United States Patent [19]

Fancher et al.

[11] 4,357,351

[45] Nov. 2, 1982

[54] LEPIDOPTERICIDAL ISOTHIOUREA COMPOUNDS

[75] Inventors: Llewellyn W. Fancher, New Castle; Herbert B. Scher, Moraga, both of Calif.

[73] Assignee: Stauffer Chemical Company, Westport, Conn.

[21] Appl. No.: 185,462

[22] Filed: Sep. 9, 1980

Related U.S. Application Data

[63] Continuation-in-part of Ser. No. 21,368, Mar. 19, 1979, abandoned.

[51] Int. Cl.$^3$ ...................... C07C 127/26; A01N 47/42

[52] U.S. Cl. ................................. 424/326; 260/453.4; 260/453.5; 260/453.6; 260/925; 544/159; 546/226; 424/200; 424/203; 424/328; 424/316; 260/239 B

[58] Field of Search ...................... 260/453.4; 424/326

[56] References Cited

U.S. PATENT DOCUMENTS

| | | | |
|---|---|---|---|
| 3,969,511 | 7/1976 | Fancher et al. | 424/326 |
| 4,062,892 | 12/1977 | Fancher et al. | 260/453.4 |
| 4,233,318 | 11/1980 | Fancher et al. | 260/453.4 |
| 4,233,318 | 11/1980 | Fancher et al. | 424/326 |

*Primary Examiner*—Alan L. Rotman
*Attorney, Agent, or Firm*—Michael J. Bradley

[57] ABSTRACT

Lepidoptericidal and herbicidal active compounds having the generic formula

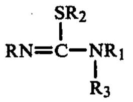

wherein R, $R^1$, $R^2$ and $R^3$ are as disclosed herein.

In general, these compounds show enhanced lepidoptericidal activity and show reduced phytotoxic effect on crops to be protected from the lepidoptera.

60 Claims, No Drawings

LEPIDOPTERICIDAL ISOTHIOUREA COMPOUNDS

This is a continuation-in-part of application Ser. No. 21,368, filed Mar. 19, 1979 now abandoned.

BACKGROUND OF THE INVENTION

Lepidoptericidal isothiuronium compounds have been disclosed in the prior art particularly those described in U.S. Pat. Nos. 3,969,511 and 4,062,892 and have the formula

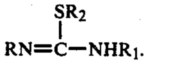

These compounds have a major disadvantage in that they show high levels of phytotoxic activity and thus, although controlling lepidoptera in the crop to be protected, are detrimental to the crop itself. To overcome this problem, applicants have discovered that substitution of the active hydrogen on the above type of isothiuronium and urea compounds with certain specific, relatively easily cleaved groups can lessen or eliminate phytotoxic effects of the parent compound while maintaining, and in some cases enhancing, the lepidoptericidal activity of the compound.

No prior art has been discovered which teaches or suggests the result that applicants have achieved.

DESCRIPTION OF THE INVENTION

The present invention is a novel group of compounds which may generally be described as certain isothioureas which are active lepidoptericides. Compounds of the present invention are represented by the generic formula

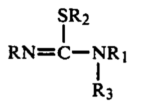

where R and $R_1$ are independently selected from the group consisting of:
- $C_2$–$C_{10}$ alkyl, preferably $C_5$–$C_9$ alkyl, more preferably $C_6$–$C_8$ alkyl,
- $C_2$–$C_{10}$ alkoxyalkyl, preferably $C_5$–$C_9$ alkoxyalkyl, more preferably $C_6$–$C_8$ alkoxyalkyl and phenyl and
- R and $R_1$ together contain from 12 to 22 carbon atoms;

wherein $R_2$ is selected from the group consisting of:
- $C_1$–$C_{14}$ alkyl, preferably $C_1$–$C_6$ alkyl, more preferably $C_1$–$C_3$ alkyl,
- $C_3$–$C_{10}$ alkenyl, preferably $C_3$–$C_5$ alkenyl, more preferably $C_2$–$C_3$ alkenyl,
- $C_3$–$C_4$ alkynyl,
- $C_2$–$C_4$ hydroxyalkyl, preferably $C_2$–$C_3$ hydroxyalkyl,
- $C_2$–$C_6$ alkylthioalkyl, preferably $C_2$–$C_4$ alkylthioalkyl,
- $C_2$–$C_6$ alkyloxyalkyl, preferably $C_2$–$C_4$ alkylthioalkyl,
- $(CH_2)_n[X(CH_2)_n]$ y where n=1 or 2, X is O or S and y=1–4, preferably 1–2,

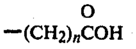

- where n=1–10, preferably 1–5, more preferably 1–3,
- phenyl and
- phenethyl;

wherein $R_3$ is selected from the group consisting of:
- carboalkoxyalkyl wherein the alkyl is $C_1$–$C_4$ alkyl, preferably $C_1$–$C_2$ alkyl,
- alkylketoalkyl wherein the alkyl is $C_1$–$C_4$ alkyl, preferably $C_1$–$C_2$ alkyl,
- hydroxyalkenyl wherein the alkenyl is $C_3$–$C_4$ alkenyl,
- hydroxyalkyl wherein the alkyl is $C_1$–$C_{12}$ alkyl, preferably $C_1$–$C_6$ alkyl, more preferably $C_1$–$C_3$ alkyl,
- formylhydroxymethyl,
- hydroxyhaloethyl wherein the halo is chloro, bromo or iodo, preferably chloro or bromo, more preferably chloro,
- substituted phenoxyalkyl wherein the alkyl is $C_1$–$C_2$ alkyl, preferably $C_1$ alkyl and the substituents are p-methoxy, Cl, $NO_3$ or CN,

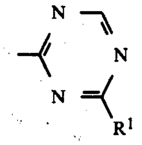

wherein $R^1$ is —OH, —$NH_2$ or $C_1$–$C_4$ alkoxy, preferably methoxy,

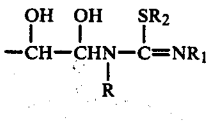

wherein R, $R_1$ and $R_2$ are as defined above,

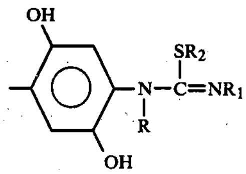

wherein R, $R_1$ and $R_2$ are as defined above, $$\overset{\ominus}{-PO_3}.B,\quad -\overset{OH}{\overset{|\ominus}{PO_2}}.B \text{ or } \overset{\ominus}{-SO_3}.B$$

wherein B is a basic cation, preferably an organic basic cation, more preferably an organic basic cation selected from the group consisting of $(CH_3)_3\overset{\oplus}{N}H$ and 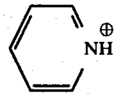,

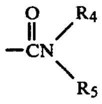

wherein $R_4$ is selected from the group consisting of:

—H,

—$C_1$–$C_{22}$ alkyl, preferably $C_1$–$C_{12}$ alkyl, more preferably $C_1$–$C_8$ alkyl and most preferably $C_1$–$C_6$ alkyl, hydroxyethyl, naphthyl, phenyl, substituted phenyl wherein the substituents are independently selected from the group of halogen, preferably chlorine, $C_1$–$C_5$ alkyl, preferably $C_1$–$C_2$ alkyl, $C_1$–$C_5$ alkoxy, preferably $C_1$–$C_2$ alkoxy, nitro, cyano and —$CF_3$,

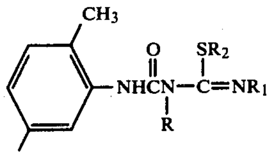

wherein R, $R_1$ and $R_2$ are as defined above,

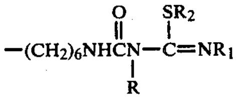

wherein R, $R_1$ and $R_2$ are as defined above,

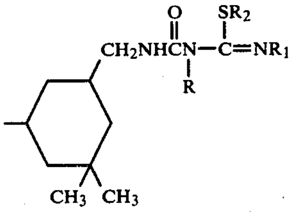

wherein R, $R_1$ and $R_2$ are as defined above,

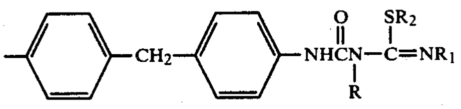

wherein R, $R_1$ and $R_2$ are as defined above,

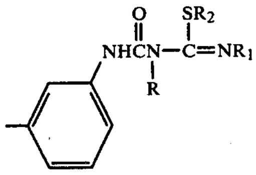

wherein R, $R_1$ and $R_2$ are as defined above,

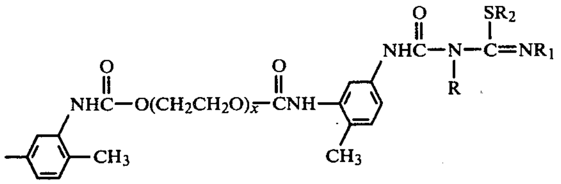

wherein x is 1 to 8 and R, $R_1$ and $R_2$ are as defined above,

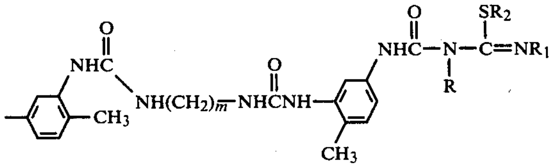

wherein m is 2 or 3, and R, $R_1$ and $R_2$ are as defined above,

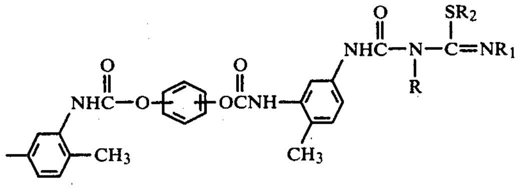

wherein R, $R_1$ and $R_2$ are as defined above,

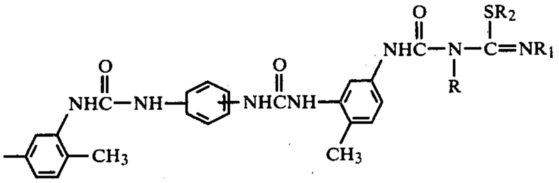

wherein R, $R_1$ and $R_2$ are as defined above,

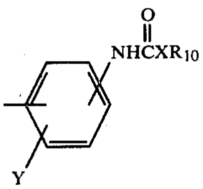

wherein X is selected from the group consisting of:

O,

S,

NH, and $NR_{11}$;

Y is hydrogen or methyl; and $R_{10}$ is selected from the group consisting of:

H, $C_1$–$C_{18}$ alkyl, preferably $C_1$–$C_8$ alkyl, more preferably $C_1$–$C_2$ alkyl, $C_3$–$C_4$ alkenyl, $C_3$–$C_4$ alkynyl, $C_2$–$C_6$ haloalkyl, preferably $C_2$–$C_3$ haloalkyl, $C_3$–$C_8$ cycloalkyl, $C_7$–$C_{20}$ polycycloalkyl, $C_2$–$C_{16}$ polyalkoxyalkyl,
$C_2$–$C_6$ hydroxyalkyl,
$C_3$–$C_{10}$ alkoxyalkyl,
$C_3$–$C_8$ carboalkoxyalkyl,
$C_4$–$C_8$ cycloalkylalkyl,
$C_4$–$C_8$ alkylcycloalkyl, preferably $C_6$–$C_8$ alkylcycloalkyl,
$C_4$–$C_7$ cycloalkylimino,
$C_2$–$C_{10}$ alkylimino,
$C_1$–$C_3$ alkylamino,
$C_4$–$C_{12}$ dialkylaminoalkyl,
$C_6$–$C_{10}$ cycloalkenyl,
phenyl,
alkylphenyl wherein the alkyl is $C_1$–$C_4$,
parachloroalkylphenyl wherein the alkyl is $C_1$–$C_4$,
naphthyl,
anthracenyl,
benzamidocycloalkyl wherein the alkyl is $C_1$–$C_2$,
pyranylmethyl,
tetrahydrofurfuryl,
thiophenemethyl,
benzhydryl,
halobenzhydryl,
polycyclic alcohol, and
substituted phenyl wherein the substituents are selected from the group consisting of:
$C_1$–$C_4$ alkyl,
halogen,
nitro,
trifluoromethyl,
formyl,
chloroacetyl,
$C_1$–$C_4$ alkoxy,
hydrogen,
benzyl,
chlorobenzyl,
phenethyl, and
substituted phenethyl wherein the substituents are selected from the group of:
$C_1$–$C_4$ alkyl and halogen, and
$R_{11}$ is selected from the group consisting of:
$C_1$–$C_4$ alkyl,
$C_3$–$C_6$ alkoxyalkyl, and
$C_3$–$C_4$ alkenyl,
$R_{10}$ and $R_{11}$ taken together form heterocyclic compounds, preferably herterocyclic compounds selected from the group consisting of:
azepinyl,
morpholinyl,
piperidinyl,
$C_1$–$C_3$ alkyl substituted peperdinyl, and
Y is hydrogen or methyl provided that when X=O or S then $R_{10}$ is other than hydrogen and substituted phenyl wherein the substituents are selected from the group consisting of:
halogen,
$C_1$–$C_4$ alkoxy,
phenoxy,
trifluoromethyl,
$C_1$–$C_6$ thioalkyl,
nitro,
isocyanato,
$C_2$–$C_4$ polyalkoxy,
$C_3$–$C_7$ cycloalkyl,
$C_3$–$C_{24}$ carboalkoxyalkyl, preferably $C_3$–$C_{10}$ carboalkoxyalkyl,
$C_1$–$C_8$ haloalkyl, preferably $C_1$–$C_4$ haloalkyl,
$C_3$–$C_{12}$ alkenyl, preferably $C_3$–$C_4$ alkenyl,
$C_2$–$C_6$ dialkylamino, phenylamino,
$C_1$–$C_{24}$ alkyl, preferably $C_1$–$C_4$ alkyl,
$C_3$–$C_{12}$ hydroxyalkylamidoalkyl;
$C_5$–$C_{10}$ N,N-hydroxyalkylureidoalkyl,
isocyanatoalkyl wherein the alkyl is $C_1$–$C_5$,
$C_3$–$C_{12}$ alkylamidoalkyl,
polyalkoxyamidoalkyl wherein the polyalkoxy moiety contains from 3–6 repeating $C_2$–$C_3$ alkoxy units and the amidoalkyl moiety contains from 4–12 carbon atoms,
—$SO_2Cl$,
—$SO_2$ polyalkoxyamidoalkyl wherein the polyalkoxy moiety contains from 3–6 repeating $C_2$–$C_3$ alkoxy units and the amidoalkyl moiety contains from 4–12 carbon atoms,
$R_5$ is selected from the group consisting of:
hydrogen,
$C_1$–$C_4$ alkyl,
$C_3$–$C_6$ alkoxyalkyl,
$C_3$–$C_4$ alkenyl,
hydroxyethyl, and
phenyl,
$R_4$ and $R_5$ taken together form heterocyclic compounds, preferably heterocyclic compounds selected from the group consisting of:
azepinyl,
morpholinyl,
piperdinyl, and
$C_1$–$C_3$ alkyl substituted piperdinyl, $$-\overset{O}{\overset{\|}{C}}X_nR_6$$

wherein X is 0 or S, n is 0 or 1, $R_6$ is selected from the group consisting of:
$C_1$–$C_{18}$ alkyl, preferably $C_1$–$C_{12}$ alkyl, more preferably $C_1$–$C_4$ alkyl,
$C_2$–$C_6$ haloalkyl,
phenyl, and
substituted phenyl wherein when N=1 the substituents are selected from the group consisting of:
nitro,
chloro,
$C_1$–$C_2$ alkyl,
$C_4$–$C_6$ polyalkoxyalkyl,
$C_3$–$C_8$ cycloalkyl,
$C_3$–$C_4$ alkenyl,
$C_3$–$C_6$ alkoxyalkyl,
$C_2$–$C_6$ hydroxyalkyl,
$C_1$–$C_3$ carboxyalkyl, and
$C_5$–$C_8$ trialkylammoniumalkyl salts,
and when n=0 the substituents are selected from the group consisting of:
chloro,
thiopotassium,
$C_1$–$C_{18}$ alkyl, preferably $C_1$–$C_{12}$ alkyl, more preferably $C_1$–$C_4$ alkyl,
benzyl,
$C_1$–$C_2$ heteroalkyl,
$C_2$–$C_4$ chlorocarboxyalkyl,
$C_4$–$C_6$ polyalkoxyalkyl, and acetyl,

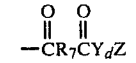

wherein $R_7$ is selected from the group consisting of:
$-(CH_2-)_n$ wherein n=0 to 8,
$-CH{=}CH-$,

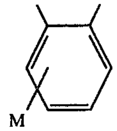

wherein M is H or Cl,

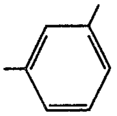

, $-CCl{=}CCl-$,
$-CH_2OCH_2-$, and
$-OCH_2CH_2O-$, and
d=0 or 1, and when d=1
Y is selected from the group consisting of:
—O,
—S, and
—NH,
Z is selected from the group consisting of:
$C_1$-$C_{18}$ alkyl, preferably $C_1$-$C_{12}$ alklyl, more preferably $C_1$-$C_4$ alkyl,
hydrogen,
$C_4$-$C_{16}$ polyalkoxyalkyl,
$C_4$-$C_8$ dialkylaminoalkyl,
$C_3$-$C_5$ alkynyl,
phenyl,
substituted phenyl,
organic salts,
inorganic salts, and
when d=0, Z is Cl or

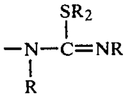

wherein R, $R_1$ and $R_2$ are as defined above,

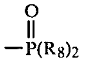

wherein $R_8$ is selected from the group consisting of:
$C_1$-$C_{10}$ alkoxy, preferably $C_1$-$C_5$ alkoxy,
amino,
$C_1$-$C_{10}$ alkoxyamino, preferably $C_1$-$C_5$ alkoxyamino,
hydroxy, and
organic base
$-SO_wR_9$ wherein w=0-2 and $R_9$ is selected from the group consisting of:
amino,
$C_1$-$C_{10}$ alkyl, preferably $C_1$-$C_5$ alkyl,
$C_1$-$C_4$ haloalkyl,
phenyl,
$C_1$-$C_{10}$ dialkylamino,
$C_1$-$C_{10}$ alkylamino,
$C_1$-$C_{10}$ alkoxy, preferably $C_1$-$C_5$ alkoxy,
substituted phenyl wherein the substituents are selected from the group consisting of:
nitro,
chloro,
$C_1$-$C_4$ alkyl, and
methoxy.

GENERAL METHODS OF PREPARATION

The compounds of the present invention are derivatives of isothioureas containing one free hydrogen atom attached to nitrogen, that is, as shown by the following formula:

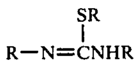

The formation of the prior art isothioureas is well known in the art. They are derived by the reaction of an isothiocyanate with a primary amine to form a thiourea followed by the reaction with an alkyl halide to produce an isothiourea salt. An unreactive solvent such as ethanol can be used for both the formation of the thiourea and the alkylation step to form the isothiourea salt. Heat is usually used to speed both reactions. The preparation of the isothiourea salt is shown below:

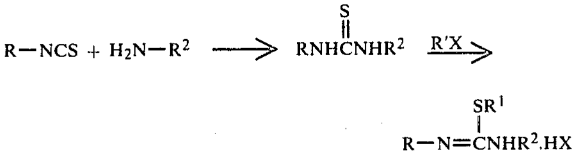

X = I, Br or Cl

The compounds of this invention are prepared by reacting the base of an isothiourea with an isocyanate or acid chloride. The free base can either be prepared by neutralization of an isothiourea salt with a cold aqueous solution of a base such as dilute sodium hydroxide, extracting the free isothiourea with a water insoluble solvent such as hexane, benzene, toluene, etc., drying over a dehydrating agent such as magnesium sulfate, filtering and evaporation under vacuum. An alternative procedure is to dissolve the isothiourea salt in a nonreactive solvent such as benzene or toluene then adding an equal molar amount of an isocyanate and the equivalent amount of a soluble tertiary base or an acid chloride and two equivalent amounts of a soluble tertiary base such as triethylamine, completing the reaction by stirring at ambient temperature for several hours or refluxing for a shorter period of time. An alternative method when using a base such as triethylamine is to treat the isothiourea salt in a solvent such as benzene in which triethylamine hydrohalide is almost totally insoluble, filtering off the triethylamine hydrohalide and treating the filtrate with the isocyanate or acid chloride, completing the reaction as discussed previously. Solvents suitable for the condensation of the isothiourea with an isocyanate or acid chloride are those which are unreactive to any of the reactants. These include hexane, benzene, toluene, tetrahydrofuran, dioxane, methylenechloride, diethylether, and the like. Depending on the reactants, reaction temperatures are generally within the range of −20° C. to 80° C. and reaction times vary from 0.5 hours to 24 hours.

In some instances, it has been found that the condensation of an isothiourea with an isocyanate or acid chloride can be hastened by the addition of such catalysts as triethylamine and dibutyltindilaurate.

Equations showing the reactions just discussed are as follows:

(A) Using isothiourea base with an isocyanate

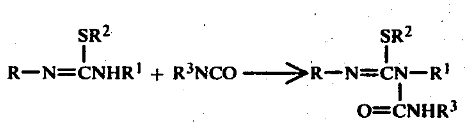

(B) Using isothiourea salt + a base

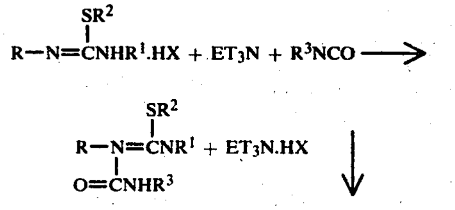

(C) Using isothiourea base with an acid chloride

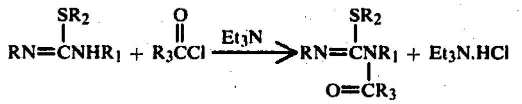

The isothiourea precursors of the prior art discussed above can in general be prepared by the methods disclosed in U.S. Pat. Nos. 3,969,511 and 4,062,892.

These compounds are useful as lepidoptericides when used in a lepidoptericidally effective amount on insects of the order lepidoptera or their habitat or feedstuffs. Some of the compounds also show phytotoxic effects which could render them useful as herbicides as well as lepidoptericides if such efficacy was desired. In addition, some of these compounds show biocidal and/or fungicidal effects.

By "lepidoptericidally effective amount" is meant the amount of the herein disclosed lepidoptericidal compounds which when applied in any conventional manner to the habitat of the lepidoptera, the feedstuffs of lepidoptera, or the insects themselves, will "control" by killing or substantially injuring a significant portion of the lepidoptera.

These compounds are useful in protecting food, fiber forage crops and ornamental crops from damage by insects and larva of other order lepidoptera. Examples of crops to be protected include forest trees such as oak and pine, fruit trees such as peach, apple and walnut, vegetables such as tomatoes, other crops such as tobacco, cotton, lettuce, cabbage, corn and rice and any crop which lepidoptera feed upon.

The novel compounds of this present invention can be prepared from the above precursors by methods shown in the following examples.

EXAMPLE 1

1,3-Diheptyl-2-ethyl-3-(O,O-dimethyl phosphoro)isothiourea 6.0 grams (g) (0.02 mole) of 1,3-diheptyl-2-ethyl isothiourea and 200 milliliters (ml) of methylene chloride were combined in a 500 ml 3-neck flask fitted with a stirrer, thermometer and dropping funnel. The solution was stirred and cooled to 0° C. 2.0 g (0.02 mole) of triethylamine was added to the flask. Next, 3.0 g (0.02 mole) of phosphorus oxychloride dissolved in 25 ml of methylene chloride was added at such a rate that the pot temperature was maintained at 0° to 5° C. After the addition was complete, the reaction mass was stirred at 0° C. for 30 minutes. Then, a solution of 8.7 g (0.04 mole) of 25 percent sodium methoxide in methanol with 25 ml of methylenechloride was added over a period of 15 minutes while the pot temperature was maintained at 0° to 5° C. The reaction mass was then stirred at 5° C. for 30 minutes and then at room temperature for 30 minutes. The resulting mixture was then washed with two 200 ml portions of water and phase separated. The methylene chloride phase was dried with anhydrous $MgSO_4$, filtered and evaporated invacuo to yield 7.4 g of the desired product, 1,3-diheptyl-2-ethyl-3-(O,O-dimethylphosphoro) isothiourea which had a $n_D^{30}$ of 1.4528. The product identification was confirmed by infrared (IR), H-nuclear magnetic resonance (NMR) and $C^{13}$-NMR spectra. Compound No. 229 in Table I.

EXAMPLE 2

1,3-diheptyl-2-ethyl-3-N-[4-methyl-3-(carbowax-350-carbamyl)] phenyl carbamyl isothiourea The title compound was formed as follows:

Intermediate (a)

3.56 g (0.02 mole) of 2-methyl-5-nitrophenylisocyanate, 7.0 g (0.02 mole) of carbowax 350, 2 drops of triethylamine, 1 drop of di- butyltindilaurate and 25 ml of methylene chloride were combined with stirring in a 100 ml round bottom flask. After the exotherm had subdivided, the solvent was removed invacuo. The residue was dissolved in a 10:1 mixture of diethylether-toluene. A white solid impurity was removed by filtration and evaporation of the filtrate invacuo gave 10.5 g of the desired compound N-(2-methyl-5-nitrophenyl) carbowax (350) carbamate, $n_D^{30}$ 1.4810. The structure was confirmed by $C^{13}$-NMR spectra.

Intermediate (b)

7 g (0.013 mole) of intermediate (a) was dissolved in 200 ml of ethanol in a Parr glass pressure bottle. 1 g of palladium on carbon catalyst was added and the mixture was shaken and reacted with hydrogen maintained at a pressure of 50 psi for 30 minutes. The reaction mass was then filtered and the filtrate was evaporated invacuo to yield 6.0 g of the desired compound N-(2-methyl-5-aminophenyl) carbowax (350) carbamate. The structure was confirmed by $C^{13}$-NMR spectra.

Intermediate (c)

5.8 g (0.0116 mole) of intermediate (b) was dissolved in 200 ml of toluene in a 250 ml 3-neck flask fitted with a condenser, stirrer and gas inlet tube. The solution was stirred, heated to 70° C. and saturated with HCl gas. The mixture was then heated to reflux and phosgene was bubbled in for 30 minutes. The reaction mass became clear. $N_2$ gas was then bubbled in to remove the excess phosgene. The solvent was removed invacuo to yield 6.1 g of N-(2-methyl-5-isocyanophenyl) carbowax (350) carbamate, $n_D^{30}$ 1.5848. The structure was confirmed by $C^{13}$-NHR spectra.

1,3-diheptyl-2-ethyl-3-N-[4-methyl-3-(carbowax-350-carbamyl)] phenyl carbamyl isothiourea 2.0 g (0.004 mole) of intermediate (c), 1.2 g (0.004 mole) of 1,3-diheptyl-2-ethylisothiourea, 2 drops of triethylamine and 15 ml of methylene chloride were combined in a 100 ml round bottom flask. After the exotherm had subsided, the solvent was removed invacuo to yield 3.3 g of the desired product, 1,3-diheptyl-2-ethyl-3-N-[4-methyl-3-(carbowax-350-carbamyl)] phenyl carbamyl isothiourea. The structure was confirmed by $C^{13}$-NMR spectra. Compound No. 216 in Table I.

EXAMPLE 3

1,3-diheptyl-2-ethyl-3-[N-(3-tergitol (15-S-7) oxycarbamylphenyl) carbamyl] isothiourea The title compound was formed as follows:

Intermediate (d)

In the same manner as intermediate (a) of Example 2 above, 3.28 g (0.02 mole) of 3-nitrophenylisocyanate, 10.1 g of tergitol (15-S-7), 2 drops of triethylamine and 25 ml of methylene chloride were combined to yield 13.2 g of the desired compound, N-(3-nitrophenyl) tergitol (15-S-7) carbamate. Structure was confirmed by IR spectra.

Intermediate (e)

In the same manner as intermediate (b) of Example 2 above, 11.2 g (0.0166 mole) of intermediate (d) was reduced with $H_2$ in ethanol using 1 g of palladium on carbon catalyst to yield 9.3 g of the desired compound, N-(3-aminophenyl) tergitol (15-S-7) carbamate. Structure was confirmed by IR spectra.

Intermediate (f)

In the same manner as intermediate (c) of Example 2 above, 9.3 g (0.0145 mole) of intermediate (e) was treated with excess HCl gas followed by excess phosgene to yield 9.4 g of the desired compound, N-(3-isocyanophenyl) tergitol (15-S-7) carbamate. Structure was confirmed by IR spectra.

1,3-diheptyl-2-ethyl-3-[N-(3-tergitol (15-S-7) oxycarbamylphenyl) carbamyl] isothiourea In the same manner as the title compound of Example 2 above, was prepared 2 g (0.003 mole) of intermediate (f) was combined with 0.9 g (0.003 mole) of 1,3-diheptyl-2-ethylisothiourea, 2 drops of triethylamine and 10 ml of methylene chloride to yield 2.9 g of the desired product, 1,3-diheptyl-2-ethyl-3-[N-(3-tergitol (15-S-7) oxycarbamylphenyl) carbamyl] isothiourea $n_D^{30}$ 1.5710. Structure was confirmed by IR spectra. Compound No. 219 in Table I.

EXAMPLE 4

1,3-diheptyl-2-ethyl-3-(O,O-diethylphosphorodithioyl acetyl) isothiourea

Intermediate (g)

30 g (0.1 mole) of 1,3-diheptyl-2-ethylisothiourea, 12.4 g (0.11 mole) of chloroacetylchloride and 250 ml of toluene were combined in a 500 ml 3-neck flask fitted with a stirrer, thermometer and dropping funnel. The solution was stirred and cooled to −30° C. with a dry-ice bath. 11.1 g (0.11 mole) of triethylamine was then added over a period of 30 minutes. After the addition was complete, the reaction mass was allowed to warm to room temperature and stirring was continued for 1 hour. The reaction mass was then washed in turn with two 200 ml portions of water, 100 ml of saturated sodium bicarbonate solution and finally with two 200 ml portions of water. The toluene phase was dried with anhydrous $MgSO_4$, filtered and evaporated invacuo to yield 36.1 g of the desired compound, 1,3-diheptyl-2-ethyl-3-chloroacetylisothiourea. The structure was confirmed by IR and NMR spectra.

1,3-diheptyl-2-ethyl-3-(O,O-diethylphosphorodithioyl acetyl isothiourea 2.2 g (0.012 mole) of O,O-diethyldithiophosphoric acid was dissolved in 25 ml of acetone and was treated with 5 g of anhydrous potassium carbonate. After neutralization, the acetone phase was decanted into a 250 ml flask containing a solution of 3.0 g (0.008 mole) of intermediate (g) in 75 ml of acetone. The resulting mixture was stirred at room temperature for 2 hours, then was poured into two 200 ml of toluene. The resulting mixture was washed with two 200 ml portions of water. The toluene phase was then dried with anhydrous $MgSO_4$, filtered and evaporated invacuo to yield 3.6 g of the desired product, 1,3-diheptyl-2-ethyl-3-(O,O-diethylphosphorodithioylacetyl) isothiourea. $n_D^{30}$ 1.5060. The structure was confirmed by IR and NMR spectra. Compound No. 261 in Table I.

EXAMPLE 5

N,N'-diheptyl-S-ethyl-N-propane sulfonyl isothiourea 1.8 g (0.018 mole) of triethylamine was added to 4.5 g (0.015 mole) N,N'-diheptyl-S-ethyl-isothiourea in 50 ml methylene chloride in a stirred round bottom flask. A solution of propanesulfonyl chloride (0.018 mole, 2.6 g) in 8 ml methylene chloride was added dropwise to the above solution at 0° C. The mixture was stirred 1.5 hours at room temperature then at 30°-35° C. for 1.5 hours. The cooled solution was washed twice with 20 ml water, once with 25 ml saturated sodium bicarbonate solution and twice more with 20 ml of water. The organic phase was dried over magnesium sulfate and evaporated invacuo to yield the product as a yellow oil. $n_D^{30}$ 1.4805. Yield was 5.2 g (85.4% of theory). The structure was confirmed by IR spectrum. Compound No. 203 in Table I.

EXAMPLE 6

N,N'-diheptyl-S-ethyl-N'-p-toluene sulfonyl isothiourea

The reaction was carried out with 0.018 mole (3.4 g) p-toluenesulfonyl chloride in the same manner as Example 5 above. The product had a $n_D^{30}$ of 1.517. Yield was 6.0 g (88% of theory). IR, NMR spectra and mass spectroscopy confirmed the structure. Compound No. 206 in Table I.

EXAMPLE 7

1,3-di-n-heptyl-1-trichloromethylthio-2-ethyl isothiourea 3 g (0.01 mole) 1,3-di-n-heptyl-2-ethyl isothiourea was mixed with 50 ml tetrahydrofuran in a stirred round bottom flask and cooled in an ice bath. 1.4 ml (0.01 mole) triethylamine was added and the mixture stirred for 10 minutes. 1.1 ml (0.01 mole) trichloromethyl sulfenyl chloride was added to the mixture dropwise over 2 minutes. A white precipitate formed and the mixture was stirred for 1 hour while coming to ambient temperature. The resultant reaction mixture was allowed to sit overnight. The mixture was suction filtered to remove the white solid which was rinsed twice with 10 ml of fresh tetrahydrofuran. The filtrate was evaporated under vacuum resulting in 4.55 g of the title product at a yield of 101.2 percent. The resulting liquid had a $n_D^{30}$ of 1.5084 and was identified as the title compound by IR spectrum and mass spectroscopy. Compound No. 297 in Table I.

EXAMPLE 8

1,3-di-n-heptyl-1-(2'-fluoro-1',1',2',2'-tetrachloroethylthio-2-ethylisothiourea 2.0 g (0.007 mole) 1,3-di-n-heptyl-2-ethyl isothiourea was dissolved in 100 ml tetrahydrofuran and placed in a stirred round bottom flask and placed in an ice bath. 0.7 g (0.0069 mole) triethylamine was added and the mixture stirred for 10 minutes. 1.68 g (0.0068 mole) 2-fluoro-1,1,2,2-tetrachloroethylsulfenyl chloride dissolved in 20 ml of tetrahydrofuran was added over approximately 15 minutes. A precipitate formed while the mixture was stirred for 2 hours. The mixture was suction filtered and the precipitate was washed twice with 20 ml tetrahydrofuran. The filtrate was vacuum evaporated. The title product's yield was 3.53 g of a liquid having a $n_D^{30}$ of 1.5091. The product identity was confirmed by IR spectrum and mass spectroscopy. Compound No. 298 in Table I.

EXAMPLE 9

1,3-di-n-heptyl-1-o-nitrophenylthio-2-ethylisothiourea 1.9 g (0.01 mole) of 2-nitro benzene sulfenyl chloride was dissolved in 50 ml of tetrahydrofuran. A mixture of 3 g (0.01 mole) 1,3-di-n-heptyl-2-ethylisothiourea in 30 ml of tetrahydrofuran was added to the mixture in a glass round bottom stirred flask cooled in an ice bath. 1.05 g (0.01 mole) of triethylamine in 10 ml of tetrahydrofuran was added over a period of 10 minutes. A white precipitate formed immediately and the reaction mixture was stirred in the bath for 3 hours while coming to ambient temperature and then suction filtered. The filtrate was vacuum evaporated to produce a light brown sticky residue which was redissolved in approximately 100 ml diethyl ether and filtered through magnesium sulfate and Dicalite 4200 by suction. The filtrate was vacuum stripped to produce 4.2 g of a liquid having a $n_D^{30}$ of 1.5463. The product was identified as the title product by IR spectrum. Compound No. 300 in Table I.

EXAMPLE 10

S-ethyl-1,3-diheptyl-3-(2-carboethoxy) ethyl-2-isothiourea 3 g (0.01 mole) of S-ethyl-1,3-diheptyl-2-isothiourea and 3 g (0.03 mole) of ethyl acrylate were placed in a 100 ml glass flask. A catalytic amount of base (0.1 g NaH) was added and the mixture heated from 25° to 85° C. and held at 85° C. for 5 hours. The reaction mixture was cooled and 150 ml of ether was added.

The ether was washed with 100 ml of water, then dried and stripped to yield 2 g of the title product. The structure was verified by IR and NMR spectra.

Compound No. 199 in Table I.

EXAMPLE 11

S-ethyl-1,3-diheptyl-3-(3-oxobutyl)-2-isothiourea

The procedure was the same as for Example 10 except ethyl acrylate was replaced with methyl vinyl ketone and the reaction was run at room temperature for 4 hours. Work-up of the product was the same. 2 g of the title product was produced and identified by IR and NMR spectra. Compound No. 200 in Table I.

EXAMPLE 12

N,N-di-n-heptyl-N'-ethyloxalyl-S-ethyl-isothiourea 5.0 g (16.6 millimoles) of S-ethyl-1,3-diheptyl-2-isothiourea and 1.8 g (18.3 millimoles) of triethylamine in 50 ml of methylene chloride were mixed together in a 100 ml single necked round bottom flask equipped with a magnetic stirrer and stopper. The clear light yellow solution was cooled to 0° C. in an ice bath. To this stirred, cooled solution was added 2.50 g (18.3 millimoles) of ethyloxalyl chloride dropwise while maintaining the temperature between 5° to 15° C. A large amount of a white precipitate formed within seconds and stirring was allowed to continue for 1 hour at 0° C. The cooling bath was removed and the mixture stirred at room temperature for 3 hours. The precipitate was dissolved by the addition of 50 ml water and the mixture transferred to a separatory funnel containing 50 ml of methylene chloride. The layers were separated and the organic phase washed once with 10 ml of saturated $NaHCO_3$, 3 times with 10 ml portions of water, once with 10 ml of saturated sodium chloride and dried over $Na_2SO_4$. The dried, clear yellow organic solution was filtered through $Na_2SO_4$ and the solvent was removed under vacuum to yield 6.63 g (99.7% yield) of the title product as a clear, yellow oil having a $n_D^{30}$ of 1.4757. The product was identified as the title product by IR and NMR spectra and mass spectroscopy. Compound No. 671 in Table I.

EXAMPLE 13

Bis-N'-(N,N'-n-heptyl-S-ethylisothioureyl)-oxalate

The procedure for Example 13 is the same as for Example 12 above with the exception that a 200 ml single necked round bottom flask was used in place of the 100 ml flask and 1.16 g (9.13 millimoles) of oxalyl chloride was substituted for the ethyloxalyl chloride of the previous example. The reaction resulted in a clear yellow solution which was stirred at 0° C. for 1 hour and then stirred at room temperature for 20 hours. The clear yellow solution was then transferred to a separatory funnel containing 50 ml of water and 50 ml of methylene chloride. The layers were phase separated and the organic phase washed once with 10 ml of 10 percent potassium carbonate, 5 times with 10 ml portions of water, once with 10 ml of saturated sodium chloride and dried over $Na_2SO_4$. The dried organic solution was filtered and the solvent removed as in Example 12 to yield 5.55 g (102.1% of theory yield) of an orange oil having a $n_D^{30}$ of 1.4932. The product was identified as the title product by IR and NMR spectra and mass spectroscopy. Compound No. 688 in Table I.

EXAMPLE 14

N,N'-Di-(1-heptyl)-N'-(ethylmercapto carbonyl)-S-ethyl isothiourea

The procedure and equipment were the same as in Example 12 above with the exception that 5.0 g (16.6 millimoles) of N,N'-di-(1-heptyl)-S-ethyl isothiourea and 1.85 g (18.3 millimoles) of triethylamine and 50 ml of methylene chloride were added to the flask followed by addition of 2.28 g (18.3 millimoles) of ethylthio chloroformate. The resultant product was phase separated, washed and dried in a manner of Example 12. The solvent was removed under vacuum to yield 6.55 g (101.5% of theory yield) of accrued yellow oil having a $n_D^{30}$ of 1.4922. The product was identified as the title product by IR and NMR spectra and mass spectroscopy. Compound No. 300 in Table I. 6

EXAMPLE 15

1,3-diheptyl-2-ethyl-3-[3'-2"-ethoxyethoxycarbonylamino)-4'-methylphenylaminocarbonyl) isothiourea The title product was prepared as follows:

Step (a)

1,3-diheptyl-2-ethyl-3-(3-isocyanato-4-methylphenylaminocarbonyl) isothiourea (Intermediate)

125 cubic centimeters (cc) of methylene chloride was pipetted under argon flow into a 200 cc 3-neck stirred flask, 15.1 g (0.86 mole) of toluene - 2,4-diisocyanate was then added to the methylene chloride. Next, 25.8 g (0.086 mole) of 1,3-diheptyl-2-ethyl isothiourea was added without cooling over a period of 5 minutes. The temperature increased from 20° to approximately 30° C. during this addition. The reaction mixture was then heated to reflux (41° C.) and held at reflux temperature for 1 hour. The resultant reaction mixture was then concentated on a rotary evaporator under high vacuum. The reaction produced 39.8 g of product having a $n_D^{30}$ of 1.5318 which was identified a the intermediate title product by IR and carbon 13 NMR spectra.

Step (b) Preparation of 1,3-diheptyl-2-ethyl-3-[3'-(2"ethoxyethoxycarbonylamino)-4'-methylphenylaminocarbonyl] isothiourea 4.74 g (0.010 mole) of the intermediate of step (a) 0.95 g (0.0105 mole) 2-ethoxyethanol, 2 drops of triethylamine, 1 drop of dibutyltindilaurate and 25 cc of tetrahydrofuran dried over a Linde Molecular Sieve 3A were charged to a 3-neck flask. The mixture was brought to reflux (67° to 68° C.) and held at reflux for 2 hours. The solvent was then removed under high vacuum at a pressure of 0.3 mm or less and at a bath temperature of 80° to 90° C. 5.6 g of a viscous oil was recovered and identified as the title product by IR and carbon 13 NMR spectra analyses. Compound No. 419 in Table I.

EXAMPLE 16

1,3-diheptyl-2-ethyl-3-[3'-(3"-chloro-4"-methylphenylureido)-4'-methylphenylaminocarbonyl] isothiourea The reaction and reactants were identical to the reaction of Example 15(b) with the exception that 1.49 g (0.0105 mole) of 3-chloro-4-methylaniline is substituted for the 2-ethoxyethanol. An insoluble by-product was formed which was removed by filtering before evaporation of the solvent. The reaction produced 3.5 g of a product identified as the title product by IR and NMR spectra analyses. Compound No. 429 in Table I.

EXAMPLE 17

1,3-diheptyl-2-ethyl-3-[3'-propylureido-4'-methylphenylaminocarbonyl] isothiourea 4.74 g (0.010 mole) of the intermediate as prepared in Example 15(a) and 25 cc of dry tetrahydrofuran were charged to a 3-neck flask. 0.62 g (0.0105 mole) of propylamine was added at room temperature without cooling. The reaction was exothermic and the temperature rose about 10° to 20° C. No heat was applied to the mixture and the reaction was completed in 1 hour. The mixture was filtered from a small amount of solid by-product and was worked up in the manner of Example 15(b). The reaction produced 5.0 g of a liquid having a $n_D^{30}$ of 1.5312 and was identified as the title product by IR and carbon 13 NMR spectra analyses. Compound No. 431 in Table I.

EXAMPLE 18

1,3-diheptyl-2-ethyl-3[3'-p-chlorobenzylthiocarbonylamino-4'-methylphenylaminocarbonyl] isothiourea The reactants were the same as in Example 15(b) with the exception that 1.66 g (0.0105 mole) of 4-chlorobenzylmercaptan was substituted for the 2-ethoxyethanol. The reaction produced 6.5 g of a viscous liquid which was identified as the title product by IR and NMR spectra analyses. Compound No. 433 in Table I.

EXAMPLE 19

1,3diheptyl-2-ethyl-3-(3'-phenoxycarbonylamino-4'-methylphenylaminocarbonyl) isothiourea The reactants were the same as in Example 15(b) with the exception that 0.99 g (0.0105 mole) of phenol was substituted for the 2-ethoxyethanol. The reaction produced 5.2 g of a liquid having a $n_D^{30}$ of 1.5488 which was identified as the title product by NMR and IR spectra analyses. Compound No. 452 in Table I.

EXAMPLE 20

1-octyl-2-ethyl-3-sec-heptyl-3-]3-(1-octyl-2-propyl-3-sec-heptyl-3-carbonylamino)-4-methylphenylcarbonylamino] isothiourea Step (a) Preparation of 1-octyl-2-ethyl-3-sec-heptyl-3-(3-isocyanato-4-methylphenylaminocarbonyl) isothiourea (Intermediate)

This intermediate was prepared as was the intermediate of Example 15(a) with the exception that 27.2 g (0.086 mole) of 1-octyl-2-ethyl-3-sec-heptyl-isothiourea was substituted for the thiourea reactant of step 25(a). The reaction produced 41.5 g (98.8 weight percent of theory) of a liquid having a $n_D^{30}$ of 1.5280 which identified as the title intermediate by IR and carbon 13 NMR spectra analyses.

Step (b) Preparation of 1-octyl-2-ethyl-3-sec-heptyl-3-[3-(1-octyl-2-propyl-3-sec-heptyl-3-carbonylamino)-4-methylphenylcarbonylamino] isothiourea The title product was prepared in the manner of step 15(b) with the exception of using 4.87 g (0.010 mole) of the intermediate prepared in step 20(a) and 3.29 g (0.010 mole) of 1-octyl-2-propyl-3-sec-heptyl isothiourea. The reaction produced 7.9 g (96.3 weight percent of theory) of a liquid having a $n_D^{30}$ of 1.5185 which was identified as the title product by IR and carbon 13 NMR spectra analyses. Compound No. 558 in Table I.

EXAMPLE 21

1,3-bis-n-heptyl-1-(carbamysulfonylchloride)-2-S-ethyl isothiourea 50 ml of dry methylene chloride and 8.49 g of chlorosulfonyl isocyanate (aldrich) were placed in a 200 ml flask provided with a magnetic stirrer, thermometer and dropping funnel. A solution of 18 g of the 1,3-dipheptyl-2-ethyl isothiourea (in 100 ml dry methylene chloride) was added dropwise over 40–45 minutes. The reaction exhibited a slight exotherm so the flask was cooled in a water bath to hold the temperature below 28° C. The solution was then stirred at about 25° C. overnight.

The solution was then filtered and the filtrate concentrated under reduced pressure. 26.2 g (99 weight percent of theory) of a thick liquid having a $n_D^{30}$ of 1.4833 was recovered. The product was identified as the title product by IR and NM spectra analyses. Compound No. 635 in Table I.

EXAMPLE 22

1,3-bis-n-heptyl-1-chlorocarbonyl-2-ethyl isothiourea 100 ml of dry $CH_2Cl_2$ was placed in a 500 ml flask equipped with a thermometer and dropping funnel and cooled to 5° C. in an ice bath. A solution of phosgene in benzene (170 g of 17.5 percent weight concentration) was then added. Next, a solution of 100 ml of dry $CH_2Cl_2$, 10.1 g triethylamine and 30 g of 1,3-diheptyl-2-ethyl isothiourea was added dropwise over a one hour period at 5° C. The mixture was then stirred overnight at ambient temperature.

The next morning the reaction mixture was warmed to about 40° C for 2½–3 hours to ensure completion of the reaction. The mixture was then subjected to reduced pressure to remove the $CH_2Cl_2$ solvent. 100 ml of dry ether was added and the mixture filtered by suction on a glass frit. The solid was washed by a little more ether and the combined filtrates concentrated under reduced pressure to remove the ether. 38.6 g of a liquid (106 weight percent of theory) having a $n_D^{30}$ of 1.4613 was recovered. The product was identified as the title product by mass spectra analyses. Compound No. 643 in Table I.

EXAMPLE 23

1,3-bis-n-heptyl-1-diethylcarbamyl-2-ethyl isothiourea 100 ml of dry benzene and 5.44 g of 1,3-diheptyl-2-ethyl isothiourea carbamyl chloride were placed in a 200 ml flask equipped with a thermometer and dropping funnel. A solution of 12 ml dry benzene and 2.19 g diethyl amine was added dropwise over 10–12 minutes. An exotherm raised the temperature from 21° to 30° C. The mixture was then heated to 45°–50° C. for 3 hours. The reaction mixture was then cooled to 15° C. and washed twice by 50 ml portions of cold water. The benzene phase was dried by $MgSO_4$, filtered and the solvent removed under reduced pressure. 5.75 g of a liquid (96 weight percent of theory) having a $n_D^{30}$ of 1.4568 was recovered. The structure was confirmed as the title compound by mass spectra analyses. Compound No. 644 in Table I.

EXAMPLE 24

1,3-bis-n-heptyl-1-(propargyloxycarbonyl)-2-ethyl isothiourea 50 ml of dry tetrahydrofuran and 0.36 g of NaH were placed in a 200 ml flask equipped with a thermometer and dropping funnel. A solution of 10 ml dry THF and 0.84 g propargyl alcohol was added dropwise over 8–10 minutes. The reaction mixture liberated hydrogen and exhibited a slight exotherm. The mixture was then stirred for 3 hours to complete the reaction.

Then a solution of 15 ml dry THF and 5.44 g of the 1,3-diheptyl-2-ethyl isothiourea carbamyl chloride was added dropwise over 10 minutes. The mixture was stirred and warmed to 45° C. for 2 hours. The reaction was cooled to 25° C. and filtered by suction on a glass frit and filter. The solvent was removed under reduced pressure. 5.0 g of a liquid (88 weight percent of theory) having a $n_D^{30}$ of 1.4553 was recovered. The structure was confirmed as the title compound by NMR and spectra analyses. Compound No. 648 in Table I.

EXAMPLE 25

1,3-bis(2-ethylhexyl)-1-(succinic anhydride adduct)2-ethyl-isothiourea·$Et_3N$ salt 200 ml of dry $CH_2Cl_2$, 32.8 g of 1,3-(2-ethylhexyl)-2-ethyl isothiourea, 11 g of succinic anhydride and 11.1 g of $Et_3N$ were placed in a 500 ml flask. There was a slight exotherm upon mixing these components. The solution stood overnight.

The reaction mixture was then stripped under reduced pressure. 47.3 g of a liquid (89 weight percent of theory) having a $n_D^{30}$ of 1.4899 was recovered. The structure was confirmed as the title compound by IR and NMR spectra analyses. Compound No. 665 in Table I.

EXAMPLE 26

Reaction product of 2 moles of 1,3-di-(2'-ethylhexyl)-2-S-ethyl isothiourea + toluene-2,4-diisocyanate In a three-neck 200 ml flask equipped with a magnetic stirrer, 3.28 g (0.01 mole) of 1,3-di-(2'-ethylhexyl-2-S-ethyl isothiourea was mixed with 20 ml of tetrahydrofuran. To this solution was added 0.87 g (0.005 mole) of toluene-2,4-diisocyanate. The temperature rose from 23° C. to 34° C. The mixture was allowed to stand at ambient temperature overnight after which it was evaporated under vacuum. Infrared analysis showed that the reaction was incomplete, therefore, the mixture was dissolved in 30 ml of methylenechloride and 1 drop of dibutyltindilaurate and 2 drops of triethylamine were added. The homogenous solution was stirred at ambient temperature for 1.5 hours. The mixture was reevaporated under vacuum to obtain the product as a viscous yellow liquid having a $n_D^{30}$ of 1.5201. The yield was 4.3 g. The product was identified as the title compound by both IR and NMR spectra analyses. Compound No. 85 in Table I.

EXAMPLE 27

1,3-di-n-heptyl-1-N-phenylcarbamyl-2-S-n-propyl isothiourea

The equipment was as in Example 26 above. 6.2 g (0.014 mole) 1,3-di-n-heptyl-2-S-n-propyl isothiuronium·hydrogen iodide was dissolved in 35 ml of tetrahydrofuran and 1.68 g (0.014 mole) phenyl isocyanate was added followed by a portion-wise addition of 1.43 g (0.014 mole) triethylamine with cooling. A solid precipitate formed on addition of the triethylamine. The reaction was stirred at ambient temperature overnight. The reaction mixture was then vacuum evaporated to remove tetrahydrofuran and the residue was dissolved in chloroform and washed two times with 150 ml portions of water. The organic phase was then dried over magnesium sulfate, filtered and vacuum evaporated to remove the chloroform. The product was 5.9 g (96.7 weight percent of theory yield) of a yellow liquid having a $n_D^{30}$ of 1.15188. The produce was identified as the title compound by IR and NMR spectra analyses. Compound No. 1 in Table I.

EXAMPLE 28

1,3-di-n-heptyl-1-N-octadecylcarbamyl-2-S-ethyl isothiourea

The equipment was the same as in Example 26 above. 4.5 g (0.015 mole) 1,3-di-n-heptyl-2-S-ethyl-isothiourea was mixed with 40 ml tetrahydrofuran and 4.43 g (0.015 mole) N-octadecylisocyanate was added. Three drops of triethylamine were added and the mixture stood overnight. The mixture was then warmed to 40° C. for 20 minutes to complete the reaction. A small amount of solid formed on cooling and was filtered off. The reaction mixture was then vacuum evaporated to produce 8.9 g (100 percent of theory yield) of a pale liquid having a $n_D^{30}$ of 1.4750. The product was identified as the title product by IR and NMR spectra analyses. Compound No. 29 In Table I.

EXAMPLE 29

1,3-di-n-heptyl-1-N-4-methylthiophenylcarbamyl-2-S-ethyl isothiourea

The equipment was the same as in Example 26 above. 3.0 g (0.01 mole) 1,3-di-n-heptyl-2-S-ethyl isothiourea was mixed with 25 ml of methylene chloride. Two drops of triethylamine and 1 drop of dibutyltindilaurate were added and then 1.65 g (0.01 mole) 4-methyl thiophenyl isocyanate was added. The temperature rose from 23° to 33°. The reaction mixture was then vacuum evaporated to remove the methylene chloride to produce 4.65 g (100 percent of theory yield) of a yellow liquid having a $n_D^{30}$ of 1.5340. The liquid solidified on standing into a semi-solid. The product was identified as the title product by IR and NMR spectra analyses. Compound No. in Table 47 in Table I.

EXAMPLE 30

1,3-di-n-heptyl-1-N-2-chloroethylcarbamyl-2-S-ethylisothiourea

The procedure, equipment and reactants were the same as in Example 29 with the exception that 1.06 g (0.01 mole) of 2-chloroethylisocyanate was substituted for the 4-methylthiolphenyl isocyanate. The reaction produced 4.14 g (102 weight percent of theory yield) of a clear liquid having a $n_D^{30}$ of 1.4930. The product was confirmed as the title compound by IR and NMR spectra analyses. Compound No. 48 in Table I.

EXAMPLE 31

1-sec-heptyl-3-n-heptyl-2-S-ethyl isothiourea (Intermediate)

The equipment was the same as in example 26 above. 11.5 g (0.1 mole) 2-aminoheptane was mixed with 50 ml ethanol 2B and 15.7 g (0.1 mole) N-heptyl isothiocyanate was added, resulting in an exothermic reaction during which the temperature rose from 25° to 65° C. The reaction mixture was refluxed on a steam bath for 1.5 hours. 17.16 g (0.11 mole) ethyl iodide was then added to the thiourea and the mixture refluxed for 1.5 hours on a steam bath. The product was vacuum evaporated to produce 44.0 g of an isothiuronium salt. The isothiuronium salt was dissolved in 200 ml of toluene and washed with 100 cc of 5 percent sodium hydroxide. The toluene layer was then washed twice with 150 cc portions of water, dried over magnesium sulfate, filtered and vacuum evaporated. The product was then stripped under high vacuum to produce 7.78 g (92.6 weight percent of theory yield) of a clear, yellow liquid having a $n_D^{30}$ of 1.4768. The product was identified as the title product by IR and NMR spectra analyses.

EXAMPLE 32

1-sec-heptyl-3-n-hexyl-2-S-ethylisothiourea (Intermediate)

The equipment, procedure and reactants were the same as in Example 31 with the exception that 10.01 g (0.07 mole) of n-hexylisothiocyanate, 8.05 g (0.07 mole) 2-aminoheptane, 35 ml ethanol 2B, 11.7 g (0.075 mole) ethyl iodide, 200 ml of toluene and a one percent solution sodium hydroxide (0.08 mole) were used as reactants and reagents in the procedure. The reaction produced 19.6 g (98 weight percent of theory yield of a clear liquid having a $n_D^{30}$ of 1.4765. The product was identified as the title product by IR and NMR spectra analyses.

EXAMPLE 33

1,3-di-n-heptyl-1-N-tert-butylcarbamyl-2-S-ethyl isothiourea

The equipment was the same as used in Example 26. 3.0 g (0.01 mole) 1,3-di-n-heptyl-2-S-ethyl isothiourea was mixed with 30 ml of methylene chloride. Two drops of triethylamine and 1 drop of dibutyltindilaurate were added to the mixture followed by 1.0 g (0.01 mole) tert-butyl isocyanate. The temperature rose from 24° to 39° C. The reaction mixture was stirred overnight at ambient temperature and then heated for one-half hour at 35° to 40° C. to complete the reaction. The reaction mixture was vacuum evaporated to produce 3.83 g (96 weight percent of theory yield) of a clear liquid having a $n_D^{30}$ of 1.4750. The product was identified as the title product by IR and NMR spectra analyses. Compound No. 40 in Table I.

EXAMPLE 34

1,3-n-heptyl-1N-ethylacetatecarbamyl-2-S-ethyl isothiourea

The procedure , equipment and reactants were the same as in Example 33 with the exception that 1.29 g (0.01 mole) ethylisothiocyanato acetate was used in place of the tert-butyl isocyanate. The reaction produced 4.3 g (100 weight percent of theory) of a clear liquid having a $n_D^{30}$ of 1.4800. The product was identified as the title product by IR and NMR spectra analyses. Compound No. 41 in Table I.

EXAMPLE 35

1,3-di-n-heptyl-3-B-hydroxyethylcarbamyl methylcarbamyl-2-S-ethyl isothiourea

The equipment was the same as in Example 26. 9.0 g (0.03 mole) 1,3-di-n-heptyl-2-S-ethyl isothiourea was mixed with 30 ml of methylene chloride to which 3.87 g (0.03 mole) ethylcyano acetate was added. The temperature rose from 23° to 45° C. during the reaction. The mixture was allowed to stand overnight. Then 10 drops of additional isothiourea were added to react residual isocyanate. To the reaction mixture was then added 1.83 g (0.03 mole) of 2-aminoethanol and the reaction mixture was stirred overnight. The reaction mixture was vacuum evaporated to remove the methylene chloride and 25 ml of ethanol were added to the remainder of the reaction mixture. The reaction mixture was then allowed to stand for 3 days. The resultant cloudy mixture was then stirred to ambient temperature overnight, then vacuum evaporated to produce 13.7 g of a yellow, turbid liquid having a $n_D^{30}$ of 1.4800. The product was identified as the title product by IR and NMR spectra analyses. Compound No. 64 in Table I.

EXAMPLE 36

Reaction product of 2 moles of 1,3-di-n-sec-heptyl-2-S-ethyl isothiourea + pp'-diphenylmethane diisocyanate The equipment was the same as in Example 26. 3.0 g (0.01 mole) of 1,3-di-sec-heptyl-2-S-ethyl isothiourea was mixed with 30 ml of toluene. 1.25 g (0.005 mole) of pp'-diphenylmethane diisocyanate was added to the mixture, and the reaction mixture was heated and held for 2 hours at 75° to 80° C. The IR showed a small isocyanate peak; so 10 drops of the isothiourea was added and heating continued for 30 minutes. The reaction mixture was then stirred at ambient temperature overnight. The reaction mixture was then vacuum evaporated to produce 4.5 g (104 weight percent of theory) of an amber colored liquid having a $n_D^{30}$ of 1.5310. The product was identified as the title product by IR and NMR spectra analyses. Compound No. 127 In Table I.

EXAMPLE 37

Reaction product of 2 moles of 1-N-sec-heptyl-3-N-n-hexyl-2-S-methyl-thiomethyl isothiourea + toluene 2,4-diisocyanate The procedure and equipment were the same as in Example 36, but the reagents were 3.8 g (0.01 mole) 1-sec-heptyl-3-N-hexyl-2-S-methyl-thiomethyl isothiourea, 0.87 g (0.005 mole) toluene-2,4-diisocyanate and 25 ml of tetrahydrofuran. After completion of the reaction 20 drops of the isothiourea was added to react with remaining isocyanate at ambient temperature overnight. The reaction mixture was then vacuum evaporated, producing a result of 4.6 g of a red colored viscous liquid having a $n_D^{30}$ of 1.5344. The product was identified as the title product by IR and NMR spectra analyses. Compound No, 138 in Table I.

EXAMPLE 38

1N-sec-heptyl-3-N-n-octyl-n-octadecylcarbamyl-2-S-allyl isothiourea

The procedure and equipment were the same as in Example 26. 1.9 g (0.006 mole) 1-sec-heptyl-3-octyl-2-S-allyl isothiourea was mixed with 25 ml of tetrahydrofuran to which 1.77 g (0.006 mole) n-octadecylisocyanate was added to the mixture. The reaction mixture was then stirred at ambient temperature overnight and then vacuum evaporated to produce 3.79 g (100 weight percent of theory yield) of a clear liquid having a $n_D^{30}$ of 1.4769. The product was identified as the title product by IR and NMR spectra analyses. Compound No. 144 in Table I.

EXAMPLE 39

Reaction product of 2 moles of 1-phenyl-3-n-heptyl-2-S-ethyl isothiourea + toluene-2,4-diisocyanate The equipment was the same as used in Example 26. 2.78 g (0.01 mole) 1-phenyl-3-n-heptyl-2-S-ethyl isothiourea in 35 ml of tetrahydrofuran were mixed with 0.87 g (0.005 mole) toluene-2,4-diisocyanate. The reaction mixture was then refluxed on a steam bath for 1 hour, then 15 drops of the isothiourea was added, and the reaction mixture was refluxed for an additional hour to react all the isocyanate. The reaction mixture was vacuum evaporated to produce 4.1 g of a viscous, yellow liquid having a $n_D^{30}$ of 1.5737. The produce was identified as the title product by IR and NMR spectra analyses. Compound No. 151 in Table I.

EXAMPLE 40

N-(5-sila-5,5-dimethyl-1-heptyl)-N'-n-heptyl,n-octadecylcarbamyl-2-S-ethyl isothiourea The equipment was the same as in Example 26. 2.4 g (0.007 mole) 1-(5'-sila-5',5'-dimethyl-N-heptyl)-3-n-heptyl-2-S-ethyl isothiourea in 25 ml tetrahydrofuran was mixed with 2.06 g (0.007 mole) N-octadecylisocyanate and stirred at ambient temperature for 2 hours. The reaction mixture was vacuum evaporated to produce 4.51 g (100 weight percent of theory yield) of a clear liquid having a $n_D^{30}$ of 1.4765. The product was identified as the title product by IR and NMR spectra analyses. Compound No. 184 in Table I.

EXAMPLE 41

N-dichloroacetyl,N,N'-di-n-heptyl,S-ethyl isothiourea 3.0 g (0.01 mole) 1,3-di-n-heptyl-2-S-ethyl isothiourea dissolved in 25 ml of methylene chloride was placed in a three-neck 200 ml flask equipped with a magnetic stirrer. 1.1 g triethylamine was added to the mixture. Then 1.5 g (0.01 mole) dichloroacetyl chloride in 10 ml of methylene chloride was added slowly while cooling the reaction mixture in an ice bath. The reaction mixture was heated to and then held at 40° C. for one-half hour. The reaction product was washed with water and the organic layer was dried with magnesium sulfate, filtered and vacuum stripped to yield 4.1 g of a liquid having a $n_D^{30}$ of 1.4723. The product was identified as the title product by NMR spectra analysis. Compound No. 332 in Table I.

EXAMPLE 42

Adduct of 1 mole 1,3-di-n-heptyl-2-S-ethyl isothiourea and 1 mole of diglycolic anhydride The equipment was the same as in Example 41, 3.0 g (0.01 mole) of 1,3-di-n-heptyl-2-S-ethyl isothiourea dissolved in 15 ml glycol and 1.2 g (0.01 mole) diglycolic anhydride dissolved in 10 ml glycol were added thereto. The reaction was heated to reflux for 10 minutes and evaporated under vacuum to produce 4.1 g of a liquid having a $n_D^{30}$ of 1.4608. The product was identified as the title product by IR and NMR spectra analyses. Compound No. 321 in Table I.

EXAMPLE 43

Adduct of 1 mole 1,3-di-n-heptyl-2-S-ethyl isothiourea and 1 mole of succinic anhydride The equipment procedures and reactants were the same as in Example 42 with the exception that 1.0 g (0.01 mole) succinic anhydride was substituted for the diglycolic anhydride. The reaction yield was 4.1 g of a semi-solid. The product was identified as the title product by NMR spectra analysis. Compound No. 331 in Table I.

EXAMPLE 44

Adduct of 1 mole 1,3-di-n-heptyl-2-S-ethyl isothiourea and 1 mole of formaldehyde The procedure, equipment and reactants were the same as in Example 42 with the exception that 1.2 g formaldehyde as a 37 percent solution in water (0.01 mole plus approximately 20 percent excess) was substituted for the diglycolic anhydride. The reaction yield was 3.3 g of a semi-solid which was identified as the title product by NMR spectra analysis. Compound No. 323 in Table I.

EXAMPLE 45

Adduct of 1 mole 1,3-di-n-heptyl-2-S-ethyl isothiourea and 1 mole of p-anisaldehyde The equipment, procedure and reactants were the same as in Example 42 with the exception that 1.4 g (0.01 mole) anisaldehyde was substituted for the diglycolic anhydride. The reaction yield was 4.3 g of a liquid having a $n_D^{30}$ of 1.4825. The product was identified as the title product by NMR spectra analysis. Compound No. 328 in Table I.

TABLE I

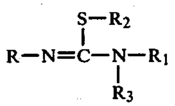

| Compound No. | R | $R_1$ | $R_2$ | $R_3$ | $n_D^{30}$ or °C. |
|---|---|---|---|---|---|
| 1 | $-C_7H_{15}$ | $-C_7H_{15}$ | $-C_2H_5$ | 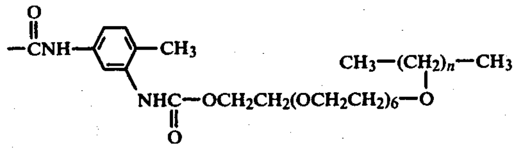 | 1.4760 |
| n average = 11<br>One of the reactants was Tergitol® 15-S-7 a product of Union Carbide Corporation in which the average Molecular Weight is 508 and n equals 9-13 and averages 11. | | | | | |
| 2 | $-C_7H_{15}$ | $-C_7H_{15}$ | $-C_2H_5$ | 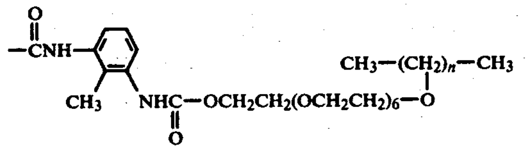 | 1.4956 |
| 3 | $-C_7H_{15}$ | $-C_7H_{15}$ | $-C_2H_5$ | 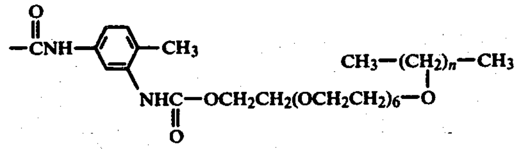 | 1.5021 |
| 4 | $-C_7H_{15}$ | $-C_7H_{15}$ | $-C_2H_5$ | 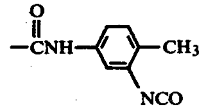 | 1.5440 |
| 5 | $-C_7H_{15}$ | $-C_7H_{15}$ | $-C_2H_5$ | 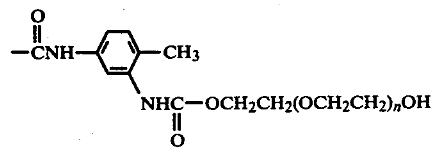 | Thick oil |
| n average = 7.7<br>One of the reactants was Carbowax® 400 a product of Union Carbide Corporation in which the average Molecular Weight is 400 and n averages 7.7. | | | | | |
| 6 | $-C_7H_{15}$ | $-C_7H_{15}$ | $-C_2H_5$ | 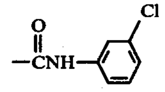 | 1.5283 |

TABLE I-continued
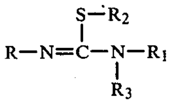
| Compound No. | R | R1 | R2 | R3 | $n_D^{30}$ or °C. |
|---|---|---|---|---|---|
| 7 | $-C_7H_{15}$ | $-C_7H_{15}$ | $-C_2H_5$ | 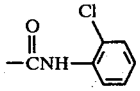 | 1.5254 |
| 8 | $-C_7H_{15}$ | $-C_7H_{15}$ | $-C_2H_5$ | 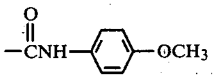 | 1.5235 |
| 9 | $-C_7H_{15}$ | $-C_7H_{15}$ | $-C_2H_5$ | 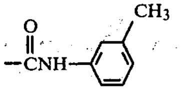 | 1.5215 |
| 10 | $-C_7H_{15}$ | $-C_7H_{15}$ | $-C_2H_5$ | 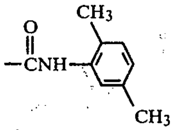 | 1.5186 |
| 11 | $-C_7H_{15}$ | $-C_7H_{15}$ | $-C_3H_7$ | 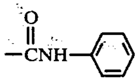 | 1.5188 |
| 12 | $-C_7H_{15}$ | $-C_7H_{15}$ | $-C_2H_5$ | 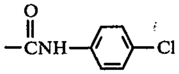 | 1.5186 |
| 13 | $-C_7H_{15}$ | $-C_7H_{15}$ | $-C_4H_9$ | 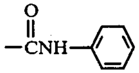 | 1.5180 |
| 14 | $-C_7H_{15}$ | $-C_7H_{15}$ | $-C_5H_{11}$ | 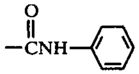 | 1.5145 |
| 15 | $-C_7H_{15}$ | $-C_7H_{15}$ | $-C_6H_{13}$ | 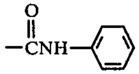 | 1.5115 |
| 16 | $-C_7H_{15}$ | $-C_7H_{15}$ | $-C_1H_3$ | 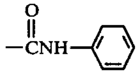 | 1.5250 |
| 17 | $-C_7H_{15}$ | $-C_7H_{15}$ | $-iC_4H_9$ | 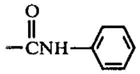 | 1.5147 |

TABLE I-continued
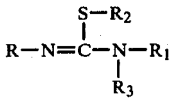
| Compound No. | R | $R_1$ | $R_2$ | $R_3$ | $n_D^{30}$ or °C. |
|---|---|---|---|---|---|
| 18 | $-C_9H_{19}$ | $-C_8H_{17}$ | $-C_2H_5$ | 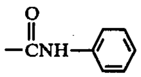 | 1.5093 |
| 19 | $-C_6H_{13}$ | $-C_7H_{15}$ | $-C_2H_5$ | 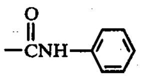 | 1.5214 |
| 20 | $-C_8H_{17}$ | $-C_8H_{17}$ | $-C_2H_5$ | 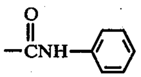 | 1.5175 |
| 21 | $-C_7H_{15}$ | $-C_9H_{19}$ | $-C_2H_5$ | 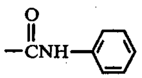 | 1.5170 |
| 22 | $-tC_8H_{17}$ | $-C_8H_{17}$ | $-C_2H_5$ | 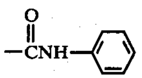 | 1.5134 |
| 23 | $-C_7H_{15}$ | $-C_8H_{17}$ | $-C_2H_5$ | 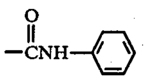 | 1.5185 |
| 24 | $-C_6H_{13}$ | $-C_{10}H_{21}$ | $-C_2H_5$ | 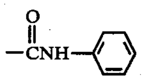 | 1.5191 |
| 25 | $-C_8H_{17}$ | $-C_8H_{17}$ | $-C_4H_9$ | 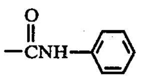 | 1.5135 |
| 26 | $-C_8H_{17}$ | $-C_8H_{17}$ | $-C_5H_{11}$ | 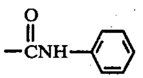 | 1.5125 |
| 27 | $-C_6H_{13}$ | $-C_9H_{19}$ | $-C_2H_5$ | 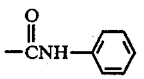 | 1.5179 |
| 28 | $-C_6H_{13}$ | $-C_9H_{19}$ | $-C_5H_{11}$ | 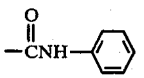 | 1.5120 |
| 29 | $-C_7H_{15}$ | $-C_7H_{15}$ | $-C_2H_5$ | 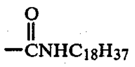 | 1.4750 |

TABLE I-continued

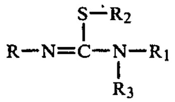

| Compound No. | R | $R_1$ | $R_2$ | $R_3$ | $n_D^{30}$ or °C. |
|---|---|---|---|---|---|
| 30 | $-C_7H_{15}$ | $-C_7H_{15}$ | $-C_2H_5$ | 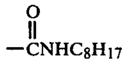 | 1.4786 |
| 31 | $-C_7H_{15}$ | $-C_7H_{15}$ | $-C_2H_5$ | 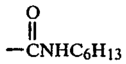 | 1.4800 |
| 32 | $-C_7H_{15}$ | $-C_7H_{15}$ | $-C_2H_5$ | 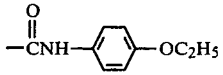 | 1.5180 |
| 33 | $-C_7H_{15}$ | $-C_7H_{15}$ | $-C_2H_5$ | 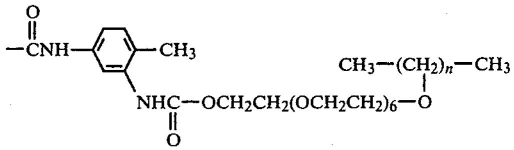 | 1.4970 |

n average = 11
One of the reactants was Tergitol® 15-S-7 a product of Union Carbide Corporation in which the average Molecular Weight is 508 and n equals 9-13 and averages 11.

| Compound No. | R | $R_1$ | $R_2$ | $R_3$ | $n_D^{30}$ or °C. |
|---|---|---|---|---|---|
| 34 | $-C_7H_{15}$ | $-C_7H_{15}$ | $-C_2H_5$ | 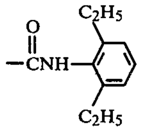 | 1.5084 |
| 35 | $-C_8H_{17}$ | $-C_8H_{17}$ | $-C_2H_5$ | 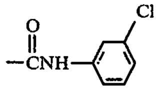 | 1.5245 |
| 36 | $-C_7H_{15}$ | $-C_7H_{15}$ | $-C_2H_5$ | 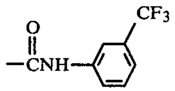 | 1.4966 |
| 37 | $-C_7H_{15}$ | $-C_7H_{15}$ | $-C_2H_5$ | 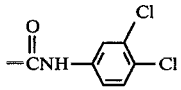 | 1.5392 |
| 38 | $-C_8H_{17}$ | $-C_6H_{13}$ | $-C_2H_5$ | 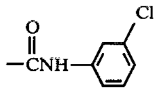 | 1.5274 |

TABLE I-continued
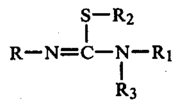
| Compound No. | R | $R_1$ | $R_2$ | $R_3$ | $n_D^{30}$ or °C. |
|---|---|---|---|---|---|
| 39 | $-C_6H_{13}$ | $-C_6H_{13}$ | $-C_2H_5$ | 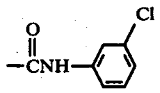 | 1.5317 |
| 40 | $-C_7H_{15}$ | $-C_7H_{15}$ | $-C_2H_5$ | 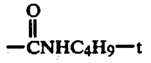 | 1.4750 |
| 41 | $-C_7H_{15}$ | $-C_7H_{15}$ | $-C_2H_5$ | 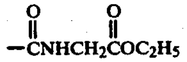 | 1.4800 |
| 42 | $-C_7H_{15}$ | $-C_7H_{15}$ | $-C_2H_5$ | 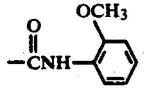 | 1.5215 |
| 43 | $-C_8H_{17}$ | $-C_6H_{13}$ | $-C_2H_5$ | 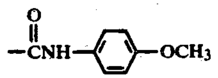 | 1.5200 |
| 44 | $-C_6H_{13}$ | $-C_6H_{13}$ | $-C_2H_5$ | 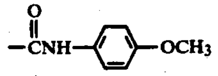 | 1.5261 |
| 45 | $-C_8H_{17}$ | $-C_8H_{17}$ | $-C_2H_5$ | 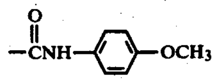 | 1.5175 |
| 46 | $-C_7H_{15}$ | $-C_7H_{15}$ | $-C_2H_5$ | 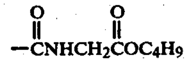 | 1.4770 |
| 47 | $-C_7H_{15}$ | $-C_7H_{15}$ | $-C_2H_5$ | 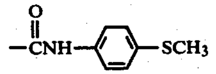 | 1.5340 |
| 48 | $-C_7H_{15}$ | $-C_7H_{15}$ | $-C_2H_5$ | 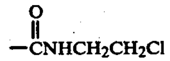 | 1.4930 |
| 49 | $-secC_7H_{15}$ | $-C_8H_{17}$ | $-C_2H_5$ | 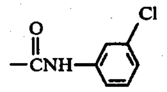 | 1.5230 |
| 50 | $-secC_7H_{15}$ | $-C_8H_{17}$ | $-C_2H_5$ | 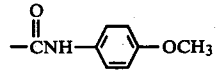 | 1.5190 |

TABLE I-continued

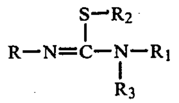

| Compound No. | R | $R_1$ | $R_2$ | $R_3$ | $n_D^{30}$ or °C. |
|---|---|---|---|---|---|
| 51 | $-C_7H_{15}$ | $-C_7H_{15}$ | $-C_2H_5$ | 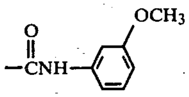 | 1.5235 |
| 52 | $-C_7H_{15}$ | $-C_7H_{15}$ | $-C_2H_5$ | $-\overset{O}{\overset{\parallel}{C}}NHC_2H_5$ | 1.4830 |
| 53 | $-C_7H_{15}$ | $-C_7H_{15}$ | $-C_2H_5$ | $-\overset{O}{\overset{\parallel}{C}}NHCH_2CH{=}CH_2$ | 1.4871 |
| 54 | $-C_7H_{15}$ | $-C_7H_{15}$ | $-C_2H_5$ | 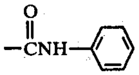 | 1.5270 |
| 55 | $-C_7H_{15}$ | $-C_7H_{15}$ | $-C_2H_5$ | $-\overset{O}{\overset{\parallel}{C}}NHC_3H_7-i$ | 1.4765 |
| 56 | $-secC_7H_{15}$ | $-C_7H_{15}$ | $-C_2H_5$ | $-\overset{O}{\overset{\parallel}{C}}NH_2$ | 1.4768 |
| 57 | $-secC_7H_{15}$ | $-C_8H_{17}$ | $-C_2H_5$ | 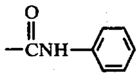 | 1.5175 |
| 58 | $-secC_7H_{15}$ | $-C_7H_{15}$ | $-C_2H_5$ | 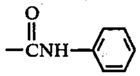 | 1.5182 |
| 59 | $-secC_7H_{15}$ | $-C_7H_{15}$ | $-C_2H_5$ | 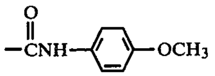 | 1.5190 |
| 60 | $-C_7H_{15}$ | $-C_7H_{15}$ | $-C_2H_5$ | 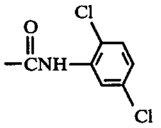 | 1.5310 |
| 61 | $-secC_7H_{15}$ | $-C_6H_{13}$ | $-C_2H_5$ | $-\overset{O}{\overset{\parallel}{C}}NH_2$ | 1.4765 |
| 62 | $-secC_7H_{15}$ | $-C_7H_{15}$ | $-C_2H_5$ | 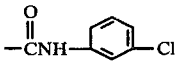 | 1.5237 |

TABLE I-continued

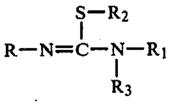

| Compound No. | R | $R_1$ | $R_2$ | $R_3$ | $n_D^{30}$ or °C. |
|---|---|---|---|---|---|
| 63 | $-C_7H_{15}$ | $-C_7H_{15}$ | $-C_2H_5$ | 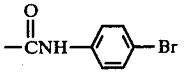 | 1.5242 |
| 64 | $-C_7H_{15}$ | $-C_7H_{15}$ | $-C_2H_5$ | $-\overset{O}{\overset{\|}{C}}NHCH_2\overset{O}{\overset{\|}{C}}NHCH_2CH_2OH$ | 1.4800 |
| 65 | —sec$C_7H_{15}$ | —sec$C_7H_{15}$ | $-C_2H_5$ | $-\overset{O}{\overset{\|}{C}}NH_2$ | 1.4725 |
| 66 | —sec$C_7H_{15}$ | $-C_6H_{13}$ | $-C_2H_5$ | 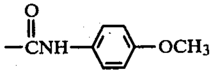 | 1.5210 |
| 67 | —sec$C_7H_{15}$ | $-C_6H_{13}$ | $-C_2H_5$ | 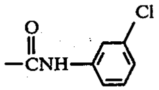 | Soft solid |
| 68 | —sec$C_7H_{15}$ | $-C_6H_{13}$ | $-C_2H_5$ | 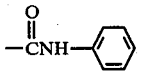 | 1.5230 |
| 69 | —sec$C_8H_{17}$ | —sec$C_7H_{15}$ | $-C_2H_5$ | 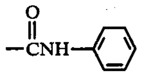 | 1.5125 |
| 70 | —sec$C_8H_{17}$ | —sec$C_7H_{15}$ | $-C_2H_5$ | 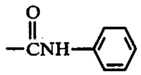 | 1.5115 |
| 71 | —sec$C_8H_{17}$ | —sec$C_7H_{15}$ | $-C_2H_5$ | 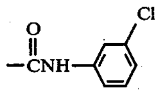 | 1.5205 |
| 72 | —sec$C_8H_{17}$ | —sec$C_7H_{15}$ | $-C_2H_5$ | $-\overset{O}{\overset{\|}{C}}NHC_{18}H_{37}$ | 1.4720 |
| 73 | $-C_7H_{15}$ | $-C_7H_{15}$ | $-C_2H_5$ | 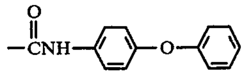 | 1.5390 |
| 74 | $-C_7H_{15}$ | $-C_7H_{15}$ | $-C_2H_5$ | $-\overset{O}{\overset{\|}{C}}NHC_{12}H_{25}$ | 1.4765 |
| 75 | —sec$C_7H_{15}$ | $-C_6H_{13}$ | $-C_2H_5$ | $-\overset{O}{\overset{\|}{C}}NHC_{18}H_{37}$ | 1.4737 |

TABLE I-continued
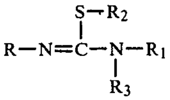
| Compound No. | R | $R_1$ | $R_2$ | $R_3$ | $n_D^{30}$ or °C. |
|---|---|---|---|---|---|
| 76 | $-secC_7H_{15}$ | $-secC_7H_{15}$ | $-C_1H_3$ | 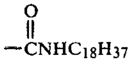 | 1.4750 |
| 77 | $-tC_8H_{17}$ | $-C_8H_{17}$ | $-C_2H_5$ | 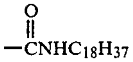 | 1.4755 |
| 78 | $-secC_7H_{15}$ | $-C_8H_{17}$ | $-C_1H_3$ | 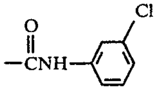 | 1.5280 |
| 79 | $-secC_7H_{15}$ | $-C_8H_{17}$ | $-C_1H_3$ | 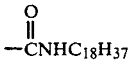 | 1.4750 |
| 80 | $-secC_7H_{15}$ | $-C_8H_{17}$ | $-C_1H_3$ | 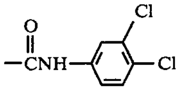 | 1.5335 |
| 81 | $-secC_7H_{15}$ | $-secC_7H_{15}$ | $-C_2H_5$ | 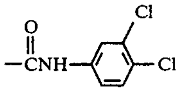 | 1.5305 |
| 82 | $-secC_7H_{15}$ | $-secC_7H_{15}$ | $-C_2H_5$ | 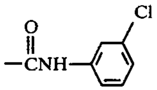 | 1.5240 |
| 83 | $-secC_7H$ | $-secC_7H_{15}$ | $-C_2H_5$ | 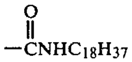 | 1.4740 |
| 84 | $-secC_7H_{15}$ | $-C_8H_{17}$ | $-C_2H_5$ | 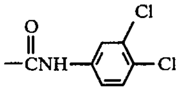 | 1.5295 |
| 85 | —2-ethyl-hexyl | —2-ethyl-hexyl | $-C_2H_5$ | 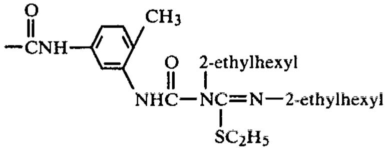 | 1.5201 |
| 86 | $-sec\text{-}C_7H_{15}$ | $-C_8H_{17}$ | $-C_2H_5$ | 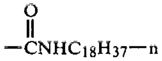 | 1.4740 |

TABLE I-continued
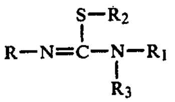
| Compound No. | R | $R_1$ | $R_2$ | $R_3$ | $n_D^{30}$ or °C. |
|---|---|---|---|---|---|
| 87 | $-tC_8H_{17}$ | $-C_8H_{17}$ | $-C_1H_3$ | 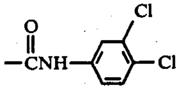 | 1.5342 |
| 88 | $-tC_8H_{17}$ | $-C_8H_{17}$ | $-C_1H_3$ | 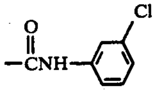 | 1.5276 |
| 89 | $-tC_8H_{17}$ | $-C_8H_{17}$ | $-C_1H_3$ | 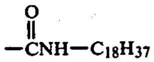 | 1.4772 |
| 90 | $-secC_7H_{15}$ | $-C_8H_{17}$ | $-C_2H_5$ | 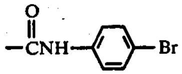 | 1.5324 |
| 91 | $-secC_7H_{15}$ | $-C_8H_{17}$ | $-C_2H_5$ | 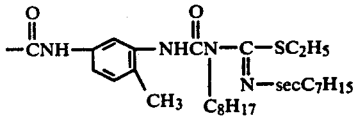 | 1.5170 |
| 92 | $-secC_7H_{15}$ | $-secC_7H_{15}$ | $-C_1H_3$ | 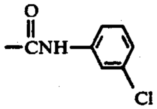 | 1.5292 |
| 93 | —2-ethyl-hexyl | —2-ethyl-hexyl | $-C_2H_5$ | 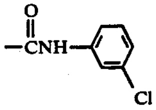 | 1.5258 |
| 94 | —2-ethyl-hexyl | —2-ethyl-hexyl | $-C_2H_5$ | 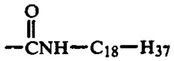 | 1.4760 |
| 95 | —2-ethyl-hexyl | —2-ethyl-hexyl | $-C_2H_5$ | 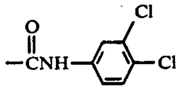 | 1.5306 |
| 96 | —2-ethyl-hexyl | —2-ethyl-hexyl | $-C_2H_5$ | 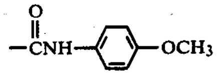 | 1.5238 |

TABLE I-continued
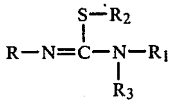
| Compound No. | R | $R_1$ | $R_2$ | $R_3$ | $n_D^{30}$ or °C. |
|---|---|---|---|---|---|
| 97 | —2-ethyl-hexyl | $-C_7H_{15}$ | $-C_2H_5$ | 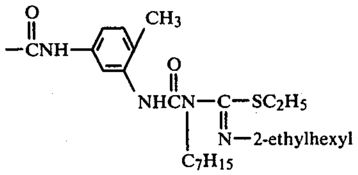 | 1.5145 |
| 98 | $-secC_7H_{15}$ | $-secC_7H_{15}$ | $-C_2H_5$ | 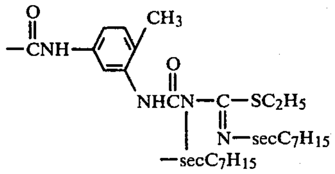 | 1.5120 |
| 99 | —2-ethyl-hexyl | —2-ethyl-hexyl | $-C_2H_5$ | 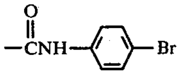 | 1.5330 |
| 100 | $-tC_8H_{17}$ | $-C_8H_{17}$ | $-C_1H_3$ | 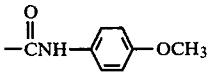 | 1.5020 |
| 101 | —2-ethyl-hexyl | $-C_7H_{15}$ | $-C_2H_5$ | 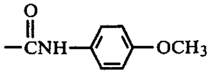 | 1.5000 |
| 102 | $-secC_7H_{15}$ | $-C_7H_{15}$ | $-C_2H_5$ | 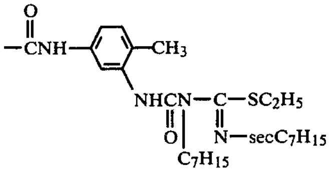 | 1.5226 |
| 103 | $-C_7H_{15}$ | $-C_7H_{15}$ | $-C_2H_5$ | 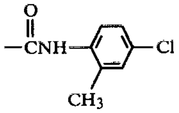 | 1.5275 |

TABLE I-continued
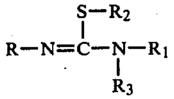
| Compound No. | R | $R_1$ | $R_2$ | $R_3$ | $n_D^{30}$ or °C. |
|---|---|---|---|---|---|
| 104 | —2-ethyl-hexyl | $-C_7H_{15}$ | $-C_3H_7$ | 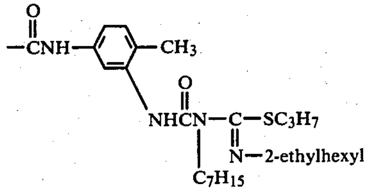 | 1.5190 |
| 105 | $-tC_8H_{17}$ | —2-ethyl-hexyl | $-C_2H_5$ | 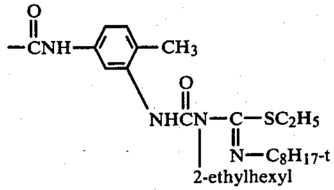 | 1.5182 |
| 106 | —2-ethyl-hexyl | $-C_7H_{15}$ | $-C_2H_5$ | 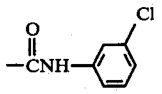 | 1.5277 |
| 107 | —2-ethyl-hexyl | $-C_7H_{15}$ | $-C_2H_5$ | 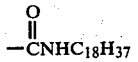 | 1.4775 |
| 108 | $-secC_7H_{15}$ | $-C_8H_{17}$ | $-CH_2SCH_3$ | 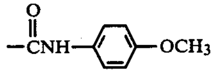 | 1.5255 |
| 109 | —2-ethyl-hexyl | $-C_7H_{15}$ | $-C_3H_7$ | 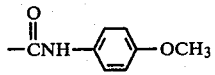 | 1.5200 |
| 110 | —2-ethyl-hexyl | $-C_7H_{15}$ | $-C_3H_7$ | 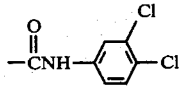 | 1.5337 |
| 111 | —2-ethyl-hexyl | $-C_7H_{15}$ | $-C_3H_7$ | 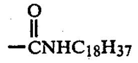 | 1.4772 |
| 112 | —2-ethyl-hexyl | $-C_7H_{15}$ | $-C_3H_7$ | 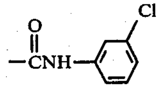 | 1.5237 |

TABLE I-continued
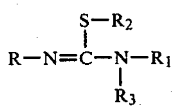
| Compound No. | R | $R_1$ | $R_2$ | $R_3$ | $n_D^{30}$ or °C. |
|---|---|---|---|---|---|
| 113 | $-secC_7H_{15}$ | $-C_7H_{15}$ | $-C_3H_7$ | 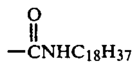 | 1.4744 |
| 114 | —2-ethyl-hexyl | $-C_8H_{17}$ | $-C_2H_5$ | 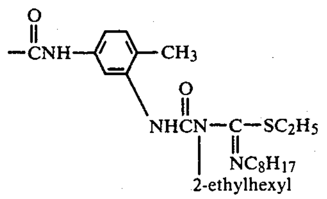 | 1.5170 |
| 115 | $-secC_7H_{15}$ | $-C_6H_{13}$ | $-C_2H_5$ | 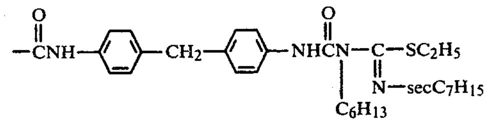 | 1.5350 |
| 116 | $-C_6H_{13}$ | $-secC_7H_{15}$ | $-C_2H_5$ | 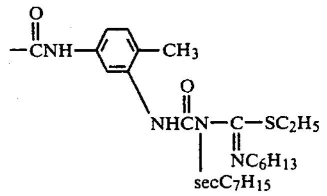 | 1.5220 |
| 117 | $-C_6H_{13}$ | 2-ethyl hexyl | $-C_2H_5$ | 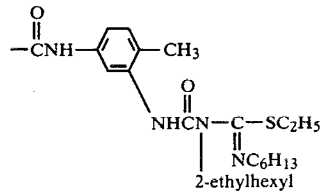 | 1.5234 |

TABLE I-continued
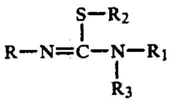
| Compound No. | R | $R_1$ | $R_2$ | $R_3$ | $n_D^{30}$ or °C. |
|---|---|---|---|---|---|
| 118 | $-C_7H_{15}$ | $-C_8H_{17}$ | $-C_1H_3$ | 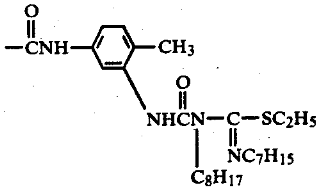 | 1.5190 |
| 119 | —2-ethyl-hexyl | $-C_8H_{17}$ | $-C_2H_5$ | 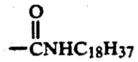 | 1.4765 |
| 120 | $-tC_8H_{17}$ | —2-ethyl-hexyl | $-C_3H_7$ | 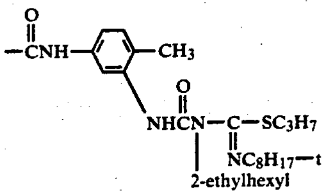 | 1.5120 |
| 121 | $-tC_8H_{17}$ | $-C_8H_{17}$ | $-C_3H_7$ | 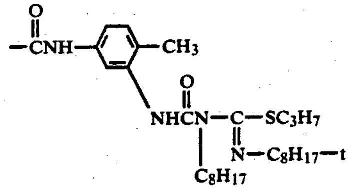 | 1.5124 |
| 122 | —2-ethyl-hexyl | $-C_8H_{17}$ | $-C_2H_5$ | 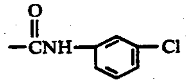 | 1.5264 |
| 123 | —2-ethyl-hexyl | $-C_6H_{13}$ | $-C_2H_5$ | 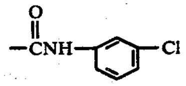 | 1.5296 |
| 124 | —2-ethyl-hexyl | $-C_6H_{13}$ | $-C_2H_5$ | 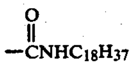 | 1.4770 |

TABLE I-continued
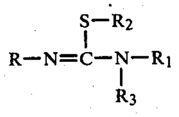
| Compound No. | R | $R_1$ | $R_2$ | $R_3$ | $n_D^{30}$ or °C. |
|---|---|---|---|---|---|
| 125 | $-C_7H_{15}$ | —2-ethyl-hexyl | $-C_2H_5$ | 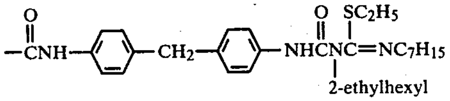 | 1.5393 |
| 126 | $-secC_7H_{15}$ | $-C_8H_{17}$ | $-C_2H_5$ | 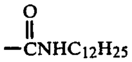 | 1.4763 |
| 127 | $-secC_7H_{15}$ | $-secC_7H_{15}$ | $-C_2H_5$ | 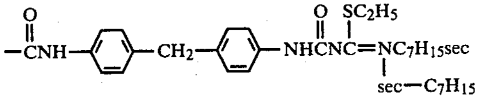 | 1.5310 |
| 128 | —2-ethyl-hexyl | —2-ethyl-hexyl | $-C_2H_5$ | 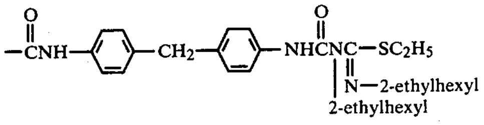 | 1.5340 |
| 129 | $-C_8H_{17}$ | —2-ethyl-hexyl | $-C_2H_5$ | 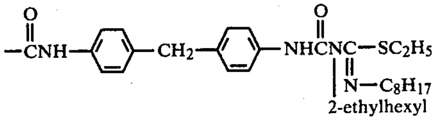 | 1.5300 |
| 130 | $-tC_8H_{17}$ | —2-ethyl-hexyl | $-C_2H_5$ | 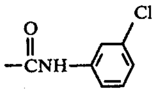 | 1.5271 |
| 131 | $-tC_8H_{17}$ | —2-ethyl-hexyl | $-C_2H_5$ | 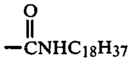 | 1.4785 |
| 132 | $-tC_8H_{17}$ | —2-ethyl-hexyl | $-C_3H_7$ | 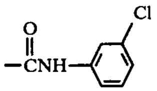 | 1.5150 |
| 133 | $-secC_7H_{15}$ | $-C_6H_{13}$ | $-C_2H_5$ | 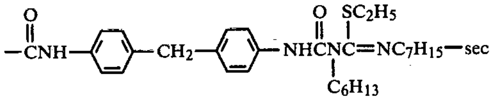 | 1.5345 |

TABLE I-continued
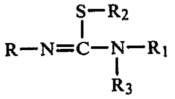
| Compound No. | R | $R_1$ | $R_2$ | $R_3$ | $n_D^{30}$ or °C. |
|---|---|---|---|---|---|
| 134 | $-secC_7H_{15}$ | —2-ethyl-hexyl | $-C_2H_5$ | 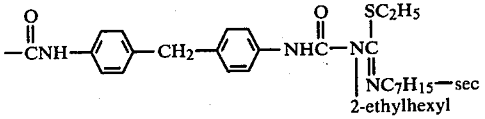 | 1.5283 |
| 135 | $-secC_7H_{15}$ | —2-ethyl-hexyl | $-C_2H_5$ | 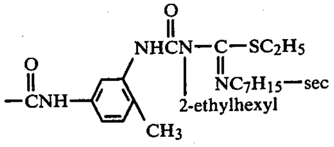 | 1.5164 |
| 136 | $-secC_7H_{15}$ | —2-ethyl-hexyl | $-C_3H_7$ | 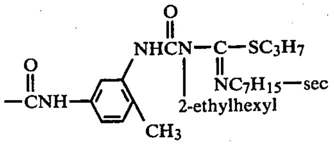 | 1.5165 |
| 137 | $-secC_7H_{15}$ | —2-ethyl-hexyl | $-C_3H_7$ | 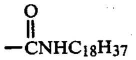 | 1.4745 |
| 138 | $-secC_7H_{15}$ | $-C_6H_{13}$ | $-CH_2SCH_3$ | 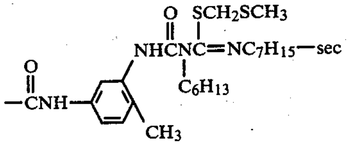 | 1.5344 |
| 139 | $-secC_7H_{15}$ | —2-ethyl-hexyl | $-C_2H_5$ | 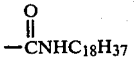 | 1.4750 |
| 140 | $-secC_7H_{15}$ | $-C_8H_{17}$ | $-C_1H_3$ | 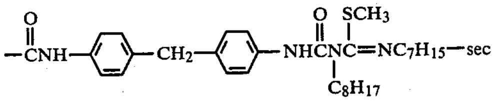 | 1.5293 |
| 141 | $-secC_7H_{15}$ | —2-ethyl-hexyl | $-C_2H_5$ | 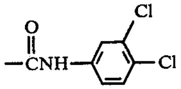 | 1.5295 |

TABLE I-continued
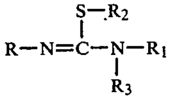
| Compound No. | R | $R_1$ | $R_2$ | $R_3$ | $n_D^{30}$ or °C. |
|---|---|---|---|---|---|
| 142 | $-tC_8H_{17}$ | —2-ethyl-hexyl | $-C_3H_7$ | 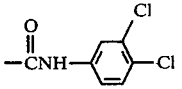 | 1.5317 |
| 143 | 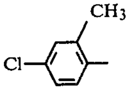 | $-C_7H_{15}$ | $-C_2H_5$ | 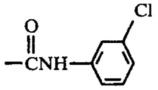 | 1.5758 |
| 144 | $-secC_7H_{15}$ | $-C_8H_{17}$ | $-CH_2CH=CH_2$ | 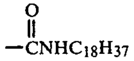 | 1.4769 |
| 145 | $-secC_7H_{15}$ | $-C_8H_{17}$ | $-CH_2CH=CH_2$ | 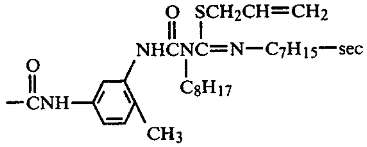 | 1.5225 |
| 146 | 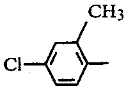 | $-C_7H_{15}$ | $-C_2H_5$ | 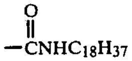 | 1.5140 |
| 147 | —2-ethyl-hexyl | $-C_7H_{15}$ | $-C_3H_7$ | 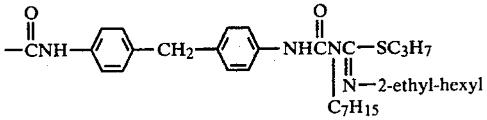 | 1.5290 |
| 148 | $-C_7H_{15}$ | $-C_8H_{17}$ | $-CH_2CH=CH_2$ | 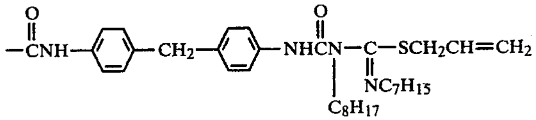 | 1.57357 |
| 149 | 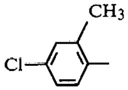 | $-C_7H_{15}$ | $-C_2H_5$ | 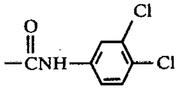 | 1.5785 |
| 150 | $-secC_7H_{15}$ | $-C_8H_{17}$ | $-CH_2CH=CH_2$ | 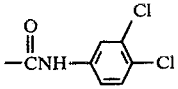 | 1.5326 |

TABLE I-continued
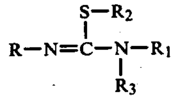
| Compound No. | R | $R_1$ | $R_2$ | $R_3$ | $n_D^{30}$ or °C. |
|---|---|---|---|---|---|
| 151 | 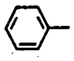 | $-C_7H_{15}$ | $-C_2H_5$ | 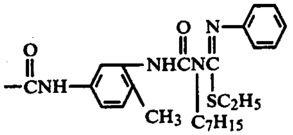 | 1.5737 |
| 152 | $-secC_7H_{15}$ | $-C_8H_{17}$ | $-C_3H_7$ | 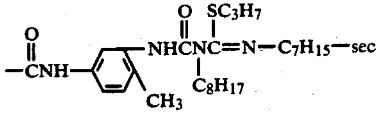 | 1.5134 |
| 153 | $-secC_7H_{15}$ | $-C_8H_{17}$ | $-C_3H_7$ | 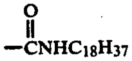 | 1.4746 |
| 154 | $-secC_7H_{15}$ | $-C_8H_{17}$ | $-C_3H_7$ | 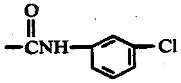 | 1.5200 |
| 155 | 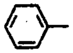 | $-C_7H_{15}$ | $-C_2H_5$ | 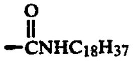 | 1.5061 |
| 156 | 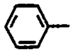 | $-C_7H_{15}$ | $-C_2H_5$ | 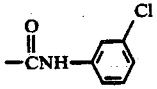 | 1.5769 |
| 157 | $(C_6H_5)_2CH-$ | $-C_7H_{15}$ | $-C_2H_5$ | 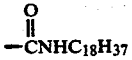 | 1.5165 |
| 158 | 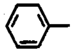 | $-C_7H_{15}$ | $-C_2H_5$ | 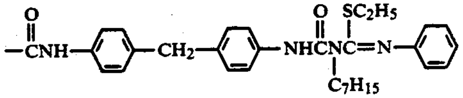 | 1.5860 |
| 159 | $-C_8H_{17}$ | $(CH_2)_6Cl$ | $-C_2H_5$ | 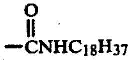 | 1.4876 |
| 160 | 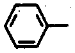 | $-C_7H_{15}$ | $-C_2H_5$ | 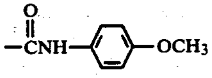 | 1.5743 |

TABLE I-continued
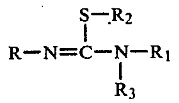
| Compound No. | R | $R_1$ | $R_2$ | $R_3$ | $n_D^{30}$ or °C. |
|---|---|---|---|---|---|
| 161 | $(C_6H_5)_2CH-$ | $-C_7H_{15}$ | $-C_2H_5$ | 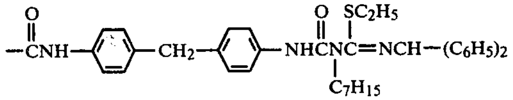 | 1.5760 |
| 162 | $-secC_7H_{15}$ | $-C_{12}H_{25}$ | $-C_2H_5$ | 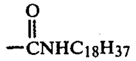 | 1.4736 |
| 163 | $-C_8H_{17}$ | $(CH_2)_2SC_5H_{11}$ | $-C_2H_5$ | 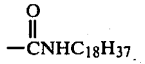 | 1.4850 |
| 164 | $-secC_7H_{15}$ | —2-ethyl-hexyl | $-iC_4H_9$ | 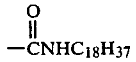 | 1.4754 |
| 165 | $-C_7H_{15}$ | $CH_2{=}C_HCH_2-$ | $-C_2H_5$ | 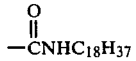 | 1.4810 |
| 166 | $-C_7H_{15}$ | $(CH_2)_3OCH_3-$ | $-C_2H_5$ | 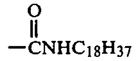 | 1.4773 |
| 167 | —2-ethyl-hexyl $O(CH_2)_3-$ | $-C_3H_7$ | $-C_2H_5$ | 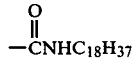 | 1.4746 |
| 168 | $-C_8H_{17}$ | 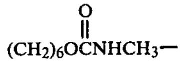 | $-C_2H_5$ | 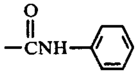 | 1.5244 |
| 169 | $-secC_7H_{15}$ | —2-ethyl-hexyl | $-iC_3H_7$ | 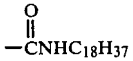 | 1.4738 |
| 170 | —2-ethyl-hexyl | 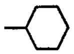 | $-C_2H_5$ | 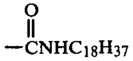 | 1.4836 |
| 171 | $-secC_7H_{15}$ | —2-ethyl-hexyl | $-C_7H_{15}$ | 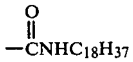 | 1.4735 |
| 172 | $-secC_7H_{15}$ | $-C_9H_{19}$ | $-C_2H_5$ | 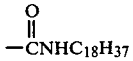 | 1.4740 |
| 173 | 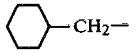 | $-C_7H_{15}$ | $-C_2H_5$ | 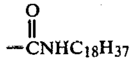 | 1.4845 |
| 174 | $-secC_7H_{15}$ | 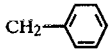 | $-C_2H_5$ | 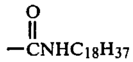 | 1.4930 |

TABLE I-continued
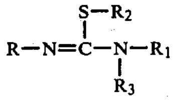
| Compound No. | R | $R_1$ | $R_2$ | $R_3$ | $n_D^{30}$ or °C. |
|---|---|---|---|---|---|
| 175 | —2-ethyl-hexyl | $(CH_2)_3Cl—$ | $—C_2H_5$ | 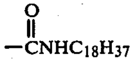 | 1.4950 |
| 176 | $—C_7H_{15}$ | $(CH_2)_3OCH_3—$ | $—C_5H_{11}$ | 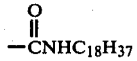 | 1.4755 |
| 177 | 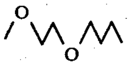 | $—C_7H_{15}$ | $—C_5H_{11}$ | 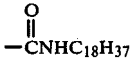 | 1.4750 |
| 178 | 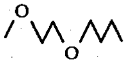 | $—C_7H_{15}$ | $—C_2H_5$ | 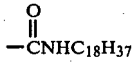 | 1.4760 |
| 179 | $—secC_7H_{15}$ | $—C_{12}H_{25}$ | $—C_2H_5$ | 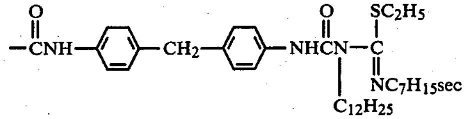 | 1.5215 |
| 180 | $—secC_7H_{15}$ | —2-ethyl-hexyl | $—iC_4H_9$ | 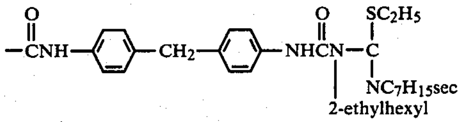 | 1.5295 |
| 181 | $—C_8H_{17}$ | 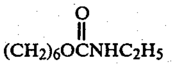 | $—C_2H_5$ | 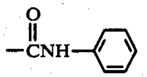 | 1.5205 |
| 182 | $—secC_7H_{15}$ | $—C_{12}H_{25}$ | $—C_2H_5$ | 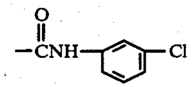 | 1.5070 |
| 183 | 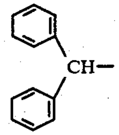 | $—C_7H_{15}$ | $—C_2H_5$ | 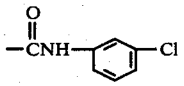 | 1.5825 |
| 184 | 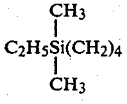 | $—C_7H_{15}$ | $—C_2H_5$ | 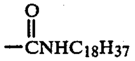 | 1.4765 |

TABLE I-continued
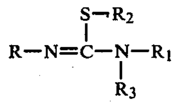
| Compound No. | R | $R_1$ | $R_2$ | $R_3$ | $n_D^{30}$ or °C. |
|---|---|---|---|---|---|
| 185 | 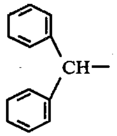 | $-C_7H_{15}$ | $-C_2H_5$ | 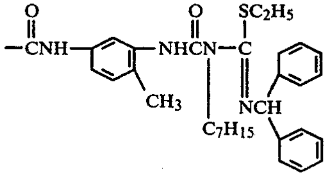 | 1.5770 |
| 186 | $-C_8H_{17}$ | 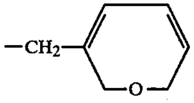 | $-C_2H_5$ | 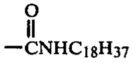 | 1.4890 |
| 187 | —2-ethyl-hexyl | —2-ethyl-hexyl | $-CH_2CH=CH_2$ | 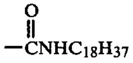 | 1.4800 |
| 188 | $-C_7H_{15}$ | $-(CH_2)_3N(C_2H_5)_2$ | $-C_2H_5$ | 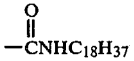 | 1.4780 |
| 189 | —2-ethyl-hexyl | —2-ethyl-hexyl | $-C_3H_7$ | 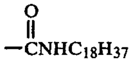 | 1.4757 |
| 190 | —sec$C_7H_{15}$ | $-C_8H_{17}$ | 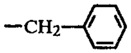 | 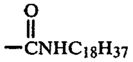 | 1.4924 |
| 191 | —sec$C_7H_{15}$ | —2-ethyl-hexyl | $-iC_4H_9$ | 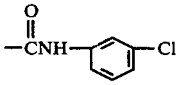 | 1.5210 |
| 192 | $-C_8H_{17}$ | $-(CH_2)_2SC_5H_{11}$ | $-C_2H_5$ | 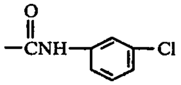 | 1.5386 |
| 193 | $-C_7H_{15}$ | $-CH_2CH=CH_2$ | $-C_2H_5$ | 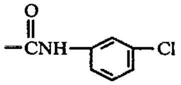 | 1.5450 |
| 194 | 2-ethylhexyl-O—$(CH_2)_3$— | $-C_3H_7$ | $-C_2H_5$ | 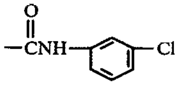 | 1.5250 |

TABLE I-continued
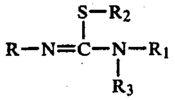
| Compound No. | R | $R_1$ | $R_2$ | $R_3$ | $n_D^{30}$ or °C. |
|---|---|---|---|---|---|
| 195 | $-secC_7H_{15}$ | —2-ethyl-hexyl | $-iC_3H_7$ | 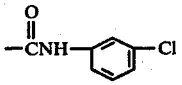 | 1.5195 |
| 196 | —2-ethyl-hexyl | 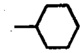 | $-C_2H_5$ | 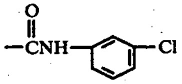 | 1.5395 |
| 197 | $-secC_7H_{15}$ | —2-ethyl-hexyl | $-C_7H_{15}$ | 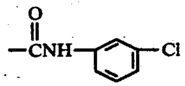 | 1.5146 |
| 198 | $-secC_7H_{15}$ | 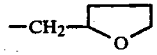 | $-C_2H_5$ | 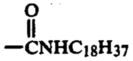 | 1.4820 |
| 199 | $-C_7H_{15}$ | $-C_7H_{15}$ | $-C_2H_5$ | 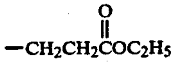 | 1.440 |
| 200 | $-C_7H_{15}$ | $-C_7H_{15}$ | $-C_2H_5$ | 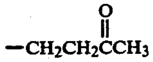 | 1.4543 |
| 201 | $-C_7H_{15}$ | $-C_7H_{15}$ | $-C_2H_5$ | 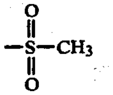 | 1.4807 |
| 202 | $-C_7H_{15}$ | $-C_7H_{15}$ | $-C_2H_5$ | 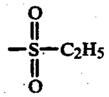 | 1.4836 |
| 203 | $-C_7H_{15}$ | $-C_7H_{15}$ | $-C_2H_5$ | 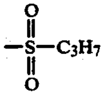 | 1.4805 |
| 204 | $-C_7H_{15}$ | $-C_7H_{15}$ | $-C_2H_5$ | 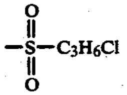 | 1.4902 |
| 205 | $-C_7H_{15}$ | $-C_7H_{15}$ | $-C_2H_5$ | 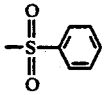 | 1.5152 |

TABLE I-continued
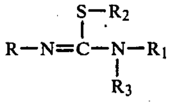
| Compound No. | R | $R_1$ | $R_2$ | $R_3$ | $n_D^{30}$ or °C. |
|---|---|---|---|---|---|
| 206 | $-C_7H_{15}$ | $-C_7H_{15}$ | $-C_2H_5$ | 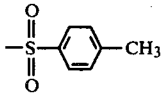 | 1.517 |
| 207 | $-C_7H_{15}$ | $-C_7H_{15}$ | $-C_2H_5$ | 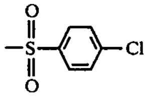 | 1.5207 |
| 208 | $-C_7H_{15}$ | $-C_7H_{15}$ | $-C_2H_5$ | 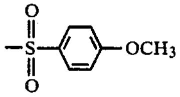 | 1.5215 |
| 209 | $-C_7H_{15}$ | $-C_7H_{15}$ | $-C_2H_5$ | 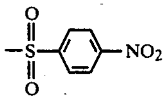 | 1.5273 |
| 210 | 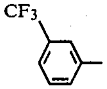 | $-C_1H_3$ | 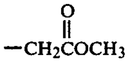 | $-CH_3$ | 1.5308 |
| 211 | 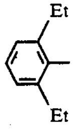 | $-C_1H_3$ | 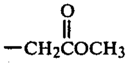 | $-CH_3$ | 1.5559 |
| 212 | 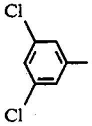 | $-C_1H_3$ | 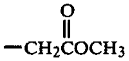 | $-CH_3$ | Dark oil |
| 213 | 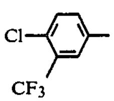 | $-C_1H_3$ | 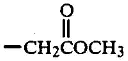 | $-CH_3$ | 1.548 |
| 214 | 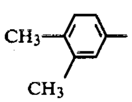 | $-C_1H_3$ | 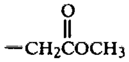 | $-CH_3$ | Dark oil |

TABLE I-continued

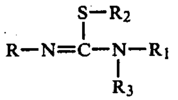

| Compound No. | R | $R_1$ | $R_2$ | $R_3$ | $n_D^{30}$ or °C. |
|---|---|---|---|---|---|
| 215 | 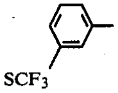 | $-C_1H_3$ | $-CH_2COCH(CH_3)_2$ | $-CH_3$ | 1.5417 |
| 216 | $-C_7H_{15}$ | $-C_7H_{15}$ | $-C_2H_5$ | 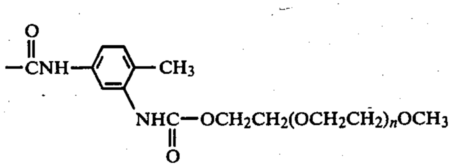 | 1.5785 |

n average = 6.2
One of the reactants was Carbowax ® 350 a product of Union Carbide Corporation in which the average Molecular Weight is 350 and n averages 6.2.

| Compound No. | R | $R_1$ | $R_2$ | $R_3$ | $n_D^{30}$ or °C. |
|---|---|---|---|---|---|
| 217 | $-C_6H_{13}$ | $-C_6H_{13}$ | $-C_2H_5$ | 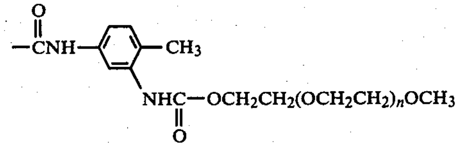 | 1.5838 |
| 218 | $-C_6H_{13}$ | $-C_8H_{17}$ | $-C_2H_5$ | 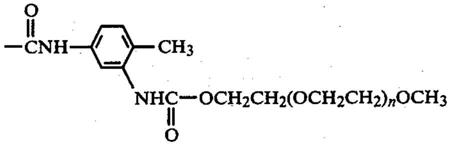 | 1.5800 |
| 219 | $-C_7H_{15}$ | $-C_7H_{15}$ | $-C_2H_5$ | 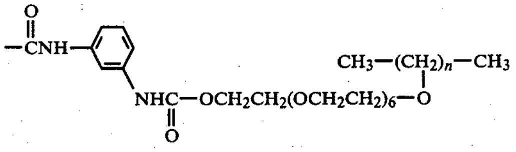 | 1.5710 |

n average = 11
One of the reactants was Tergitol ® 15-S-7 a product of Union Carbide Corporation in which the average Molecular Weight is 508 and n equals 9-13 and averages 11.

| Compound No. | R | $R_1$ | $R_2$ | $R_3$ | $n_D^{30}$ or °C. |
|---|---|---|---|---|---|
| 220 | $-C_8H_{17}$ | $-C_8H_{17}$ | $-C_2H_5$ | 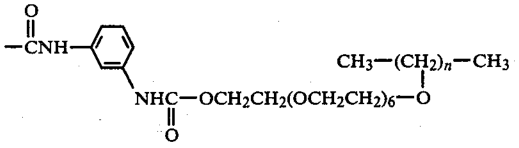 | 1.5700 |

TABLE I-continued
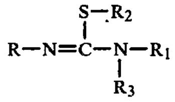
| Compound No. | R | $R_1$ | $R_2$ | $R_3$ | $n_D^{30}$ or °C. |
|---|---|---|---|---|---|
| 221 | $-C_8H_{17}$ | $-C_6H_{13}$ | $-C_2H_5$ | 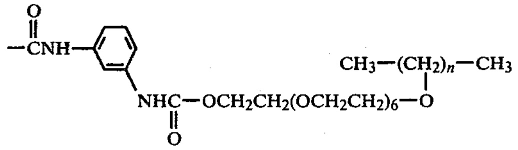 | 1.5680 |
| 222 | $-C_6H_{13}$ | $-C_6H_{13}$ | $-C_2H_5$ | 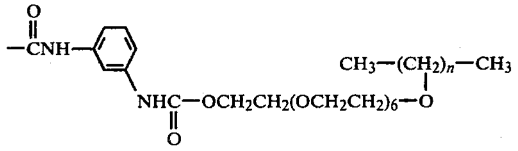 | 1.5720 |
| 223 | $-C_6H_{13}$ | $-C_8H_{17}$ | $-C_2H_5$ | 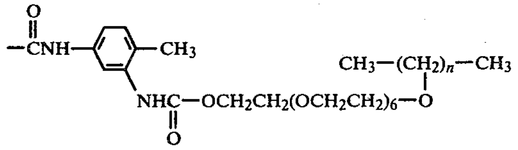 | 1.5746 |
| 224 | $-C_8H_{17}$ | $-C_8H_{17}$ | $-C_2H_5$ | 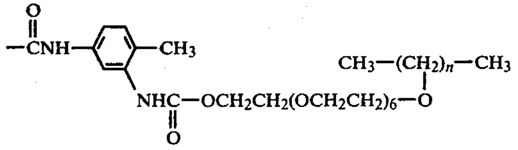 | 1.5726 |
| 225 | $-C_6H_{13}$ | $-C_6H_{13}$ | $-C_2H_5$ | 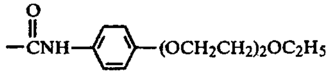 | 1.4930 |
| 226 | $-C_7H_{15}$ | $-C_7H_{15}$ | $-C_2H_5$ | 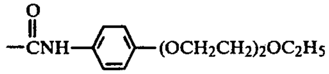 | 1.4895 |
| 227 | $-C_8H_{17}$ | $-C_8H_{17}$ | $-C_2H_5$ | 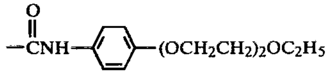 | 1.4885 |
| 228 | $-C_8H_{17}$ | $-C_6H_{13}$ | $-C_2H_5$ | 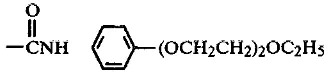 | 1.4892 |

TABLE I-continued
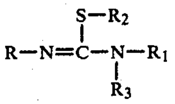
| Compound No. | R | $R_1$ | $R_2$ | $R_3$ | $n_D^{30}$ or °C. |
|---|---|---|---|---|---|
| 229 | $-C_7H_{15}$ | $-C_7H_{15}$ | $-C_2H_5$ | 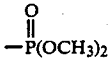 | 1.4528 |
| 230 | $-tC_8H_{17}$ | $-C_8H_{17}$ | $-C_2H_5$ | 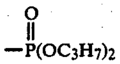 | 1.5460 |
| 231 | $-tC_8H_{17}$ | $-C_8H_{17}$ | $-C_2H_5$ | 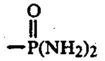 | 1.4552 |
| 232 | $-tC_8H_{17}$ | $-C_8H_{17}$ | $-C_2H_5$ | 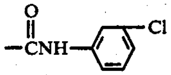 | 1.5035 |
| 233 | $-tC_8H_{17}$ | $-C_8H_{17}$ | $-C_2H_5$ | 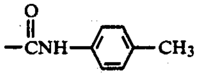 | 1.4913 |
| 234 | $-tC_8H_{17}$ | $-C_8H_{17}$ | $-C_2H_5$ | 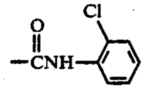 | 1.4950 |
| 235 | $-tC_8H_{17}$ | $-C_8H_{17}$ | $-C_2H_5$ | 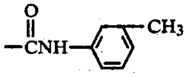 | 1.4863 |
| 236 | $-tC_8H_{17}$ | $-C_8H_{17}$ | $-C_2H_5$ | 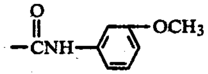 | 1.5010 |
| 237 | $-tC_8H_{17}$ | $-C_8H_{17}$ | $-C_2H_5$ | 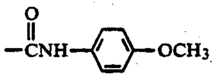 | 1.5020 |
| 238 | $-C_7H_{15}$ | $-C_7H_{15}$ | $-C_2H_5$ | 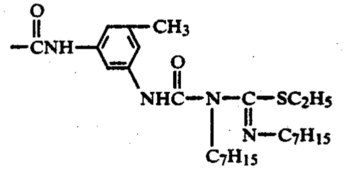 | 1.5018 |
| 239 | $-tC_8H_{17}$ | $-C_6H_{13}$ | $-C_2H_5$ | 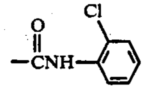 | 1.5082 |

TABLE I-continued
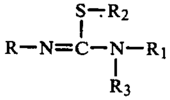
| Compound No. | R | R₁ | R₂ | R₃ | $n_D^{30}$ or °C. |
|---|---|---|---|---|---|
| 240 | $-tC_8H_{17}$ | $-C_6H_{13}$ | $-C_2H_5$ | 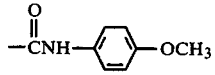 | 1.5063 |
| 241 | $-tC_8H_{17}$ | $-C_7H_{15}$ | $-C_2H_5$ | 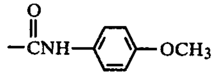 | 1.5215 |
| 242 | $-tC_8H_{17}$ | $-C_7H_{15}$ | $-C_2H_5$ | 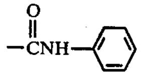 | Crude solid |
| 243 | $-tC_8H_{17}$ | $-C_7H_{15}$ | $-C_2H_5$ | 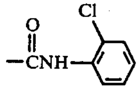 | 1.5033 |
| 244 | $-tC_8H_{17}$ | $-C_7H_{15}$ | $-C_2H_5$ | 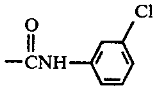 | 1.5044 |
| 245 | $-tC_8H_{17}$ | $-C_7H_{15}$ | $-C_2H_5$ | 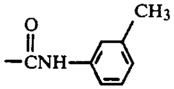 | 1.4985 |
| 246 | $-tC_8H_{17}$ | $-C_7H_{15}$ | $-C_2H_5$ | 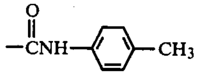 | 1.4923 |
| 247 | $-tC_8H_{17}$ | $-C_7H_{15}$ | $-C_2H_5$ | 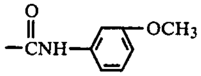 | 1.4990 |
| 248 | $-tC_8H_{17}$ | $-C_7H_{15}$ | $-C_2H_5$ | 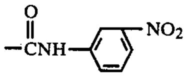 | 1.4942 |
| 249 | $-tC_8H_{17}$ | $-C_4H_9$ | $-C_2H_5$ | 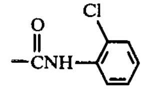 | 1.5140 |
| 250 | $-tC_8H_{17}$ | $-C_4H_9$ | $-C_2H_5$ | 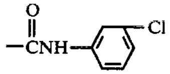 | 1.5135 |

TABLE I-continued
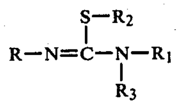
| Compound No. | R | $R_1$ | $R_2$ | $R_3$ | $n_D^{30}$ or °C. |
|---|---|---|---|---|---|
| 251 | $-tC_8H_{17}$ | $-C_7H_{15}$ | $-C_2H_5$ | 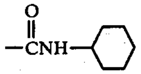 | 1.4673 |
| 252 | $-tC_8H_{17}$ | $-C_4H_9$ | $-C_2H_5$ | 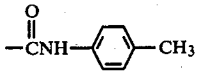 | 1.5060 |
| 253 | $-tC_8H_{17}$ | $-C_4H_9$ | $-C_2H_5$ | 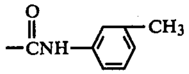 | 1.5052 |
| 254 | $-tC_8H_{17}$ | $-C_4H_9$ | $-C_2H_5$ | 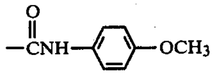 | Crude solid |
| 255 | $-tC_8H_{17}$ | $-C_4H_9$ | $-C_2H_5$ | 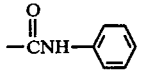 | 1.4953 |
| 256 | $-tC_8H_{17}$ | $-C_4H_9$ | $-iC_4H_9$ | 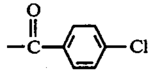 | 1.4953 |
| 257 | $-tC_8H_{17}$ | $-C_4H_9$ | $-iC_4H_9$ | 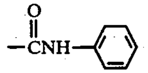 | 1.5078 |
| 258 | $-tC_8H_{17}$ | $-C_4H_9$ | $-iC_3H_7$ | 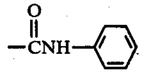 | 1.5048 |
| 259 | $-tC_8H_{17}$ | $-C_4H_9$ | $-iC_3H_7$ | 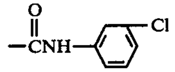 | 1.5120 |
| 260 | $-C_7H_{15}$ | $-C_1H_3$ | $-C_2H_5$ | 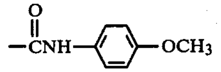 | 1.5240 |
| 261 | $-C_7H_{15}$ | $-C_7H_{15}$ | $-C_2H_5$ | 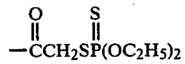 | 1.5060 |
| 262 | $-C_7H_{15}$ | $-C_7H_{15}$ | $-C_2H_5$ | 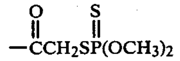 | 1.5100 |

TABLE I-continued

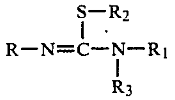

| Compound No. | R | $R_1$ | $R_2$ | $R_3$ | $n_D^{30}$ or °C. |
|---|---|---|---|---|---|
| 263 | $-C_7H_{15}$ | $-C_7H_{15}$ | $-C_2H_5$ | 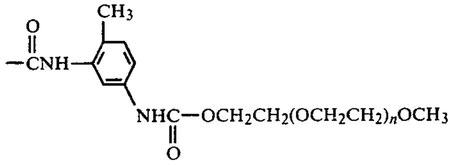 | 1.5030 |

n average = 6.2
One of the reactants was Carbowax® 350 a product of Union Carbide Corporation in which the average Molecular Weight is 350 and n averages 6.2

| Compound No. | R | $R_1$ | $R_2$ | $R_3$ | $n_D^{30}$ or °C. |
|---|---|---|---|---|---|
| 264 | $-C_6H_{13}$ | $-C_8H_{17}$ | $-C_2H_5$ | 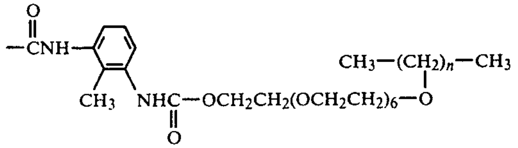 | 1.4960 |

n average = 11
One of the reactants was Tergitol® 15-S-7 a product of Union Carbide Corporation in which the average Molecular Weight is 508 and n equals 9-13 and averages 11.

| Compound No. | R | $R_1$ | $R_2$ | $R_3$ | $n_D^{30}$ or °C. |
|---|---|---|---|---|---|
| 265 | $-C_8H_{17}$ | $-C_8H_{17}$ | $-C_2H_5$ | 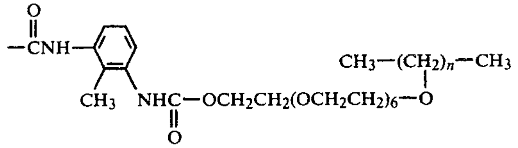 | 1.4942 |
| 266 | $-C_6H_{13}$ | $-C_6H_{13}$ | $-C_2H_5$ | 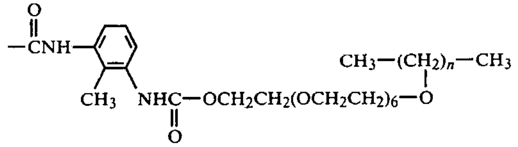 | 1.4955 |
| 267 | $-C_6H_{13}$ | $-C_8H_{17}$ | $-C_2H_5$ | 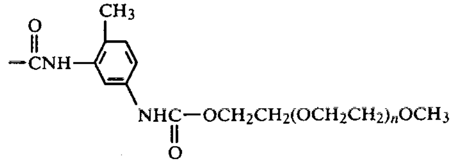 | 1.5025 |

n average = 6.2
One of the reactants was Carbowax® 350 a product of Union Carbide Corporation in which the average Molecular Weight is 350 and n averages 6.2.

TABLE I-continued
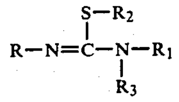
| Compound No. | R | $R_1$ | $R_2$ | $R_3$ | $n_D^{30}$ or °C. |
|---|---|---|---|---|---|
| 268 | $-C_8H_{17}$ | $-C_8H_{17}$ | $-C_2H_5$ | 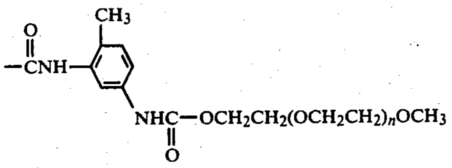 | 1.5005 |
| 269 | $-C_6H_{13}$ | $-C_6H_{13}$ | $-C_2H_5$ | 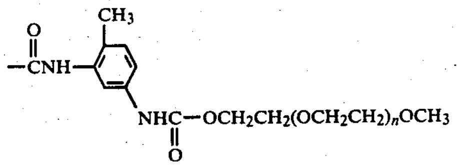 | 1.5065 |
| 270 | $-C_8H_{17}$ | $-C_6H_{13}$ | $-C_2H_5$ | 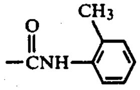 | Soft wax |
| 271 | $-C_8H_{17}$ | $-C_8H_{17}$ | $-C_2H_5$ | 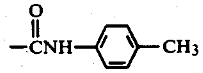 | 1.5166 |
| 272 | $-C_8H_{17}$ | $-C_6H_{13}$ | $-C_2H_5$ | 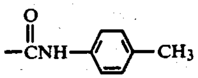 | 1.5200 |
| 273 | $-C_8H_{17}$ | $-C_6H_{13}$ | $-C_2H_5$ | 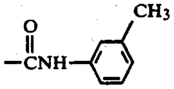 | 1.5024 |
| 274 | $-C_8H_{17}$ | $-C_6H_{13}$ | $-C_2H_5$ | 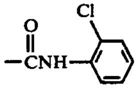 | 1.5240 |
| 275 | $-C_8H_{17}$ | $-C_6H_{13}$ | $-C_2H_5$ | 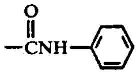 | 1.5205 |
| 276 | $-C_8H_{17}$ | $-C_6H_{13}$ | $-C_2H_5$ | 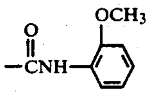 | 1.5215 |

TABLE I-continued
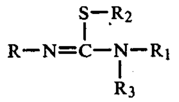
| Compound No. | R | $R_1$ | $R_2$ | $R_3$ | $n_D^{30}$ or °C. |
|---|---|---|---|---|---|
| 277 | $-C_8H_{17}$ | $-C_7H_{15}$ | $-C_2H_5$ | 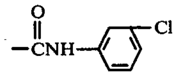 | 1.5256 |
| 278 | $-C_8H_{17}$ | $-C_7H_{15}$ | $-C_2H_5$ | 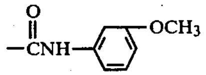 | 1.5219 |
| 279 | $-C_8H_{17}$ | $-C_7H_{15}$ | $-C_2H_5$ | 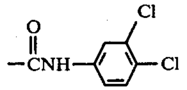 | 1.5351 |
| 280 | $-C_8H_{17}$ | $-C_7H_{15}$ | $-C_2H_5$ | 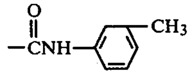 | 1.585 |
| 281 | $-C_8H_{17}$ | $-C_7H_{15}$ | $-C_2H_5$ | 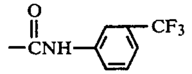 | 1.4974 |
| 282 | $-C_8H_{17}$ | $-C_8H_{17}$ | $-C_2H_5$ | 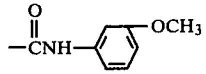 | 1.5205 |
| 283 | $-C_8H_{17}$ | $-C_8H_{17}$ | $-C_2H_5$ | 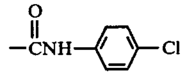 | 1.5246 |
| 284 | $-C_8H_{17}$ | $-C_6H_{13}$ | $-iC_3H_7$ | 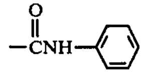 | 1.5072 |
| 285 | $-C_8H_{17}$ | $-C_6H_{13}$ | $-iC_3H_7$ | 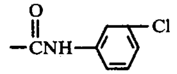 | 1.5242 |
| 286 | $-C_8H_{17}$ | $-C_7H_{15}$ | $-C_2H_5$ | 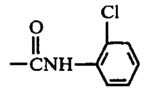 | 1.5228 |
| 287 | $-C_8H_{17}$ | $-C_6H_{13}$ | $-C_2H_5$ | 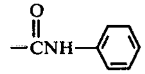 | 1.5244 |
| 288 | $-C_8H_{17}$ | $-C_6H_{13}$ | $-iC_3H_7$ | 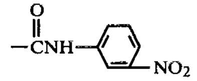 | 1.5286 |

TABLE I-continued
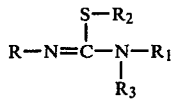
| Compound No. | R | $R_1$ | $R_2$ | $R_3$ | $n_D^{30}$ or °C. |
|---|---|---|---|---|---|
| 289 | $-C_8H_{17}$ | $-C_7H_{15}$ | $-C_2H_5$ | 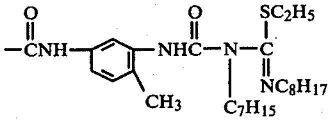 | 1.5217 |
| 290 | $-C_8H_{17}$ | $-C_6H_{13}$ | $-C_2H_5$ | 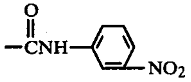 | 1.5331 |
| 291 | $-C_8H_{17}$ | $-C_6H_{13}$ | $-iC_3H_7$ | 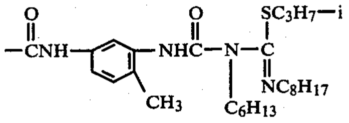 | 1.5201 |
| 292 | $-C_8H_{17}$ | $-C_5H_{11}$ | $-C_2H_5$ | 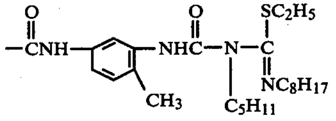 | 1.5258 |
| 293 | $-C_8H_{17}$ | $-C_8H_{17}$ | $-C_2H_5$ | 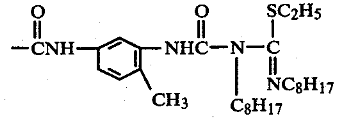 | 1.5193 |
| 294 | $-C_8H_{17}$ | $-C_6H_{13}$ | $-C_2H_5$ | 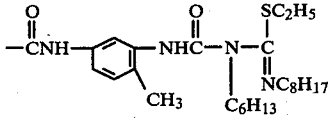 | 1.5177 |
| 295 | $-C_6H_{13}$ | $-C_6H_{13}$ | $-C_2H_5$ | 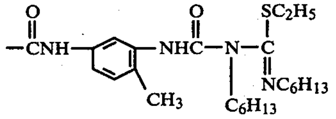 | 1.5266 |
| 296 | $-C_8H_{17}$ | $-C_6H_{13}$ | $-C_3H_7$ | 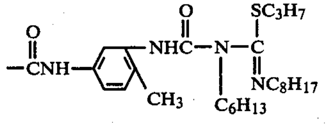 | 1.5182 |

TABLE I-continued
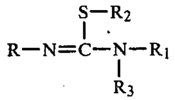
| Compound No. | R | $R_1$ | $R_2$ | $R_3$ | $n_D^{30}$ or °C. |
|---|---|---|---|---|---|
| 297 | $-C_7H_{15}$ | $-C_7H_{15}$ | $-C_2H_5$ | $-SCCl_3$ | 1.5084 |
| 298 | $-C_7H_{15}$ | $-C_7H_{15}$ | $-C_2H_5$ | $-SCCl_2CFCl_2$ | 1.5091 |
| 299 | $-C_7H_{15}$ | $-C_7H_{15}$ | $-C_2H_5$ | $-SCCl_2CHCl_2$ | 1.5192 |
| 300 | $-C_7H_{15}$ | $-C_7H_{15}$ | $-C_2H_5$ | 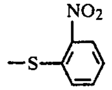 | 1.5463 |
| 301 | —2-ethyl-hexyl | —2-ethyl-hexyl | $-C_2H_5$ | $-SCCl_3$ | 1.5060 |
| 302 | $-C_7H_{15}$ | $-C_7H_{15}$ | $-C_2H_5$ | 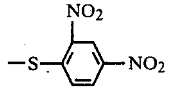 | 1.5580 |
| 303 | $-C_4H_9$ | $-C_4H_9$ | $-C_8H_{17}$ | 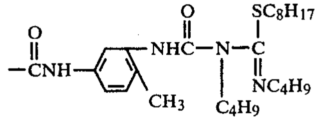 | 1.5245 |
| 304 | $-C_8H_{17}$ | —3,7-dimethyl-2,6-octadienyl | $-C_2H_5$ | 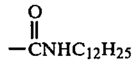 | 1.4882 |
| 305 | $-C_4H_9$ | —3,7-dimethyl-2,6-octadienyl | $-C_2H_5$ | 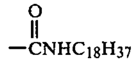 | 1.4848 |
| 306 | $-C_1H_3$ | $-C_1H_3$ | $-C_{14}H_{29}$ | 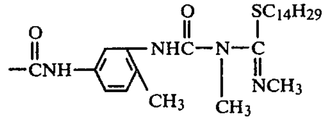 | 1.5141 |
| 307 | $-C_2H_5$ | $-C_2H_5$ | $-C_{12}H_{25}$ | 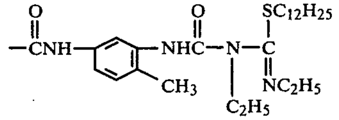 | 1.5091 |
| 308 | —2-ethyl-hexyl | —2-ethyl-hexyl | 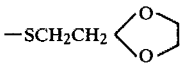 | 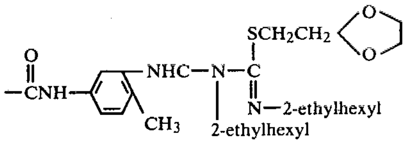 | 1.5029 |

TABLE I-continued
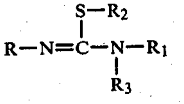
| Compound No. | R | $R_1$ | $R_2$ | $R_3$ | $n_D^{30}$ or °C. |
|---|---|---|---|---|---|
| 309 | —2-ethyl-hexyl | —2-ethyl-hexyl | 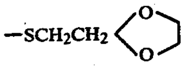 | 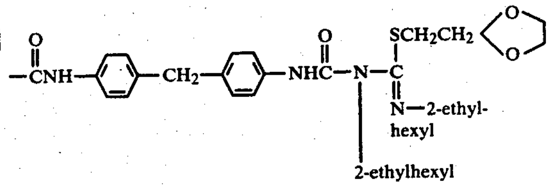 | 1.5253 |
| 310 | —2-ethyl-hexyl | —2-ethyl-hexyl | 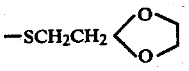 | 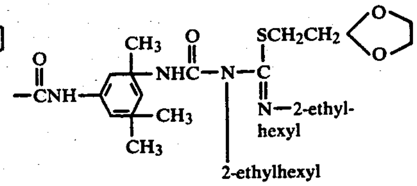 | 1.4600 |
| 311 | $—C_7H_{15}$ | $—C_7H_{15}$ | $—C_2H_5$ | 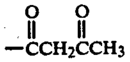 | |
| 312 | $—C_7H_{15}$ | $—C_7H_{15}$ | $—C_2H_5$ | 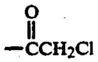 | |
| 313 | $—C_7H_{15}$ | $—C_7H_{15}$ | $—C_2H_5$ | 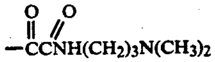 | Low melting material |
| 314 | $—C_7H_{15}$ | $—C_7H_{15}$ | $—C_2H_5$ | 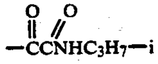 | Low-melting material |
| 315 | $—C_7H_{15}$ | $—C_7H_{15}$ | $—C_2H_5$ | 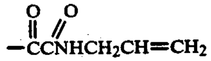 | Low-melting material |
| 316 | $—C_7H_{15}$ | $—C_7H_{15}$ | $—C_2H_5$ | 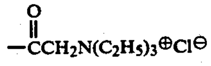 | Semi-solid |
| 317 | $—C_7H_{15}$ | $—C_7H_{15}$ | $—C_2H_5$ | 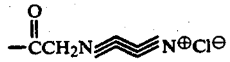 | Semi-solid |
| 318 | $—C_7H_{15}$ | $—C_7H_{15}$ | $—C_2H_5$ | 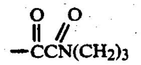 | Hygroscopic |

TABLE I-continued
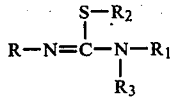
| Compound No. | R | $R_1$ | $R_2$ | $R_3$ | $n_D^{30}$ or °C. |
|---|---|---|---|---|---|
| 319 | $-C_7H_{15}$ | $-C_7H_{15}$ | $-C_2H_5$ | 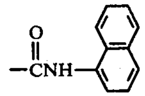 | 1.5425 |
| 320 | $-C_7H_{15}$ | $-C_7H_{15}$ | $-C_2H_5$ | 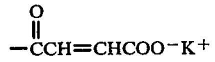 | Semi-solid |
| 321 | $-C_7H_{15}$ | $-C_7H_{15}$ | $-C_2H_5$ | 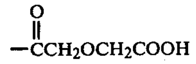 | 1.4608 |
| 322 | $-C_7H_{15}$ | $-C_7H_{15}$ | $-C_2H_5$ | 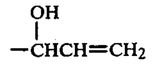 | 1.4630 |
| 323 | $-C_7H_{15}$ | $-C_7H_{15}$ | $-C_2H_5$ | $-CH_2OH$ | Semi-solid |
| 324 | $-C_7H_{15}$ | $-C_7H_{15}$ | $-C_2H_5$ | 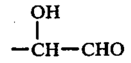 | 1.4513 |
| 325 | $-C_7H_{15}$ | $-C_7H_{15}$ | $-C_2H_5$ | 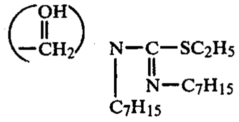 | 1.4563 |
| 326 | $-C_7H_{15}$ | $-C_7H_{15}$ | $-C_2H_5$ | 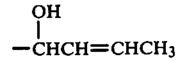 | 1.4588 |
| 327 | $-C_7H_{15}$ | $-C_7H_{15}$ | $-C_2H_5$ | 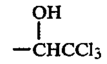 | 1.4638 |
| 328 | $-C_7H_{15}$ | $-C_7H_{15}$ | $-C_2H_5$ | 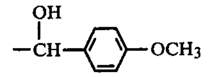 | 1.4825 |
| 329 | $-C_7H_{15}$ | $-C_7H_{15}$ | $-C_2H_5$ | 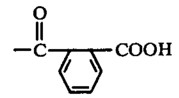 | Semi-solid |
| 330 | $-C_7H_{15}$ | $-C_7H_{15}$ | $-C_2H_5$ | 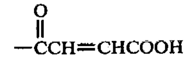 | No line |
| 331 | $-C_7H_{15}$ | $-C_7H_{15}$ | $-C_2H_5$ | 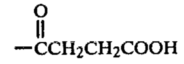 | Semi-solid |

TABLE I-continued

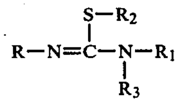

| Compound No. | R | R1 | R2 | R3 | $n_D^{30}$ or °C. |
|---|---|---|---|---|---|
| 332 | $-C_7H_{15}$ | $-C_7H_{15}$ | $-C_2H_5$ | O<br>‖<br>$-CCHCl_2$ | 1.4729 |
| 333 | $-C_7H_{15}$ | $-C_7H_{15}$ | $-C_2H_5$ | O<br>‖<br>$-CCH{=}CHCOO^-H_2N^+(CH_2CH_2OH)_2$ | No line |
| 334 | $-C_7H_{15}$ | $-C_7H_{15}$ | $-C_2H_5$ | 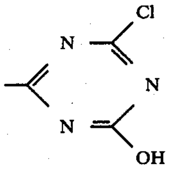 | 1.4920 |
| 335 | $-C_7H_{15}$ | $-C_7H_{15}$ | $-C_2H_5$ | O<br>‖<br>$-CCH{=}CH_2$ | 1.4672 |
| 336 | $-C_7H_{15}$ | $-C_7H_{15}$ | $-C_2H_5$ | 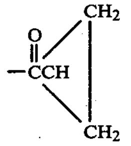 | 1.4856 |
| 337 | $-C_7H_{15}$ | $-C_7H_{15}$ | $-C_2H_5$ | O CH3<br>‖ \|<br>$-C-C{=}CH_2$ | 1.4673 |
| 338 | $-C_7H_{15}$ | $-C_7H_{15}$ | $-C_2H_5$ | O<br>‖<br>$-CCH_2OCH_2COO^{\ominus}.HNEt_3^{\oplus}$ | 1.4560 |
| 339 | $-C_7H_{15}$ | $-C_7H_{15}$ | $-C_2H_5$ | 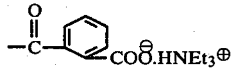 | 1.4870 |
| 340 | $-C_7H_{15}$ | $-C_7H_{15}$ | $-C_2H_5$ | O<br>‖<br>$-CCH_2CH_2COO^{\ominus}.HNEt_3^{\oplus}$ | 1.4830 |
| 341 | $-C_7H_{15}$ | $-C_7H_{15}$ | $-C_2H_5$ | $-SO_2NH_2$ | 1.4660 |
| 342 | $-C_7H_{15}$ | $-C_7H_{15}$ | $-C_2H_5$ | O<br>‖<br>$-CNH_2$ | 1.4632 |
| 343 | $-C_7H_{15}$ | $-C_7H_{15}$ | $-C_2H_5$ | O<br>‖<br>$-SNH_2$ | 1.4670 |

TABLE I-continued
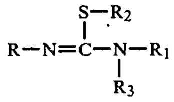
| Compound No. | R | $R_1$ | $R_2$ | $R_3$ | $n_D^{30}$ or °C. |
|---|---|---|---|---|---|
| 344 | $-C_7H_{15}$ | $-C_7H_{15}$ | $-C_2H_5$ | 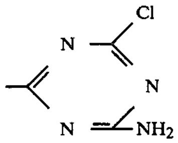 | 1.4874 |
| 345 | $-C_7H_{15}$ | $-C_7H_{15}$ | $-C_2H_5$ | 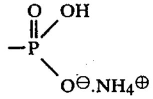 | 1.4670 |
| 346 | $-C_7H_{15}$ | $-C_7H_{15}$ | $-C_2H_5$ | $-SO_3CH_3$ | 1.4325 |
| 347 | $-C_7H_{15}$ | $-C_7H_{15}$ | $-C_2H_5$ | $-SO_2NHC_4H_9$ | 1.5264 |
| 348 | $-C_7H_{15}$ | $-C_7H_{15}$ | $-C_2H_5$ | 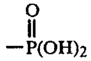 | Glass |
| 349 | $-C_7H_{15}$ | $-C_7H_{15}$ | $-C_2H_5$ | $-SO_2N(C_2H_5)_2$ | 1.4356 |
| 350 | $-C_7H_{15}$ | $-C_7H_{15}$ | $-C_2H_5$ | 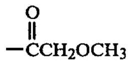 | 1.5140 |
| 351 | $-C_7H_{15}$ | $-C_7H_{15}$ | $-C_2H_5$ | 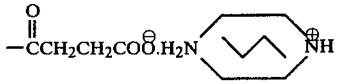 | Semi-solid |
| 352 | $-C_7H_{15}$ | $-C_7H_{15}$ | $-C_2H_5$ | 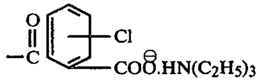 | 1.5472 |
| 353 | $-C_7H_{15}$ | $-C_7H_{15}$ | $-C_2H_5$ | 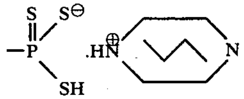 | 1.5464 |
| 354 | $-C_7H_{15}$ | $-C_7H_{15}$ | $-C_2H_5$ | 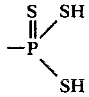 | Stench |
| 355 | $-C_7H_{15}$ | $-C_7H_{15}$ | $-C_2H_5$ | 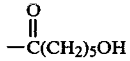 | 1.4600 |

TABLE I-continued
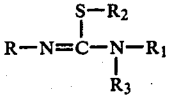
| Compound No. | R | $R_1$ | $R_2$ | $R_3$ | $n_D^{30}$ or °C. |
| --- | --- | --- | --- | --- | --- |
| 356 | $-C_7H_{15}$ | $-C_7H_{15}$ | $-C_2H_5$ | 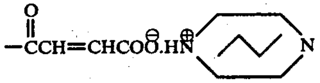 | 1.4467 |
| 357 | $-C_7H_{15}$ | $-C_7H_{15}$ | $-C_2H_5$ | 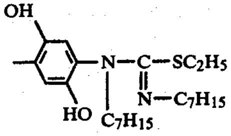 | 1.5730 |
| 358 | $-C_7H_{15}$ | $-C_7H_{15}$ | $-C_2H_5$ | 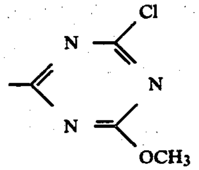 | Semi-solid |
| 359 | $-C_7H_{15}$ | $-C_7H_{15}$ | $-C_2H_5$ | $-SCCl_3$ | 1.4880 |
| 360 | $-C_7H_{15}$ | $-C_7H_{15}$ | $-C_2H_5$ | 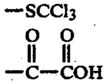 | 1.4640 |
| 361 | $-C_7H_{15}$ | $-C_7H_{15}$ | $-C_2H_5$ | 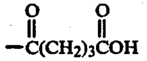 | 1.4670 |
| 362 | $-C_7H_{15}$ | $-C_7H_{15}$ | $-C_2H_5$ | 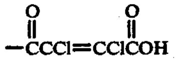 | 1.4780 |
| 363 | $-C_7H_{15}$ | $-C_7H_{15}$ | $-C_2H_5$ | 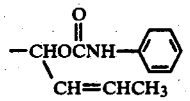 | 1.4990 |
| 364 | $-C_7H_{15}$ | $-C_7H_{15}$ | $-C_2H_5$ | 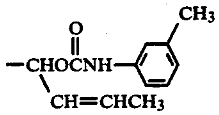 | 1.4970 |
| 365 | $-C_7H_{15}$ | $-C_7H_{15}$ | $-C_2H_5$ | 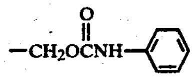 | 1.4915 |

TABLE I-continued

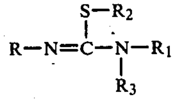

| Compound No. | R | $R_1$ | $R_2$ | $R_3$ | $n_D^{30}$ or °C. |
|---|---|---|---|---|---|
| 366 | $-C_7H_{15}$ | $-C_7H_{15}$ | $-C_2H_5$ | 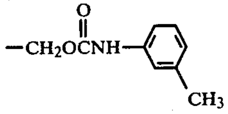 | 1.4922 |
| 367 | $-C_7H_{15}$ | $-C_7H_{15}$ | $-C_2H_5$ | 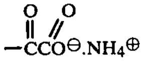 | Semi-solid |
| 368 | $-C_7H_{15}$ | $-C_7H_{15}$ | $-C_2H_5$ | 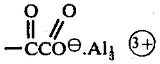 | Semi-solid |
| 369 | $-C_7H_{15}$ | $-C_7H_{15}$ | $-C_2H_5$ | 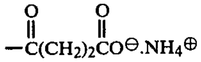 | 1.4620 |
| 370 | $-C_7H_{15}$ | $-C_7H_{15}$ | $-C_2H_5$ | 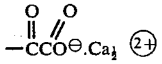 | |
| 371 | $-C_7H_{15}$ | $-C_7H_{15}$ | $-C_2H_5$ | 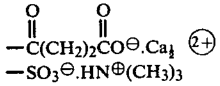 | Semi-solid |
| 372 | $-C_7H_{15}$ | $-C_7H_{15}$ | $-C_2H_5$ | $-SO_3^{\ominus}.HN^{\oplus}(CH_3)_3$ | Semi-solid |
| 373 | $-C_7H_{15}$ | $-C_7H_{15}$ | $-C_2H_5$ | 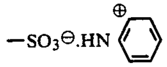 | 1.4630 |
| 374 | $-C_7H_{15}$ | $-C_7H_{15}$ | $-C_2H_5$ | 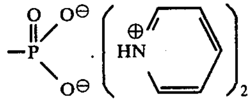 | Semi-solid |
| 375 | —2-ethyl-hexyl | —2-ethyl-hexyl | $-C_2H_5$ | 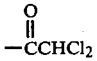 | 1.4664 |
| 376 | $-secC_7H_{15}$ | $-C_6H_{13}$ | $-C_2H_5$ | 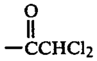 | 1.4666 |
| 377 | $-secC_7H_{15}$ | $-C_8H_{17}$ | $-C_2H_5$ | 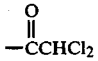 | 1.4633 |
| 378 | $-secC_7H_{15}$ | $-secC_7H_{15}$ | $-C_2H_5$ | 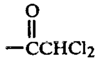 | 1.4680 |
| 379 | $-secC_7H_{15}$ | $-C_7H_{15}$ | $-C_2H_5$ | 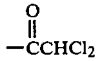 | 1.4683 |

TABLE I-continued

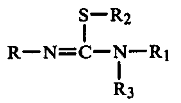

| Compound No. | R | $R_1$ | $R_2$ | $R_3$ | $n_D^{30}$ or °C. |
|---|---|---|---|---|---|
| 380 | —2-ethyl-hexyl | —2-ethyl-hexyl | $-C_2H_5$ | 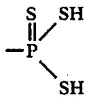 | 1.5487 |
| 381 | $-secC_7H_{15}$ | $-C_7H_{15}$ | $-C_2H_5$ | 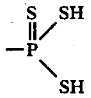 | 1.5638 |
| 382 | $-secC_7H_{15}$ | $-C_8H_{17}$ | $-C_2H_5$ | 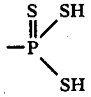 | 1.5567 |
| 383 | $-secC_7H_{15}$ | $-secC_7H_{15}$ | $-C_2H_5$ | 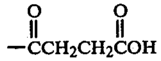 | 1.4612 |
| 384 | —2-ethyl-hexyl | —2-ethyl-hexyl | $-C_2H_5$ | 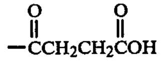 | 1.4653 |
| 385 | $-secC_7H_{15}$ | $-C_8H_{17}$ | $-C_2H_5$ | 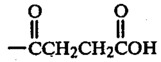 | 1.4673 |
| 386 | $-C_7H_{15}$ | $-C_7H_{15}$ | $-C_2H_5$ | 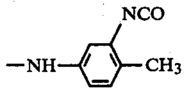 | 1.5440 |
| 387 | $-C_7H_{15}$ | $-C_7H_{15}$ | $-C_2H_5$ | 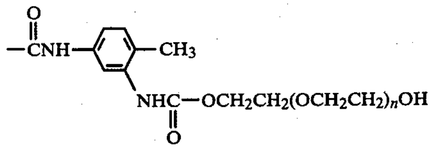 | Thick oil |
| n average = 7.7<br>One of the reactants was Carbowax® 400 a product of Union Carbide Corporation in which the average Molecular Weight is 400 and n averages 7.7. | | | | | |
| 388 | $-C_7H_{15}$ | $-C_7H_{15}$ | $-C_2H_5$ | 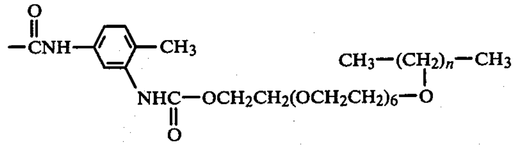 | 1.5021 |

n average = 11
One of the reactants was Tergitol® 15-S-7 a product of Union Carbide Corporation in which the average Molecular Weight is 508 and n equals 9-13 and averages 11.

TABLE I-continued

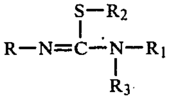

| Compound No. | R | $R_1$ | $R_2$ | $R_3$ | $n_D^{30}$ or °C. |
|---|---|---|---|---|---|
| 389 | $-C_7H_{15}$ | $-C_7H_{15}$ | $-C_2H_5$ | 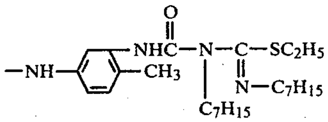 | 1.5000 |
| 390 | $-C_7H_{15}$ | $-C_7H_{15}$ | $-C_2H_5$ | 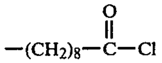 | |
| 391 | $-C_7H_{15}$ | $-C_7H_{15}$ | $-C_2H_5$ | 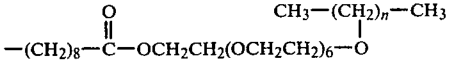 | |
| n average = 11<br>One of the reactants was Tergitol ® 15-S-7 a product of Union Carbide Corporation in which the average Molecular Weight is 508 and n equals 9-13 and averages 11. | | | | | |
| 392 | $-C_7H_{15}$ | $-C_7H_{15}$ | $-C_2H_5$ | 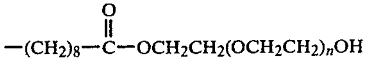 | |
| n average = 7.7<br>One of the reactants was Carbowax ® 400 a product of Union Carbide Corporation in which the average Molecular Weight is 400 and n averages 7.7. | | | | | |
| 393 | $-C_7H_{15}$ | $-C_7H_{15}$ | $-C_2H_5$ | 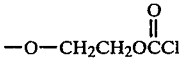 | |
| 394 | $-C_7H_{15}$ | $-C_7H_{15}$ | $-C_2H_5$ | 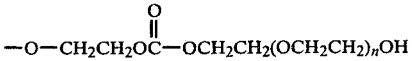 | |
| n average = 7.7<br>One of the reactants was Carbowax ® 400 a product of Union Carbide Corporation in which the average Molecular Weight is 400 and n averages 7.7. | | | | | |
| 395 | $-C_7H_{15}$ | $-C_7H_{15}$ | $-C_2H_5$ | 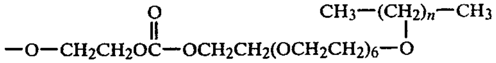 | |
| n average = 11<br>One of the reactants was Tergitol ® 15-S-7 a product of Union Carbide Corporation in which the average Molecular Weight is 508 and n equals 9-13 and averages 11. | | | | | |
| 396 | $-C_7H_{15}$ | $-C_7H_{15}$ | $-C_2H_5$ | 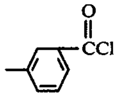 | |
| 397 | $-C_7H_{15}$ | $-C_7H_{15}$ | $-C_2H_5$ | 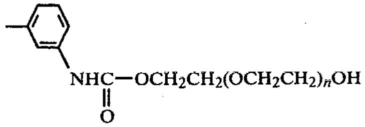 | |
| n average = 7.7<br>One of the reactants was Carbowax ® 400 a product of Union Carbide Corporation in which the average Molecular Weight is 400 and n averages 7.7. | | | | | |

TABLE I-continued

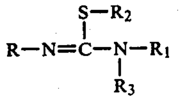

| Compound No. | R | $R_1$ | $R_2$ | $R_3$ | $n_D^{30}$ or °C. |
|---|---|---|---|---|---|
| 398 | $-C_7H_{15}$ | $-C_7H_{15}$ | $-C_2H_5$ | 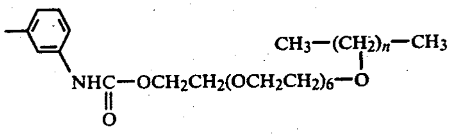 | |

n average = 11
One of the reactants was Tergitol® 15-S-7 a product of Union Carbide Corporation in which the average Molecular Weight is 508 and n equals 9-13 and averages 11.

| Compound No. | R | $R_1$ | $R_2$ | $R_3$ | $n_D^{30}$ or °C. |
|---|---|---|---|---|---|
| 399 | $-C_7H_{15}$ | $-C_7H_{15}$ | $-C_2H_5$ | 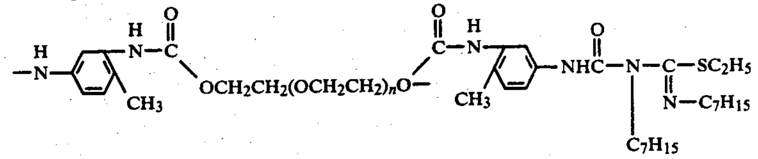 | |

n average = 7.7
One of the reactants was Carbowax® 400 a product of Union Carbide Corporation in which the average Molecular Weight is 400 and n averages 7.7.

| Compound No. | R | $R_1$ | $R_2$ | $R_3$ | $n_D^{30}$ or °C. |
|---|---|---|---|---|---|
| 400 | $-C_7H_{15}$ | $-C_7H_{15}$ | $-C_2H_5$ | $-NH-(CH_2)_6NCO$ | |
| 401 | $-C_7H_{15}$ | $-C_7H_{15}$ | $-C_2H_5$ | 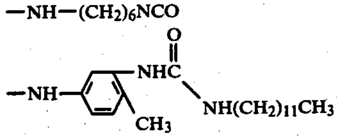 | |
| 402 | $-C_7H_{15}$ | $-C_7H_{15}$ | $-C_2H_5$ | 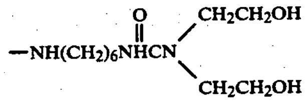 | |
| 403 | $-C_7H_{15}$ | $-C_7H_{15}$ | $-C_2H_5$ | 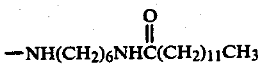 | |
| 404 | $-C_7H_{15}$ | $-C_7H_{15}$ | $-C_2H_5$ | 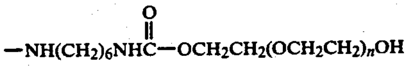 | |

n average = 7.7
One of the reactants was Carbowax® 400 a product of Union Carbide Corporation in which the average Molecular Weight is 400 and n averages 7.7.

| Compound No. | R | $R_1$ | $R_2$ | $R_3$ | $n_D^{30}$ or °C. |
|---|---|---|---|---|---|
| 405 | $-C_7H_{15}$ | $-C_7H_{15}$ | $-C_2H_5$ | 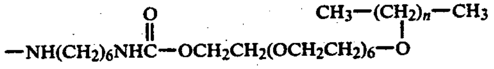 | |

n average = 11
One of the reactants was Tergitol® 15-S-7 a product of Union Carbide Corporation in which the average Molecular Weight is 508 and n equals 9-13 and averages 11.

TABLE I-continued
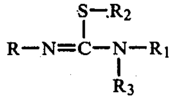
| Compound No. | R | $R_1$ | $R_2$ | $R_3$ | $n_D^{30}$ or °C. |
|---|---|---|---|---|---|
| 406 | $-C_7H_{15}$ | $-C_7H_{15}$ | $-C_2H_5$ | 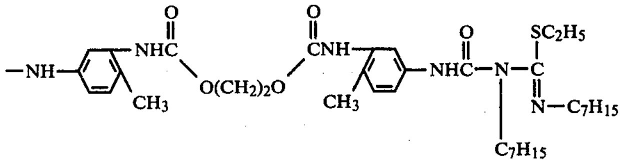 | |
| 407 | $-C_7H_{15}$ | $-C_7H_{15}$ | $-C_2H_5$ | 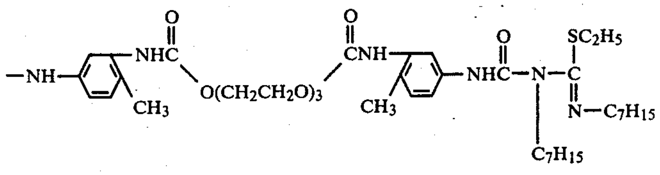 | |
| 408 | $-C_7H_{15}$ | $-C_7H_{15}$ | $-C_2H_5$ | 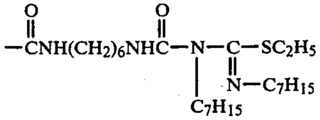 | |
| 409 | $-C_7H_{15}$ | $-C_7H_{15}$ | $-C_2H_5$ | 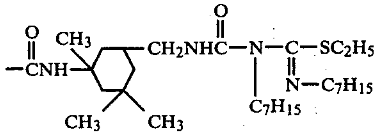 | |
| 410 | $-C_7H_{15}$ | $-C_7H_{15}$ | $-C_2H_5$ | 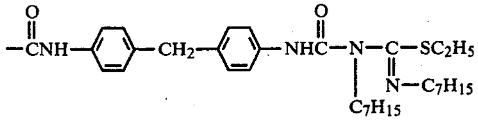 | Liquid |
| 411 | $-C_7H_{15}$ | $-C_7H_{15}$ | $-C_2H_5$ | 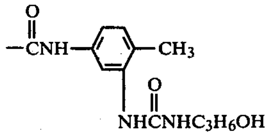 | Wax |

TABLE I-continued
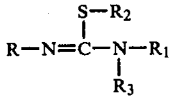
| Compound No. | R | $R_1$ | $R_2$ | $R_3$ | $n_D^{30}$ or °C. |
|---|---|---|---|---|---|
| 412 | $-C_7H_{15}$ | $-C_7H_{15}$ | $-C_2H_5$ | 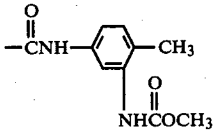 | Wax |
| 413 | $-C_7H_{15}$ | $-C_7H_{15}$ | $-C_2H_5$ | 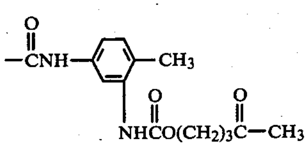 | Viscous liquid |
| 414 | $-C_7H_{15}$ | $-C_7H_{15}$ | $-C_2H_5$ | 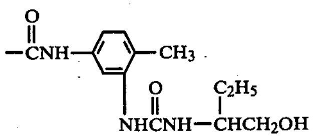 | Wax |
| 415 | $-C_7H_{15}$ | $-C_7H_{15}$ | $-C_2H_5$ | 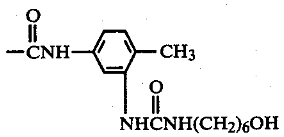 | Wax |
| 416 | $-C_7H_{15}$ | $-C_7H_{15}$ | $-C_2H_5$ | 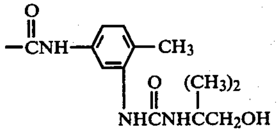 | Viscous liquid |
| 417 | $-C_7H_{15}$ | $-C_7H_{15}$ | $-C_2H_5$ | 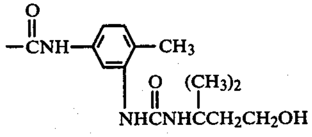 | Paste |

TABLE I-continued
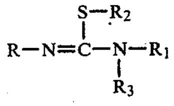
| Compound No. | R | $R_1$ | $R_2$ | $R_3$ | $n_D^{30}$ or °C. |
|---|---|---|---|---|---|
| 418 | $-C_7H_{15}$ | $-C_7H_{15}$ | $-C_2H_5$ | 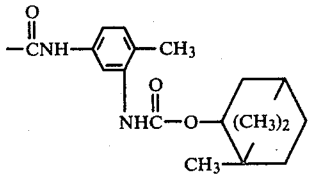 | Viscous liquid |
| 419 | $-C_7H_{15}$ | $-C_7H_{15}$ | $-C_2H_5$ | 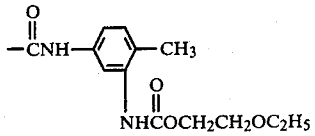 | Paste |
| 420 | $-C_7H_{15}$ | $-C_7H_{15}$ | $-C_2H_5$ | 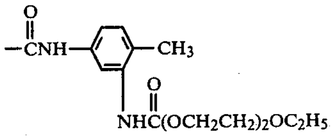 | Viscous liquid |
| 421 | $-C_7H_{15}$ | $-C_7H_{15}$ | $-C_2H_5$ | 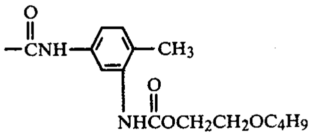 | Viscous liquid |
| 422 | $-C_7H_{15}$ | $-C_7H_{15}$ | $-C_2H_5$ | 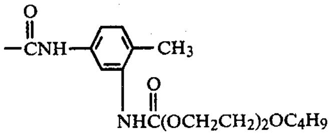 | Viscous liquid |
| 423 | $-C_7H_{15}$ | $-C_7H_{15}$ | $-C_2H_5$ | 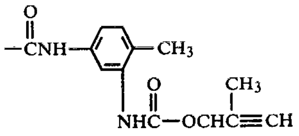 | Viscous liquid |

TABLE I-continued
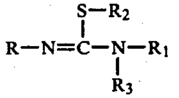
| Compound No. | R | $R_1$ | $R_2$ | $R_3$ | $n_D^{30}$ or °C. |
|---|---|---|---|---|---|
| 424 | $-C_7H_{15}$ | $-C_7H_{15}$ | $-C_2H_5$ | 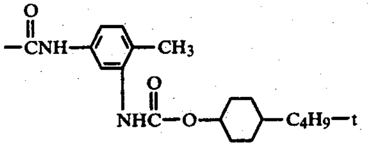 | Viscous liquid |
| 425 | $-C_7H_{15}$ | $-C_7H_{15}$ | $-C_2H_5$ | 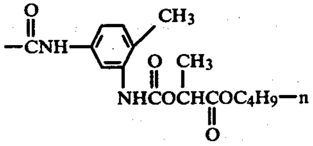 | Viscous liquid |
| 426 | $-C_7H_{15}$ | $-C_7H_{15}$ | $-C_2H_5$ | 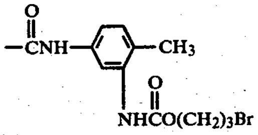 | Viscous liquid |
| 427 | $-C_7H_{15}$ | $-C_7H_{15}$ | $-C_2H_5$ | 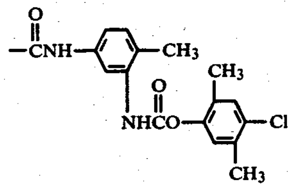 | Viscous liquid |
| 428 | $-C_7H_{15}$ | $-C_7H_{15}$ | $-C_2H_5$ | 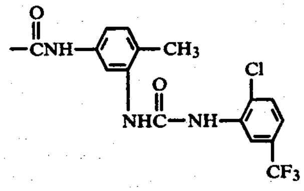 | Viscous liquid |

TABLE I-continued
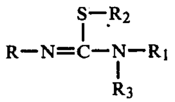
| Compound No. | R | $R_1$ | $R_2$ | $R_3$ | $n_D^{30}$ or °C. |
|---|---|---|---|---|---|
| 429 | $-C_7H_{15}$ | $-C_7H_{15}$ | $-C_2H_5$ | 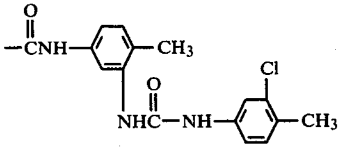 | Viscous liquid |
| 430 | $-C_7H_{15}$ | $-C_7H_{15}$ | $-C_2H_5$ | 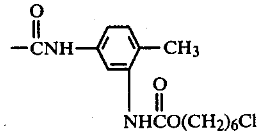 | 1.5260 |
| 431 | $-C_7H_{15}$ | $-C_7H_{15}$ | $-C_2H_5$ | 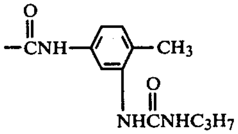 | 1.5312 |
| 432 | $-C_7H_{15}$ | $-C_7H_{15}$ | $-C_2H_5$ | 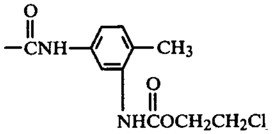 | 1.5339 |
| 433 | $-C_7H_{15}$ | $-C_7H_{15}$ | $-C_2H_5$ | 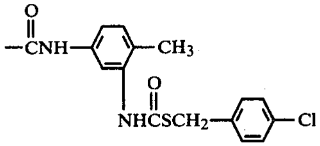 | Wax |
| 434 | $-C_7H_{15}$ | $-C_7H_{15}$ | $-C_2H_5$ | 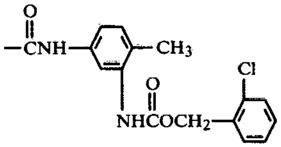 | Viscous liquid |

TABLE I-continued
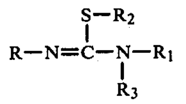
| Compound No. | R | $R_1$ | $R_2$ | $R_3$ | $n_D^{30}$ or °C. |
|---|---|---|---|---|---|
| 435 | $-C_7H_{15}$ | $-C_7H_{15}$ | $-C_2H_5$ | 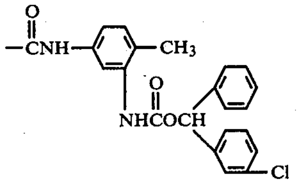 | 1.5628 |
| 436 | $-C_7H_{15}$ | $-C_7H_{15}$ | $-C_2H_5$ | 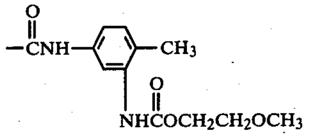 | 1.52526 |
| 437 | $-C_7H_{15}$ | $-C_7H_{15}$ | $-C_2H_5$ | 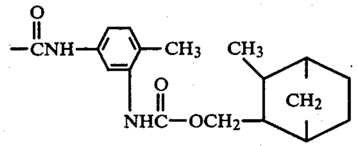 | 1.531 |
| 438 | $-C_7H_{15}$ | $-C_7H_{15}$ | $-C_2H_5$ | 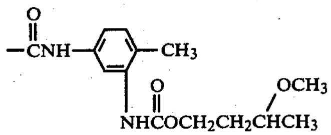 | 1.5210 |
| 439 | $-C_7H_{15}$ | $-C_7H_{15}$ | $-C_2H_5$ | 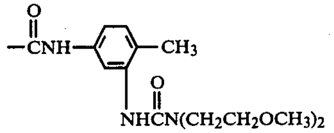 | 1.5282 |
| 440 | $-C_7H_{15}$ | $-C_7H_{15}$ | $-C_2H_5$ | 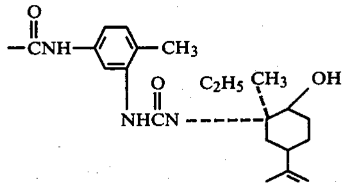 | 1.540 |

TABLE I-continued
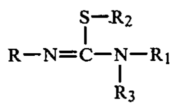
| Compound No. | R | $R_1$ | $R_2$ | $R_3$ | $n_D^{30}$ or °C. |
|---|---|---|---|---|---|
| 441 | $-C_7H_{15}$ | $-C_7H_{15}$ | $-C_2H_5$ | 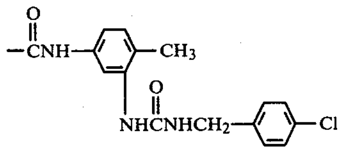 | 1.5524 |
| 442 | $-C_7H_{15}$ | $-C_7H_{15}$ | $-C_2H_5$ | 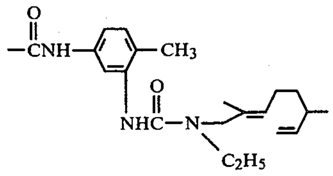 | 1.5277 |
| 443 | $-C_7H_{15}$ | $-C_7H_{15}$ | $-C_2H_5$ | 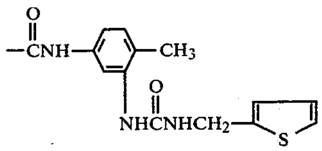 | Soft wax |
| 444 | $-C_7H_{15}$ | $-C_7H_{15}$ | $-C_2H_5$ | 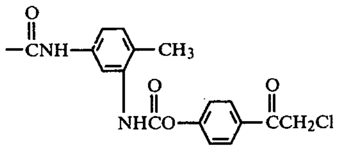 | Viscous liquid |
| 445 | $-C_7H_{15}$ | $-C_7H_{15}$ | $-C_2H_5$ | 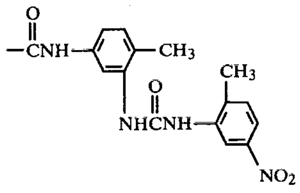 | Viscous liquid |

TABLE I-continued
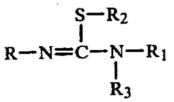
| Compound No. | R | $R_1$ | $R_2$ | $R_3$ | $n_D^{30}$ or °C. |
|---|---|---|---|---|---|
| 446 | $-C_7H_{15}$ | $-C_7H_{15}$ | $-C_2H_5$ | 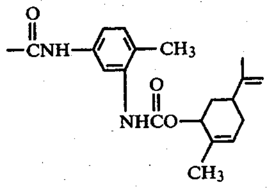 | 1.5355 |
| 447 | $-C_7H_{15}$ | $-C_7H_{15}$ | $-C_2H_5$ | 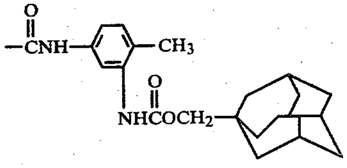 | Viscous liquid |
| 448 | $-C_7H_{15}$ | $-C_7H_{15}$ | $-C_2H_5$ | 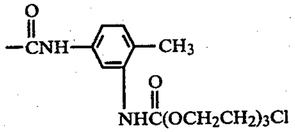 | Viscous liquid |
| 449 | $-C_7H_{15}$ | $-C_7H_{15}$ | $-C_2H_5$ | 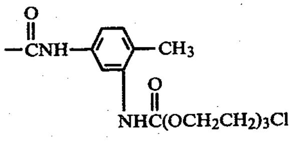 | 1.5251 |
| 450 | $-C_7H_{15}$ | $-C_7H_{15}$ | $-C_2H_5$ | 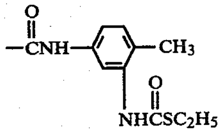 | 1.5461 |
| 451 | $-C_7H_{15}$ | $-C_7H_{15}$ | $-C_2H_5$ | 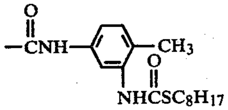 | 1.5269 |

TABLE I-continued
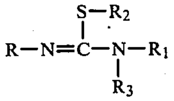
| Compound No. | R | $R_1$ | $R_2$ | $R_3$ | $n_D^{30}$ or °C. |
|---|---|---|---|---|---|
| 452 | $-C_7H_{15}$ | $-C_7H_{15}$ | $-C_2H_5$ | 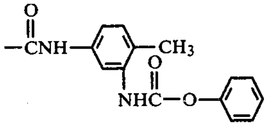 | 1.5488 |
| 453 | $-C_7H_{15}$ | $-C_7H_{15}$ | $-C_2H_5$ | 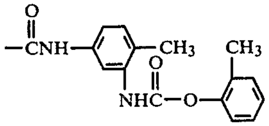 | 1.5481 |
| 454 | $-C_7H_{15}$ | $-C_7H_{15}$ | $-C_2H_5$ | 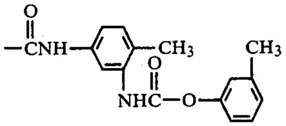 | 1.5481 |
| 455 | $-C_7H_{15}$ | $-C_7H_{15}$ | $-C_2H_5$ | 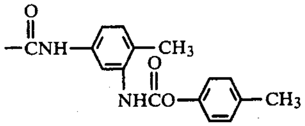 | 1.5472 |
| 456 | $-C_7H_{15}$ | $-C_7H_{15}$ | $-C_2H_5$ | 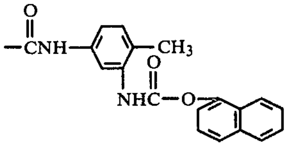 | Viscous liquid |
| 457 | $-C_7H_{15}$ | $-C_7H_{15}$ | $-C_2H_5$ | 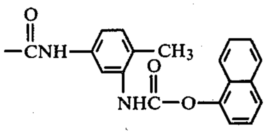 | Viscous liquid |
| 458 | $-C_7H_{15}$ | $-C_7H_{15}$ | $-C_2H_5$ | 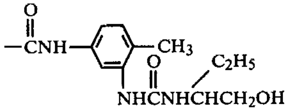 | Viscous liquid |

TABLE I-continued
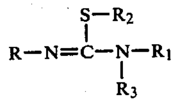
| Compound No. | R | $R_1$ | $R_2$ | $R_3$ | $n_D^{30}$ or °C. |
|---|---|---|---|---|---|
| 459 | $-C_7H_{15}$ | $-C_7H_{15}$ | $-C_2H_5$ | 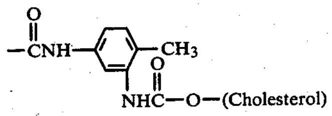 | Viscous liquid |
| 460 | $-C_7H_{15}$ | $-C_7H_{15}$ | $-C_2H_5$ | 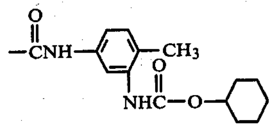 | Viscous liquid |
| 461 | $-C_7H_{15}$ | $-C_7H_{15}$ | $-C_2H_5$ | 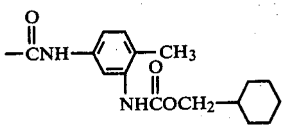 | 1.5304 |
| 462 | $-C_7H_{15}$ | $-C_7H_{15}$ | $-C_2H_5$ | 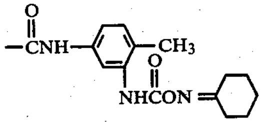 | 1.5416 |
| 463 | $-C_7H_{15}$ | $-C_7H_{15}$ | $-C_2H_5$ | 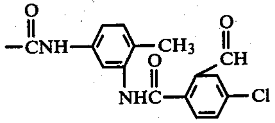 | Viscous liquid |
| 464 | $-C_7H_{15}$ | $-C_7H_{15}$ | $-C_2H_5$ | 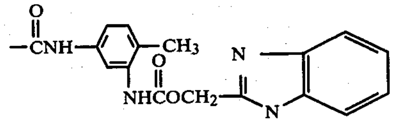 | Viscous liquid |
| 465 | $-C_7H_{15}$ | $-C_7H_{15}$ | $-C_2H_5$ | 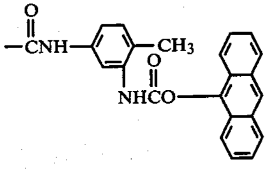 | Wax |

TABLE I-continued
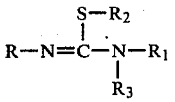
| Compound No. | R | $R_1$ | $R_2$ | $R_3$ | $n_D^{30}$ or °C. |
|---|---|---|---|---|---|
| 466 | $-C_7H_{15}$ | $-C_7H_{15}$ | $-C_2H_5$ | 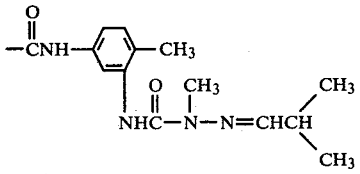 | 1.5396 |
| 467 | $-C_7H_{15}$ | $-C_7H_{15}$ | $-C_2H_5$ | 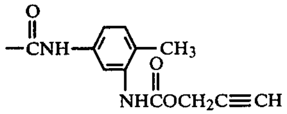 | Wax |
| 468 | $-C_7H_{15}$ | $-C_7H_{15}$ | $-C_2H_5$ | 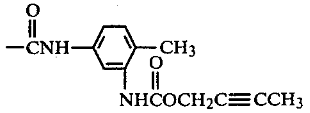 | 1.5325 |
| 469 | $-C_7H_{15}$ | $-C_7H_{15}$ | $-C_2H_5$ | 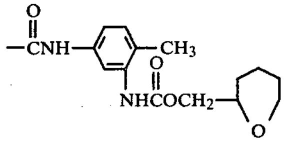 | 1.5304 |
| 470 | $-C_7H_{15}$ | $-C_7H_{15}$ | $-C_2H_5$ | 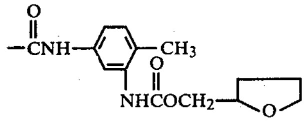 | 1.5311 |
| 471 | $-C_7H_{15}$ | $-C_7H_{15}$ | $-C_2H_5$ | 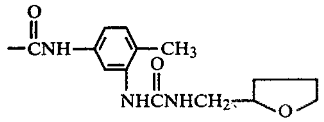 | 1.5378 |
| 472 | $-C_7H_{15}$ | $-C_7H_{15}$ | $-C_2H_5$ | 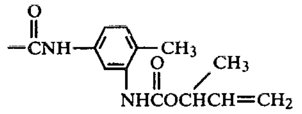 | 1.5250 |

TABLE I-continued
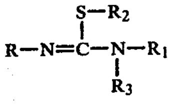
| Compound No. | R | $R_1$ | $R_2$ | $R_3$ | $n_D^{30}$ or °C. |
|---|---|---|---|---|---|
| 473 | $-C_7H_{15}$ | $-C_7H_{15}$ | $-C_2H_5$ | 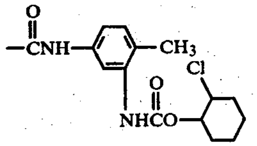 | Viscous liquid |
| 474 | $-C_7H_{15}$ | $-C_7H_{15}$ | $-C_2H_5$ | 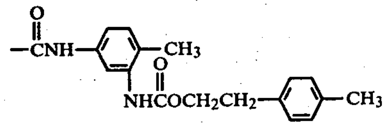 | 1.5484 |
| 475 | $-C_7H_{15}$ | $-C_7H_{15}$ | $-C_2H_5$ | 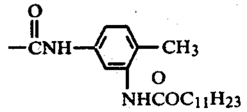 | 1.5124 |
| 476 | $-C_7H_{15}$ | $-C_7H_{15}$ | $-C_2H_5$ | 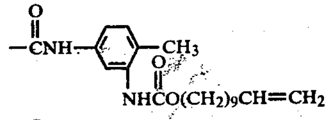 | 1.5172 |
| 477 | $-C_7H_{15}$ | $-C_7H_{15}$ | $-C_2H_5$ | 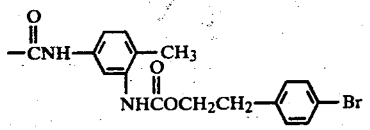 | 1.5548 |
| 478 | $-C_7H_{15}$ | $-C_7H_{15}$ | $-C_2H_5$ | 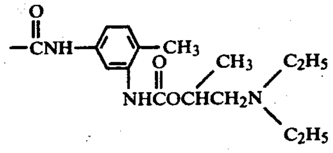 | 1.5206 |
| 479 | $-C_7H_{15}$ | $-C_7H_{15}$ | $-C_2H_5$ | 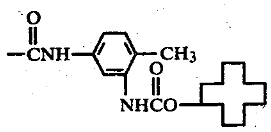 | 1.5288 |

TABLE I-continued
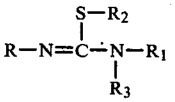
| Compound No. | R | $R_1$ | $R_2$ | $R_3$ | $n_D^{30}$ or °C. |
|---|---|---|---|---|---|
| 480 | $-C_7H_{15}$ | $-C_7H_{15}$ | $-C_2H_5$ | 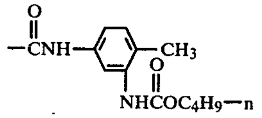 | 1.5233 |
| 481 | $-C_7H_{15}$ | $-C_7H_{15}$ | $-C_2H_5$ | 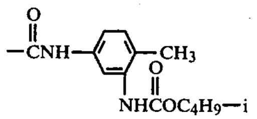 | 1.5220 |
| 482 | $-C_7H_{15}$ | $-C_7H_{15}$ | $-C_2H_5$ | 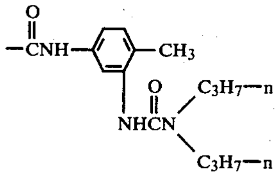 | 1.5278 |
| 483 | $-C_7H_{15}$ | $-C_7H_{15}$ | $-C_2H_5$ | 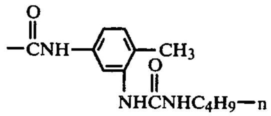 | Wax |
| 484 | $-C_7H_{15}$ | $-C_7H_{15}$ | $-C_2H_5$ | 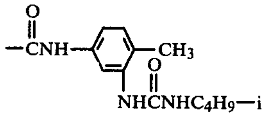 | Viscous liquid |
| 485 | $-C_7H_{15}$ | $-C_7H_{15}$ | $-C_2H_5$ | 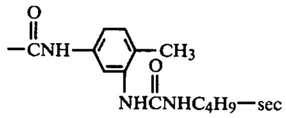 | Viscous liquid |
| 486 | $-C_7H_{15}$ | $-C_7H_{15}$ | $-C_2H_5$ | 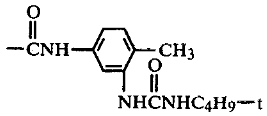 | Viscous liquid |

TABLE I-continued
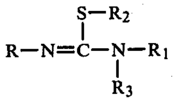
| Compound No. | R | $R_1$ | $R_2$ | $R_3$ | $n_D^{30}$ or °C. |
|---|---|---|---|---|---|
| 487 | $-C_7H_{15}$ | $-C_7H_{15}$ | $-C_2H_5$ | 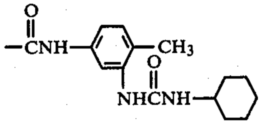 | Viscous liquid |
| 488 | $-C_7H_{15}$ | $-C_7H_{15}$ | $-C_2H_5$ | 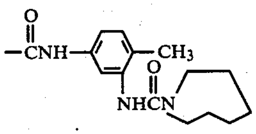 | Viscous liquid |
| 489 | $-C_7H_{15}$ | $-C_7H_{15}$ | $-C_2H_5$ | 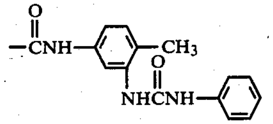 | 1.550 |
| 490 | $-C_7H_{15}$ | $-C_7H_{15}$ | $-C_2H_5$ | 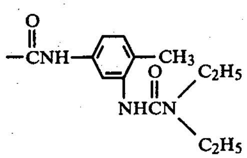 | 1.5329 |
| 491 | $-C_7H_{15}$ | $-C_7H_{15}$ | $-C_2H_5$ | 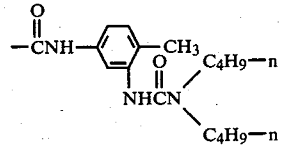 | 1.5234 |
| 492 | $-C_7H_{15}$ | $-C_7H_{15}$ | $-C_2H_5$ | 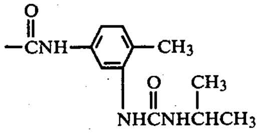 | 1.532 |

TABLE I-continued
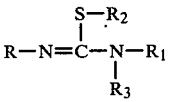
| Compound No. | R | $R_1$ | $R_2$ | $R_3$ | $n_D^{30}$ or °C. |
|---|---|---|---|---|---|
| 493 | $-C_7H_{15}$ | $-C_7H_{15}$ | $-C_2H_5$ | 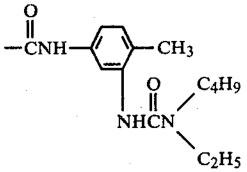 | 1.5280 |
| 494 | $-C_7H_{15}$ | $-C_7H_{15}$ | $-C_2H_5$ | 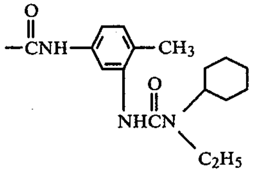 | 1.537 |
| 495 | $-C_7H_{15}$ | $-C_7H_{15}$ | $-C_2H_5$ | 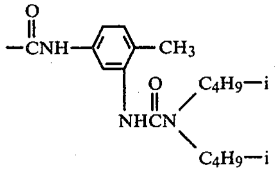 | 1.5236 |
| 496 | $-C_7H_{15}$ | $-C_7H_{15}$ | $-C_2H_5$ | 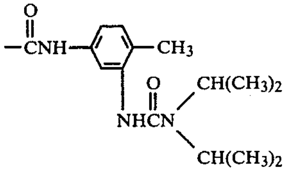 | Pasty solid |
| 497 | $-C_7H_{15}$ | $-C_7H_{15}$ | $-C_2H_5$ | 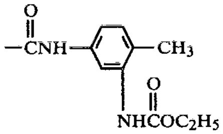 | 1.5280 |

TABLE I-continued
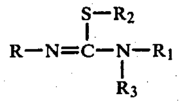
| Compound No. | R | $R_1$ | $R_2$ | $R_3$ | $n_D^{30}$ or °C. |
|---|---|---|---|---|---|
| 498 | $-C_7H_{15}$ | $-C_7H_{15}$ | $-C_2H_5$ | 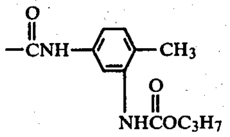 | 1.5254 |
| 499 | $-C_7H_{15}$ | $-C_7H_{15}$ | $-C_2H_5$ | 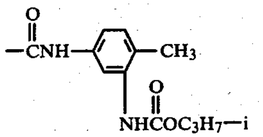 | 1.5258 |
| 500 | $-C_7H_{15}$ | $-C_7H_{15}$ | $-C_2H_5$ | 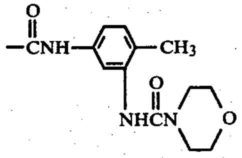 | 1.5401 |
| 501 | $-C_7H_{15}$ | $-C_7H_{15}$ | $-C_2H_5$ | 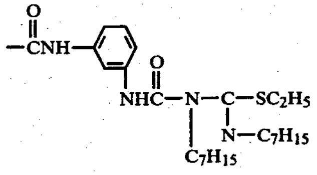 | 1.5250 |
| 502 | $-C_7H_{15}$ | $-C_7H_{15}$ | $-C_2H_5$ | 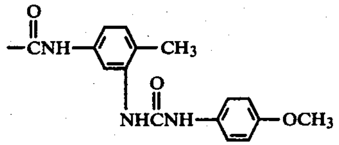 | 1.553 |
| 503 | $-C_7H_{15}$ | $-C_7H_{15}$ | $-C_2H_5$ | 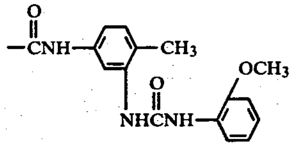 | Viscous liquid |

TABLE I-continued
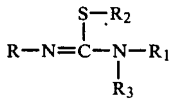
| Compound No. | R | $R_1$ | $R_2$ | $R_3$ | $n_D^{30}$ or °C. |
|---|---|---|---|---|---|
| 504 | $-C_7H_{15}$ | $-C_7H_{15}$ | $-C_2H_5$ | 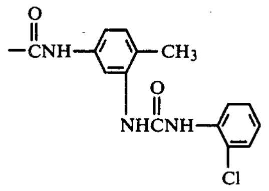 | 1.567 |
| 505 | $-C_7H_{15}$ | $-C_7H_{15}$ | $-C_2H_5$ | 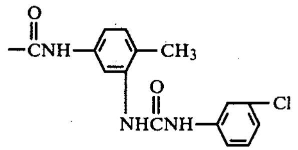 | Viscous liquid |
| 506 | $-C_7H_{15}$ | $-C_7H_{15}$ | $-C_2H_5$ | 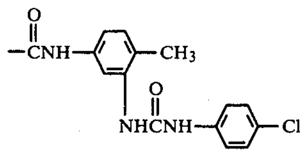 | 1.552 |
| 507 | $-C_7H_{15}$ | $-C_7H_{15}$ | $-C_2H_5$ | 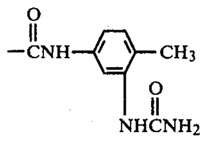 | Viscous liquid |
| 508 | $-C_7H_{15}$ | $-C_7H_{15}$ | $-C_2H_5$ | 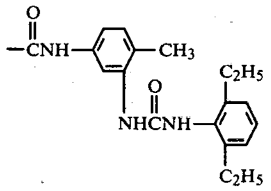 | 1.542 |

TABLE I-continued
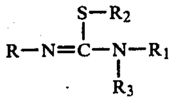
| Compound No. | R | R1 | R2 | R3 | $n_D^{30}$ or °C. |
|---|---|---|---|---|---|
| 509 | $-C_7H_{15}$ | $-C_7H_{15}$ | $-C_2H_5$ | 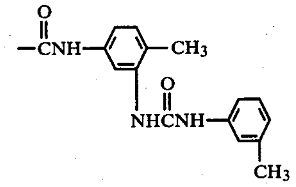 | Viscous liquid |
| 510 | $-C_7H_{15}$ | $-C_7H_{15}$ | $-C_2H_5$ | 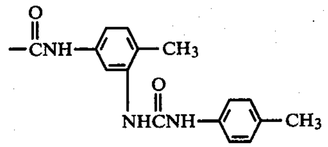 | 1.5494 |
| 511 | $-C_7H_{15}$ | $-C_7H_{15}$ | $-C_2H_5$ | 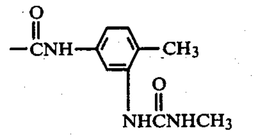 | Viscous liquid |
| 512 | $-C_7H_{15}$ | $-C_7H_{15}$ | $-C_2H_5$ | 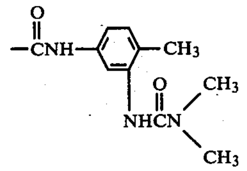 | 1.542 |
| 513 | $-C_7H_{15}$ | $-C_7H_{15}$ | $-C_2H_5$ | 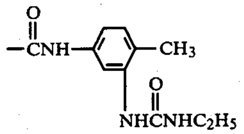 | 1.5311 |

TABLE I-continued
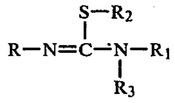
| Compound No. | R | $R_1$ | $R_2$ | $R_3$ | $n_D^{30}$ or °C. |
| --- | --- | --- | --- | --- | --- |
| 514 | $-C_7H_{15}$ | $-C_7H_{15}$ | $-C_2H_5$ | 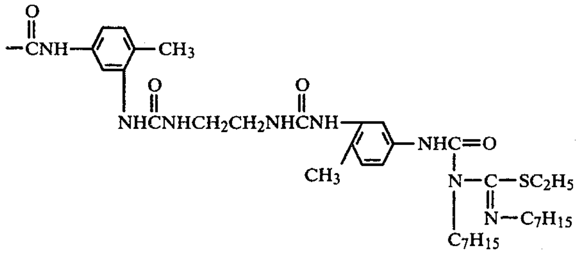 | Soft glass |
| 515 | $-C_7H_{15}$ | $-C_7H_{15}$ | $-C_2H_5$ | 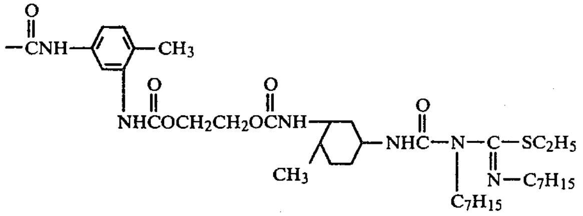 | 1.5398 |
| 516 | $-C_7H_{15}$ | $-C_7H_{15}$ | $-C_2H_5$ | 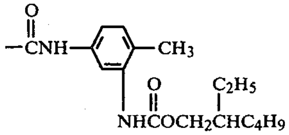 | 1.5180 |
| 517 | $-C_7H_{15}$ | $-C_7H_{15}$ | $-C_2H_5$ | 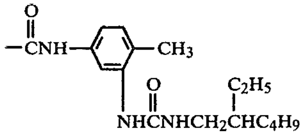 | 1.5246 |
| 518 | $-C_7H_{15}$ | $-C_7H_{15}$ | $-C_2H_5$ | 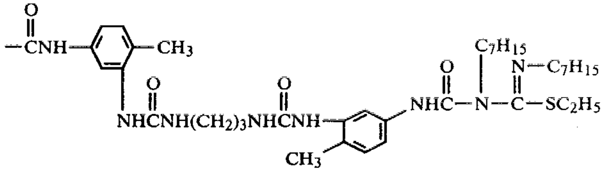 | Soft glass |

TABLE I-continued
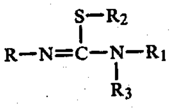
| Compound No. | R | $R_1$ | $R_2$ | $R_3$ | $n_D^{30}$ or °C. |
|---|---|---|---|---|---|
| 519 | $-C_7H_{15}$ | $-C_7H_{15}$ | $-C_2H_5$ | 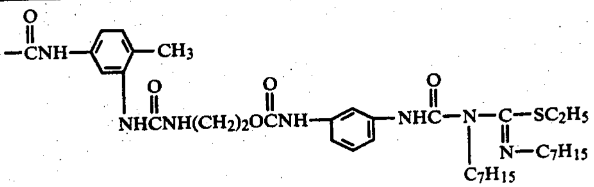 | Very viscous liquid |
| 520 | $-C_7H_{15}$ | $-C_7H_{15}$ | $-C_2H_5$ | 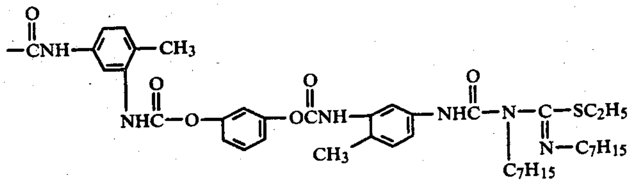 | Viscous liquid |
| 521 | $-C_7H_{15}$ | $-C_7H_{15}$ | $-C_2H_5$ | 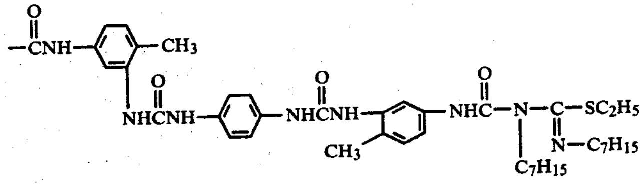 | Amber gel |
| 522 | $-C_7H_{15}$ | $-C_7H_{15}$ | $-C_2H_5$ | 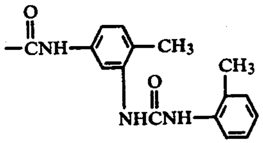 | Viscous liquid |
| 523 | $-C_7H_{15}$ | $-C_7H_{15}$ | $-C_2H_5$ | 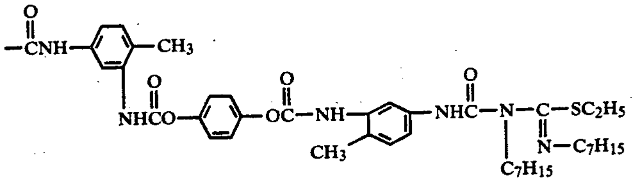 | Soft glass |

TABLE I-continued
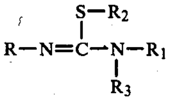
| Compound No. | R | R1 | R2 | R3 | $n_D^{30}$ or °C. |
|---|---|---|---|---|---|
| 524 | —2-ethyl-hexyl | —2-ethyl-hexyl | $-C_2H_5$ | 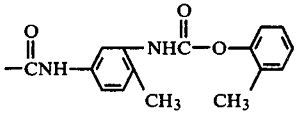 | 1.5429 |
| 525 | —2-ethyl-hexyl | —2-ethyl-hexyl | $-C_2H_5$ | 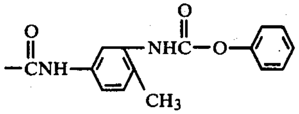 | 1.5460 |
| 526 | —2-ethyl-hexyl | —2-ethyl-hexyl | $-C_2H_5$ | 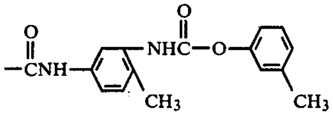 | 1.5430 |
| 527 | —2-ethyl-hexyl | —2-ethyl-hexyl | $-C_2H_5$ | 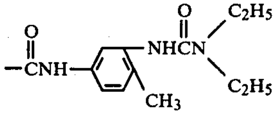 | Tacky solid |
| 528 | —2-ethyl-hexyl | —2-ethyl-hexyl | $-C_2H_5$ | 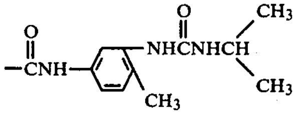 | 1.5228 |
| 529 | —2-ethyl-hexyl | —2-ethyl-hexyl | $-C_2H_5$ | 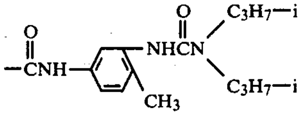 | Wax |
| 530 | —2-ethyl-hexyl | —2-ethyl-hexyl | $-C_2H_5$ | 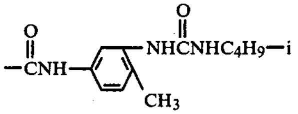 | Wax |
| 531 | —2-ethyl-hexyl | —2-ethyl-hexyl | $-C_2H_5$ | 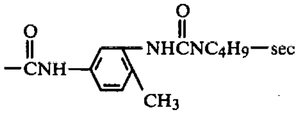 | 1.5231 |

TABLE I-continued
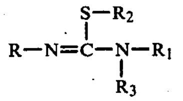
| Compound No. | R | $R_1$ | $R_2$ | $R_3$ | $n_D^{30}$ or °C. |
|---|---|---|---|---|---|
| 532 | —2-ethyl-hexyl | —2-ethyl-hexyl | $-C_2H_5$ | 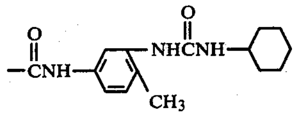 | 1.5265 |
| 533 | —2-ethyl-hexyl | —2-ethyl-hexyl | $-C_2H_5$ | 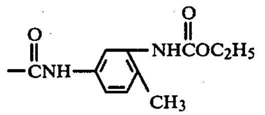 | 1.5257 |
| 534 | —2-ethyl-hexyl | —2-ethyl-hexyl | $-C_2H_5$ | 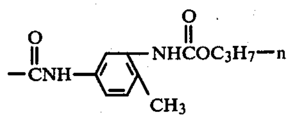 | 1.5235 |
| 535 | —2-ethyl-hexyl | —2-ethyl-hexyl | $-C_2H_5$ | 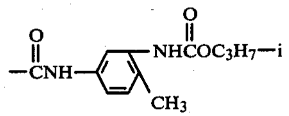 | 1.5215 |
| 536 | —2-ethyl-hexyl | —2-ethyl-hexyl | $-C_2H_5$ | 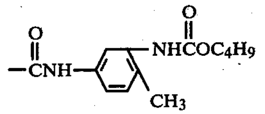 | 1.5216 |
| 537 | —2-ethyl-hexyl | —2-ethyl-hexyl | $-C_2H_5$ | 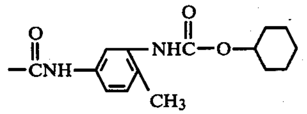 | 1.5294 |
| 538 | —2-ethyl-hexyl | —2-ethyl-hexyl | $-C_2H_5$ | 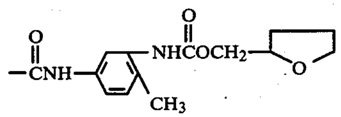 | 1.5290 |
| 539 | —2-ethyl-hexyl | —2-ethyl-hexyl | $-C_2H_5$ | 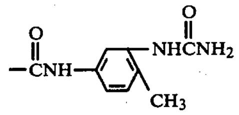 | 1.5309 |

TABLE I-continued
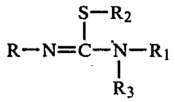
| Compound No. | R | $R_1$ | $R_2$ | $R_3$ | $n_D^{30}$ or °C. |
|---|---|---|---|---|---|
| 540 | —2-ethyl-hexyl | $—secC_7H_{15}$ | $—C_2H_5$ | 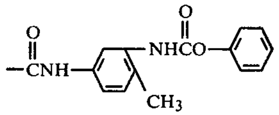 | 1.5475 |
| 541 | —2-ethyl-hexyl | $—secC_7H_{15}$ | $—C_2H_5$ | 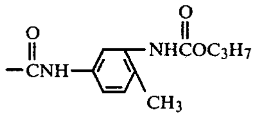 | 1.5215 |
| 542 | $—C_8H_{17}$ | $—C_8H_{17}$ | $—C_2H_5$ | 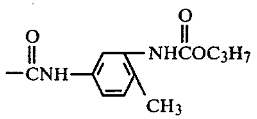 | 1.5209 |
| 543 | $—C_8H_{17}$ | $—secC_7H_{15}$ | $—C_2H_5$ | 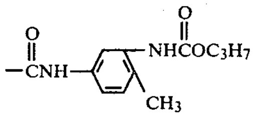 | 1.5234 |
| 544 | —2-ethyl-hexyl | $—secC_7H_{15}$ | $—C_2H_5$ | 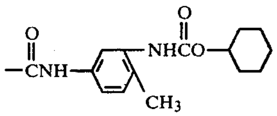 | 1.5275 |
| 545 | $—C_8H_{17}$ | $—C_8H_{17}$ | $—C_2H_5$ | 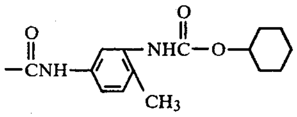 | 1.5298 |
| 546 | $—C_8H_{17}$ | $—secC_7H_{15}$ | $—C_2H_5$ | 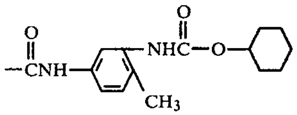 | 1.5280 |
| 547 | $—C_8H_{17}$ | $—secC_7H_{15}$ | $—C_3H_7$ | 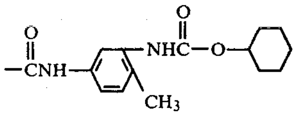 | 1.5260 |

TABLE I-continued
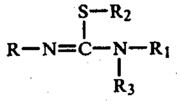
| Compound No. | R | $R_1$ | $R_2$ | $R_3$ | $n_D^{30}$ or °C. |
|---|---|---|---|---|---|
| 548 | $-C_8H_{17}$ | $-secC_7H_{15}$ | $-C_3H_7$ | 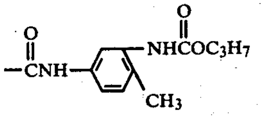 | 1.5455 |
| 549 | $-C_8H_{17}$ | $-secC_7H_{15}$ | $-C_2H_5$ | 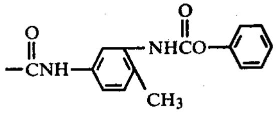 | 1.5455 |
| 550 | $-C_8H_{17}$ | $-secC_7H_{15}$ | $-C_3H_7$ | 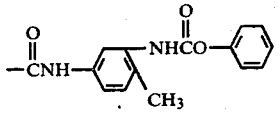 | 1.5451 |
| 551 | $-C_8H_{17}$ | $-C_8H_{17}$ | $-C_2H_5$ | 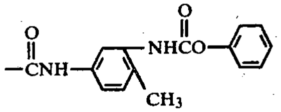 | 1.5445 |
| 552 | $-C_8H_{17}$ | $-secC_7H_{15}$ | $-C_2H_5$ | 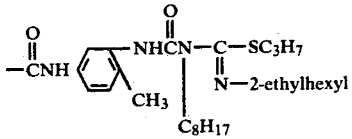 | 1.5195 |
| 553 | $-C_8H_{17}$ | $-secC_7H_{15}$ | $-C_2H_5$ | 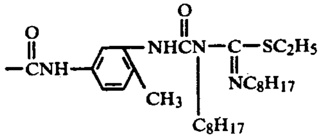 | 1.5204 |
| 554 | $-C_8H_{17}$ | $-secC_7H_{15}$ | $-C_2H_5$ | 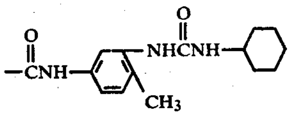 | 1.5268 |

TABLE I-continued
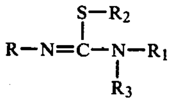
| Compound No. | R | $R_1$ | $R_2$ | $R_3$ | $n_D^{30}$ or °C. |
|---|---|---|---|---|---|
| 555 | $-C_8H_{17}$ | —2-ethyl-hexyl | $-C_2H_5$ | 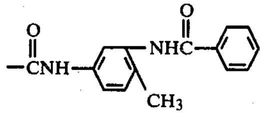 | 1.5466 |
| 556 | $-C_8H_{17}$ | $-secC_7H_{15}$ | $-C_2H_5$ | 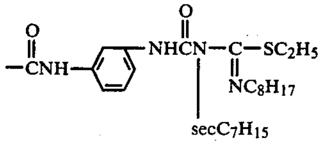 | 1.5007 |
| 557 | $-C_8H_{17}$ | $-secC_7H_{15}$ | $-C_3H_7$ | 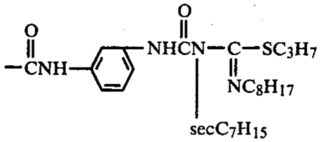 | 1.5180 |
| 558 | $-C_8H_{17}$ | $-secC_7H_{15}$ | $-C_2H_5$ | 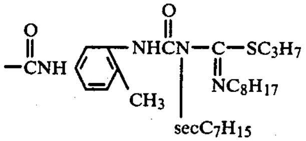 | 1.5185 |
| 559 | —2-ethyl-hexyl | —2-ethyl-hexyl | $-C_3H_7$ | 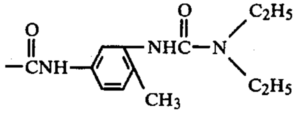 | Waxy white solid |
| 560 | —2-ethyl-hexyl | —2-ethyl-hexyl | $-C_3H_7$ | 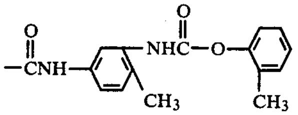 | 1.5420 |
| 561 | —2-ethyl-hexyl | —2-ethyl-hexyl | $-C_3H_7$ | 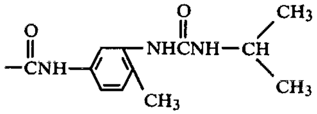 | 1.5210 |

TABLE I-continued
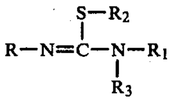
| Compound No. | R | $R_1$ | $R_2$ | $R_3$ | $n_D^{30}$ or °C. |
|---|---|---|---|---|---|
| 562 | —2-ethyl-hexyl | —2-ethyl-hexyl | $-C_3H_7$ | 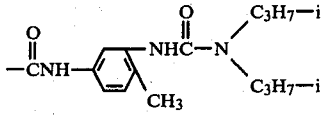 | 1.522 |
| 563 | —2-ethyl-hexyl | —2-ethyl-hexyl | $-C_3H_7$ | 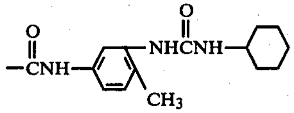 | 1.5236 |
| 564 | —2-ethyl-hexyl | —2-ethyl-hexyl | $-C_2H_5$ | 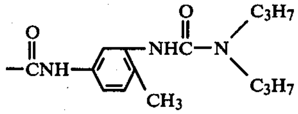 | 1.5231 |
| 565 | $-C_8H_{17}$ | —2-ethyl-hexyl | $-C_2H_5$ | 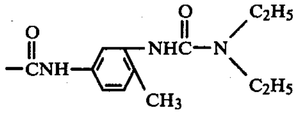 | 1.5279 |
| 566 | —2-ethyl-hexyl | $-secC_7H_{15}$ | $-C_2H_5$ | 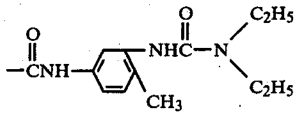 | 1.5278 |
| 567 | $-C_8H_{17}$ | $-secC_7H_{15}$ | $-C_3H_7$ | 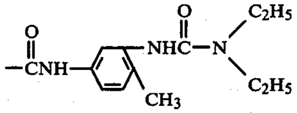 | 1.5278 |
| 568 | $-C_8H_{17}$ | $-secC_7H_{15}$ | $-C_3H_7$ | 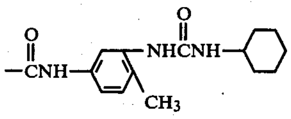 | 1.5270 |
| 569 | —2-ethyl-hexyl | $-secC_7H_{15}$ | $-C_2H_5$ | 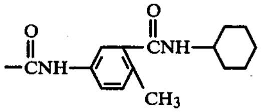 | 1.5240 |

TABLE I-continued
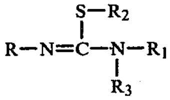
| Compound No. | R | $R_1$ | $R_2$ | $R_3$ | $n_D^{30}$ or °C. |
|---|---|---|---|---|---|
| 570 | —2-ethyl-hexyl | $-secC_7H_{15}$ | $-C_2H_5$ | 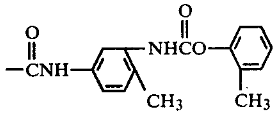 | 1.5410 |
| 571 | —2-ethyl-hexyl | $-secC_7H_{15}$ | $-C_2H_5$ | 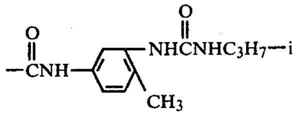 | 1.5209 |
| 572 | —2-ethyl-hexyl | $-secC_7H_{15}$ | $-C_2H_5$ | 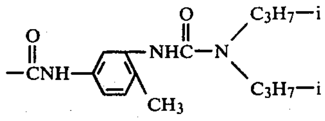 | Opaque white wax |
| 573 | $-C_8H_{17}$ | —2-ethyl-hexyl | $-C_2H_5$ | 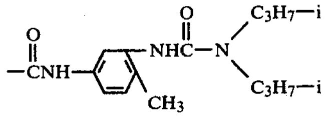 | 1.524 |
| 574 | $-C_8H_{17}$ | —2-ethyl-hexyl | $-C_2H_5$ | 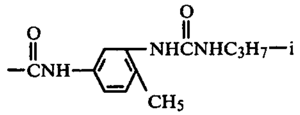 | 1.5239 |
| 575 | $-C_8H_{17}$ | —2-ethyl-hexyl | $-C_2H_5$ | 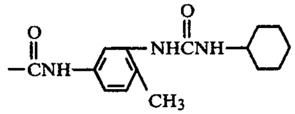 | 1.5262 |
| 576 | —2-ethyl-hexyl | $-secC_7H_{15}$ | $-C_2H_5$ | 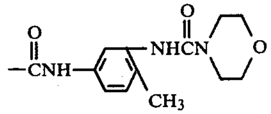 | 1.5270 |
| 577 | —2-ethyl-hexyl | $-secC_7H_{15}$ | $-C_2H_5$ | 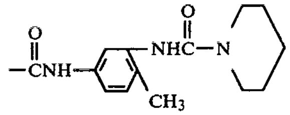 | 1.5304 |

TABLE I-continued
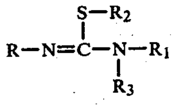
| Compound No. | R | $R_1$ | $R_2$ | $R_3$ | $n_D^{30}$ or °C. |
|---|---|---|---|---|---|
| 578 | —2-ethyl-hexyl | —sec$C_7H_{15}$ | —$C_2H_5$ | 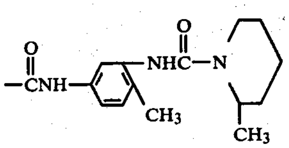 | 1.5330 |
| 579 | —2-ethyl-hexyl | —sec$C_7H_{15}$ | —$C_2H_5$ | 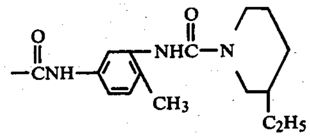 | 1.5305 |
| 580 | —2-ethyl-hexyl | —sec$C_7H_{15}$ | —$C_2H_5$ | 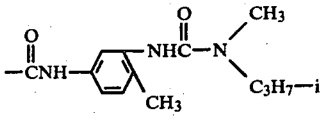 | 1.5268 |
| 581 | —2-ethyl-hexyl | —sec$C_7H_{15}$ | —$C_2H_5$ | 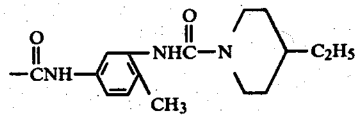 | 1.5321 |
| 582 | —2-ethyl-hexyl | —sec$C_7H_{15}$ | —$C_2H_5$ | 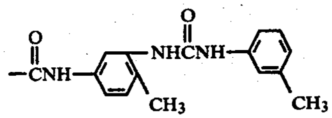 | 1.5415 |
| 583 | —2-ethyl-hexyl | —2-ethyl-hexyl | —$C_2H_5$ | 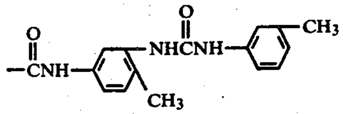 | 1.5406 |
| 584 | —2-ethyl-hexyl | —2-ethyl-hexyl | —$C_2H_5$ | 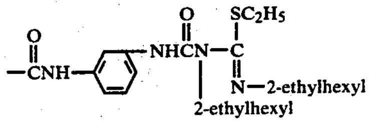 | 1.5233 |

TABLE I-continued
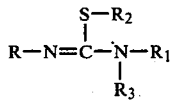
| Compound No. | R | $R_1$ | $R_2$ | $R_3$ | $n_D^{30}$ or °C. |
|---|---|---|---|---|---|
| 585 | —2-ethyl-hexyl | —2-ethyl-hexyl | $-C_2H_5$ | 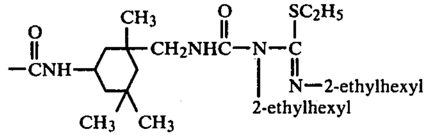 | 1.4991 |
| 586 | 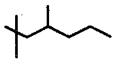 | 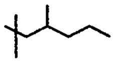 | $-C_2H_5$ | 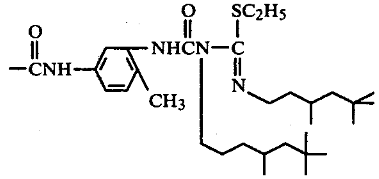 | 1.5163 |
| 587 | 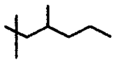 | 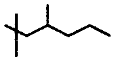 | $-C_2H_5$ | 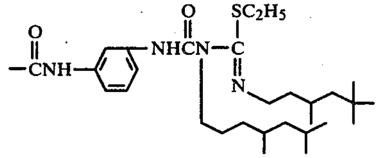 | 1.5162 |
| 588 | 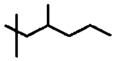 | 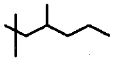 | $-C_2H_5$ | 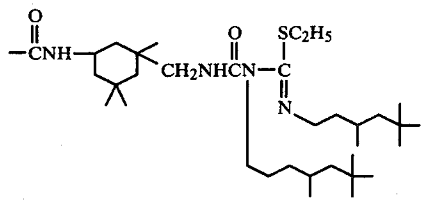 | 1.4948 |
| 589 | 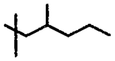 | 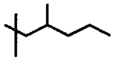 | $-C_2H_5$ | 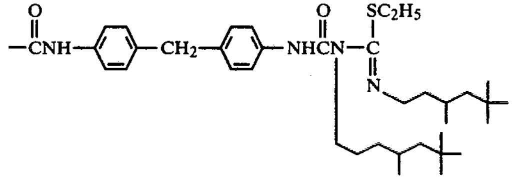 | 1.5292 |

TABLE I-continued
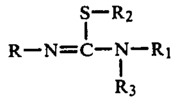
| Compound No. | R | $R_1$ | $R_2$ | $R_3$ | $n_D^{30}$ or °C. |
|---|---|---|---|---|---|
| 590 | 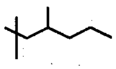 | 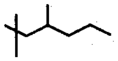 | $-C_2H_5$ | 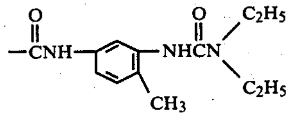 | 1.5212 |
| 591 | 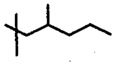 | 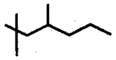 | $-C_2H_5$ | 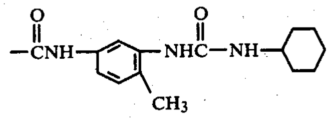 | 1.5153 |
| 592 | 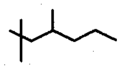 | 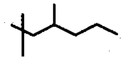 | $-C_2H_5$ | 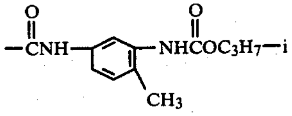 | 1.5181 |
| 593 | 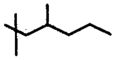 | 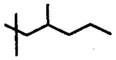 | $-C_2H_5$ | 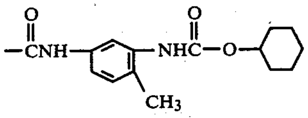 | 1.5228 |
| 594 | 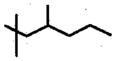 | 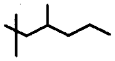 | $-C_2H_5$ | 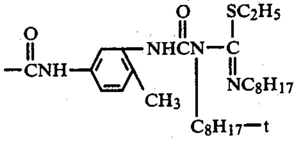 | 1.5178 |
| 595 | 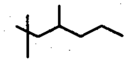 | 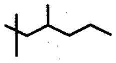 | $-C_2H_5$ | 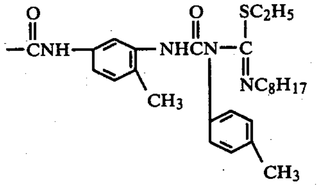 | 1.5447 |
| 596 | 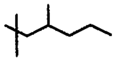 | 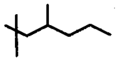 | $-C_2H_5$ | 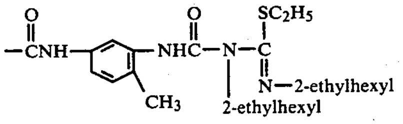 | 1.5195 |

TABLE I-continued
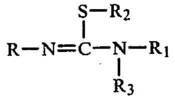
| Compound No. | R | $R_1$ | $R_2$ | $R_3$ | $n_D^{30}$ or °C. |
|---|---|---|---|---|---|
| 597 | 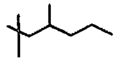 | 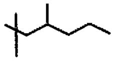 | $-C_2H_5$ | 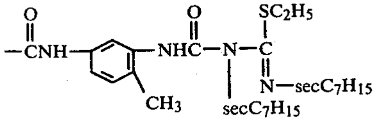 | 1.5166 |
| 598 | 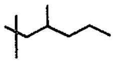 | 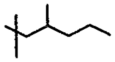 | $-C_2H_5$ | 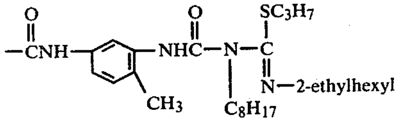 | 1.5178 |
| 599 | 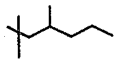 | 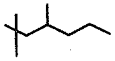 | $-C_2H_5$ | 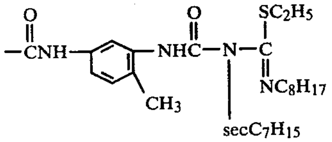 | 1.5187 |
| 600 | 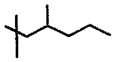 | 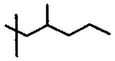 | $-C_2H_5$ | 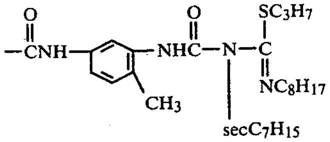 | 1.5176 |
| 601 | 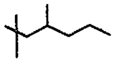 | 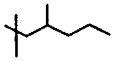 | $-C_2H_5$ | 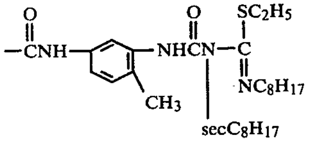 | 1.5166 |
| 602 | $-secC_7H_{15}$ | $-tC_8H_{17}$ | $-C_2H_5$ | 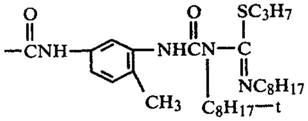 | 1.5184 |
| 603 | $-secC_7H_{15}$ | $-secC_7H_{15}$ | $-C_2H_5$ | 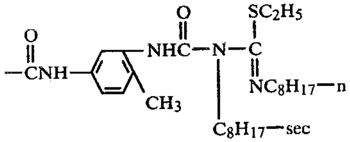 | 1.5196 |

TABLE I-continued
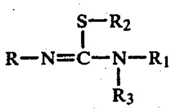
| Compound No. | R | $R_1$ | $R_2$ | $R_3$ | $n_D^{30}$ or °C. |
|---|---|---|---|---|---|
| 604 | $-secC_7H_{15}$ | $-secC_7H_{15}$ | $-C_2H_5$ | 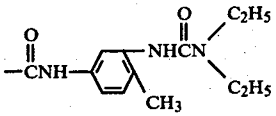 | 1.5178 |
| 605 | 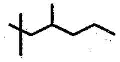 | 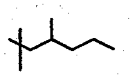 | $-C_3H_7$ | 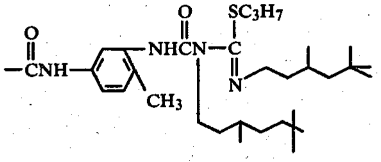 | 1.5142 |
| 606 | 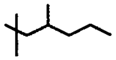 | 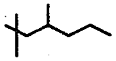 | $-C_3H_7$ | 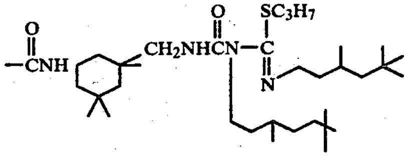 | 1.4930 |
| 607 | 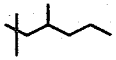 | 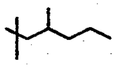 | $-C_3H_7$ | 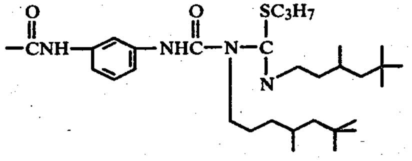 | 1.5133 |
| 608 | 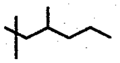 | 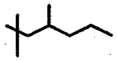 | $-C_3H_7$ | 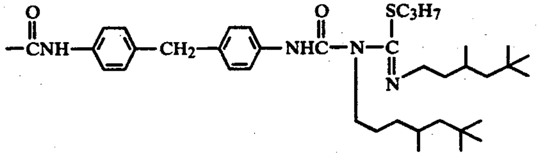 | 1.5244 |
| 609 | $-secC_7H_{15}$ | $-secC_7H_{15}$ | $-C_2H_5$ | 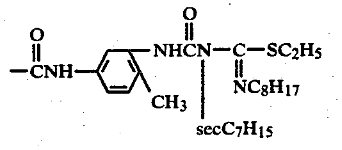 | 1.5182 |

TABLE I-continued
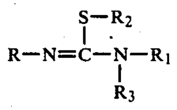
| Compound No. | R | R1 | R2 | R3 | $n_D^{30}$ or °C. |
|---|---|---|---|---|---|
| 610 | $-secC_7H_{15}$ | $-secC_7H_{15}$ | $-C_2H_5$ | 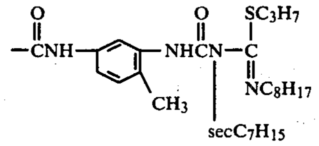 | 1.5166 |
| 611 | $-secC_7H_{15}$ | $-secC_7H_{15}$ | $-C_2H_5$ | 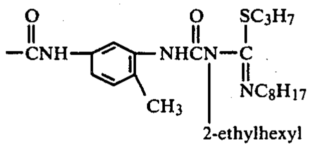 | 1.5177 |
| 612 | $-secC_7H_{15}$ | $-secC_7H_{15}$ | $-C_2H_5$ | 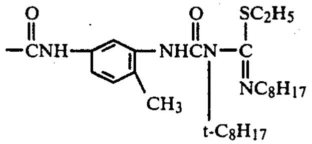 | 1.5202 |
| 613 | $-secC_7H_{15}$ | $-secC_7H_{15}$ | $-C_2H_5$ | 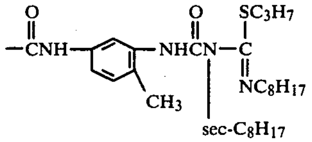 | 1.5156 |
| 614 | $-secC_7H_{15}$ | $-secC_7H_{15}$ | $-C_2H_5$ | 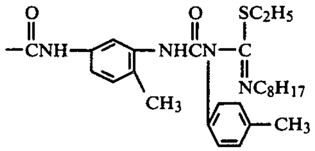 | 1.5507 |
| 615 | $-secC_7H_{15}$ | $-secC_7H_{15}$ | $-C_2H_5$ | 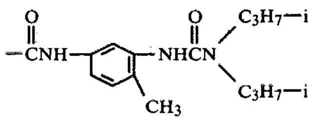 | 1.514 |

TABLE I-continued
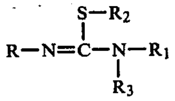
| Compound No. | R | $R_1$ | $R_2$ | $R_3$ | $n_D^{30}$ or °C. |
|---|---|---|---|---|---|
| 616 | $-secC_7H_{15}$ | $-secC_7H_{15}$ | $-C_2H_5$ | 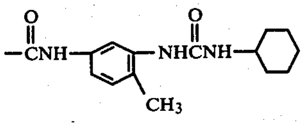 | 1.509 |
| 617 | $-secC_7H_{15}$ | $-secC_7H_{15}$ | $-C_2H_5$ | 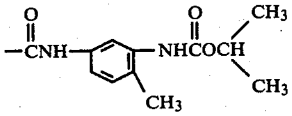 | 1.5164 |
| 618 | $-secC_7H_{15}$ | $-secC_7H_{15}$ | $-C_2H_5$ | 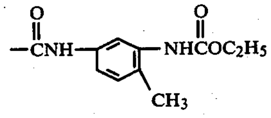 | 1.5128 |
| 619 | $-secC_7H_{15}$ | $-secC_7H_{15}$ | $-C_2H_5$ | 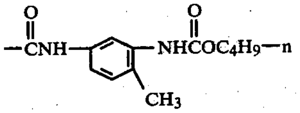 | 1.5145 |
| 620 | $-secC_7H_{15}$ | $-secC_7H_{15}$ | $-C_2H_5$ | 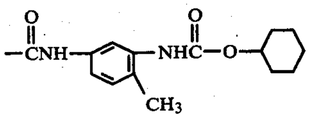 | 1.5211 |
| 621 | $-secC_7H_{15}$ | $-secC_7H_{15}$ | $-C_2H_5$ | 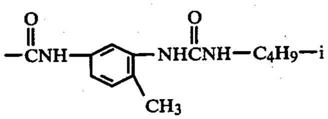 | 1.514 |
| 622 | 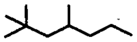 | 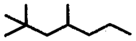 | $-C_3H_7$ | 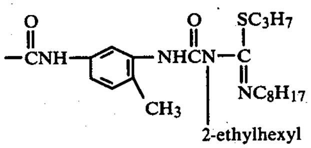 | 1.5118 |

TABLE I-continued
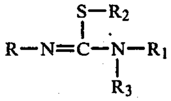
| Compound No. | R | R1 | R2 | R3 | $n_D^{30}$ or °C. |
|---|---|---|---|---|---|
| 623 | 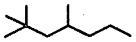 | 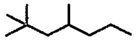 | $-C_3H_7$ | 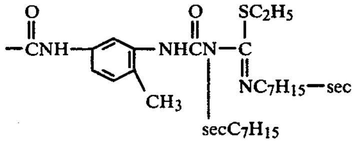 | 1.5157 |
| 624 | 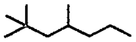 | 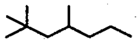 | $-C_3H_7$ | 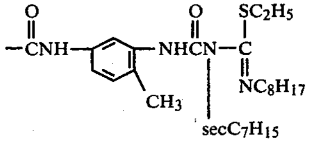 | 1.5169 |
| 625 | 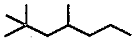 | 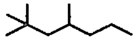 | $-C_3H_7$ | 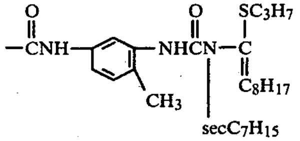 | 1.5154 |
| 626 | 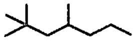 | 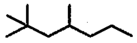 | $-C_3H_7$ | 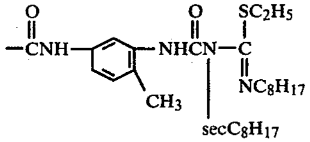 | 1.5137 |
| 627 | 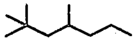 | 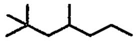 | $-C_3H_7$ | 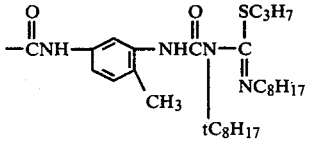 | 1.5163 |
| 628 | 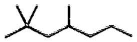 | 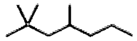 | $-C_3H_7$ | 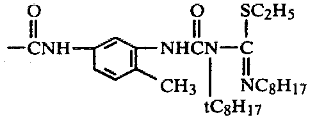 | 1.5170 |

TABLE I-continued
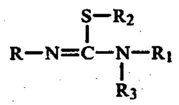
| Compound No. | R | $R_1$ | $R_2$ | $R_3$ | $n_D^{30}$ or °C. |
|---|---|---|---|---|---|
| 629 | $-C_8H_{17}$ | $-secC_7H_{15}$ | $-C_2H_5$ | 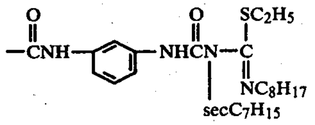 | 1.5239 |
| 630 | 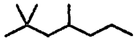 | 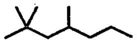 | $-C_3H_7$ | 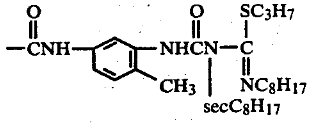 | 1.5154 |
| 631 | 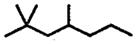 | 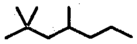 | $-C_3H_7$ | 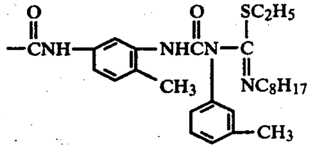 | 1.5423 |
| 632 | $-C_7H_{15}$ | $-C_7H_{15}$ | $-SC_2H_5$ | 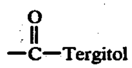 | 1.4488 |
| 633 | $-C_7H_{15}$ | $-C_7H_{15}$ | $-SC_2H_5$ | 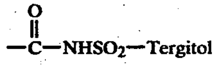 | 1.4564 |
| 634 | $-C_7H_{15}$ | $-C_7H_{15}$ | $-SC_2H_5$ | 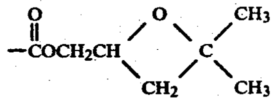 | 1.5583 |
| 635 | $-C_7H_{15}$ | $-C_7H_{15}$ | $-SC_2H_5$ | 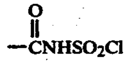 | 62°-77° |
| 636 | $-C_7H_{15}$ | $-C_7H_{15}$ | $-SC_2H_5$ | 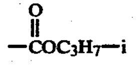 | 1.4425 |
| 637 | $-C_7H_{15}$ | $-C_7H_{15}$ | $-SC_2H_5$ | 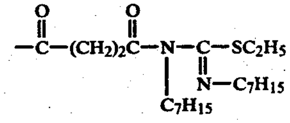 | 1.4954 |

TABLE I-continued

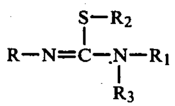

| Compound No. | R | $R_1$ | $R_2$ | $R_3$ | $n_D^{30}$ or °C. |
|---|---|---|---|---|---|
| 638 | $-C_7H_{15}$ | $-C_7H_{15}$ | $-SC_2H_5$ | 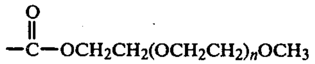 | 1.5592 |
| n average = 6.2<br>One of the reactants was Carbowax® 350 a product of Union Carbide Corporation in which the average Molecular Weight is 350 and n averages 6.2. | | | | | |
| 639 | $-C_7H_{15}$ | $-C_7H_{15}$ | 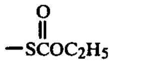 | 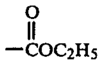 | 1.4841 |
| 640 | $-C_7H_{15}$ | $-C_7H_{15}$ | $-SCH_2CH_2OH$ | 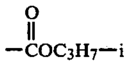 | Waxy-semi-solid |
| 641 | $-C_7H_{15}$ | $-C_7H_{15}$ | $-SCH_2CH_2OH$ | 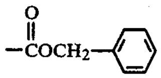 | Waxy solid |
| 642 | $-C_7H_{15}$ | $-C_7H_{15}$ | $-C_2H_5$ | 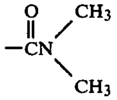 | 1.4621 |
| 643 | $-C_7H_{15}$ | $-C_7H_{15}$ | $-C_2H_5$ | 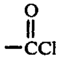 | 1.4613 |
| 644 | $-C_7H_{15}$ | $-C_7H_{15}$ | $-C_2H_5$ | 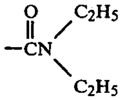 | 1.4568 |
| 645 | $-C_7H_{15}$ | $-C_7H_{15}$ | $-C_2H_5$ | 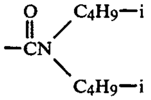 | 1.4538 |
| 646 | $-C_7H_{15}$ | $-C_7H_{15}$ | $-C_2H_5$ | 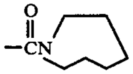 | 1.4708 |
| 647 | $-C_7H_{15}$ | $-C_7H_{15}$ | $-C_2H_5$ | 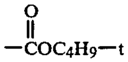 | 1.4412 |
| 648 | $-C_7H_{15}$ | $-C_7H_{15}$ | $-C_2H_5$ | 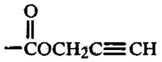 | 1.4553 |
| 649 | $-C_7H_{15}$ | $-C_7H_{15}$ | $-C_2H_5$ | 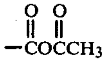 | 1.4501 |

TABLE I-continued
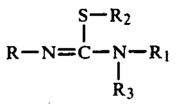
| Compound No. | R | $R_1$ | $R_2$ | $R_3$ | $n_D^{30}$ or °C. |
|---|---|---|---|---|---|
| 650 | $-C_7H_{15}$ | $-C_7H_{15}$ | $-C_2H_5$ | 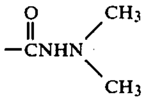 | 1.4654 |
| 651 | $-C_7H_{15}$ | $-C_7H_{15}$ | $-C_2H_5$ | 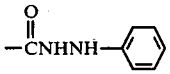 | 1.4990 |
| 652 | $-C_7H_{15}$ | $-C_7H_{15}$ | $-C_2H_5$ | 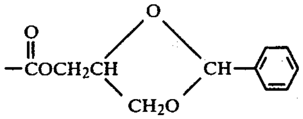 | 1.4764 |
| 653 | $-C_7H_{15}$ | $-C_7H_{15}$ | $-C_2H_5$ | 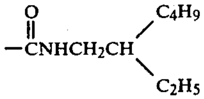 | 1.4563 |
| 654 | $-C_7H_{15}$ | $-C_7H_{15}$ | $-C_2H_5$ | 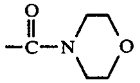 | 1.4689 |
| 655 | $-C_7H_{15}$ | $-C_7H_{15}$ | $-C_2H_5$ | 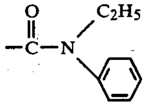 | 1.4836 |
| 656 | $-C_7H_{15}$ | $-C_7H_{15}$ | $-C_2H_5$ | 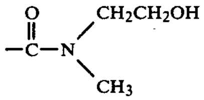 | 1.4660 |
| 657 | $-C_7H_{15}$ | $-C_7H_{15}$ | $-C_2H_5$ | 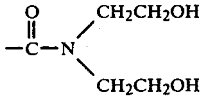 | 1.4623 |
| 658 | $-C_7H_{15}$ | $-C_7H_{15}$ | $-C_2H_5$ | 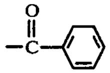 | 1.5095 |
| 659 | $-C_7H_{15}$ | $-C_7H_{15}$ | $-C_2H_5$ | 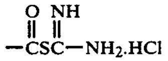 | Glass |

TABLE I-continued
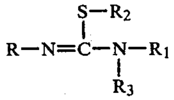
| Compound No. | R | $R_1$ | $R_2$ | $R_3$ | $n_D^{30}$ or °C. |
|---|---|---|---|---|---|
| 660 | $-C_7H_{15}$ | $-C_7H_{15}$ | $-C_2H_5$ | 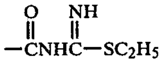 | 1.5209 |
| 661 | $-C_7H_{15}$ | $-C_7H_{15}$ | $-C_2H_5$ | 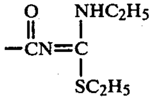 | 1.5156 |
| 662 | $-C_7H_{15}$ | $-C_7H_{15}$ | $-C_2H_5$ | 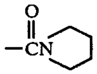 | 1.4929 |
| 663 | $-C_7H_{15}$ | $-C_7H_{15}$ | $-C_2H_5$ | 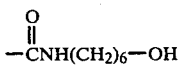 | 1.4897 |
| 664 | $-C_7H_{15}$ | $-C_7H_{15}$ | $-C_2H_5$ | 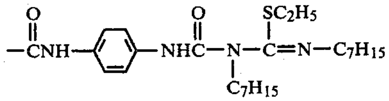 | 1.5228 |
| 665 | —2-ethyl-hexyl | —2-ethyl-hexyl | $-C_2H_5$ | 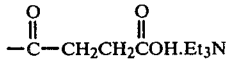 | 1.4899 |
| 666 | —2-ethyl-hexyl | $-C_8H_{17}$ | $-C_2H_5$ | 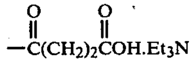 | 1.4879 |
| 667 | $-secC_7H_{15}$ | $-C_8H_{17}$ | $-C_2H_5$ | 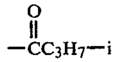 | 1.4746 |
| 668 | —2-ethyl-hexyl | —2-ethyl-hexyl | $-C_2H_5$ | 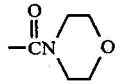 | 1.4930 |
| 669 | $-C_7H_{15}$ | $-C_7H_{15}$ | $-C_2H_5$ | 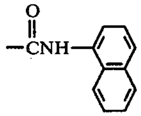 | Waxy semi-solid |
| 670 | $-C_7H_{15}$ | $-C_7H_{15}$ | $-C_2H_5$ | 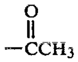 | 1.4793 |
| 671 | $-C_7H_{15}$ | $-C_7H_{15}$ | $-C_2H_5$ | 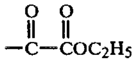 | 1.4757 |

TABLE I-continued

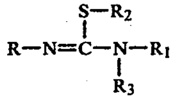

| Compound No. | R | $R_1$ | $R_2$ | $R_3$ | $n_D^{30}$ or °C. |
|---|---|---|---|---|---|
| 672 | $-C_7H_{15}$ | $-C_7H_{15}$ | $-C_2H_5$ | $-\overset{O}{\overset{\parallel}{C}}(CH_2)_{16}CH_3$ | Slush |
| 673 | $-C_7H_{15}$ | $-C_7H_{15}$ | $-C_2H_5$ | $-\overset{O}{\overset{\parallel}{C}}C_2H_5$ | 1.4778 |
| 674 | $-C_7H_{15}$ | $-C_7H_{15}$ | $-C_2H_5$ | $-\overset{O}{\overset{\parallel}{C}}C_{15}H_{31}$ | Slush |
| 675 | $-C_7H_{15}$ | $-C_7H_{15}$ | $-C_2H_5$ | $-\overset{O}{\overset{\parallel}{C}}C_3H_7$ | 1.4740 |
| 676 | $-C_7H_{15}$ | $-C_7H_{15}$ | $-C_2H_5$ | $-\overset{O}{\overset{\parallel}{C}}C_4H_9$ | 1.4746 |
| 677 | $-C_7H_{15}$ | $-C_7H_{15}$ | $-C_2H_5$ | $-\overset{O}{\overset{\parallel}{C}}C_{11}H_{23}$ | 1.4725 |
| 678 | $-C_7H_{15}$ | $-C_7H_{15}$ | $-C_2H_5$ | 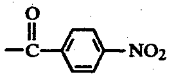 | Slush |
| 679 | $-C_7H_{15}$ | $-C_7H_{15}$ | $-C_2H_5$ | $-\overset{O}{\overset{\parallel}{C}}CCl_3$ | 1.4960 |
| 680 | $-C_7H_{15}$ | $-C_7H_{15}$ | $-C_2H_5$ | $-\overset{O}{\overset{\parallel}{C}}CF_3$ | 1.4533 |
| 681 | $-C_7H_{15}$ | $-C_7H_{15}$ | $-C_2H_5$ | $-\overset{O}{\overset{\parallel}{C}}C_9H_{19}$ | 1.4727 |
| 682 | $-C_7H_{15}$ | $-C_7H_{15}$ | $-C_2H_5$ | $-\overset{O}{\overset{\parallel}{C}}C_{10}H_{21}$ | 1.4732 |
| 683 | $-C_7H_{15}$ | $-C_7H_{15}$ | $-C_2H_5$ | $-\overset{O}{\overset{\parallel}{C}}C_5H_{11}$ | 1.4748 |
| 684 | $-C_7H_{15}$ | $-C_7H_{15}$ | $-C_2H_5$ | $-\overset{O}{\overset{\parallel}{C}}C_6H_{13}$ | 1.4724 |
| 685 | $-C_7H_{15}$ | $-C_7H_{15}$ | $-C_2H_5$ | $-\overset{O}{\overset{\parallel}{C}}C_7H_{15}$ | 1.4730 |

TABLE I-continued
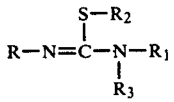
| Compound No. | R | $R_1$ | $R_2$ | $R_3$ | $n_D^{30}$ or °C. |
|---|---|---|---|---|---|
| 686 | $-C_7H_{15}$ | $-C_7H_{15}$ | $-C_2H_5$ | 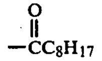 | 1.4730 |
| 687 | $-C_7H_{15}$ | $-C_7H_{15}$ | $-C_2H_5$ | 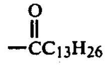 | Slush |
| 688 | $-C_7H_{15}$ | $-C_7H_{15}$ | $-C_2H_5$ | 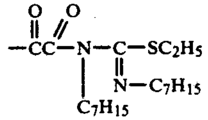 | 1.4932 |
| 689 | $-C_7H_{15}$ | $-C_7H_{15}$ | $-C_2H_5$ | 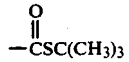 | 1.4872 |
| 690 | $-C_7H_{15}$ | $-C_7H_{15}$ | $-C_2H_5$ | 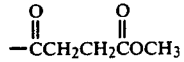 | 1.4776 |
| 691 | $-tC_8H_{17}$ | $-C_8H_{17}$ | $-C_2H_5$ | 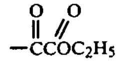 | 1.4809 |
| 692 | $-C_8H_{17}$ | $-C_5H_{11}$ | $-C_2H_5$ | 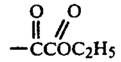 | 1.4765 |
| 693 | $-C_6H_{13}$ | $-C_6H_{13}$ | $-C_2H_5$ | 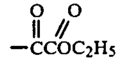 | 1.4771 |
| 694 | $-secC_7H_{15}$ | $-C_7H_{15}$ | $-C_2H_5$ | 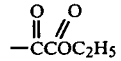 | 1.4757 |
| 695 | $-secC_7H_{15}$ | $-C_6H_{13}$ | $-C_2H_5$ | 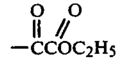 | 1.4766 |
| 696 | $-secC_7H_{15}$ | $-C_8H_{17}$ | $-C_2H_5$ | 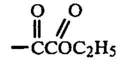 | 1.4760 |
| 697 | $-tC_8H_{17}$ | $-C_7H_{15}$ | $-C_2H_5$ | 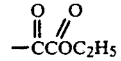 | 1.4817 |
| 698 | $-tC_8H_{17}$ | $-C_4H_9$ | $-C_2H_5$ | 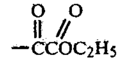 | 1.4835 |
| 699 | $-tC_8H_{17}$ | $-C_6H_{13}$ | $-C_2H_5$ | 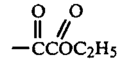 | 1.4821 |

TABLE I-continued
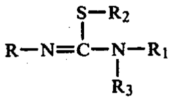
| Compound No. | R | R1 | R2 | R3 | $n_D^{30}$ or °C. |
|---|---|---|---|---|---|
| 700 | $-secC_8H_{17}$ | $-secC_7H_{15}$ | $-C_2H_5$ | 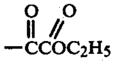 | 1.4752 |
| 701 | $-tC_4H_9$ | $-secC_7H_{15}$ | $-C_2H_5$ | 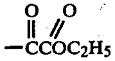 | 1.4789 |
| 702 | $-secC_7H_{15}$ | $-secC_7H_{15}$ | $-C_1H_3$ | 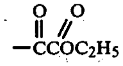 | 1.4770 |
| 703 | $-secC_7H_{15}$ | $-secC_7H_{15}$ | $-C_2H_5$ | 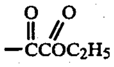 | 1.4745 |
| 704 | $-tC_8H_{17}$ | $-C_8H_{17}$ | $-C_1H_3$ | 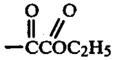 | 1.4809 |
| 705 | $-secC_7H_{15}$ | $-C_7H_{15}$ | $-C_3H_7$ | 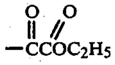 | 1.4748 |
| 706 | —2-ethyl-hexyl | —2-ethyl-hexyl | $-C_2H_5$ | 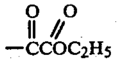 | 1.4782 |
| 707 | $-C_7H_{15}$ | $-C_7H_{15}$ | $-C_2H_5$ | 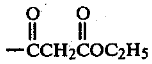 | 1.4822 |
| 708 | $-secC_7H_{15}$ | $-C_7H_{15}$ | $-C_3H_7$ | 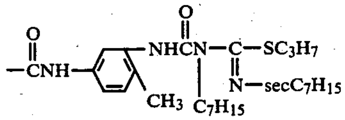 | 1.5166 |
| 709 | —2-ethyl-hexyl | $-C_7H_{15}$ | $-C_2H_5$ | 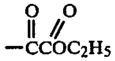 | 1.4784 |
| 710 | $-tC_8H_{17}$ | —2-ethyl-hexyl | $-C_2H_5$ | 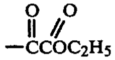 | 1.4837 |
| 711 | $-tC_8H_{17}$ | —2-ethyl-hexyl | $-C_3H_7$ | 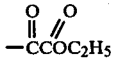 | 1.4818 |
| 712 | $-secC_7H_{15}$ | $-C_7H_{15}$ | $-C_4H_9$ | 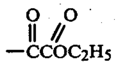 | 1.4748 |

TABLE I-continued
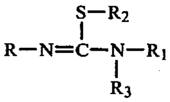
| Compound No. | R | $R_1$ | $R_2$ | $R_3$ | $n_D^{30}$ or °C. |
|---|---|---|---|---|---|
| 713 | $-secC_7H_{15}$ | $-C_7H_{15}$ | $-C_4H_9$ | 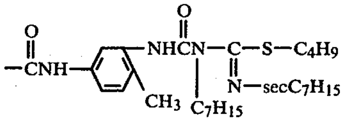 | 1.5152 |
| 714 | $-tC_8H_{17}$ | $-C_8H_{17}$ | $-C_3H_7$ | 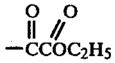 | 1.4808 |
| 715 | $-secC_7H_{15}$ | $-C_8H_{17}$ | $-CH_2SCH_3$ | 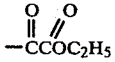 | 1.4960 |
| 716 | $-C_2H_5$ | $-C_2H_5$ | $-C_2H_5$ | 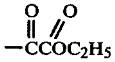 | 1.4883 |
| 717 | —2-ethyl-hexyl | $-C_6H_{13}$ | $-C_2H_5$ | 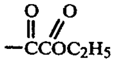 | 1.4788 |
| 718 | $-secC_7H_{15}$ | $-C_8H_{17}$ | $-C_2H_5$ | 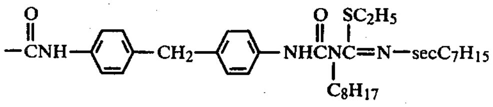 | 1.5305 |
| 719 | $-secC_7H_{15}$ | $-C_7H_{15}$ | $-C_3H_7$ | 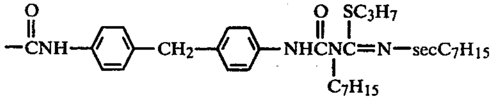 | 1.5307 |
| 720 | $-secC_7H_{15}$ | —2-ethyl-hexyl | $-C_2H_5$ | 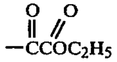 | 1.4776 |
| 721 | $-secC_7H_{15}$ | —2-ethyl-hexyl | $-C_3H_7$ | 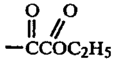 | 1.4785 |
| 722 | —2-ethyl-hexyl | $-C_6H_{13}$ | $-CH_2SCH_3$ | 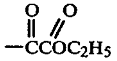 | 1.4983 |
| 723 | 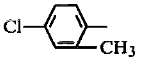 | $-C_7H_{15}$ | $-C_2H_5$ | 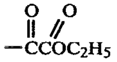 | 1.5295 |
| 724 | $-C_7H_{15}$ | $-C_{17}H_{15}$ | $-C_2H_5$ | 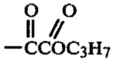 | 1.4766 |

TABLE I-continued
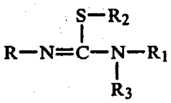
| Compound No. | R | R1 | R2 | R3 | $n_D^{30}$ or °C. |
|---|---|---|---|---|---|
| 725 | $-C_7H_{15}$ | $-C_7H_{15}$ | $-C_2H_5$ | 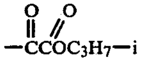 | 1.4738 |
| 726 | $-secC_7H_{15}$ | $-CH_8H_{17}$ | $-CH_2CH_2$ | 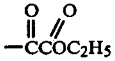 | 1.4814 |
| 727 | $-C_7H_{15}$ | $-C_7H_{15}$ | $-C_2H_5$ | 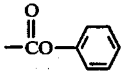 | 1.5008 |
| 728 | $-C_7H_{15}$ | $-C_7H_{15}$ | $-C_2H_5$ | 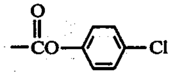 | Slurry |
| 729 | $-secC_7H_{15}$ | $-C_8H_{17}$ | $-C_1H_3$ | 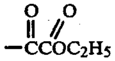 | 1.4752 |
| 730 | 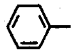 | $-C_7H_{15}$ | $-C_2H_5$ | 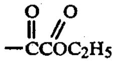 | 1.5255 |
| 731 | $-secC_7H_{15}$ | $-C_8H_{17}$ | $-C_3H_7$ | 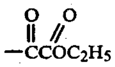 | 1.4757 |
| 732 | 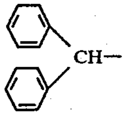 | $-C_7H_{15}$ | $-C_2H_5$ | 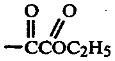 | 1.5398 |
| 733 | $-C_7H_{15}$ | $-(CH_2)_3OCH_3$ | $-C_2H_5$ | 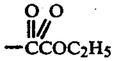 | 1.4803 |
| 734 | $-secC_7H_{15}$ | $-C_{12}H_{25}$ | $-C_2H_5$ | 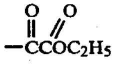 | 1.4739 |
| 735 | $-C_5H_{11}S(CH_2)_2$ | $-C_8H_{17}$ | $-C_2H_5$ | 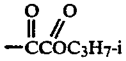 | 1.4898 |
| 736 | $-C_7H_{15}$ | $-(CH_2)_3OCH_3$ | $-C_5H_{11}$ | 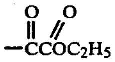 | 1.4772 |
| 737 | $-secC_7H_{15}$ | —2-ethyl-hexyl | $-iC_4H_9$ | 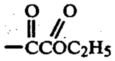 | 1.4794 |

TABLE I-continued

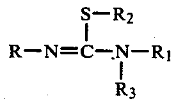

| Compound No. | R | $R_1$ | $R_2$ | $R_3$ | $n_D^{30}$ or °C. |
|---|---|---|---|---|---|
| 738 | $-C_7H_{15}$ | $-CH_2CH{=}CH_2$ | $-C_2H_5$ | $-\overset{O}{\overset{\|}{C}}\overset{O}{\overset{/\!/}{C}}OC_2H_5$ | 1.4857 |
| 739 | $-CH_3O(CH_2)_2O(CH_2)_3$ | $-C_7H_{15}$ | $-C_2H_5$ | $-\overset{O}{\overset{\|}{C}}\overset{O}{\overset{/\!/}{C}}OC_2H_5$ | 1.4777 |
| 740 | —2-ethyl-hexyl-$O(CH_2)_3$ | $-C_3H_7$ | $-C_2H_5$ | $-\overset{O}{\overset{\|}{C}}\overset{O}{\overset{/\!/}{C}}OCH(CH_3)_2$ | 1.4723 |
| 741 | $-C_8H_{17}$ | $-\overset{O}{\overset{\|}{C}}\overset{O}{\overset{/\!/}{C}}OC_2H_5$ | $-C_2H_5$ | $-\overset{O}{\overset{\|}{C}}\overset{O}{\overset{/\!/}{C}}OC_2H_5$ | 1.4792 |
| 742 | $-secC_7H_{15}$ | —2-ethyl-hexyl | $-iC_3H_7$ | $-\overset{O}{\overset{\|}{C}}\overset{O}{\overset{/\!/}{C}}OC_2H_5$ | 1.4764 |
| 743 | $-secC_7H_{15}$ | —2-ethyl-hexyl | $-C_7H_{15}$ | $-\overset{O}{\overset{\|}{C}}\overset{O}{\overset{/\!/}{C}}OC_2H_5$ | 1.4721 |
| 744 | $-CH_3O(CH_2)_2O(CH_2)_3$ | $-C_7H_{15}$ | $-C_5H_{11}$ | $-\overset{O}{\overset{\|}{C}}\overset{O}{\overset{/\!/}{C}}OC_2H_5$ | 1.4757 |
| 745 | 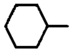 | —2-ethyl-hexyl | $-C_2H_5$ | $-\overset{O}{\overset{\|}{C}}\overset{O}{\overset{/\!/}{C}}OC_2H_5$ | 1.4915 |
| 746 | 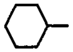 | $-C_7H_{15}$ | $-C_2H_5$ | $-\overset{O}{\overset{\|}{C}}\overset{O}{\overset{/\!/}{C}}OC_2H_5$ | 1.4943 |
| 747 | $-secC_7H_{15}$ | $-C_9H_{19}$ | $-C_2H_5$ | $-\overset{O}{\overset{\|}{C}}\overset{O}{\overset{/\!/}{C}}OC_2H_5$ | 1.4750 |
| 748 | $-secC_7H_{15}$ | 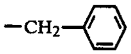 | $-C_2H_5$ | $-\overset{O}{\overset{\|}{C}}\overset{O}{\overset{/\!/}{C}}OC_2H_5$ | 1.5105 |
| 749 | 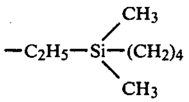 | $-C_7H_{15}$ | $-C_2H_5$ | $-\overset{O}{\overset{\|}{C}}\overset{O}{\overset{\|}{C}}OC_3H_7-i$ | 1.4740 |
| 750 | $-C_8H_{17}$ | 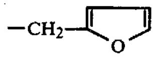 | $-C_2H_5$ | $-\overset{O}{\overset{\|}{C}}\overset{O}{\overset{\|}{C}}OC_3H_7-i$ | 1.4936 |
| 751 | $-C_7H_{15}$ | $-C_7H_{15}$ | $-C_2H_5$ | $-\overset{O}{\overset{\|}{C}}SCH_3$ | 1.4948 |

TABLE I-continued
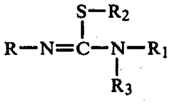
| Compound No. | R | $R_1$ | $R_2$ | $R_3$ | $n_D^{30}$ or °C. |
|---|---|---|---|---|---|
| 752 | $-C_7H_{15}$ | $-C_7H_{15}$ | $-C_2H_5$ | 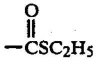 | 1.4922 |
| 753 | $-C_7H_{15}$ | $-C_7H_{15}$ | $-C_2H_5$ | 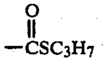 | 1.4916 |
| 754 | $-C_7H_{15}$ | $-C_7H_{15}$ | $-C_2H_5$ | 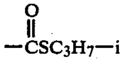 | 1.4894 |
| 755 | $-C_7H_{15}$ | $-C_7H_{15}$ | $-C_2H_5$ | 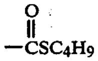 | 1.4898 |
| 756 | $-C_7H_{15}$ | $-C_7H_{15}$ | $-C_2H_5$ | 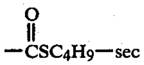 | 1.4892 |
| 757 | $-C_7H_{15}$ | $-C_7H_{15}$ | $-C_2H_5$ | 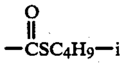 | 1.4879 |
| 758 | $-C_7H_{15}$ | $-C_7H_{15}$ | $-C_2H_5$ | 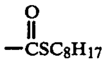 | 1.4860 |
| 759 | $-C_7H_{15}$ | $-C_7H_{15}$ | $-C_2H_5$ | 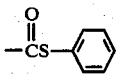 | 1.5287 |
| 760 | $-C_7H_{15}$ | $-C_7H_{15}$ | $-C_2H_5$ | 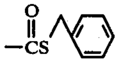 | 1.5250 |
| 761 | $-C_7H_{15}$ | $-C_7H_{15}$ | $-C_2H_5$ | 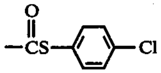 | 1.5366 |
| 762 | —2-ethyl-hexyl | —2-ethyl-hexyl | $-CH_2CH{=}CH_2$ | 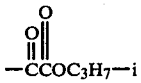 | 1.4800 |
| 763 | —2-ethyl-hexyl | —2-ethyl-hexyl | $-C_3H_7$ | 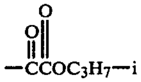 | 1.4749 |
| 764 | $-secC_7H_{15}$ | $-C_8H_{17}$ | 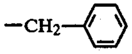 | 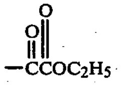 | 1.5052 |

TABLE I-continued

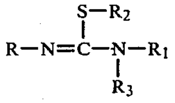

| Compound No. | R | $R_1$ | $R_2$ | $R_3$ | $n_D^{30}$ or °C. |
|---|---|---|---|---|---|
| 765 | 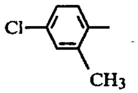 | $-secC_7H_{15}$ | $-C_2H_5$ | $-\overset{O}{\overset{\|}{C}}\overset{O}{\overset{\|}{C}}OC_2H_5$ | 1.5298 |
| 766 | $-C_7H_{15}$ | $-(CH_2)_3N(C_2H_5)_2$ | $-C_2H_5$ | $-\overset{O}{\overset{\|}{C}}\overset{O}{\overset{\|}{C}}OC_3H_7-i$ | 1.4786 |
| 767 | $-secC_7H_{15}$ | 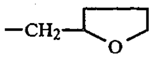 | $-C_2H_5$ | $-\overset{O}{\overset{\|}{C}}\overset{O}{\overset{\|}{C}}OC_2H_5$ | 1.4909 |
| 768 | $-secC_7H_{15}$ | $-C_8H_{17}$ | 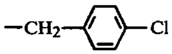 | $-\overset{O}{\overset{\|}{C}}\overset{O}{\overset{\|}{C}}OC_2H_5$ | 1.5114 |
| 769 | 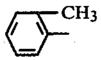 | 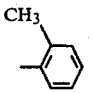 | $-C_2H_5$ | $-\overset{O}{\overset{\|}{C}}\overset{O}{\overset{\|}{C}}OC_2H_5$ | 1.5632 |
| 770 | 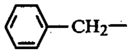 | 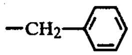 | $-C_2H_5$ | $-\overset{O}{\overset{\|}{C}}\overset{O}{\overset{\|}{C}}OC_3H_7-i$ | 1.5526 |
| 771 | 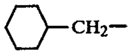 | $-C_7H_{15}$ | $-C_2H_5$ | $-\overset{O}{\overset{\|}{C}}\overset{O}{\overset{\|}{C}}OC_3H_7-i$ | 1.4882 |
| 772 | $-secC_{17}H_{15}$ | $-C_6H_{13}$ | $-C_2H_5$ | $-\overset{O}{\overset{\|}{C}}\overset{O}{\overset{\|}{C}}OCH_3$ | 1.4784 |
| 773 | $-secC_7H_{15}$ | $-C_6H_{13}$ | $-C_2H_5$ | $-\overset{O}{\overset{\|}{C}}\overset{O}{\overset{\|}{C}}OC_3H_7-i$ | 1.4730 |
| 774 | $-secC_7H_{15}$ | $-C_8H_{17}$ | $-C_2H_5$ | $-\overset{O}{\overset{\|}{C}}NHC_8H_{17}$ | 1.4756 |
| 775 | $-secC_7H_{15}$ | $-C_8H_{17}$ | $-C_2H_5$ | $-\overset{O}{\overset{\|}{C}}NH-sec-C_7H_{15}$ | 1.4766 |

TABLE I-continued
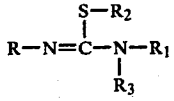
| Compound No. | R | $R_1$ | $R_2$ | $R_3$ | $n_D^{30}$ or °C. |
|---|---|---|---|---|---|
| 776 | $-secC_7H_{15}$ | $-C_8H_{17}$ | $-C_2H_5$ | 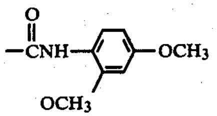 | 1.5215 |
| 777 | $-secC_7H_{15}$ | $-C_8H_{17}$ | $-C_2H_5$ | 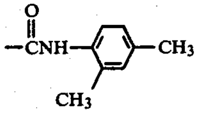 | 1.5145 |
| 778 | $-secC_7H_{15}$ | $-C_8H_{17}$ | $-C_2H_5$ | 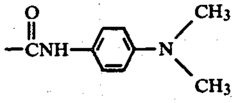 | 1.5219 |
| 779 | —3,5,5-trimethylhexyl | —3,5,5-trimethylhexyl | $-C_3H_7$ | 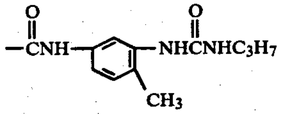 | 1.5125 |
| 780 | —3,5,5-trimethylhexyl | —3,5,5-trimethylhexyl | $-C_3H_7$ | 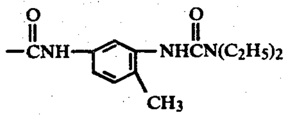 | 1.5152 |
| 781 | —3,5,5-trimethylhexyl | —3,5,5-trimethylhexyl | $-C_3H_7$ | 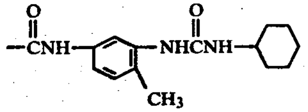 | 1.511 |
| 782 | —3,5,5-trimethylhexyl | —3,5,5-trimethylhexyl | $-C_3H_7$ | 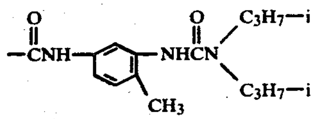 | 1.510 |
| 783 | —3,5,5-trimethylhexyl | —3,5,5-trimethylhexyl | $-C_3H_7$ | 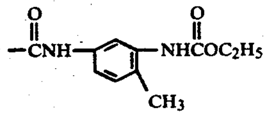 | 1.5165 |

TABLE I-continued
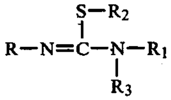
| Compound No. | R | $R_1$ | $R_2$ | $R_3$ | $n_D^{30}$ or °C. |
|---|---|---|---|---|---|
| 784 | —3,5,5-trimethylhexyl | —3,5,5-trimethylhexyl | $-C_3H_7$ | 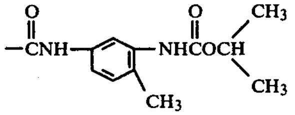 | 1.5147 |
| 785 | —3,5,5-trimethylhexyl | —3,5,5-trimethylhexyl | $-C_3H_7$ | 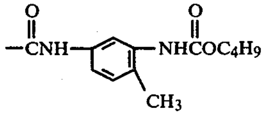 | 1.5124 |
| 786 | —3,5,5-trimethylhexyl | —3,5,5-trimethylhexyl | $-C_3H_7$ | 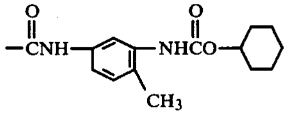 | 1.5160 |
| 787 | —3,5,5-trimethylhexyl | —3,5,5-trimethylhexyl | $-C_3H_7$ | 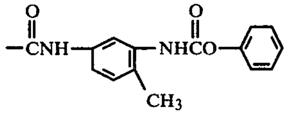 | 1.5250 |
| 788 | —2-ethyl hexyl | —2-ethyl hexyl | Allyl | 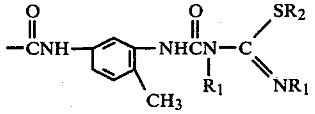 | 1.5253 |
| 789 | —sec$C_7H_{15}$ | —2-ethyl hexyl | $-iC_3H_7$ | 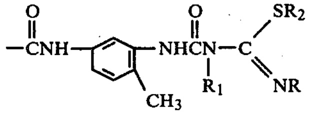 | 1.5114 |
| 790 | —sec$C_7H_{15}$ | $-C_8H_{17}$ | $-C_2H_5$ | $-SCCl_3$ | 1.5001 |
| 791 | —sec$C_7H_{15}$ | $-C_8H_{17}$ | $-C_2H_5$ | 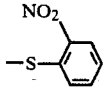 | Waxy solid |
| 792 | —sec$C_7H_{15}$ | $-C_8H_{17}$ | $-C_1H_3$ | 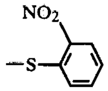 | 39-45° C. |

TABLE I-continued
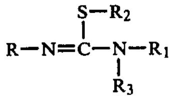
| Compound No. | R | $R_1$ | $R_2$ | $R_3$ | $n_D^{30}$ or °C. |
|---|---|---|---|---|---|
| 793 | $-secC_7H_{15}$ | $-C_8H_{17}$ | Allyl | 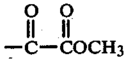 | 1.4837 |
| 794 | $-secC_7H_{15}$ | $-C_8H_{17}$ | Allyl | 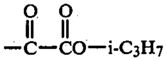 | 1.4784 |
| 795 | $-secC_7H_{15}$ | $-C_8H_{17}$ | $-C_3H_7$ | 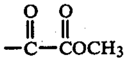 | 1.4765 |
| 796 | $-secC_7H_{15}$ | $-C_8H_{17}$ | $-C_3H_7$ | 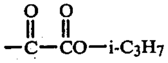 | 1.4720 |
| 797 | 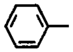 | 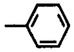 | Allyl | 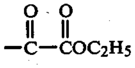 | 1.5777 |
| 798 | $-C_7H_{15}$ | $-C_7H_{15}$ | $-C_2H_5$ | 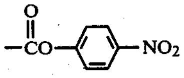 | 1.5608 |
| 799 | $-secC_7H_{15}$ | $-C_8H_{17}$ | $-C_1H_3$ | 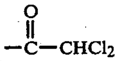 | 1.4919 |
| 800 | $-secC_7H_{15}$ | $-C_8H_{17}$ | Allyl | 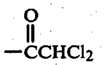 | 1.4960 |
| 801 | $-secC_7H_{15}$ | $-C_8H_{17}$ | $-C_1H_3$ | 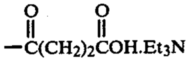 | 1.4855 |
| 802 | $-secC_7H_{15}$ | $-C_8H_{17}$ | Allyl | 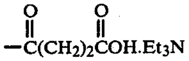 | 1.4907 |
| 803 | $-secC_7H_{15}$ | $-C_8H_{17}$ | $-C_2H_5$ | 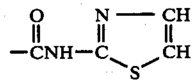 | 1.5218 |
| 804 | $-secC_7H_{15}$ | $-C_8H_{17}$ | $-C_2H_5$ | 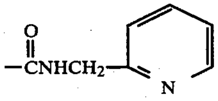 | 1.4985 |

TABLE I-continued

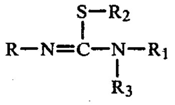

| Compound No. | R | $R_1$ | $R_2$ | $R_3$ | $n_D^{30}$ or °C. |
|---|---|---|---|---|---|
| 805 | $-secC_7H_{15}$ | $-C_8H_{17}$ | $-C_2H_5$ | 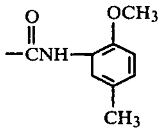 | 1.4652 |
| 806 | —2-ethyl hexyl | —2-ethyl hexyl | $-C_2H_5$ | $-\overset{O}{\overset{\|}{C}}NH(CH_2)_6OH$ | 1.4882 |
| 807 | $-secC_7H_{15}$ | $-C_8H_{17}$ | $-C_2H_5$ | $-\overset{O}{\overset{\|}{C}}NHCH_3$ | 1.4817 |
| 808 | $-secC_7H_{15}$ | $-C_8H_{17}$ | $-C_2H_5$ | $-\overset{O}{\overset{\|}{C}}NHC_2H_5$ | 1.4784 |
| 809 | $-secC_7H_{15}$ | $-C_8H_{17}$ | $-C_2H_5$ | $-\overset{O}{\overset{\|}{C}}NHC_4H_9$ | 1.4768 |
| 810 | $-secC_7H_{17}$ | $-C_8H_{17}$ | $-C_2H_5$ | $-\overset{O}{\overset{\|}{C}}NHC_6H_{13}$ | 1.4745 |
| 811 | $CH_3\overset{CH_3}{\overset{\|}{C}}HCH_2CH_2\overset{CH_3}{\overset{\|}{C}}H-$ | $-C_8H_{17}$ | $-C_2H_5$ | $-\overset{O}{\overset{\|}{C}}NHC_{18}H_{37}$ | 1.4740 |
| 812 | $-C_7H_{15}$ | $-C_7H_{15}$ | $-C_2H_5$ | $-\overset{O}{\overset{\|}{C}}NHC_{14}H_{29}$ | 1.4750 |
| 813 | $-C_7H_{15}$ | $-C_7H_{15}$ | $-C_2H_5$ | 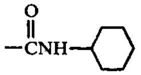 | 1.4005 |
| 814 | $[(CH_3)_2CHCH_2]_2-$ | $-C_6H_{13}$ | $-C_2H_5$ | $-\overset{O}{\overset{\|}{C}}NHC_{18}H_{37}$ | 1.4740 |
| 815 | —3-methyl hexyl | $-C_8H_{17}$ | $-C_2H_5$ | $-\overset{O}{\overset{\|}{C}}NHC_{18}H_{37}$ | 1.4760 |
| 816 | $-secC_7H_{15}$ | $-C_8H_{17}$ | $-C_2H_5$ | $-\overset{O}{\overset{\|}{C}}NHC_{11}H_{23}$ | 1.4750 |
| 817 | $-secC_7H_{15}$ | $-C_8H_{17}$ | $-C_2H_5$ | 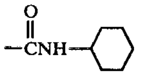 | 1.4873 |

TABLE I-continued
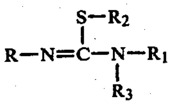
| Compound No. | R | $R_1$ | $R_2$ | $R_3$ | $n_D^{30}$ or °C. |
|---|---|---|---|---|---|
| 818 | $-secC_7H_{15}$ | $-C_8H_{17}$ | $-C_2H_5$ | 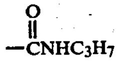 | 1.4780 |
| 819 | $-secC_7H_{15}$ | $-C_8H_{17}$ | $-C_2H_5$ | 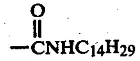 | 1.4730 |
| 820 | 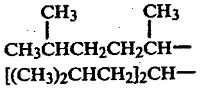 | $-C_8H_{17}$ | $-C_2H_5$ | 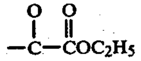 | 1.4745 |
| 821 | $[(CH_3)_2CHCH_2]_2CH-$ | $-C_6H_{13}$ | $-C_2H_5$ | 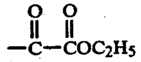 | 1.4740 |
| 822 | —3-methyl hexyl | $-C_8H_{17}$ | $-C_2H_5$ | 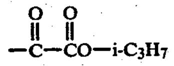 | 1.4736 |
| 823 | $-C_8H_{17}$ | $-C_6H_{13}$ | $-C_3H_7$ | 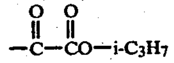 | 1.4735 |
| 824 | $-C_7H_{15}$ | $-C_7H_{15}$ | $-C_2H_5$ | 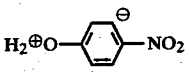 | 1.5612 |
| 825 | $-C_8H_{17}$ | $-C_6H_{13}$ | $-C_3H_7$ | $-SCCl_3$ | 1.5048 |
| 826 | $-C_8H_{17}$ | $-C_6H_{13}$ | $-C_3H_7$ | 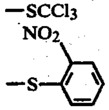 | 1.5367 |
| 827 | $-C_8H_{17}$ | $-C_6H_{13}$ | $-C_3H_7$ | 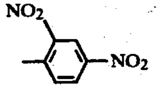 | 1.5375 |
| 828 | $-secC_7H_{15}$ | $-C_8H_{17}$ | $-C_2H_5$ | 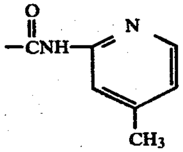 | 1.5194 |
| 829 | $-secC_7H_{15}$ | $-C_8H_{17}$ | $-C_2H_5$ | 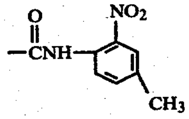 | 1.5310 |

TABLE I-continued

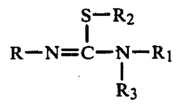

| Compound No. | R | $R_1$ | $R_2$ | $R_3$ | $n_D^{30}$ or °C. |
|---|---|---|---|---|---|
| 830 | $-secC_7H_{15}$ | $-C_8H_{17}$ | $-C_2H_5$ | 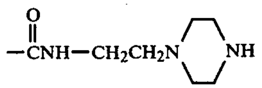 | 1.4982 |
| 831 | $-secC_7H_{15}$ | $-C_8H_{17}$ | $-C_2H_5$ | $-\overset{O}{\overset{\|}{C}}NH-t\text{-}C_4H_9$ | 1.4742 |
| 832 | $-secC_7H_{15}$ | $-C_8H_{17}$ | $-C_2H_5$ | $-\overset{O}{\overset{\|}{C}}NH(CH_2)_8CH=CH_2$ | 1.4796 |
| 833 | $-secC_7H_{15}$ | $-C_8H_{17}$ | $-C_2H_5$ | $-\overset{O}{\overset{\|}{C}}NH-i\text{-}C_3H_7$ | 1.4747 |
| 834 | $-secC_7H_{15}$ | $-C_8H_{17}$ | $-C_2H_5$ | $-\overset{O}{\overset{\|}{C}}NHCH_2CH_2Cl$ | 1.3265 |
| 835 | —2-ethyl hexyl | —2-ethyl hexyl | Allyl | $-\overset{O}{\overset{\|}{C}}NHC_{14}H_{29}$ | 1.4800 |
| 836 | —2-ethyl hexyl | —2-ethyl hexyl | $-C_3H_7$ | $-\overset{O}{\overset{\|}{C}}NHC_{14}H_{29}$ | 1.4755 |
| 837 | $CH_3(CH_2)_3\underset{}{CH}(C_2H_5)-$ | $-C_8H_{17}$ | $-C_2H_5$ | $\overset{O}{\overset{\|}{C}}NHC_{18}H_{37}$ | 1.4750 |
| 838 | $-C_8H_{17}$ | $-C_6H_{13}$ | Allyl | 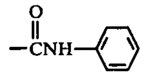 | 1.5239 |
| 839 | $-C_8H_{17}$ | $-C_6H_{13}$ | Allyl | $-\overset{O}{\overset{\|}{C}}NHC_{18}H_{37}$ | 1.4806 |
| 840 | $-C_8H_{17}$ | $-C_6H_{13}$ | Allyl | 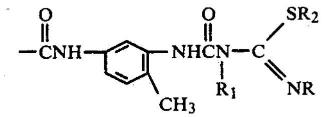 | 1.5257 |
| 841 | $-C_8H_{17}$ | $-C_6H_{13}$ | $-C_3H_7$ | 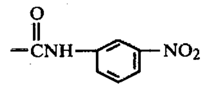 | 1.5318 |
| 842 | $-C_7H_{15}$ | $-C_7H_{15}$ | $-C_2H_5$ | $-\overset{O}{\overset{\|}{C}}OC(CH_3)_2CCl_3$ | 1.4822 |

TABLE I-continued
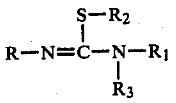
| Compound No. | R | $R_1$ | $R_2$ | $R_3$ | $n_D^{30}$ or °C. |
|---|---|---|---|---|---|
| 843 | $-C_8H_{17}$ | $-C_6H_{13}$ | Allyl | 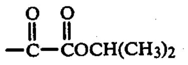 | 1.4796 |
| 844 | $-secC_7H_{15}$ | $-C_8H_{17}$ | $-C_2H_5$ | 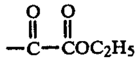 | 1.4775 |
| 845 | $(CH_3)_2CH$ / $(CH_3)_2CHCH-$ | $-C_8H_{17}$ | $-C_2H_5$ | 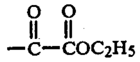 | 1.4818 |
| 846 | $-C_8H_{17}$ | $-secC_7H_{15}$ | $-C_2H_5$ | 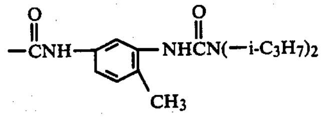 | 1.5245 |
| 847 | $-secC_7H_{15}$ | $-C_8H_{17}$ | $-C_2H_5$ | 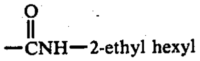 | 1.4764 |
| 848 | $-secC_7H_{15}$ | $-C_8H_{17}$ | $-C_2H_5$ | 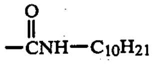 | 1.4772 |
| 849 | $-secC_7H_{15}$ | $-C_8H_{15}$ | $-C_2H_5$ | 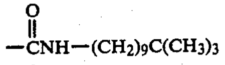 | 1.4791 |
| 850 | $-secC_7H_{15}$ | $-C_8H_{17}$ | $-C_2H_5$ | 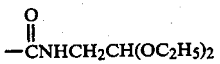 | 1.4769 |
| 851 | —2-ethyl hexyl | $-C_7H_{15}$ | $-C_2H_5$ | 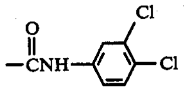 | 1.5325 |
| 852 | $CH(CH_3)_2$ / $(CH_3)_2CHCH-$ | $-C_8H_{17}$ | $-C_2H_5$ | 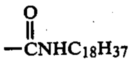 | 1.4785 |
| 853 | $(CH_3CH_2CH_2)_2CH-$ | $-C_8H_{17}$ | $-C_2H_5$ | 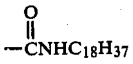 | 1.4755 |
| 854 | $-C_7H_{15}$ | $-C_7H_{15}$ | 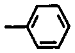 | 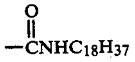 | 1.5021 |
| 855 | $-secC_7H_{15}$ | $-C_8H_{17}$ | $-C_2H_5$ | 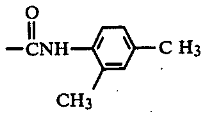 | 1.5145 |

TABLE I-continued
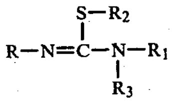
| Compound No. | R | $R_1$ | $R_2$ | $R_3$ | $n_D^{30}$ or °C. |
|---|---|---|---|---|---|
| 856 | $-secC_7H_{15}$ | $-C_8H_{17}$ | $-C_2H_5$ | 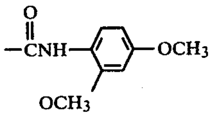 | 1.5215 |
| 857 | $-secC_7H_{15}$ | $-C_8H_{17}$ | $-C_2H_5$ | 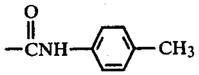 | 1.5171 |
| 858 | $(n-C_3H_7)_2CH-$ | $-C_8H_{17}$ | $-C_2H_5$ | 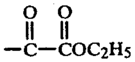 | 1.4775 |
| 859 | $-secC_7H_{15}$ | $-C_8H_{17}$ | $-C_2H_5$ | 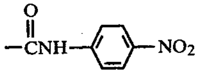 | 1.5400 |
| 860 | $-secC_7H_{15}$ | $-C_8H_{17}$ | $-C_2H_5$ | 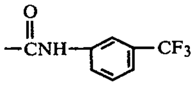 | 1.4945 |
| 861 | $-secC_7H_{15}$ | $-C_8H_{17}$ | $-C_2H_5$ | 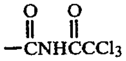 | 1.5076 |
| 862 | $(CH_3CH_2CH_2)_2CH-$ | $-C_8H_{17}$ | $-C_2H_5$ | 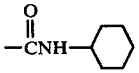 | 1.4895 |
| 863 | $(CH_3CH_2CH_2)_2CH-$ | $-C_8H_{17}$ | $-C_2H_5$ | 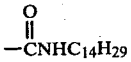 | 1.4755 |
| 864 | $-secC_7H_{15}$ | $-C_8H_{17}$ | $-C_2H_5$ | 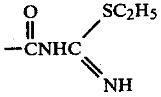 | 1.5119 |
| 865 | $-secC_7H_{15}$ | $-C_8H_{17}$ | $-C_2H_5$ | 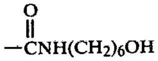 | 1.4848 |
| 866 | $-secC_7H_{15}$ | $-C_8H_{17}$ | $-C_2H_5$ | 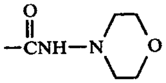 | 1.4851 |

TABLE I-continued
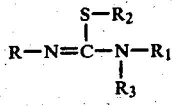
| Compound No. | R | $R_1$ | $R_2$ | $R_3$ | $n_D^{30}$ or °C. |
|---|---|---|---|---|---|
| 867 | $-secC_7H_{15}$ | $-C_8H_{17}$ | $-C_2H_5$ | 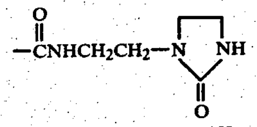 | 1.4974 |
| 868 | $-secC_7H_{15}$ | $-C_8H_{17}$ | $-C_2H_5$ | 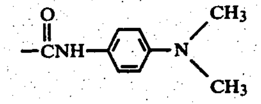 | 1.5219 |
| 869 | $-secC_7H_{15}$ | $-C_8H_{17}$ | $-C_2H_5$ | 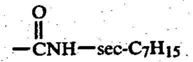 | 1.4766 |
| 870 | $-secC_7H_{15}$ | $-C_8H_{17}$ | $-C_2H_5$ | 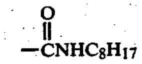 | 1.4756 |
| 871 | $-secC_7H_{15}$ | $-secC_7H_{15}$ | $-C_2H_5$ | 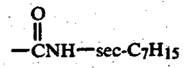 | 1.4765 |
| 872 | —3-methyl hexyl | $-C_8H_{17}$ | $-C_2H_5$ | 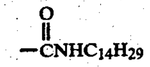 | 1.4747 |
| 873 | 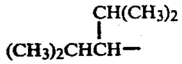 | $-C_8H_{17}$ | $-C_2H_5$ | 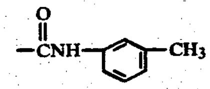 | 1.5230 |
| 874 | 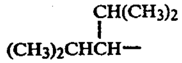 | $-C_8H_{17}$ | $-C_2H_5$ | 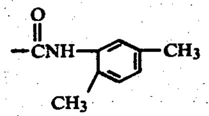 | 1.5165 |
| 875 | $-secC_7H_{15}$ | $-C_8H_{17}$ | $-C_2H_5$ | 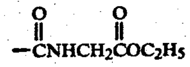 | 1.4782 |
| 876 | $-secC_7H_{15}$ | $-C_8H_{17}$ | $-C_2H_5$ | 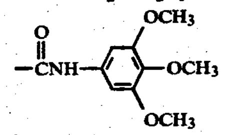 | 1.5194 |
| 877 | $-secC_7H_{15}$ | $-C_8H_{17}$ | $-C_1H_3$ | 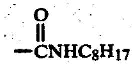 | 1.4775 |

TABLE I-continued
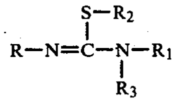
| Compound No. | R | $R_1$ | $R_2$ | $R_3$ | $n_D^{30}$ or °C. |
|---|---|---|---|---|---|
| 878 | $-secC_7H_{15}$ | $-C_8H_{17}$ | $-C_1H_3$ | 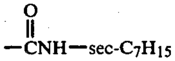 | 1.4765 |
| 879 | $-C_8H_{17}$ | $-C_8H_{17}$ | $-C_2H_5$ | 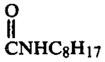 | 1.4776 |
| 880 | $-secC_7H_{15}$ | $-C_8H_{17}$ | $-C_2H_5$ | 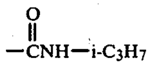 | 1.4766 |
| 881 | $-secC_7H_{15}$ | $-C_8H_{17}$ | $-C_2H_5$ | 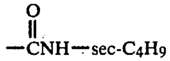 | 1.4745 |
| 882 | $-secC_7H_{15}$ | $-C_8H_{17}$ | $-C_2H_5$ | 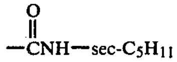 | 1.4733 |
| 883 | $-secC_7H_{15}$ | $-C_8H_{17}$ | $-C_2H_5$ | 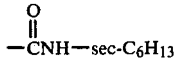 | 1.4732 |
| 884 | $-secC_7H_{15}$ | $-C_8H_{17}$ | $-C_2H_5$ | 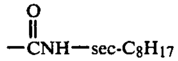 | 1.4725 |
| 885 | $-secC_7H_{15}$ | $-C_8H_{17}$ | $-C_2H_5$ | 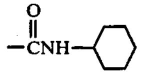 | 1.4883 |
| 886 | $-secC_7H_{15}$ | $-C_8H_{17}$ | $-C_2H_5$ | 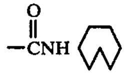 | 1.4892 |
| 887 | $-secC_7H_{15}$ | $-C_8H_{17}$ | $-C_2H_5$ | 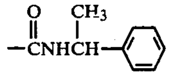 | 1.5030 |
| 888 | $-secC_7H_{15}$ | $-C_8H_{17}$ | $-C_2H_5$ | 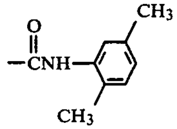 | 1.5136 |
| 889 | $-secC_7H_{15}$ | $-C_8H_{17}$ | $-C_2H_5$ | 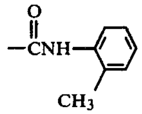 | 1.5200 |

TABLE I-continued
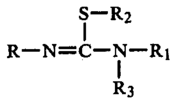
| Compound No. | R | R₁ | R₂ | R₃ | $n_D^{30}$ or °C. |
|---|---|---|---|---|---|
| 890 | $-secC_7H_{15}$ | $-C_8H_{17}$ | $-C_2H_5$ | 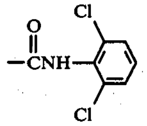 | 1.5195 |
| 891 | $-secC_7H_{15}$ | $-C_8H_{17}$ | $-C_2H_5$ | 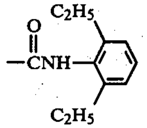 | 1.5053 |
| 892 | $-secC_7H_{15}$ | $-C_8H_{17}$ | $-C_2H_5$ | 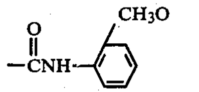 | 1.5217 |
| 893 | 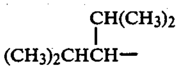 | $-C_1H_3$ | $-C_2H_5$ | 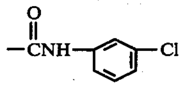 | 1.5550 |
| 894 | 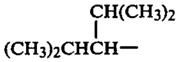 | $-C_1H_3$ | $-C_2H_5$ | 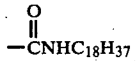 | 29-32° C. |
| 895 | 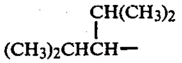 | $-C_1H_3$ | $-C_2H_5$ | 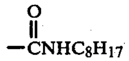 | 1.4856 |
| 896 | $-secC_7H_{15}$ | $-C_8H_{17}$ | $-C_2H_5$ | 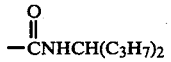 | 1.4725 |
| 897 | $-secC_7H_{15}$ | $-C_8H_{17}$ | $-C_2H_5$ | 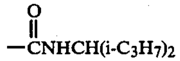 | 1.4761 |
| 898 | $-secC_7H_{15}$ | $-C_8H_{17}$ | $-C_2H_5$ | 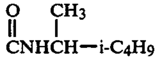 | 1.4716 |
| 899 | $-secC_7H_{15}$ | $-C_8H_{17}$ | $-C_2H_5$ | 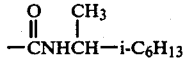 | 1.4714 |
| 900 | $-secC_7H_{15}$ | $-C_8H_{17}$ | $-C_2H_5$ | 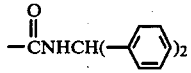 | 1.5220 |
| 901 | $-secC_7H_{15}$ | $-C_8H_{17}$ | $-C_2H_5$ | 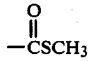 | 1.4930 |

TABLE I-continued
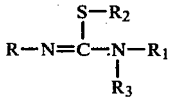
| Compound No. | R | $R_1$ | $R_2$ | $R_3$ | $n_D^{30}$ or °C. |
|---|---|---|---|---|---|
| 902 | $-C_7H_{15}$ | $-C_7H_{15}$ | $-C_2H_5$ | 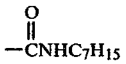 | 1.4817 |
| 903 | 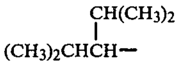 | $-C_8H_{17}$ | $-C_2H_5$ | 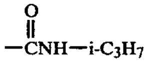 | 1.5805 |
| 904 | 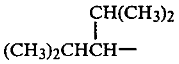 | $-C_8H_{17}$ | $-C_2H_5$ | 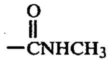 | 1.4864 |
| 905 | $-secC_7H_{15}$ | $-C_8H_{17}$ | $-C_2H_5$ | 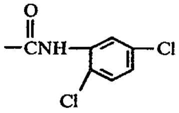 | 1.5255 |
| 906 | $-secC_7H_{15}$ | $-C_8H_{17}$ | $-C_2H_5$ | 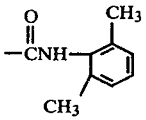 | 1.5069 |
| 907 | $-secC_7H_{15}$ | $-C_8H_{17}$ | $-C_2H_5$ | 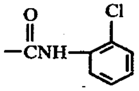 | 1.5232 |
| 908 | $-secC_7H_{15}$ | $-C_8H_{17}$ | $-C_2H_5$ | 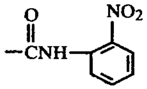 | 1.5332 |
| 909 | $-secC_7H_{15}$ | $-C_8H_{17}$ | Allyl | 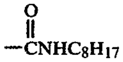 | 1.4801 |
| 910 | $-C_8H_{17}$ | $-C_8H_{17}$ | $-C_2H_5$ | 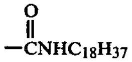 | 1.4762 |
| 911 | $-C_8H_{17}$ | $-C_8H_{17}$ | $-C_2H_5$ | 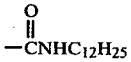 | 1.4772 |
| 912 | $secC_7H_{15}$ | $-C_8H_{17}$ | $-C_2H_5$ | 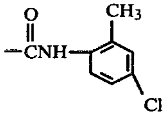 | 1.5230 |

TABLE I-continued
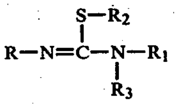
| Compound No. | R | $R_1$ | $R_2$ | $R_3$ | $n_D^{30}$ or °C. |
|---|---|---|---|---|---|
| 913 | $-secC_7H_{15}$ | $-C_8H_{17}$ | $-C_2H_5$ | 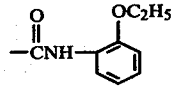 | 1.5152 |
| 914 | $-secC_7H_{15}$ | $-C_8H_{17}$ | Allyl | 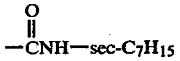 | 1.4774 |
| 915 | $-secC_7H_{15}$ | $-C_8H_{17}$ | Allyl | 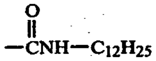 | 1.4792 |
| 916 | $-secC_7H_{15}$ | $-C_8H_{17}$ | $-C_2H_5$ | 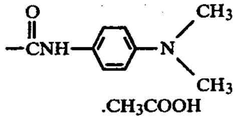 | 1.5074 |
| 917 | $-secC_7H_{15}$ | $-C_8H_{17}$ | Allyl | 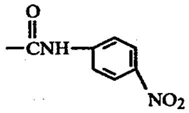 | 1.5471 |
| 918 | $-secC_7H_{15}$ | $-C_8H_{17}$ | $-C_2H_5$ | 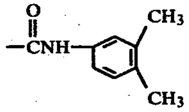 | 1.5191 |
| 919 | $-secC_7H_{15}$ | $-C_8H_{17}$ | $-C_2H_5$ | 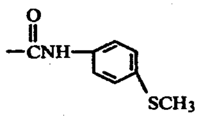 | 1.5400 |
| 920 | 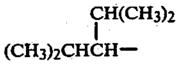 | $-C_2H_5$ | $-C_2H_5$ | 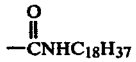 | 1.4795 |
| 921 | $-C_7H_{15}$ | $-C_7H_{15}$ | $-C_2H_5$ | 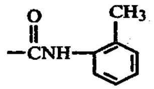 | 1.5180 |

TABLE I-continued
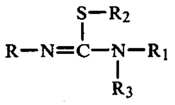
| Compound No. | R | $R_1$ | $R_2$ | $R_3$ | $n_D^{30}$ or °C. |
|---|---|---|---|---|---|
| 922 | $-C_7H_{15}$ | $-C_7H_{15}$ | $-C_2H_5$ | 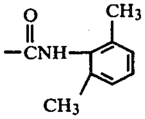 | 1.5065 |
| 923 | $-C_7H_{15}$ | $-C_7H_{15}$ | $-C_2H_5$ | 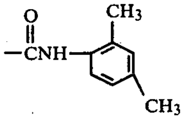 | 1.5180 |
| 924 | $-C_7H_{15}$ | $-C_7H_{15}$ | $-C_2H_5$ | 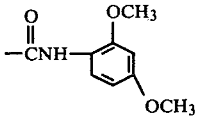 | 1.5230 |
| 925 | $-C_7H_{15}$ | $-C_7H_{15}$ | $-C_2H_5$ | 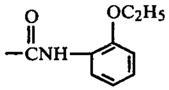 | 1.5195 |
| 926 | $-C_7H_{15}$ | $-C_7H_{15}$ | $-C_2H_5$ | 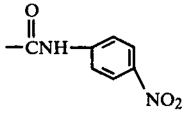 | 1.5495 |
| 927 | $-C_7H_{15}$ | $-C_7H_{15}$ | $-C_2H_5$ | 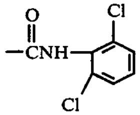 | 1.5245 |
| 928 | $-C_7H_{15}$ | $-C_7H_{15}$ | $-C_2H_5$ | 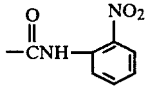 | 1.5360 |
| 929 | —2-ethyl hexyl | —2-ethyl hexyl | $-C_3H_7$ | 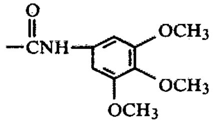 | 1.5181 |

TABLE I-continued
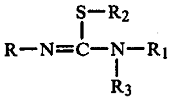
| Compound No. | R | $R_1$ | $R_2$ | $R_3$ | $n_D^{30}$ or °C. |
|---|---|---|---|---|---|
| 930 | $-C_7H_{15}$ | $-C_7H_{15}$ | $-C_2H_5$ | 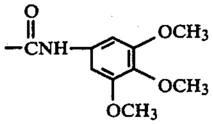 | 1.5222 |
| 931 | $-secC_7H_{15}$ | $-C_8H_{17}$ | $-C_2H_5$ | 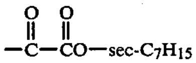 | 1.4724 |
| 932 | —2-ethyl hexyl | —2-ethyl hexyl | $-C_2H_5$ | 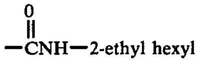 | 1.4765 |
| 933 | $-C_7H_{15}$ | $-C_7H_{15}$ | $-C_2H_5$ | 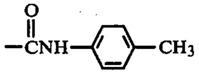 | 1.5180 |
| 934 | $-C_7H_{15}$ | $-C_7H_{15}$ | $-C_2H_5$ | 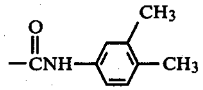 | 1.5247 |
| 935 | —2-ethyl hexyl | —2-ethyl hexyl | $-C_1H_3$ | 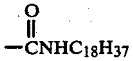 | 1.4775 |
| 936 | —2-ethyl hexyl | —2-ethyl hexyl | $-C_1H_3$ | 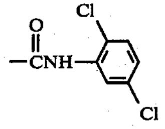 | 1.5317 |
| 937 | —2-ethyl hexyl | —2-ethyl hexyl | $-C_1H_3$ | 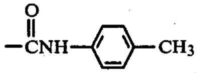 | 1.5210 |
| 938 | —2-ethyl hexyl | —2-ethyl hexyl | $-C_2H_5$ | 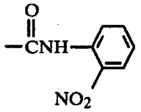 | 1.5332 |
| 939 | —2-ethyl hexyl | —2-ethyl hexyl | $-C_2H_5$ | 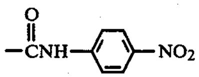 | 1.5440 |

TABLE I-continued
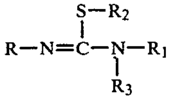
| Compound No. | R | R1 | R2 | R3 | $n_D^{30}$ or °C. |
|---|---|---|---|---|---|
| 940 | —2-ethyl hexyl | —2-ethyl hexyl | $-C_2H_5$ | 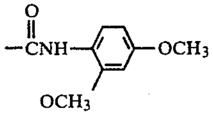 | 1.5210 |
| 941 | —2-ethyl hexyl | —2-ethyl hexyl | $-C_2H_5$ | 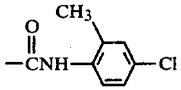 | 1.5220 |
| 942 | —2-ethyl hexyl | —2-ethyl hexyl | $-C_2H_5$ | 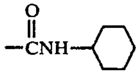 | 1.4890 |
| 943 | —2-ethyl hexyl | —2-ethyl hexyl | $-C_2H_5$ | 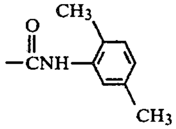 | 1.5165 |
| 944 | —2-ethyl hexyl | —2-ethyl hexyl | $-C_2H_5$ | 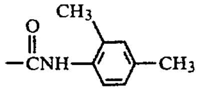 | 1.5150 |
| 945 | —2-ethyl hexyl | —2-ethyl hexyl | $-C_2H_5$ | 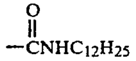 | 1.4770 |
| 946 | $-secC_7H_{15}$ | $-C_8H_{17}$ | $-C_2H_5$ | 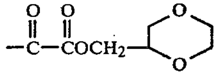 | (Spectroscopic data IR & NMR) |
| 947 | $-secC_7H_{15}$ | $-C_8H_{17}$ | $-C_1H_3$ | 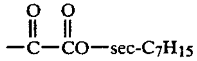 | 1.4726 |
| 948 | —2-ethyl hexyl | —2-ethyl hexyl | $-C_2H_5$ | 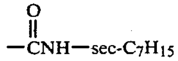 | 1.4730 |
| 949 | —2-ethyl hexyl | —2-ethyl hexyl | $-C_2H_5$ | 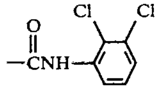 | 1.5300 |
| 950 | $-secC_7H_{15}$ | $-C_8H_{17}$ | $-C_2H_5$ | 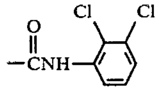 | 1.5282 |

TABLE I-continued
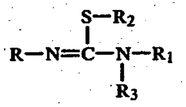
| Compound No. | R | $R_1$ | $R_2$ | $R_3$ | $n_D^{30}$ or °C. |
|---|---|---|---|---|---|
| 951 | $-C_7H_{15}$ | $-C_7H_{15}$ | $-C_2H_5$ | 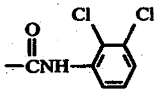 | 1.5312 |
| 952 | —2-ethyl hexyl | —2-ethyl hexyl | $-C_2H_5$ | 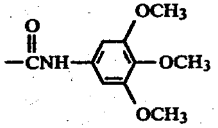 | 1.5210 |
| 953 | —2-ethyl hexyl | —2-ethyl hexyl | $-C_1H_3$ | 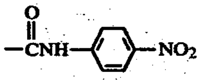 | 1.5473 |
| 954 | —2-ethyl hexyl | —2-ethyl hexyl | $-C_1H_3$ | 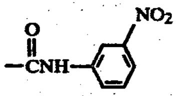 | 1.5326 |
| 955 | —2-ethyl hexyl | —2-ethyl hexyl | $-C_2H_5$ | 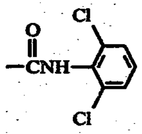 | 1.5234 |
| 956 | $-secC_7H_{15}$ | $-C_8H_{17}$ | $-C_1H_3$ | 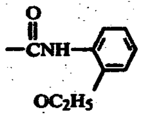 | 1.5180 |
| 957 | —2-ethyl hexyl | —2-ethyl hexyl | $-C_1H_3$ | 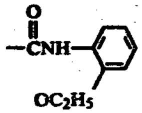 | 1.5172 |
| 958 | $-C_8H_{17}$ | $-C_8H_{17}$ | $-C_2H_5$ | 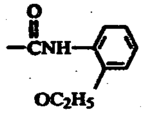 | 1.5122 |
| 959 | $(CH_3CH_2CH_2)_2CH-$ | $-C_4H_9$ | $-C_2H_5$ | 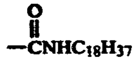 | 1.4756 |

TABLE I-continued
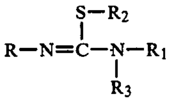
| Compound No. | R | $R_1$ | $R_2$ | $R_3$ | $n_D^{30}$ or °C. |
|---|---|---|---|---|---|
| 960 | 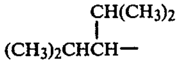 | $-C_8H_{17}$ | $-C_2H_5$ | 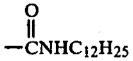 | 1.4789 |
| 961 | —2-ethyl hexyl | —2-ethyl hexyl | $-C_2H_5$ | 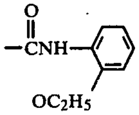 | 1.5135 |
| 962 | $-secC_7H_{15}$ | $-C_8H_{17}$ | Allyl | 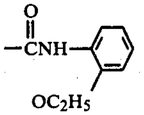 | 1.5176 |
| 963 | $-secC_7H_{15}$ | $-C_8H_{17}$ | $-C_3H_7$ | 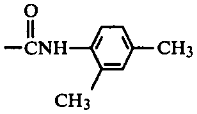 | 1.5130 |
| 964 | $-secC_7H_{15}$ | $-C_8H_{17}$ | $-C_3H_7$ | 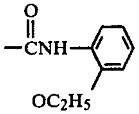 | 1.5138 |
| 965 | —2-ethyl hexyl | —2-ethyl hexyl | $-C_2H_5$ | 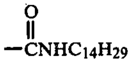 | 1.4765 |
| 966 | $-secC_7H_{15}$ | $-C_8H_{17}$ | $-C_2H_5$ | 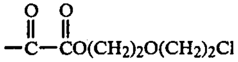 | 1.4840 |
| 967 | $-secC_7H_{15}$ | $-C_6H_{13}$ | $-C_2H_5$ | 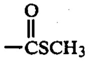 | 1.4962 |
| 968 | $-secC_7H_{15}$ | $-C_8H_{17}$ | $-C_1H_3$ | 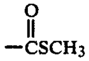 | 1.4955 |
| 969 | $-secC_7H_{15}$ | $-C_7H_{15}$ | $-C_3H_7$ | 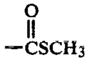 | 1.4920 |
| 970 | $-secC_7H_{15}$ | $-C_7H_{15}$ | $-C_4H_9$ | 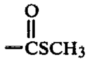 | 1.4909 |

TABLE I-continued

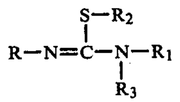

| Compound No. | R | $R_1$ | $R_2$ | $R_3$ | $n_D^{30}$ or °C. |
|---|---|---|---|---|---|
| 971 | $-C_8H_{17}$ | $-C_5H_{11}$ | $-C_2H_5$ | $-\overset{O}{\overset{\|}{C}}SCH_3$ | 1.4970 |
| 972 | —2-ethyl hexyl | —2-ethyl hexyl | $-C_2H_5$ | $-\overset{O}{\overset{\|}{C}}SCH_3$ | 1.4953 |
| 973 | $-secC_7H_{15}$ | —2-ethyl hexyl | $-C_3H_7$ | $-\overset{O}{\overset{\|}{C}}SCH_3$ | 1.4929 |
| 974 | —2-ethyl hexyl | —2-ethyl hexyl | $-C_1H_3$ | $-\overset{O}{\overset{\|}{C}}SCH_3$ | 1.4983 |
| 975 | $-secC_7H_{15}$ | $-C_8H_{17}$ | $-C_2H_5$ | $-\overset{O}{\overset{\|}{C}}NHCH_2CH=CH_2$ | 1.4890 |
| 976 | $-secC_7H_{15}$ | $-C_8H_{17}$ | $-C_3H_7$ | $-\overset{O}{\overset{\|}{C}}NHC_{14}H_{29}$ | 1.4726 |
| 977 | $-secC_7H_{15}$ | $-C_8H_{17}$ | $-C_3H_7$ | $-\overset{O}{\overset{\|}{C}}NHC_3H_7$ | 1.4735 |
| 978 | —2-ethyl hexyl | —2-ethyl hexyl | $-C_2H_5$ | 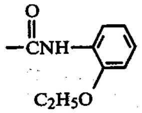 | 1.5165 |
| 979 | $-secC_7H_{15}$ | $-C_8H_{17}$ | $-C_1H_3$ | 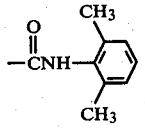 | 1.5080 |
| 980 | $-C_8H_{17}$ | $-C_8H_{17}$ | $-C_2H_5$ | 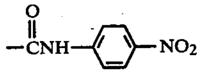 | 1.5414 |
| 981 | $-C_8H_{17}$ | $-C_8H_{17}$ | $-C_2H_5$ | 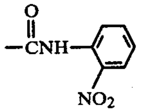 | 1.5333 |
| 982 | $-C_8H_{17}$ | $-C_8H_{17}$ | $-C_2H_5$ | 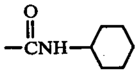 | 1.4880 |

TABLE I-continued
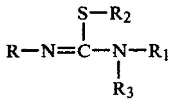
| Compound No. | R | $R_1$ | $R_2$ | $R_3$ | $n_D^{30}$ or °C. |
|---|---|---|---|---|---|
| 983 | $-C_8H_{17}$ | $-C_8H_{17}$ | $-C_2H_5$ | 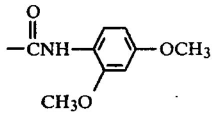 | 1.5182 |
| 984 | $-C_8H_{17}$ | $-C_8H_{17}$ | $-C_2H_5$ | $-\overset{\overset{O}{\|}}{C}NHCH(CH_3)_2$ | 1.4743 |
| 985 | $-C_8H_{17}$ | $-C_8H_{17}$ | $-C_2H_5$ | 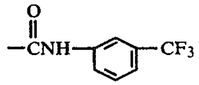 | 1.4948 |
| 986 | $-C_8H_{17}$ | $-C_8H_{17}$ | $-C_2H_5$ | 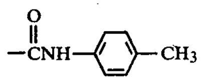 | 1.5157 |
| 987 | —2-ethyl hexyl | —2-ethyl hexyl | $-C_1H_3$ | 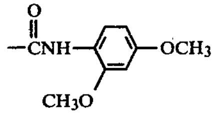 | 1.5211 |
| 988 | —2-ethyl hexyl | —2-ethyl hexyl | $-C_2H_5$ | $-\overset{\overset{O}{\|}}{C}NHCH(CH_3)_2$ | 1.4762 |
| 989 | $-secC_7H_{15}$ | —2-ethyl hexyl | $-C_3H_7$ | 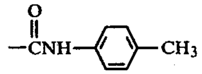 | 1.5145 |
| 990 | $-secC_7H_{15}$ | —2-ethyl hexyl | $-C_3H_7$ | 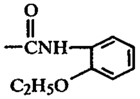 | 1.5110 |
| 991 | $-secC_7H_{15}$ | —2-ethyl hexyl | $-C_3H_7$ | 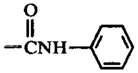 | 1.5118 |
| 992 | $-secC_7H_{15}$ | —2-ethyl hexyl | $-C_3H_7$ | 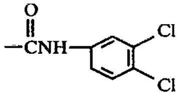 | 1.5287 |

TABLE I-continued
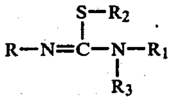
| Compound No. | R | $R_1$ | $R_2$ | $R_3$ | $n_D^{30}$ or °C. |
|---|---|---|---|---|---|
| 993 | $-secC_7H_{15}$ | —2-ethyl hexyl | $-C_3H_7$ | 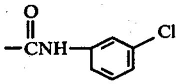 | 1.5199 |
| 994 | $-C_7H_{15}$ | $-C_7H_{15}$ | $-C_3H_7$ | 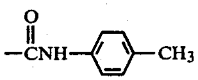 | 1.5177 |
| 995 | $-C_7H_{15}$ | $-C_7H_{15}$ | $-C_3H_7$ | 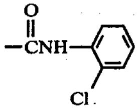 | 1.5205 |
| 996 | $-C_7H_{15}$ | $-C_7H_{15}$ | $-C_3H_7$ | 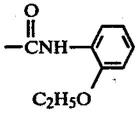 | 1.5145 |
| 997 | $-C_7H_{15}$ | $-C_7H_{15}$ | $-C_3H_7$ | 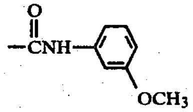 | 1.5194 |
| 998 | $-C_7H_{15}$ | $-C_7H_{15}$ | $-C_3H_7$ | 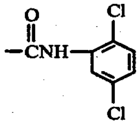 | 1.5281 |
| 999 | $-C_7H_{15}$ | $-C_7H_{15}$ | $-C_3H_7$ | 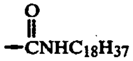 | 1.4729 |
| 1000 | $-C_7H_{15}$ | $-C_7H_{15}$ | $-C_3H_7$ | 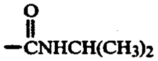 | 1.4756 |
| 1001 | $-C_7H_{15}$ | $-C_7H_{15}$ | $-C_3H_7$ | 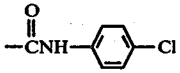 | 1.5241 |
| 1002 | $-C_7H_{15}$ | $-C_7H_{15}$ | $-C_3H_7$ | 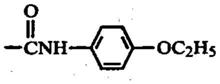 | 1.5164 |

TABLE I-continued
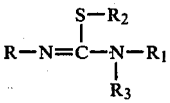
| Compound No. | R | $R_1$ | $R_2$ | $R_3$ | $n_D^{30}$ or °C. |
|---|---|---|---|---|---|
| 1003 | $-C_7H_{15}$ | $-C_7H_{15}$ | Allyl | 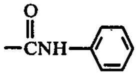 | 1.5229 |
| 1004 | $-C_7H_{15}$ | $-C_7H_{15}$ | Allyl | 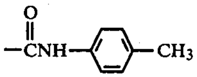 | 1.5241 |
| 1005 | $-C_7H_{15}$ | $-C_7H_{15}$ | Allyl | 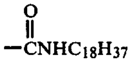 | 1.4772 |
| 1006 | $-C_7H_{15}$ | $-C_7H_{15}$ | Allyl | 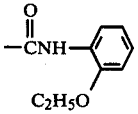 | 1.5142 |
| 1007 | $-C_7H_{15}$ | $-C_7H_{15}$ | Allyl | 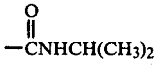 | 1.4816 |
| 1008 | $-C_7H_{15}$ | $-C_7H_{15}$ | Allyl | 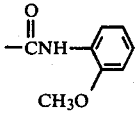 | 1.5249 |
| 1009 | $-C_7H_{15}$ | $-C_7H_{15}$ | Allyl | 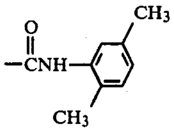 | 1.5196 |
| 1010 | $-C_7H_{15}$ | $-C_7H_{15}$ | Allyl | 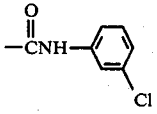 | 1.5300 |
| 1011 | $-secC_7H_{15}$ | $-C_6H_{13}$ | $-C_2H_5$ | 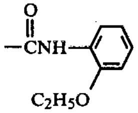 | 1.5182 |

TABLE I-continued
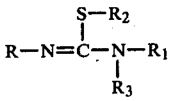
| Compound No. | R | $R_1$ | $R_2$ | $R_3$ | $n_D^{30}$ or °C. |
|---|---|---|---|---|---|
| 1012 | $-C_7H_{15}$ | $-C_7H_{15}$ | Allyl | 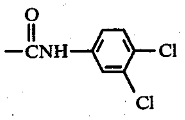 | 1.5365 |
| 1013 | $-secC_7H_{15}$ | $-secC_7H_{15}$ | $-C_2H_5$ | 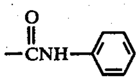 | 1.5150 |
| 1014 | $-secC_7H_{15}$ | $-secC_7H_{15}$ | $-C_2H_5$ | 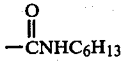 | 1.4776 |
| 1015 | $-secC_7H_{15}$ | $-secC_7H_{15}$ | $-C_2H_5$ | 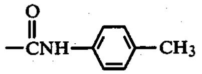 | 1.5154 |
| 1016 | $-secC_7H_{15}$ | $-secC_7H_{15}$ | $-C_2H_5$ | 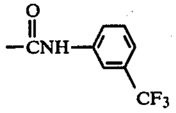 | 1.4936 |
| 1017 | $-secC_7H_{15}$ | $-C_7H_{15}$ | $-C_3H_7$ | 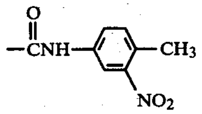 | 1.5255 |
| 1018 | $-secC_7H_{15}$ | $-C_7H_{15}$ | $-C_3H_7$ | 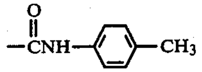 | 1.5132 |
| 1019 | $-secC_7H_{15}$ | $-C_7H_{15}$ | $-C_3H_7$ | 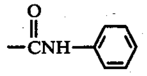 | 1.5140 |
| 1020 | $-secC_7H_{15}$ | $-C_7H_{15}$ | $-C_3H_7$ | 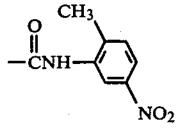 | 1.5280 |
| 1021 | $-secC_7H_{15}$ | $-C_7H_{15}$ | $-C_3H_7$ | 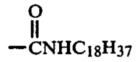 | 1.4718 |

TABLE I-continued
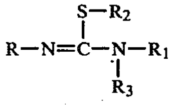
| Compound No. | R | $R_1$ | $R_2$ | $R_3$ | $n_D^{30}$ or °C. |
|---|---|---|---|---|---|
| 1022 | $-secC_7H_{15}$ | $-C_7H_{15}$ | $-C_3H_7$ | 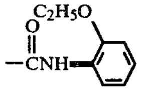 | 1.5032 |
| 1023 | $-secC_7H_{15}$ | $-C_7H_{15}$ | $-C_3H_7$ | 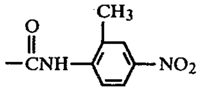 | 1.5390 |
| 1024 | $-secC_7H_{15}$ | $-C_7H_{15}$ | $-C_3H_7$ | 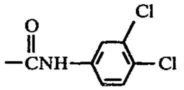 | 1.5291 |
| 1025 | $-secC_7H_{15}$ | $-C_7H_{15}$ | $-C_3H_7$ | 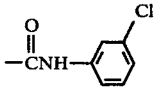 | 1.5188 |
| 1026 | $-secC_7H_{15}$ | $-C_7H_{15}$ | $-C_3H_7$ | 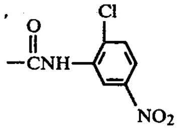 | 1.5303 |
| 1027 | $-secC_7H_{15}$ | $-C_7H_{15}$ | $-C_3H_7$ | 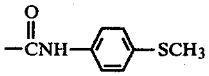 | 1.5352 |
| 1028 | $-secC_7H_{15}$ | $-C_7H_{15}$ | $-C_3H_7$ | 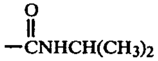 | 1.4344 |
| 1029 | $-secC_7H_{15}$ | $-C_7H_{15}$ | $-C_3H_7$ | 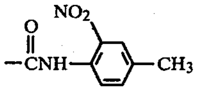 | 1.5278 |
| 1030 | $-secC_7H_{15}$ | $-C_8H_{17}$ | $-C_1H_3$ | 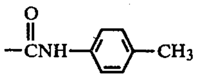 | 1.5175 |
| 1031 | $-secC_7H_{15}$ | $-C_8H_{17}$ | $-C_1H_3$ | 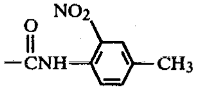 | 1.5322 |
| 1032 | $-secC_7H_{15}$ | $-C_8H_{17}$ | $-C_1H_3$ | 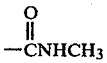 | 1.4846 |

TABLE I-continued
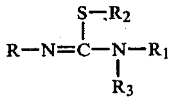
| Compound No. | R | $R_1$ | $R_2$ | $R_3$ | $n_D^{30}$ or °C. |
|---|---|---|---|---|---|
| 1033 | $-secC_7H_{15}$ | $-C_8H_{17}$ | $-C_1H_3$ | 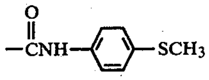 | 1.5388 |
| 1034 | $-secC_7H_{15}$ | $-C_8H_{17}$ | $-C_1H_3$ | 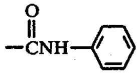 | 1.5160 |
| 1035 | $-secC_7H_{15}$ | $-C_8H_{17}$ | $-C_1H_3$ | 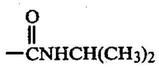 | 1.4723 |
| 1036 | $-secC_7H_{15}$ | $-C_8H_{17}$ | $-C_1H_3$ | 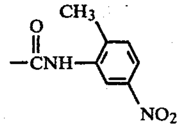 | 1.5319 |
| 1037 | $-secC_7H_{15}$ | $-C_8H_{17}$ | $-C_1H_3$ | 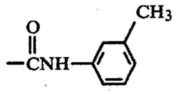 | 1.4956 |
| 1038 | $-secC_7H_{15}$ | $-C_8H_{17}$ | $-C_1H_3$ | 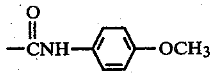 | 1.5185 |
| 1039 | $-secC_7H_{15}$ | $-C_8H_{17}$ | $-C_1H_3$ | 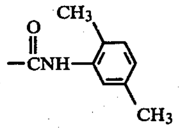 | 1.5152 |
| 1040 | $-secC_7H_{15}$ | $-C_8H_{17}$ | $-C_1H_3$ | 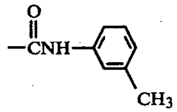 | 1.5162 |
| 1041 | $-secC_7H_{15}$ | $-C_8H_{17}$ | $-C_1H_3$ | 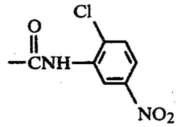 | 1.5356 |

TABLE I-continued
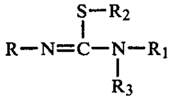
| Compound No. | R | $R_1$ | $R_2$ | $R_3$ | $n_D^{30}$ or °C. |
|---|---|---|---|---|---|
| 1042 | $-secC_7H_{15}$ | $-C_8H_{17}$ | $-C_1H_3$ | 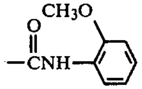 | 1.5216 |
| 1043 | $-secC_7H_{15}$ | $-C_8H_{17}$ | $-C_1H_3$ | 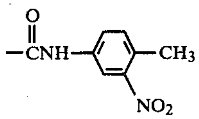 | 1.5286 |
| 1044 | $-secC_7H_{15}$ | $-C_8H_{17}$ | $-C_1H_3$ | 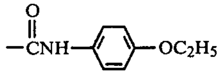 | 1.5187 |
| 1045 | $-secC_7H_{15}$ | $-C_8H_{17}$ | $-C_1H_3$ | 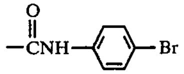 | 1.5316 |
| 1046 | $-secC_7H_{15}$ | $-C_8H_{17}$ | $-C_1H_3$ | 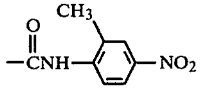 | 1.5432 |
| 1047 | $-secC_7H_{15}$ | $-C_8H_{17}$ | $-C_1H_3$ | 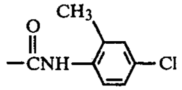 | 1.5229 |
| 1048 | $-secC_7H_{15}$ | $-C_8H_{17}$ | $-C_1H_3$ | 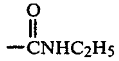 | 1.4804 |
| 1049 | $-secC_7H_{15}$ | $-C_8H_{17}$ | $-C_1H_3$ | 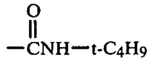 | 1.4709 |
| 1050 | $-secC_7H_{15}$ | $-C_8H_{17}$ | $-C_1H_3$ | 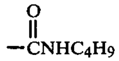 | 1.4790 |
| 1051 | $-secC_7H_{15}$ | $-C_8H_{17}$ | $-C_1H_3$ | 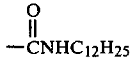 | 1.4754 |
| 1052 | $-secC_7H_{15}$ | $-C_8H_{17}$ | $-C_1H_3$ | 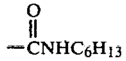 | 1.4775 |
| 1053 | $-secC_7H_{15}$ | $-C_8H_{17}$ | $-C_1H_3$ | 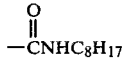 | 1.4742 |

TABLE I-continued

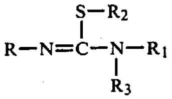

| Compound No. | R | $R_1$ | $R_2$ | $R_3$ | $n_D^{30}$ or °C. |
|---|---|---|---|---|---|
| 1054 | $-secC_7H_{15}$ | $-C_8H_{17}$ | $-C_1H_3$ | 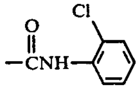 | 1.5245 |
| 1055 | $-secC_7H_{15}$ | $-secC_6H_{13}$ | $-C_5H_{11}$ | $-\overset{O}{\overset{\|}{C}}NHCH_3$ | 1.4805 |
| 1056 | $-secC_7H_{15}$ | $-secC_6H_{13}$ | $-C_5H_{11}$ | $-\overset{O}{\overset{\|}{C}}NHCH(CH_3)_2$ | 1.4734 |
| 1057 | $-secC_7H_{15}$ | $-secC_7H_{15}$ | $-C_2H_5$ | $-\overset{O}{\overset{\|}{C}}SCH_3$ | 1.4910 |
| 1058 | $-secC_7H_{15}$ | —2-ethyl hexyl | $-i-C_3H_7$ | $-\overset{O}{\overset{\|}{C}}SCH_3$ | 1.4885 |
| 1059 | —3-methyl hexyl | $-C_8H_{17}$ | $-C_2H_5$ | $-\overset{O}{\overset{\|}{C}}SCH_3$ | 1.4954 |
| 1060 | 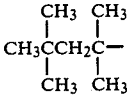 | $-C_8H_{17}$ | $-C_1H_3$ | $-\overset{O}{\overset{\|}{C}}SCH_3$ | 1.4985 |
| 1061 | 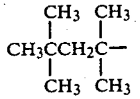 | $-C_8H_{17}$ | $-C_3H_7$ | $-\overset{O}{\overset{\|}{C}}SCH_3$ | 1.4985 |
| 1062 | $(n-C_3H_7)_2CH-$ | $-C_8H_{17}$ | $-C_2H_5$ | $-\overset{O}{\overset{\|}{C}}SCH_3$ | 1.4936 |
| 1063 | 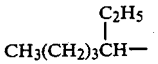 | $-C_8H_{17}$ | $-C_2H_5$ | $-\overset{O}{\overset{\|}{C}}SCH_3$ | 1.4960 |
| 1064 | 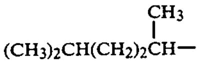 | $-C_8H_{17}$ | $-C_2H_5$ | $-\overset{O}{\overset{\|}{C}}SCH_3$ | 1.4926 |
| 1065 | 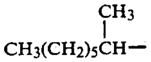 | $-C_8H_{17}$ | $-C_3H_7$ | $-\overset{O}{\overset{\|}{C}}SCH_3$ | 1.4902 |
| 1066 | 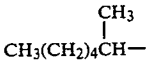 | $-C_8H_{17}$ | $-C_3H_7$ | $-\overset{O}{\overset{\|}{C}}SCH_3$ | 1.4915 |

TABLE I-continued
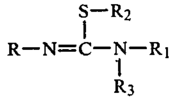
| Compound No. | R | $R_1$ | $R_2$ | $R_3$ | $n_D^{30}$ or °C. |
|---|---|---|---|---|---|
| 1067 | 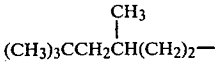 | 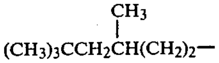 | $-C_3H_7$ | 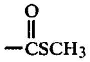 | 1.4909 |
| 1068 | $-secC_7H_{15}$ | $-secC_6H_{13}$ | $-C_5H_{11}$ | 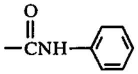 | 1.5122 |
| 1069 | $-secC_7H_{15}$ | $-secC_6H_{13}$ | $-C_5H_{11}$ | 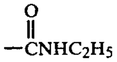 | 1.4786 |
| 1070 | $-secC_7H_{15}$ | $-secC_6H_{13}$ | $-C_5H_{11}$ | 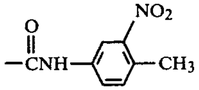 | 1.5213 |
| 1071 | $-secC_7H_{15}$ | $-C_8H_{17}$ | $-C_1H_3$ | 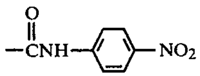 | 1.5325 |
| 1072 | $-secC_8H_{17}$ | $-C_7H_{15}$ | $-C_1H_3$ | 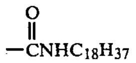 | 1.4720 |
| 1073 | $-secC_8H_{17}$ | $-C_7H_{15}$ | $-C_1H_3$ | 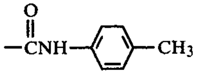 | 1.5153 |
| 1074 | $-secC_8H_{17}$ | $-C_7H_{15}$ | $-C_1H_3$ | 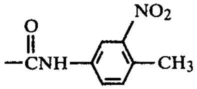 | 1.5286 |
| 1075 | $-secC_8H_{17}$ | $-C_7H_{15}$ | $-C_1H_3$ | 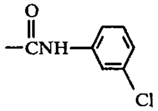 | 1.5620 |
| 1076 | $-secC_8H_{17}$ | $-C_7H_{15}$ | $-C_1H_3$ | 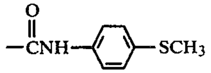 | 1.5403 |
| 1077 | $-secC_8H_{17}$ | $-C_7H_{15}$ | $-C_1H_3$ | 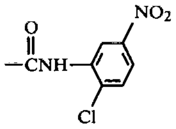 | 1.5318 |

TABLE I-continued
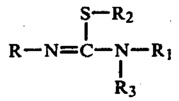
| Compound No. | R | $R_1$ | $R_2$ | $R_3$ | $n_D^{30}$ or °C. |
|---|---|---|---|---|---|
| 1078 | $-secC_8H_{17}$ | $-C_7H_{15}$ | $-C_1H_3$ | 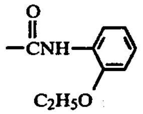 | 1.4750 |
| 1079 | $-secC_8H_{17}$ | $-C_7H_{15}$ | $-C_1H_3$ | 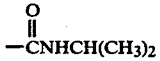 | 1.5141 |
| 1080 | $-secC_8H_{17}$ | $-C_7H_{15}$ | $-C_1H_3$ | 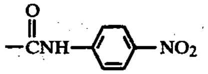 | 1.5380 |
| 1081 | $-secC_8H_{17}$ | $-C_7H_{15}$ | $-C_1H_3$ | 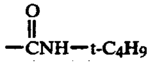 | 1.4712 |
| 1082 | $-secC_8H_{17}$ | $-C_7H_{15}$ | $-C_1H_3$ | 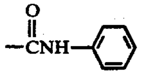 | 1.5152 |
| 1083 | $-secC_8H_{17}$ | $-C_7H_{15}$ | $-C_1H_3$ | 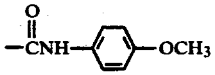 | 1.5167 |
| 1084 | $-secC_8H_{17}$ | $-C_7H_{15}$ | $-C_1H_3$ | 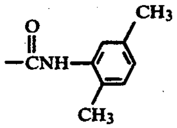 | 1.5159 |
| 1085 | $-secC_8H_{17}$ | $-C_7H_{15}$ | $-C_1H_3$ | 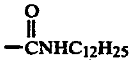 | 1.4739 |
| 1086 | $-secC_8H_{17}$ | $-C_7H_{15}$ | $-C_1H_3$ | 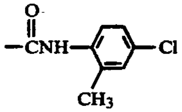 | 1.5220 |
| 1087 | $-secC_8H_{17}$ | $-secC_7H_{15}$ | $-C_1H_3$ | 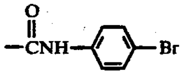 | 1.5317 |

TABLE I-continued
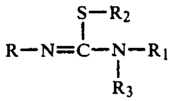
| Compound No. | R | $R_1$ | $R_2$ | $R_3$ | $n_D^{30}$ or °C. |
| --- | --- | --- | --- | --- | --- |
| 1088 | $-secC_8H_{17}$ | $-C_7H_{15}$ | $-C_1H_3$ | 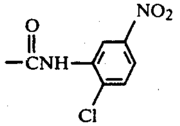 | 1.5298 |
| 1089 | $-secC_8H_{17}$ | $-C_7H_{15}$ | $-C_1H_3$ | 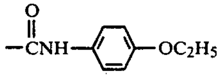 | 1.5167 |
| 1090 | $-secC_8H_{17}$ | $-C_7H_{15}$ | $-C_1H_3$ | 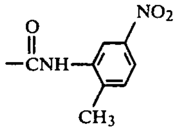 | 1.5254 |
| 1091 | $-secC_8H_{17}$ | $-C_7H_{15}$ | $-C_1H_3$ | 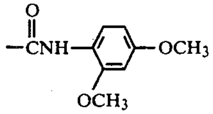 | 1.5231 |
| 1092 | $-secC_8H_{17}$ | $-C_7H_{15}$ | $-C_1H_3$ | 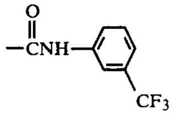 | 1.4950 |
| 1093 | $-secC_8H_{17}$ | $-C_7H_{15}$ | $-C_1H_3$ | 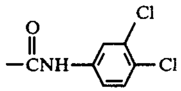 | 1.5301 |
| 1094 | $-secC_8H_{17}$ | $-C_7H_{15}$ | $-C_1H_3$ | 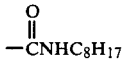 | 1.4765 |
| 1095 | $-secC_8H_{17}$ | $-C_7H_{15}$ | $-C_1H_3$ | 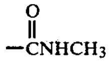 | 1.4821 |
| 1096 | $-secC_8H_{17}$ | $-C_7H_{15}$ | $-C_1H_3$ | 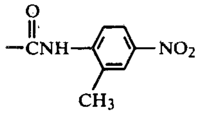 | 1.5443 |

TABLE I-continued
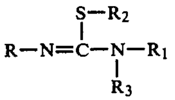
| Compound No. | R | $R_1$ | $R_2$ | $R_3$ | $n_D^{30}$ or °C. |
|---|---|---|---|---|---|
| 1097 | 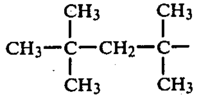 | —2-ethyl hexyl | $-C_3H_7$ | 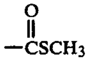 | 1.4938 |
| 1098 | 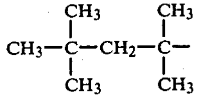 | —2-ethyl hexy l | $-C_2H_5$ | 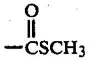 | 1.4955 |
| 1099 | $-C_7H_{15}$ | $-C_7H_{15}$ | $-C_1H_3$ | 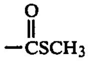 | 1.4987 |
| 1100 | 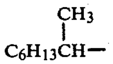 | —2-ethyl hexyl | $-C_2H_5$ | 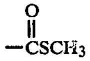 | 1.4934 |
| 1101 | —2-ethyl hexyl | $-C_8H_{17}$ | $-C_3H_7$ | 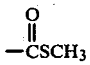 | 1.4926 |
| 1102 | —2-ethyl hexyl | —2-ethyl hexyl | $-C_3H_7$ | 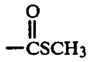 | 1.4940 |
| 1103 | 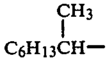 | $-C_7H_{15}$ | $-C_1H_3$ | 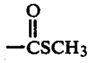 | 1.4940 |
| 1104 | 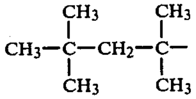 | $-C_8H_{17}$ | $-C_2H_5$ | 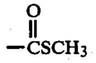 | 1.4959 |
| 1105 | 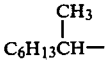 | $-C_7H_{15}$ | $-C_1H_3$ | 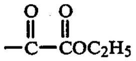 | 1.4752 |
| 1106 | 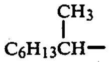 | $-C_8H_{17}$ | $-C_2H_5$ | 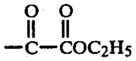 | 1.4750 |
| 1107 | 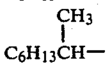 | $-C_8H_{17}$ | $-C_3H_7$ | 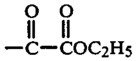 | 1.4747 |
| 1108 | $-C_6H_{13}$ | $-C_8H_{17}$ | $-C_1H_3$ | 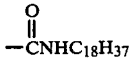 | 1.4751 |
| 1109 | $-C_6H_{13}$ | $-C_8H_{17}$ | $-C_1H_3$ | 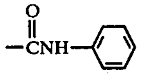 | 1.5224 |

TABLE I-continued
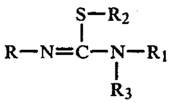
| Compound No. | R | $R_1$ | $R_2$ | $R_3$ | $n_D^{30}$ or °C. |
|---|---|---|---|---|---|
| 1110 | $-C_6H_{13}$ | $-C_8H_{17}$ | $-C_1H_3$ | 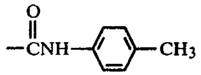 | 1.5194 |
| 1111 | $-C_6H_{13}$ | $-C_8H_{17}$ | $-C_1H_3$ | 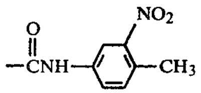 | 1.5306 |
| 1112 | $-C_6H_{13}$ | $-C_8H_{17}$ | $-C_1H_3$ | 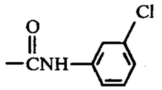 | 1.5292 |
| 1113 | $-C_6H_{13}$ | $-C_8H_{17}$ | $-C_1H_3$ | 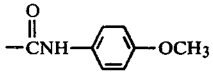 | 1.5234 |
| 1114 | $-C_6H_{13}$ | $-C_8H_{17}$ | $-C_1H_3$ | 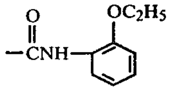 | 1.5182 |
| 1115 | $-C_6H_{13}$ | $-C_8H_{17}$ | $-C_1H_3$ | 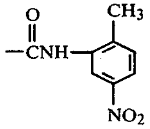 | 1.5238 |
| 1116 | $-C_6H_{13}$ | $-C_8H_{17}$ | $-C_1H_3$ | 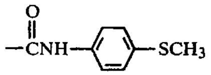 | 1.5441 |
| 1117 | $-C_6H_{13}$ | $-C_8H_{17}$ | $-C_1H_3$ | 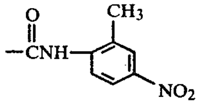 | 1.5410 |
| 1118 | $-C_6H_{13}$ | $-C_8H_{17}$ | $-C_1H_3$ | 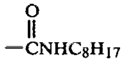 | 1.4786 |
| 1119 | $-C_6H_{13}$ | $-C_8H_{17}$ | $-C_1H_3$ | 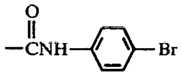 | 1.5354 |

TABLE I-continued
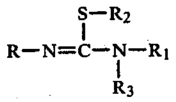
| Compound No. | R | $R_1$ | $R_2$ | $R_3$ | $n_D^{30}$ or °C. |
|---|---|---|---|---|---|
| 1120 | $-C_6H_{13}$ | $-C_8H_{17}$ | $-C_1H_3$ | 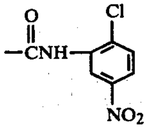 | 1.5354 |
| 1121 | $-C_6H_{13}$ | $-C_8H_{17}$ | $-C_1H_3$ | 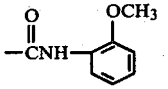 | 1.5232 |
| 1122 | $-C_6H_{13}$ | $-C_8H_{17}$ | $-C_1H_3$ | 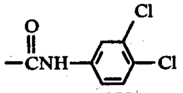 | 1.5380 |
| 1123 | $-C_6H_{13}$ | $-C_8H_{17}$ | $-C_1H_3$ | 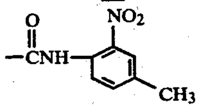 | 1.5376 |
| 1124 | $-C_6H_{13}$ | $-C_8H_{17}$ | $-C_1H_3$ | 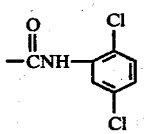 | 1.5296 |
| 1125 | $-C_6H_{13}$ | $-C_8H_{17}$ | $-C_1H_3$ | 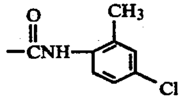 | 1.5249 |
| 1126 | $-secC_7H_{15}$ | $-C_7H_{15}$ | $-C_1H_3$ | 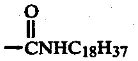 | 1.4730 |
| 1127 | $-secC_7H_{15}$ | $-C_7H_{15}$ | $-C_1H_3$ | 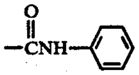 | 1.5231 |
| 1128 | $-secC_7H_{15}$ | $-C_7H_{15}$ | $-C_1H_3$ | 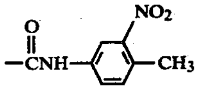 | 1.5232 |
| 1129 | $-secC_7H_{15}$ | $-C_7H_{15}$ | $-C_1H_3$ | 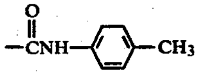 | 1.5218 |

TABLE I-continued
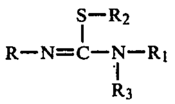
| Compound No. | R | $R_1$ | $R_2$ | $R_3$ | $n_D^{30}$ or °C. |
|---|---|---|---|---|---|
| 1130 | $-secC_7H_{15}$ | $-C_7H_{15}$ | $-C_1H_3$ | 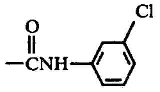 | 1.5278 |
| 1131 | $-secC_7H_{15}$ | $-C_7H_{15}$ | $-C_1H_3$ | 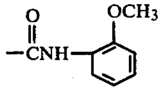 | 1.5227 |
| 1132 | $-secC_7H_{15}$ | $-C_7H_{15}$ | $-C_1H_3$ | 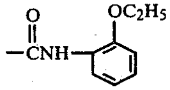 | 1.5174 |
| 1133 | $-secC_7H_{15}$ | $-C_7H_{15}$ | $-C_1H_3$ | 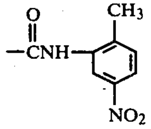 | 1.5299 |
| 1134 | 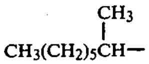 | $-C_8H_{17}$ | $-C_2H_5$ | 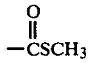 | 1.4920 |
| 1135 | $-C_7H_{15}$ | $-C_7H_{15}$ | $-C_2H_5$ | 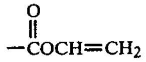 | 1.4803 |
| 1136 | $-secC_7H_{15}$ | $-C_8H_{17}$ | $-C_2H_5$ | 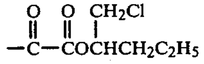 | 1.4950 |

III. Tobacco Budworm [*Heliothis virescens* (F.)]

Larvae of the tobacco budworm are used in this test in a procedure identical to that used for saltmarsh caterpillar larvae, except that a Romaine lettuce (*Latuca sativa*) leaf section of approximately the same size as the curly dock leaf section is used in place of the latter. The primary screening level for this test is 0.1 percent by weight of the test compound in the solution.

Table II summarizes the results of the lepidoptericidal tests performed on the compounds of Table I. These test results are expressed as $LD_{50}$ values, which represent the dose of test compound which was lethal to 50 percent of the insect population in the test. The entries in Table II were obtained as follows:

For a particular lepidoptera, each compound was initially tested at the primary screening level. Those compounds showing less than 50 percent kill at this level are represented in the table by the primary screening level preceded by a "greater than" sign (>). Those compounds showing approximately 50 percent kill are represented by the primary screening level alone. Those compounds showing greater than 50 percent kill were subjected to further testing at successively lower levels, until the level was found at which approximately 50 percent kill was achieved. The latter level is listed as the $LD_{50}$ for this group.

Phytotoxicity Tests

Phytotoxicity tests are conducted on cotton (*Gossaypium hirsutum*) and hyzini squash (*Calabacita abobrinha*) seedlings. Plants are grown and treated in Kaiser No. 1059 6"×9"×3" aluminum flats. Each flat contains one row of cotton and one row of squash, with 6–8 plants per row. The plants are grown in the greenhouse and are treated when they are approximately 8 days old and 2" tall.

Technical test compounds are diluted in a 50–50 acetone-water solution and formulated compounds are diluted in water. These test solutions are then sprayed on the flats in a Ducon-Savko Model 3400 linear spray table at rates of ½, 1, 2, and 4 lbs a.i./80 gallons/acre. The treated plants are then placed in the greenhouse and watered in such a way that the foliage is not wet.

One week later, the treated plants are inspected and the degree of phytotoxicity is subjectively rated from 0 to 5 as follows:

0=no injury
1=slight injury
2=slight to moderate injury
3=moderate injury
4=moderate to severe injury
5=severe injury or dead Table II also summarizes the results of the phytotoxicity tests performed on the compounds of Table I.

The primary screening level in each of the above tests was selected for purposes of convenience only, and none of the figures in the table are to be understood as representing the highest level at which a viable test for lepidoptericidal activity can be conducted.

TABLE II

| Compound No. | Lepidoptericidal Activity | | | Phytotoxicity Cotton | | | Phytotoxicity Squash | | |
|---|---|---|---|---|---|---|---|---|---|
| | SMC | CL | TBW | ½ | 1 | 2 | ½ | 1 | 2 |
| 1 | .008 | .01 | >.05 | 0 | 0 | 2 | 0 | 0 | 2 |
| 2 | .008 | .003 | .04 | 0 | 0 | 1 | 0 | 1 | 2 |
| 3 | .0024 | .006 | .03 | 0 | 0 | 3 | 0 | 1 | 1 |

TABLE II-continued

| Compound No. | Lepidoptericidal Activity | | | Phytotoxicity Cotton | | | Phytotoxicity Squash | | |
|---|---|---|---|---|---|---|---|---|---|
| | SMC | CL | TBW | ½ | 1 | 2 | ½ | 1 | 2 |
| 4 | .016 | .0016 | >.08 | 0 | 0 | 0 | 0 | 0 | 0 |
| 5 | .003 | .009 | .15 | 1 | 4 | 4 | 1 | 4 | 4 |
| 6 | .001 | .005 | .05 | 0 | 0 | 2 | 0 | 0 | 2 |
| 7 | .002 | .0008 | .02 | 0 | 1 | 4 | 0 | 1 | 4 |
| 8 | .0009 | .0009 | .02 | 0 | 1 | 4 | 0 | 0 | 3 |
| 9 | .0007 | .002 | .01 | 1 | 3 | 5 | 0 | 2 | 5 |
| 10 | .005 | .0007 | .02 | 1 | 3 | 5 | 1 | 3 | 5 |
| 11 | .008 | .002 | >.05 | 0 | 2 | 5 | 0 | 2 | 5 |
| 12 | .001 | .002 | >.05 | 0 | 1 | 5 | 0 | 2 | 5 |
| 13 | .003 | .003 | >.05 | 1 | 2 | 5 | 1 | 2 | 5 |
| 14 | .003 | .005 | >.05 | 1 | 3 | 5 | 0 | 2 | 4 |
| 15 | .008 | .008 | >.05 | 1 | 2 | 5 | 0 | 1 | 3 |
| 16 | .008 | .008 | >.05 | 1 | 3 | 4 | 0 | 2 | 4 |
| 17 | .001 | .002 | >.05 | 1 | 2 | 4 | 0 | 1 | 4 |
| 18 | .05 | .003 | >.05 | 1 | 2 | 4 | 0 | 1 | 3 |
| 19 | .003 | .005 | >.05 | 0 | 2 | 5 | 0 | 2 | 5 |
| 20 | .008 | .002 | >.05 | 1 | 2 | 4 | 0 | 1 | 3 |
| 21 | .01 | .003 | >.05 | 0 | 1 | 2 | 0 | 1 | 2 |
| 22 | .005 | .0008 | >.05 | 0 | 0 | 1 | 0 | 0 | 1 |
| 23 | .003 | .0005 | >.05 | 0 | 1 | 3 | 0 | 2 | 4 |
| 24 | >.05 | .01 | >.05 | 0 | 1 | 3 | 0 | 1 | 2 |
| 25 | .03 | .005 | >.05 | 0 | 2 | 4 | 0 | 2 | 3 |
| 26 | >.05 | .01 | >.05 | 1 | 2 | 3 | 0 | 1 | 2 |
| 27 | .005 | .001 | >.05 | 0 | 1 | 3 | 0 | 1 | 3 |
| 28 | >.05 | .003 | .05 | 0 | 1 | 3 | 0 | 1 | 2 |
| 29 | .002 | .002 | >.05 | 0 | 0 | 0 | 0 | 0 | 1 |
| 30 | .005 | .002 | .05 | 0 | 1 | 2 | 0 | 0 | 1 |
| 31 | .005 | .003 | .05 | 0 | 1 | 2 | 0 | 1 | 3 |
| 32 | .001 | .002 | .01 | 0 | 1 | 3 | 0 | 1 | 3 |
| 33 | .008 | .01 | >.05 | 0 | 0 | 1 | 0 | 0 | 1 |
| 34 | .005 | .002 | >.05 | 1 | 1 | 2 | 1 | 2 | 3 |
| 35 | .01 | .0005 | >.05 | 0 | 1 | 2 | 1 | 2 | 3 |
| 36 | .005 | .002 | >.05 | 0 | 1 | 2 | 0 | 1 | 3 |
| 37 | .002 | .002 | .05 | 0 | 0 | 1 | 0 | 0 | 2 |
| 38 | .003 | .005 | >.05 | 0 | 1 | 3 | 1 | 2 | 4 |
| 39 | >.05 | .1 | >.05 | 0 | 0 | 2 | 0 | 1 | 3 |
| 40 | .001 | .001 | .01 | 1 | 3 | 5 | 1 | 4 | 5 |
| 41 | .003 | .03 | >.05 | 0 | 0 | 1 | 0 | 1 | 2 |
| 42 | .001 | .002 | .05 | 0 | 2 | 3 | 1 | 2 | 5 |
| 43 | .002 | .002 | >.05 | 0 | 2 | 5 | 1 | 3 | 5 |
| 44 | >.05 | .03 | >.05 | 0 | 1 | 3 | 0 | 2 | 4 |
| 45 | .01 | .0005 | .05 | 1 | 2 | 5 | 1 | 3 | 5 |
| 46 | .01 | .002 | .05 | 0 | 0 | 1 | 0 | 1 | 2 |
| 47 | .001 | .001 | .03 | 0 | 1 | 3 | 0 | 2 | 4 |
| 48 | .005 | .001 | .03 | 1 | 2 | 4 | 1 | 3 | 5 |
| 49 | .0003 | .0002 | .05 | 1 | 2 | 5 | 1 | 3 | 5 |
| 50 | .0003 | .0003 | .05 | 1 | 3 | 5 | 1 | 3 | 5 |
| 51 | .001 | .001 | .05 | 0 | 2 | 5 | 0 | 2 | 5 |
| 52 | .005 | .003 | | 0 | 1 | 2 | 0 | 0 | 2 |
| 53 | .008 | .005 | | 0 | 0 | 1 | 0 | 0 | 1 |
| 54 | .008 | .005 | | 0 | 0 | 0 | 0 | 0 | 2 |
| 55 | .002 | .002 | | 0 | 1 | 2 | 0 | 1 | 2 |
| 56 | .001 | .0003 | .02 | 1 | 2 | 3 | 1 | 3 | 4 |
| 57 | .001 | .0003 | .02 | 0 | 2 | 4 | 1 | 2 | 5 |
| 58 | .002 | .0005 | .05 | 0 | 2 | 3 | 0 | 3 | 5 |
| 59 | .002 | .0005 | .05 | 0 | 1 | 3 | 0 | 1 | 3 |
| 60 | .003 | .002 | >.05 | 0 | 0 | 0 | 0 | 0 | 0 |
| 61 | .008 | .005 | .05 | 0 | 2 | 5 | 0 | 3 | 5 |
| 62 | .0008 | .001 | .05 | 0 | 1 | 2 | 0 | 1 | 2 |
| 63 | .001 | .005 | >.05 | 0 | 0 | 1 | 0 | 0 | 2 |
| 64 | .005 | .008 | >.05 | 0 | 0 | 1 | 0 | 0 | 1 |
| 65 | .0002 | .0005 | .02 | 1 | 2 | 5 | 1 | 3 | 5 |
| 66 | .002 | .03 | .05 | 0 | 1 | 3 | 0 | 2 | 3 |
| 67 | .001 | .002 | .05 | 0 | 0 | 0 | 0 | 0 | 0 |
| 68 | .0008 | .005 | .05 | 0 | 1 | 3 | 0 | 2 | 5 |
| 69 | .0003 | .002 | >.05 | 0 | 1 | 3 | 0 | 1 | 5 |
| 70 | .001 | .002 | >.05 | 0 | 1 | 3 | 0 | 1 | 4 |
| 71 | .001 | .0005 | .05 | 0 | 1 | 4 | 0 | 1 | 4 |
| 72 | .0008 | .002 | .05 | 0 | 0 | 1 | 0 | 1 | 2 |
| 73 | .002 | .003 | .06 | 0 | 0 | 1 | 0 | 0 | 1 |
| 74 | .002 | .002 | .03 | 0 | 0 | 0 | 0 | 1 | 0 |
| 75 | .003 | .03 | >.05 | 0 | 0 | 0 | 0 | 0 | 0 |
| 76 | .003 | .03 | >.05 | 0 | 0 | 1 | 0 | 0 | 1 |
| 77 | .01 | .002 | >.05 | 0 | 0 | 1 | 0 | 0 | 1 |
| 78 | .002 | .0005 | .05 | 0 | 1 | 2 | 0 | 1 | 3 |
| 79 | .005 | .002 | >.05 | 0 | 0 | 0 | 0 | 0 | 0 |
| 80 | .002 | .0005 | .01 | 0 | 0 | 1 | 0 | 0 | 1 |
| 81 | .003 | .002 | .05 | 0 | 0 | 0 | 0 | 0 | 1 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 82 | .008 | .002 | >.05 | 0 | 1 | 3 | 0 | 1 | 4 |
| 83 | .005 | .003 | >.05 | 0 | 0 | 1 | 0 | 0 | 1 |
| 84 | .001 | .0003 | >.05 | 0 | 1 | 4 | 0 | 1 | 5 |
| 85 | .005 | .0003 | .03 | 0 | 0 | 3 | 0 | 0 | 2 |
| 86 | .002 | .0008 | >.05 | 0 | 0 | 0 | 0 | 0 | 0 |
| 87 | .002 | .002 | >.05 | 0 | 0 | 3 | 0 | 1 | 4 |
| 88 | .003 | .0002 | >.05 | 0 | 0 | 3 | 0 | 0 | 4 |
| 89 | .001 | .002 | .05 | 0 | 0 | 0 | 0 | 0 | 0 |
| 90 | .001 | .0002 | .04 | 0 | 0 | 1 | 0 | 0 | 1 |
| 91 | .0003 | .0002 | .01 | 0 | 0 | 0 | 0 | 0 | 1 |
| 92 | .005 | .03 | >.05 | 0 | 0 | 0 | 0 | 0 | 0 |
| 93 | .001 | .001 | >.05 | 0 | 0 | 2 | 0 | 1 | 3 |
| 94 | .005 | .002 | >.05 | 0 | 0 | 1 | 0 | 0 | 1 |
| 95 | .002 | .0008 | >.05 | 0 | 0 | 0 | 0 | 0 | 1 |
| 96 | .001 | .0003 | >.05 | 0 | 2 | 4 | 1 | 3 | 5 |
| 97 | .0008 | .0008 | >.05 | 0 | 0 | 0 | 0 | 0 | 0 |
| 98 | .001 | .001 | .05 | 0 | 1 | 3 | 0 | 1 | 3 |
| 99 | .002 | .0005 | >.05 | 0 | 0 | 1 | 0 | 0 | 2 |
| 100 | .003 | .0005 | .05 | 0 | 1 | 3 | 0 | 1 | 4 |
| 101 | .001 | .002 | .05 | 1 | 2 | 4 | 1 | 3 | 5 |
| 102 | .0003 | .002 | .06 | 0 | 0 | 0 | 0 | 0 | 1 |
| 103 | <.05 | .002 | .03 | 1 | 2 | 4 | 1 | 2 | 5 |
| 104 | .003 | .002 | .05 | 0 | 0 | 0 | 0 | 0 | 0 |
| 105 | .005 | .002 | .05 | 0 | 0 | 0 | 0 | 0 | 0 |
| 106 | .005 | .0005 | .05 | 0 | 1 | 4 | 0 | 2 | 4 |
| 107 | .003 | .0008 | .05 | 0 | 0 | 1 | 0 | 0 | 2 |
| 108 | .002 | .001 | >.05 | 0 | 1 | 2 | 0 | 1 | 3 |
| 109 | .003 | .002 | .05 | 0 | 2 | 4 | 0 | 3 | 5 |
| 110 | .01 | .0005 | >.05 | 0 | 0 | 2 | 0 | 0 | 2 |
| 111 | .008 | .05 | >.05 | 0 | 0 | 0 | 0 | 0 | 0 |
| 112 | .001 | .0003 | .05 | 0 | 0 | 2 | 0 | 1 | 3 |
| 113 | .005 | .003 | .05 | 0 | 0 | 0 | 0 | 0 | 0 |
| 114 | .002 | .0005 | .05 | 0 | 0 | 2 | 0 | 1 | 3 |
| 115 | .003 | .008 | >.05 | 0 | 0 | 0 | 0 | 0 | 0 |
| 116 | .002 | .003 | <.05 | 0 | 0 | 0 | 0 | 0 | 0 |
| 117 | .002 | .002 | >.05 | 0 | 0 | 0 | 0 | 0 | 1 |
| 118 | .001 | .0005 | <.05 | 0 | 0 | 1 | 1 | 2 | 3 |
| 119 | .05 | .002 | >.05 | 0 | 0 | 0 | 0 | 0 | 1 |
| 120 | .002 | .001 | .05 | 0 | 0 | 0 | 0 | 0 | 0 |
| 121 | .0005 | .0005 | .03 | 0 | 0 | 1 | 0 | 0 | 2 |
| 122 | .0001 | .0005 | .03 | 0 | 1 | 3 | 1 | 3 | 5 |
| 123 | .0003 | .001 | .05 | 1 | 3 | 4 | 1 | 4 | 5 |
| 124 | .05 | .002 | .05 | 0 | 1 | 2 | 0 | 1 | 3 |
| 125 | .0008 | .001 | <.05 | 0 | 0 | 1 | 0 | 0 | 1 |
| 126 | .0005 | .0005 | .03 | 0 | 1 | 3 | 1 | 2 | 4 |
| 127 | .0008 | .005 | >.05 | 0 | 1 | 2 | 1 | 2 | 5 |
| 128 | .001 | .001 | <.05 | 0 | 0 | 0 | 0 | 0 | 0 |
| 129 | .005 | .0005 | .05 | 0 | 0 | 1 | 0 | 1 | 2 |
| 130 | .002 | .002 | <.05 | 0 | 0 | 0 | 0 | 0 | 3 |
| 131 | .008 | .002 | .05 | 0 | 0 | 0 | 0 | 0 | 0 |
| 132 | .003 | .002 | <.05 | 0 | 0 | 1 | 0 | 1 | 3 |
| 133 | .001 | .005 | <.05 | 0 | 0 | 1 | 0 | 0 | 2 |
| 134 | .003 | .001 | >.1 | 0 | 0 | 0 | 0 | 0 | 1 |
| 135 | .0008 | .0005 | <.05 | 0 | 0 | 2 | 0 | 1 | 3 |
| 136 | .0002 | .003 | .05 | 0 | 0 | 0 | 0 | 0 | 1 |
| 137 | .001 | .03 | >.1 | 0 | 0 | 0 | 0 | 0 | 0 |
| 138 | .005 | .01 | >.05 | 0 | 1 | 2 | 0 | 1 | 2 |
| 139 | .003 | .002 | <.05 | 0 | 0 | 0 | 0 | 0 | 1 |
| 140 | .002 | .001 | <.05 | 0 | 0 | 1 | 0 | 0 | 0 |
| 141 | .0005 | .0005 | .05 | 0 | 0 | 2 | 0 | 0 | 1 |
| 142 | .01 | .002 | .05 | 0 | 0 | 0 | 0 | 0 | 0 |
| 143 | >.05 | .03 | .05 | 0 | 0 | 0 | 0 | 0 | 0 |
| 144 | .001 | .002 | <.05 | 0 | 0 | 0 | 0 | 0 | 0 |
| 145 | .0003 | .0005 | <.05 | 0 | 0 | 1 | 0 | 0 | 2 |
| 146 | >.05 | .005 | .05 | 0 | 0 | 0 | 0 | 0 | 0 |
| 147 | .005 | .002 | <.05 | 0 | 0 | 2 | 0 | 0 | 2 |
| 148 | .005 | .0005 | <.05 | 0 | 0 | 1 | 0 | 0 | 1 |
| 149 | .005 | .002 | .05 | 0 | 0 | 0 | 0 | 0 | 0 |
| 150 | .0001 | .0003 | <.05 | 0 | 1 | 2 | 0 | 1 | 3 |
| 151 | >.05 | .008 | <.05 | 0 | 0 | 0 | 0 | 0 | 0 |
| 152 | .002 | .0003 | .05 | 0 | 1 | 3 | 0 | 2 | 3 |
| 153 | .002 | .001 | .08 | 0 | 0 | 0 | 0 | 0 | 0 |
| 154 | .0003 | <.001 | .02 | 0 | 0 | 1 | 0 | 0 | 1 |
| 155 | >.05 | >.05 | >.05 | 0 | 0 | 0 | 0 | 0 | 0 |
| 156 | .03 | .03 | >.05 | 0 | 0 | 0 | 0 | 0 | 1 |
| 157 | >.05 | >.05 | .04 | 0 | 0 | 0 | 0 | 0 | 1 |
| 158 | >.05 | >.05 | .05 | 0 | 0 | 0 | 0 | 0 | 0 |
| 159 | .05 | .008 | >.05 | 0 | 0 | 0 | 0 | 0 | 1 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 160 | >.05 | .05 | >.05 | 0 | 0 | 1 | 0 | 0 | 1 |
| 161 | >.05 | .03 | .05 | 0 | 0 | 0 | 0 | 0 | 0 |
| 162 | >.05 | .1 | >.05 | 0 | 0 | 0 | 0 | 0 | 0 |
| 163 | >.05 | .01 | .04 | 0 | 0 | 0 | 0 | 0 | 0 |
| 164 | .008 | >.05 | .05 | 0 | 0 | 1 | 0 | 0 | 1 |
| 165 | >.05 | >.05 | .05 | 0 | 0 | 1 | 0 | 0 | 1 |
| 166 | >.05 | >.05 | >.05 | 0 | 0 | 1 | 0 | 0 | 1 |
| 167 | >.05 | >.05 | .05 | 0 | 1 | 2 | 0 | 0 | 1 |
| 168 | >.05 | .01 | .05 | 0 | 0 | 0 | 0 | 0 | 0 |
| 169 | .03 | .005 | >.05 | 0 | 0 | 0 | 0 | 0 | 0 |
| 170 | >.05 | >.05 | >.05 | 0 | 0 | 0 | 0 | 0 | 0 |
| 171 | >.05 | .4 | >.05 | 0 | 0 | 0 | 0 | 0 | 0 |
| 172 | .003 | <.001 | .05 | 0 | 0 | 0 | 0 | 0 | 0 |
| 173 | .01 | .003 | >.05 | 0 | 0 | 0 | 0 | 0 | 0 |
| 174 | >.05 | .03 | >.05 | 0 | 0 | 1 | 0 | 0 | 0 |
| 175 | >.05 | >.05 | >.05 | 0 | 0 | 1 | 0 | 1 | 2 |
| 176 | .05 | >.05 | >.05 | 0 | 0 | 1 | 0 | 0 | 1 |
| 177 | >.05 | .2 | >.05 | 0 | 0 | 1 | 0 | 0 | 1 |
| 178 | >.05 | .05 | >.05 | 0 | 0 | 1 | 0 | 0 | 1 |
| 179 | >.05 | .01 | >.05 | 0 | 0 | 1 | 0 | 0 | 1 |
| 180 | .005 | >.05 | >.05 | 0 | 1 | 3 | 0 | 1 | 2 |
| 181 | .05 | .01 | >.05 | 0 | 0 | 0 | 0 | 0 | 1 |
| 182 | .03 | .008 | >.05 | 1 | 2 | 4 | 1 | 2 | 4 |
| 183 | >.05 | >.05 | .05 | 0 | 0 | 0 | 0 | 0 | 0 |
| 184 | .01 | .003 | >.05 | 0 | 0 | 0 | 0 | 0 | 0 |
| 185 | >.05 | .5 | .05 | 0 | 0 | 0 | 0 | 0 | 0 |
| 186 | >.05 | .05 | >.05 | 0 | 0 | 0 | 0 | 0 | 0 |
| 187 | >.05 | .01 | >.05 | 0 | 0 | 0 | 0 | 0 | 0 |
| 188 | >.05 | .5 | >.05 | 0 | 0 | 1 | 0 | 0 | 0 |
| 189 | .003 | .01 | >.05 | 0 | 0 | 1 | 0 | 0 | 1 |
| 190 | >.05 | .008 | >.05 | 0 | 0 | 0 | 0 | 0 | 0 |
| 191 | .01 | .15 | >.05 | 0 | 2 | 3 | 0 | 2 | 4 |
| 192 | >.05 | .01 | >.05 | 0 | 1 | 2 | 0 | 1 | 3 |
| 193 | | .4 | | 0 | 0 | 1 | 0 | 0 | 2 |
| 194 | | .2 | | 0 | 0 | 2 | 0 | 0 | 2 |
| 195 | .001 | .002 | >.05 | 0 | 1 | 2 | 0 | 1 | 3 |
| 196 | >.05 | .01 | >.05 | 0 | 1 | 2 | 0 | 0 | 2 |
| 197 | | .2 | | 0 | 0 | 1 | 0 | 1 | 2 |
| 198 | | .5 | | 0 | 1 | 2 | 0 | 0 | 1 |
| 199 | >.05 | .2 | >.05 | 1 | 2 | 4 | 1 | 3 | 5 |
| 200 | .01 | .0025 | >.05 | 1 | 3 | 5 | 2 | 3 | 5 |
| 201 | .05 | >.05 | >.05 | 0 | 0 | 0 | 0 | 0 | 0 |
| 202 | .05 | >.05 | >.05 | 0 | 0 | 0 | 0 | 0 | 0 |
| 203 | >.05 | >.05 | .03 | 0 | 0 | 0 | 0 | 0 | 0 |
| 204 | >.05 | .1 | >.05 | 0 | 0 | 0 | 0 | 0 | 0 |
| 205 | >.05 | .1 | >.05 | 0 | 0 | 0 | 0 | 0 | 0 |
| 206 | .03 | .03 | >.05 | 0 | 0 | 0 | 0 | 0 | 0 |
| 207 | .03 | .03 | >.05 | 0 | 0 | 0 | 0 | 0 | 0 |
| 208 | .03 | .008 | .05 | 0 | 0 | 0 | 0 | 0 | 0 |
| 209 | .01 | .01 | >.05 | 0 | 0 | 0 | 0 | 0 | 0 |
| 210 | >.05 | >.05 | >.05 | 0 | 0 | 0 | 0 | 0 | 0 |
| 211 | .05 | >.05 | >.05 | 0 | 0 | 0 | 0 | 0 | 0 |
| 212 | .01 | .002 | .05 | 0 | 0 | 1 | 0 | 0 | 1 |
| 213 | >.5 | >.05 | >.5 | 0 | 0 | 0 | 0 | 0 | 1 |
| 214 | | >.05 | | 0 | 0 | 0 | 0 | 0 | 1 |
| 215 | | >.05 | | 0 | 0 | 0 | 0 | 0 | 0 |
| 216 | .008 | .005 | >.05 | 0 | 0 | 2 | 0 | 0 | 1 |
| 217 | .05 | >.05 | >.05 | 0 | 0 | 1 | 0 | 1 | 2 |
| 218 | .05 | .003 | >.05 | 0 | 1 | 2 | 0 | 1 | 2 |
| 219 | .005 | .008 | >.05 | 0 | 0 | 0 | 0 | 0 | 2 |
| 220 | .03 | .004 | .05 | 0 | 0 | 1 | 0 | 0 | 1 |
| 221 | .01 | .004 | .05 | 0 | 0 | 1 | 0 | 1 | 2 |
| 222 | >.05 | .3 | >.05 | 0 | 0 | 0 | 0 | 0 | 0 |
| 223 | .003 | .008 | >.05 | 0 | 0 | 0 | 0 | 0 | 0 |
| 224 | .03 | .002 | >.05 | 0 | 0 | 0 | 0 | 0 | 1 |
| 225 | .01 | .03 | >.05 | 0 | 0 | 1 | 0 | 0 | 2 |
| 226 | .005 | .005 | >.05 | 0 | 0 | 1 | 0 | 0 | 1 |
| 227 | .03 | .0008 | >.05 | 0 | 1 | 2 | 0 | 1 | 3 |
| 228 | .003 | .002 | .05 | 0 | 1 | 2 | 0 | 1 | 2 |
| 229 | .01 | .009 | >.1 | 0 | 1 | 3 | 0 | 2 | 4 |
| 230 | .003 | .001 | >.1 | 1 | 3 | 5 | 1 | 3 | 5 |
| 231 | .001 | .0005 | >.1 | 2 | 5 | 5 | 1 | 5 | 5 |
| 232 | .001 | .0005 | >.1 | 0 | 2 | 5 | 0 | 2 | 5 |
| 233 | .003 | .0008 | >.1 | 1 | 4 | 5 | 0 | 3 | 5 |
| 234 | .002 | .002 | .1 | 0 | 2 | 5 | 0 | 2 | 5 |
| 235 | .003 | .0008 | .1 | 1 | 4 | 5 | 0 | 3 | 5 |
| 236 | .003 | .0005 | >.1 | 1 | 3 | 5 | 1 | 3 | 5 |
| 237 | .002 | .0005 | >.1 | 1 | 5 | 5 | 1 | 5 | 5 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 238 | .002 | .003 | >.05 | 0 | 0 | 0 | 0 | 0 | 1 |
| 239 | .03 | .03 | >.05 | 0 | 0 | 2 | 0 | 0 | 2 |
| 240 | .03 | .03 | >.05 | 0 | 1 | 2 | 0 | 1 | 3 |
| 241 | >.05 | .005 | >.05 | 0 | 0 | 3 | 0 | 1 | 5 |
| 242 | .01 | .005 | >.05 | 0 | 0 | 2 | 0 | 1 | 5 |
| 243 | .03 | .005 | >.05 | 0 | 0 | 3 | 0 | 1 | 4 |
| 244 | .03 | .01 | >.05 | 0 | 1 | 3 | 0 | 1 | 4 |
| 245 | .008 | .03 | .05 | 0 | 1 | 3 | 0 | 1 | 4 |
| 246 | .05 | .005 | >.05 | 0 | 0 | 2 | 0 | 1 | 3 |
| 247 | .01 | .002 | >.05 | 0 | 0 | 1 | 0 | 0 | 2 |
| 248 | .01 | .01 | >.05 | 0 | 0 | 0 | 0 | 0 | 0 |
| 249 | >.05 | >.05 | .05 | 0 | 0 | 0 | 0 | 0 | 0 |
| 250 | >.05 | .2 | >.05 | 0 | 0 | 0 | 0 | 0 | 0 |
| 251 | .01 | .005 | >.05 | 0 | 0 | 2 | 0 | 1 | 4 |
| 252 | >.05 | .03 | .05 | 0 | 0 | 1 | 0 | 0 | 1 |
| 253 | >.05 | .03 | >.05 | 0 | 0 | 0 | 0 | 0 | 0 |
| 254 | >.05 | .05 | >.05 | 0 | 0 | 0 | 0 | 0 | 0 |
| 255 | >.05 | >.05 | .05 | 0 | 0 | 0 | 0 | 0 | 0 |
| 256 | >.05 | .15 | >.05 | 0 | 0 | 0 | 0 | 0 | 1 |
| 257 | >.05 | .1 | >.1 | 0 | 0 | 0 | 0 | 0 | 0 |
| 258 | >.05 | >.05 | >.1 | 0 | 0 | 0 | 0 | 0 | 0 |
| 259 | >.05 | >.05 | .01 | 0 | 0 | 0 | 0 | 0 | 0 |
| 260 | .008 | .03 | >.05 | 0 | 0 | 0 | 0 | 0 | 1 |
| 261 | >.05 | .05 | >.05 | 0 | 0 | 0 | 0 | 0 | 0 |
| 262 | .05 | >.05 | >.05 | 0 | 0 | 0 | 0 | 0 | 0 |
| 263 | .005 | .005 | >.05 | 0 | 1 | 1 | 0 | 1 | 2 |
| 264 | .005 | .005 | >.05 | 0 | 0 | 1 | 0 | 0 | 1 |
| 265 | .03 | .003 | >.05 | 0 | 0 | 2 | 0 | 1 | 3 |
| 266 | >.05 | .4 | >.05 | 0 | 0 | 1 | 0 | 1 | 2 |
| 267 | .005 | .003 | >.05 | 0 | 0 | 0 | 0 | 1 | 2 |
| 268 | .03 | .002 | >.05 | 0 | 0 | 2 | 0 | 0 | 2 |
| 269 | .03 | >.05 | >.05 | 0 | 0 | 1 | 0 | 1 | 2 |
| 270 | .003 | .002 | .03 | 0 | 1 | 3 | 0 | 1 | 4 |
| 271 | .003 | .002 | .05 | 0 | 2 | 5 | 1 | 2 | 5 |
| 272 | .002 | .002 | .05 | 1 | 2 | 4 | 1 | 3 | 5 |
| 273 | .005 | .002 | .05 | 1 | 2 | 4 | 1 | 3 | 5 |
| 274 | .002 | .001 | .05 | 0 | 1 | 2 | 0 | 1 | 3 |
| 275 | .001 | .0005 | .05 | 0 | 0 | 2 | 0 | 1 | 3 |
| 276 | .003 | .0008 | >.05 | 0 | 0 | 2 | 0 | 1 | 3 |
| 277 | .001 | .002 | >.05 | 0 | 1 | 2 | 0 | 1 | 2 |
| 278 | .003 | .001 | .05 | 0 | 1 | 4 | 0 | 1 | 5 |
| 279 | .003 | .001 | >.05 | 0 | 1 | 2 | 0 | 1 | 3 |
| 280 | .003 | .0005 | .05 | 0 | 1 | 4 | 0 | 1 | 5 |
| 281 | .001 | .001 | .06 | 1 | 2 | 4 | 0 | 2 | 5 |
| 282 | .005 | .0005 | .05 | 1 | 2 | 4 | 0 | 1 | 5 |
| 283 | .01 | .002 | .05 | 0 | 1 | 2 | 0 | 1 | 3 |
| 284 | .001 | .0008 | .05 | 1 | 4 | 5 | 1 | 4 | 5 |
| 285 | .001 | .0002 | >.05 | 0 | 1 | 3 | 0 | 3 | 5 |
| 286 | .001 | .0002 | .05 | 0 | 0 | 2 | 0 | 0 | 3 |
| 287 | .005 | .0005 | .02 | 0 | 0 | 3 | 0 | 0 | 4 |
| 288 | .002 | .0005 | .02 | 0 | 0 | 1 | 0 | 0 | 1 |
| 289 | .002 | .001 | >.05 | 0 | 0 | 0 | 0 | 0 | 0 |
| 290 | .002 | .0008 | .03 | 0 | 0 | 0 | 0 | 0 | 0 |
| 291 | .001 | .002 | .05 | 0 | 0 | 0 | 0 | 0 | 0 |
| 292 | .003 | .005 | .01 | 0 | 0 | 0 | 0 | 0 | 0 |
| 293 | .001 | .0005 | .01 | 0 | 0 | 0 | 0 | 0 | 0 |
| 294 | .001 | .0002 | >.05 | 0 | 0 | 0 | 0 | 0 | 1 |
| 295 | .002 | .03 | >.05 | 0 | 0 | 0 | 0 | 0 | 0 |
| 296 | .0005 | .001 | .05 | 0 | 0 | 0 | 0 | 0 | 0 |
| 297 | .002 | .002 | .05 | 0 | 0 | 0 | 0 | 0 | 1 |
| 298 | .003 | .005 | >.05 | 0 | 0 | 2 | 0 | 1 | 2 |
| 299 | .008 | .003 | >.05 | 0 | 1 | 3 | 0 | 2 | 3 |
| 300 | .005 | .003 | .05 | 0 | 0 | 0 | 0 | 0 | 0 |
| 301 | .003 | .001 | .05 | 0 | 0 | 0 | 0 | 0 | 1 |
| 302 | .03 | .03 | >.05 | 0 | 0 | 1 | 0 | 1 | 2 |
| 303 | >.05 | .03 | >.05 | 0 | 0 | 0 | 0 | 0 | 1 |
| 304 | >.05 | .01 | >.05 | 0 | 0 | 0 | 0 | 0 | 0 |
| 305 | >.05 | >.05 | .04 | 0 | 0 | 0 | 0 | 0 | 0 |
| 306 | >.05 | >.05 | .05 | 0 | 0 | 1 | 0 | 1 | 2 |
| 307 | >.05 | >.05 | >.05 | 0 | 0 | 1 | 0 | 2 | 3 |
| 308 | >.05 | >.05 | >.05 | 0 | 0 | 1 | 0 | 0 | 1 |
| 309 | >.05 | >.05 | >.05 | 0 | 0 | 0 | 0 | 0 | 1 |
| 310 | >.05 | >.05 | .05 | 0 | 0 | 0 | 0 | 0 | 0 |
| 311 | .05 | >.05 | >.05 | 0 | 0 | 0 | 0 | 0 | 0 |
| 312 | .04 | .05 | >.05 | 0 | 0 | 0 | 0 | 0 | 0 |
| 313 | .002 | .003 | .04 | 0 | 2 | 4 | 1 | 3 | 5 |
| 314 | .002 | .005 | >.05 | 2 | 3 | 5 | 3 | 4 | 5 |
| 315 | <.008 | <.008 | .05 | 1 | 3 | 5 | 2 | 3 | 5 |
| 316 | .04 | .04 | >.05 | 0 | 0 | 0 | 0 | 0 | 0 |
| 317 | .05 | | >.05 | 0 | 0 | 0 | 0 | 0 | 1 |
| 318 | >.05 | | >.05 | 0 | 0 | 0 | 0 | 0 | 0 |
| 319 | .002 | .002 | .04 | 1 | 2 | 3 | 1 | 2 | 4 |
| 320 | .005 | .008 | >.05 | 0 | 0 | 1 | 0 | 0 | 2 |
| 321 | .002 | .002 | .02 | 1 | 2 | 4 | 2 | 3 | 5 |
| 322 | .002 | .003 | .03 | 1 | 3 | 5 | 1 | 3 | 5 |
| 323 | .005 | .01 | .05 | 0 | 1 | 2 | 0 | 1 | 2 |
| 324 | >.05 | .5 | >.05 | 0 | 0 | 0 | 0 | 0 | 0 |
| 325 | .03 | .003 | >.05 | 0 | 0 | 1 | 0 | 0 | 0 |
| 326 | .002 | .001 | .03 | 1 | 2 | 5 | 2 | 3 | 5 |
| 327 | .003 | .002 | .05 | 1 | 2 | 5 | 2 | 3 | 5 |
| 328 | .002 | .003 | .04 | 1 | 2 | 5 | 2 | 3 | 5 |
| 329 | .002 | .003 | >.05 | 0 | 1 | 3 | 1 | 2 | 3 |
| 330 | .002 | .005 | >.05 | 0 | 0 | 0 | 0 | 0 | 0 |
| 331 | .001 | .003 | >.05 | 0 | 0 | 0 | 0 | 0 | 0 |
| 332 | .002 | .005 | >.05 | 0 | 0 | 0 | 0 | 0 | 0 |
| 333 | >.05 | >.05 | >.05 | 0 | 0 | 0 | 0 | 0 | 0 |
| 334 | .03 | .008 | >.05 | 0 | 0 | 0 | 0 | 0 | 0 |
| 335 | >.05 | .1 | >.05 | 0 | 0 | 0 | 2 | 4 | 5 |
| 336 | >.05 | .1 | >.05 | 0 | 0 | 0 | 0 | 0 | 0 |
| 337 | .03 | >.05 | >.05 | 0 | 0 | 0 | 0 | 0 | 0 |
| 338 | .005 | .002 | >.05 | 1 | 3 | 5 | 1 | 2 | 5 |
| 339 | .005 | .002 | >.05 | 1 | 3 | 4 | 1 | 2 | 3 |
| 340 | .03 | .005 | .03 | 0 | 1 | 3 | 1 | 2 | 3 |
| 341 | .01 | .008 | >.05 | 0 | 2 | 3 | 1 | 2 | 3 |
| 342 | .01 | .009 | .05 | 0 | 0 | 1 | 0 | 1 | 2 |
| 343 | .002 | .005 | >.05 | 0 | 2 | 3 | 1 | 2 | 4 |
| 344 | >.05 | .1 | >.05 | 0 | 0 | 0 | 0 | 0 | 0 |
| 345 | .002 | .003 | .03 | 0 | 1 | 3 | 1 | 2 | 3 |
| 346 | .03 | .008 | >.05 | 0 | 0 | 0 | 0 | 0 | 1 |
| 347 | .03 | .009 | >.05 | 0 | 0 | 0 | 0 | 0 | 0 |
| 348 | .005 | .002 | .05 | 0 | 1 | 4 | 0 | 1 | 3 |
| 349 | >.05 | .05 | >.05 | 0 | 2 | 4 | 0 | 2 | 3 |
| 350 | .005 | .005 | .03 | 0 | 1 | 4 | 1 | 2 | 3 |
| 351 | .03 | .005 | >.05 | 0 | 1 | 2 | 1 | 2 | 3 |
| 352 | .005 | .003 | >.05 | 0 | 0 | 2 | 1 | 1 | 2 |
| 353 | .03 | .002 | .05 | 0 | 0 | 0 | 0 | 0 | 0 |
| 354 | .002 | .002 | .01 | 0 | 0 | 0 | 0 | 0 | 0 |
| 355 | .002 | .001 | .05 | 0 | 3 | 4 | 1 | 2 | 5 |
| 356 | .005 | .005 | >.05 | 0 | 1 | 2 | 0 | 2 | 4 |
| 357 | .03 | .005 | .05 | 0 | 0 | 0 | 0 | 0 | 0 |
| 358 | .05 | >.05 | .05 | 0 | 0 | 0 | 0 | 0 | 0 |
| 359 | .002 | .005 | .05 | 0 | 2 | 3 | 1 | 2 | 2 |
| 360 | .005 | .002 | .05 | 0 | 1 | 3 | 1 | 2 | 3 |
| 361 | .01 | .003 | >.05 | 0 | 0 | 0 | 0 | 0 | 0 |
| 362 | .008 | .008 | >.05 | 0 | 0 | 0 | 0 | 0 | 0 |
| 363 | .05 | .002 | .05 | 0 | 0 | 0 | 0 | 0 | 0 |
| 364 | .005 | .002 | .05 | 0 | 0 | 1 | 0 | 0 | 1 |
| 365 | >.05 | .2 | >.05 | 0 | 0 | 0 | 0 | 0 | 0 |
| 366 | >.05 | >.05 | .05 | 0 | 0 | 0 | 0 | 0 | 0 |
| 367 | .003 | .005 | >.05 | 0 | 1 | 2 | 0 | 1 | 2 |
| 368 | >.05 | .03 | .05 | 0 | 0 | 0 | 0 | 0 | 0 |
| 369 | .003 | .003 | .05 | 0 | 1 | 2 | 0 | 1 | 2 |
| 370 | .005 | .005 | .05 | 0 | 0 | 2 | 0 | 0 | 2 |
| 371 | .003 | .008 | .05 | 0 | 1 | 3 | 0 | 1 | 2 |
| 372 | .002 | .002 | >.05 | 0 | 0 | 1 | 0 | 1 | 2 |
| 373 | .002 | .005 | >.05 | 0 | 2 | 4 | 1 | 2 | 3 |
| 374 | .001 | .002 | >.05 | 0 | 1 | 2 | 0 | 1 | 2 |
| 375 | .002 | .002 | >.05 | 0 | 0 | 0 | 0 | 0 | 0 |
| 376 | .003 | .005 | .05 | | | | | | |
| 377 | .002 | .0005 | .05 | 0 | 0 | 0 | 0 | 0 | 1 |
| 378 | .003 | .005 | .05 | 0 | 0 | 0 | 0 | 0 | 1 |
| 379 | .002 | .003 | .05 | 0 | 0 | 0 | 0 | 0 | 0 |
| 380 | .002 | .0003 | .05 | 0 | 0 | 0 | 0 | 0 | 0 |
| 381 | .002 | .003 | >.05 | 0 | 0 | 0 | 0 | 0 | 0 |
| 382 | .002 | .0005 | .1 | 0 | 0 | 0 | 0 | 0 | 0 |
| 383 | .001 | .002 | .05 | 0 | 1 | 2 | 1 | 2 | 3 |
| 384 | .002 | .0008 | .05 | 0 | 0 | 0 | 0 | 0 | 1 |
| 385 | .002 | .0005 | .05 | 0 | 0 | 1 | 0 | 0 | 2 |
| 386 | .016 | .0016 | >.08 | 0 | 0 | 0 | 0 | 0 | 0 |
| 387 | .003 | .009 | .15 | 1 | 4 | 4 | 1 | 4 | 4 |
| 388 | .0024 | .006 | .03 | 0 | 0 | 3 | 0 | 1 | 1 |
| 389 | .004 | .0008 | >.1 | 0 | 0 | 2 | 0 | 0 | 2 |
| 390 | .05 | .03 | .05 | | | | | | |
| 391 | >.05 | >.05 | >.05 | | | | | | |
| 392 | >.05 | >.05 | .05 | | | | | | |
| 393 | .01 | .01 | >.1 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 394 | .05 | .03 | >.1 | 0 | 0 | 0 | 0 | 0 | 0 |
| 395 | .05 | >.05 | >.1 | 0 | 1 | 3 | 0 | 1 | 2 |
| 396 | .01 | .005 | >.1 | 0 | 0 | 0 | 0 | 0 | 0 |
| 397 | .05 | >.05 | >.1 | 0 | 0 | 0 | 0 | 0 | 2 |
| 398 | .05 | .003 | >.1 | 0 | 1 | 3 | 0 | 2 | 3 |
| 399 | .01 | .01 | .03 | 0 | 0 | 0 | 0 | 0 | 0 |
| 400 | .05 | .04 | | 0 | 0 | 0 | 0 | 0 | 0 |
| 401 | .002 | .002 | | 1 | 2 | 5 | 1 | 3 | 5 |
| 402 | .05 | >.05 | | 0 | 0 | 0 | 0 | 0 | 0 |
| 403 | .001 | .002 | | 0 | 2 | 4 | 1 | 2 | 5 |
| 404 | .03 | .008 | | 0 | 0 | 0 | 0 | 0 | 0 |
| 405 | .03 | .01 | | 0 | 0 | 0 | 0 | 0 | 1 |
| 406 | .03 | .03 | | 0 | 0 | 0 | 0 | 0 | 0 |
| 407 | .03 | .008 | | 0 | 0 | 0 | 0 | 0 | 1 |
| 408 | .03 | .03 | >.05 | 0 | 0 | 0 | 0 | 0 | 0 |
| 409 | .003 | .005 | >.05 | 0 | 0 | 0 | 0 | 0 | 0 |
| 410 | .0008 | .002 | .05 | 0 | 0 | 0 | 0 | 0 | 1 |
| 411 | .005 | .002 | .04 | 0 | 1 | 3 | 1 | 3 | 4 |
| 412 | .003 | .002 | >.05 | 0 | 0 | 2 | 0 | 0 | 2 |
| 413 | .003 | .001 | .04 | 0 | 0 | 0 | 0 | 0 | 0 |
| 414 | .005 | .003 | .04 | 0 | 0 | 1 | 0 | 0 | 1 |
| 415 | .002 | .001 | .04 | 0 | 1 | 3 | 0 | 1 | 2 |
| 416 | .005 | .002 | .04 | 0 | 0 | 0 | 0 | 0 | 1 |
| 417 | .003 | .0025 | >.05 | 0 | 0 | 0 | 0 | 0 | 0 |
| 418 | .008 | .003 | >.05 | 0 | 0 | 0 | 0 | 0 | 0 |
| 419 | .002 | .0025 | .05 | 0 | 0 | 0 | 0 | 0 | 0 |
| 420 | .01 | .003 | >.05 | 0 | 0 | 0 | 0 | 0 | 0 |
| 421 | .002 | .005 | .03 | 0 | 0 | 1 | 0 | 0 | 2 |
| 422 | .005 | .002 | .05 | 0 | 0 | 1 | 0 | 0 | 2 |
| 423 | .008 | .003 | <.01 | 0 | 0 | 0 | 0 | 0 | 2 |
| 424 | .03 | .001 | .05 | 0 | 0 | 0 | 0 | 0 | 0 |
| 425 | .01 | .002 | >.05 | 0 | 0 | 2 | 0 | 0 | 2 |
| 426 | .01 | .005 | >.05 | 0 | 1 | 2 | 0 | 1 | 2 |
| 427 | .01 | .002 | >.05 | 0 | 0 | 0 | 0 | 0 | 0 |
| 428 | .03 | .005 | >.05 | 0 | 0 | 0 | 0 | 0 | 0 |
| 429 | .002 | .001 | >.05 | 0 | 0 | 0 | 0 | 0 | 0 |
| 430 | .005 | .002 | >.05 | 0 | 0 | 0 | 0 | 0 | 1 |
| 431 | .01 | .002 | >.05 | 0 | 0 | 0 | 0 | 0 | 2 |
| 432 | .005 | .005 | >.05 | 0 | 0 | 2 | 0 | 0 | 2 |
| 433 | .005 | .005 | >.05 | 0 | 0 | 0 | 0 | 0 | 0 |
| 434 | .01 | .03 | >.05 | 0 | 0 | 0 | 0 | 0 | 0 |
| 435 | .01 | .002 | >.05 | 0 | 0 | 0 | 0 | 0 | 0 |
| 436 | .003 | .001 | .05 | 0 | 0 | 0 | 0 | 0 | 1 |
| 437 | .005 | .001 | >.05 | 0 | 0 | 0 | 0 | 0 | 0 |
| 438 | .003 | .002 | >.05 | 0 | 0 | 1 | 0 | 0 | 1 |
| 439 | .003 | .003 | >.05 | 0 | 0 | 0 | 0 | 0 | 0 |
| 440 | .003 | .003 | >.05 | 0 | 0 | 0 | 0 | 0 | 0 |
| 441 | .005 | .002 | >.05 | 0 | 0 | 0 | 0 | 0 | 0 |
| 442 | .003 | .005 | >.05 | 0 | 0 | 0 | 0 | 0 | 2 |
| 443 | .003 | .005 | >.05 | 0 | 0 | 0 | 0 | 0 | 0 |
| 444 | .008 | .01 | >.05 | 0 | 0 | 0 | 0 | 0 | 0 |
| 445 | .001 | .01 | >.05 | 0 | 0 | 0 | 0 | 0 | 0 |
| 446 | .003 | .008 | >.05 | 0 | 0 | 0 | 0 | 0 | 0 |
| 447 | .008 | .01 | >.05 | 0 | 0 | 0 | 0 | 0 | 0 |
| 448 | .005 | .005 | >.05 | 0 | 0 | 0 | 0 | 0 | 1 |
| 449 | .008 | .005 | >.05 | 0 | 0 | 0 | 0 | 0 | 0 |
| 450 | .005 | .005 | >.05 | 0 | 0 | 0 | 0 | 0 | 0 |
| 451 | .005 | .03 | .05 | 0 | 0 | 0 | 0 | 0 | 0 |
| 452 | .001 | .001 | .05 | 0 | 0 | 0 | 0 | 0 | 0 |
| 453 | .002 | .005 | .05 | 0 | 0 | 0 | 0 | 0 | 0 |
| 454 | .001 | .003 | >.05 | 0 | 0 | 0 | 0 | 0 | 0 |
| 455 | .008 | .002 | .06 | 0 | 0 | 1 | 0 | 0 | 1 |
| 456 | .002 | .002 | .05 | 0 | 0 | 0 | 0 | 0 | 0 |
| 457 | .005 | .002 | .05 | 0 | 0 | 0 | 0 | 0 | 0 |
| 458 | .005 | .01 | >.05 | 0 | 0 | 0 | 0 | 0 | 0 |
| 459 | .008 | .01 | .05 | 0 | 0 | 0 | 0 | 0 | 0 |
| 460 | .003 | .002 | <.05 | 0 | 0 | 0 | 0 | 0 | 0 |
| 461 | .005 | .002 | >.05 | 0 | 0 | 0 | 0 | 0 | 0 |
| 462 | .005 | .002 | >.05 | 0 | 0 | 0 | 0 | 0 | 0 |
| 463 | .005 | .005 | .05 | 0 | 0 | 0 | 0 | 0 | 0 |
| 464 | .002 | .005 | .05 | 0 | 0 | 0 | 0 | 0 | 0 |
| 465 | .005 | .002 | >.05 | 0 | 0 | 0 | 0 | 0 | 0 |
| 466 | .003 | .002 | .05 | 0 | 0 | 0 | 0 | 0 | 0 |
| 467 | .003 | .002 | >.05 | 0 | 0 | 1 | 1 | 0 | 2 |
| 468 | .002 | .002 | >.05 | 0 | 0 | 0 | 0 | 0 | 0 |
| 469 | .002 | .002 | >.05 | 0 | 0 | 0 | 0 | 0 | 0 |
| 470 | .002 | .003 | .05 | 0 | 0 | 0 | 0 | 0 | 0 |
| 471 | .002 | .005 | >.05 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 472 | .003 | .005 | >.05 | 0 | 0 | 0 | 0 | 0 | 1 |
| 473 | .002 | .002 | >.05 | 0 | 0 | 0 | 0 | 0 | 0 |
| 474 | .002 | .002 | .05 | 0 | 0 | 0 | 0 | 0 | 1 |
| 475 | .002 | .005 | >.05 | 0 | 0 | 0 | 0 | 0 | 1 |
| 476 | .002 | .002 | .05 | 0 | 0 | 0 | 0 | 0 | 0 |
| 477 | .005 | .002 | >.05 | 0 | 0 | 0 | 0 | 0 | 0 |
| 478 | .003 | .002 | >.05 | 0 | 0 | 0 | 0 | 0 | 0 |
| 479 | .005 | .01 | .05 | 0 | 0 | 0 | 0 | 0 | 0 |
| 480 | .003 | .002 | >.05 | 0 | 0 | 0 | 0 | 0 | 0 |
| 481 | .003 | .002 | .03 | 0 | 0 | 0 | 0 | 0 | 1 |
| 482 | .008 | .003 | .05 | 0 | 0 | 0 | 0 | 0 | 1 |
| 483 | .005 | .002 | >.05 | 0 | 0 | 0 | 0 | 0 | 0 |
| 484 | .003 | .002 | >.05 | 0 | 0 | 0 | 0 | 0 | 0 |
| 485 | .003 | .002 | >.05 | 0 | 0 | 0 | 0 | 0 | 0 |
| 486 | .005 | .002 | >.05 | 0 | 0 | 0 | 0 | 0 | 0 |
| 487 | .001 | .005 | >.05 | 0 | 0 | 0 | 0 | 0 | 0 |
| 488 | .003 | .002 | .05 | 0 | 0 | 0 | 0 | 0 | 1 |
| 489 | .01 | .002 | >.05 | 0 | 0 | 0 | 0 | 0 | 0 |
| 490 | .002 | .002 | >.05 | 0 | 0 | 0 | 0 | 0 | 0 |
| 491 | .005 | .003 | >.05 | 0 | 0 | 0 | 0 | 0 | 0 |
| 492 | .003 | .002 | >.05 | 0 | 0 | 0 | 0 | 0 | 0 |
| 493 | .005 | .005 | >.05 | 0 | 0 | 0 | 0 | 0 | 1 |
| 494 | .01 | .005 | >.05 | 0 | 0 | 0 | 0 | 0 | 0 |
| 495 | .01 | .002 | >.05 | 0 | 0 | 0 | 0 | 0 | 0 |
| 496 | .003 | .001 | >.05 | 0 | 0 | 0 | 0 | 0 | 0 |
| 497 | .001 | .002 | .01 | 0 | 0 | 0 | 0 | 0 | 0 |
| 498 | .0008 | .005 | .03 | 0 | 0 | 0 | 0 | 0 | 0 |
| 499 | .002 | .002 | .01 | 0 | 0 | 0 | 0 | 0 | 0 |
| 500 | .003 | .002 | .05 | 0 | 0 | 0 | 0 | 0 | 0 |
| 501 | .002 | .002 | .03 | 0 | 0 | 0 | 0 | 0 | 0 |
| 502 | .003 | .002 | >.05 | 0 | 0 | 0 | 0 | 0 | 0 |
| 503 | .002 | .001 | >.05 | 0 | 0 | 0 | 0 | 0 | 0 |
| 504 | .005 | .002 | >.05 | 0 | 0 | 0 | 0 | 0 | 0 |
| 505 | .008 | .001 | >.05 | 0 | 0 | 0 | 0 | 0 | 0 |
| 506 | .002 | >.003 | .01 | 0 | 0 | 0 | 0 | 0 | 0 |
| 507 | .002 | .005 | >.05 | 0 | 0 | 0 | 0 | 0 | 0 |
| 508 | .001 | .002 | .03 | 0 | 0 | 0 | 0 | 0 | 0 |
| 509 | .001 | .002 | .05 | 0 | 0 | 0 | 0 | 0 | 0 |
| 510 | .005 | .001 | >.05 | 0 | 0 | 0 | 0 | 0 | 0 |
| 511 | .001 | .005 | >.05 | 0 | 0 | 0 | 0 | 0 | 0 |
| 512 | .001 | .005 | .05 | 0 | 0 | 1 | 0 | 0 | 1 |
| 513 | .002 | .005 | >.05 | 0 | 0 | 1 | 0 | 0 | 1 |
| 514 | .005 | .006 | >.05 | 0 | 0 | 0 | 0 | 0 | 0 |
| 515 | .002 | .002 | .05 | 0 | 0 | 0 | 0 | 0 | 0 |
| 516 | .001 | .005 | >.05 | 0 | 0 | 0 | 0 | 0 | 0 |
| 517 | .002 | .002 | >.05 | 0 | 0 | 1 | 0 | 0 | 1 |
| 518 | .003 | .005 | >.05 | 0 | 0 | 0 | 0 | 0 | 1 |
| 519 | .001 | .005 | >.05 | 0 | 0 | 0 | 0 | 0 | 0 |
| 520 | .001 | .005 | >.05 | 0 | 0 | 0 | 0 | 0 | 0 |
| 521 | .008 | .003 | >.05 | 0 | 0 | 0 | 0 | 0 | 0 |
| 522 | .005 | .003 | >.05 | 0 | 0 | 0 | 0 | 0 | 0 |
| 523 | .005 | .005 | >.05 | 0 | 0 | 0 | 0 | 0 | 0 |
| 524 | .002 | .0002 | >.05 | 0 | 0 | 0 | 0 | 0 | 0 |
| 525 | .002 | .001 | >.05 | 0 | 0 | 0 | 0 | 0 | 0 |
| 526 | .002 | .0005 | >.05 | 0 | 0 | 0 | 0 | 0 | 0 |
| 527 | .002 | .0003 | >.05 | 0 | 0 | 0 | 0 | 0 | 0 |
| 528 | .002 | .0002 | .05 | 0 | 0 | 1 | 0 | 1 | 3 |
| 529 | .002 | .0002 | >.05 | 0 | 0 | 0 | 0 | 0 | 0 |
| 530 | .002 | .001 | >.05 | 0 | 0 | 0 | 0 | 0 | 0 |
| 531 | .002 | .001 | >.05 | 0 | 0 | 0 | 0 | 0 | 0 |
| 532 | .001 | .0002 | .05 | 0 | 0 | 0 | 0 | 0 | 2 |
| 533 | .002 | .0001 | <.05 | 0 | 0 | 0 | 0 | 0 | 0 |
| 534 | .002 | .002 | .05 | 0 | 0 | 0 | 0 | 0 | 0 |
| 535 | .002 | .0002 | <.05 | 0 | 0 | 0 | 0 | 0 | 0 |
| 536 | .002 | .0005 | >.05 | 0 | 0 | 0 | 0 | 0 | 0 |
| 537 | .001 | .0005 | .05 | 0 | 0 | 0 | 0 | 0 | 0 |
| 538 | .002 | .002 | .05 | 0 | 0 | 0 | 0 | 0 | 0 |
| 539 | .001 | .0005 | .05 | 0 | 0 | 0 | 0 | 0 | 0 |
| 540 | .002 | .0001 | .05 | 0 | 0 | 0 | 0 | 0 | 0 |
| 541 | .0002 | .001 | .05 | 0 | 0 | 0 | 0 | 0 | 0 |
| 542 | .03 | .002 | .05 | 0 | 0 | 0 | 0 | 0 | 0 |
| 543 | .0005 | .0003 | <.05 | 0 | 0 | 0 | 0 | 0 | 0 |
| 544 | .002 | .0001 | .05 | 0 | 0 | 0 | 0 | 0 | 0 |
| 545 | .03 | .002 | .05 | 0 | 0 | 0 | 0 | 0 | 0 |
| 546 | .001 | .0001 | .05 | 0 | 0 | 0 | 0 | 0 | 0 |
| 547 | .0005 | .0005 | .05 | 0 | 0 | 1 | 0 | 0 | 3 |
| 548 | .001 | .0003 | <.05 | 0 | 0 | 1 | 0 | 0 | 1 |
| 549 | .002 | .0002 | .05 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 550 | .002 | .0002 | .05 | 0 | 0 | 0 | 0 | 0 | 0 |
| 551 | .03 | .001 | .05 | 0 | 0 | 1 | 0 | 0 | 1 |
| 552 | .0003 | .0002 | .05 | 0 | 0 | 0 | 0 | 0 | 1 |
| 553 | .001 | .0003 | <.05 | 0 | 0 | 0 | 0 | 0 | 1 |
| 554 | .001 | .0003 | .05 | 0 | 0 | 0 | 0 | 0 | 0 |
| 555 | .002 | .0008 | >.05 | 0 | 0 | 0 | 0 | 0 | 0 |
| 556 | .0005 | .0001 | <.05 | 0 | 0 | 0 | 0 | 0 | 1 |
| 557 | .0005 | .0002 | .05 | 0 | 0 | 0 | 0 | 0 | 2 |
| 558 | .0002 | .0003 | <.05 | 0 | 0 | 0 | 0 | 0 | 0 |
| 559 | .003 | .002 | .05 | 0 | 0 | 1 | 0 | 0 | 1 |
| 560 | .003 | .002 | >.05 | 0 | 0 | 0 | 0 | 0 | 1 |
| 561 | .001 | .002 | .03 | 0 | 1 | 3 | 0 | 1 | 5 |
| 562 | .001 | .001 | .05 | 0 | 0 | 2 | 0 | 0 | 2 |
| 563 | .001 | .0003 | .05 | 0 | 0 | 0 | 0 | 0 | 0 |
| 564 | .003 | .0005 | >.05 | 0 | 0 | 2 | 0 | 1 | 3 |
| 565 | .002 | .0005 | >.05 | 0 | 1 | 2 | 0 | 1 | 2 |
| 566 | .0005 | .0005 | .05 | 0 | 0 | 2 | 0 | 1 | 3 |
| 567 | .0003 | .0005 | .05 | 0 | 0 | 2 | 0 | 1 | 2 |
| 568 | .0003 | .0002 | >.05 | 0 | 0 | 1 | 0 | 1 | 2 |
| 569 | .0008 | .0003 | .02 | 0 | 0 | 0 | 0 | 0 | 1 |
| 570 | .0003 | .0003 | .05 | 0 | 0 | 1 | 0 | 0 | 1 |
| 571 | .0005 | .0003 | >.05 | 0 | 0 | 2 | 0 | 1 | 2 |
| 572 | .0002 | .0002 | .05 | 0 | 0 | 2 | 0 | 1 | 3 |
| 573 | .001 | .0005 | >.05 | 0 | 0 | 1 | 0 | 1 | 2 |
| 574 | .001 | .0005 | >.05 | 0 | 0 | 2 | 0 | 1 | 2 |
| 575 | .01 | .0008 | >.05 | 0 | 0 | 1 | 0 | 1 | 2 |
| 576 | .0002 | .0005 | >.05 | 0 | 0 | 1 | 0 | 0 | 2 |
| 577 | .0002 | .0003 | .05 | 0 | 0 | 1 | 0 | 0 | 2 |
| 578 | .0005 | .0005 | >.05 | 0 | 0 | 1 | 0 | 0 | 2 |
| 579 | .0005 | .0005 | >.05 | 0 | 0 | 0 | 0 | 1 | 2 |
| 580 | .0005 | .0008 | >.05 | 0 | 0 | 0 | 0 | 0 | 1 |
| 581 | .0002 | .0005 | .05 | 0 | 0 | 0 | 0 | 0 | 1 |
| 582 | .0002 | .0005 | .005 | 0 | 0 | 1 | 0 | 0 | 2 |
| 583 | .0003 | .0003 | >.05 | 0 | 0 | 1 | 0 | 0 | 2 |
| 584 | .002 | .001 | .05 | 0 | 0 | 0 | 0 | 0 | 0 |
| 585 | .003 | .002 | .05 | 0 | 0 | 0 | 0 | 0 | 0 |
| 586 | .03 | .005 | .05 | 0 | 0 | 1 | 0 | 0 | 0 |
| 587 | .01 | .002 | .05 | 0 | 0 | 0 | 0 | 0 | 0 |
| 588 | >.05 | .05 | .05 | 0 | 0 | 0 | 0 | 0 | 0 |
| 589 | >.05 | .008 | .05 | 0 | 0 | 0 | 0 | 0 | 0 |
| 590 | .05 | .002 | >.05 | 0 | 1 | 3 | 0 | 1 | 2 |
| 591 | .05 | .01 | .05 | 0 | 0 | 1 | 0 | 0 | 0 |
| 592 | .01 | .01 | <.05 | 0 | 0 | 0 | 0 | 0 | 0 |
| 593 | .03 | .01 | >.05 | 0 | 0 | 0 | 0 | 0 | 0 |
| 594 | .005 | .002 | .05 | 0 | 0 | 0 | 0 | 0 | 0 |
| 595 | >.05 | .005 | .05 | 0 | 0 | 0 | 0 | 0 | 0 |
| 596 | .002 | .002 | .04 | 0 | 0 | 0 | 0 | 0 | 0 |
| 597 | .005 | .005 | .05 | 0 | 0 | 0 | 0 | 0 | 1 |
| 598 | .005 | .01 | >.05 | 0 | 0 | 0 | 0 | 0 | 1 |
| 599 | .001 | .0002 | .02 | 0 | 0 | 0 | 0 | 0 | 1 |
| 600 | <.001 | .0005 | .04 | 0 | 0 | 0 | 0 | 0 | 0 |
| 601 | <.001 | .0003 | .005 | 0 | 0 | 1 | 0 | 0 | 1 |
| 602 | .002 | .003 | >.05 | 0 | 1 | 2 | 0 | 1 | 2 |
| 603 | .002 | .0003 | .08 | 0 | 0 | 0 | 0 | 0 | 1 |
| 604 | .003 | .003 | .05 | 0 | 0 | 1 | 0 | 0 | 1 |
| 605 | .003 | .05 | >.05 | 0 | 0 | 0 | 0 | 0 | 0 |
| 606 | >.05 | .4 | >.05 | 0 | 0 | 0 | 0 | 0 | 0 |
| 607 | >.05 | .05 | >.05 | 0 | 0 | 0 | 0 | 0 | 0 |
| 608 | >.05 | .2 | >.05 | 0 | 0 | 0 | 0 | 0 | 0 |
| 609 | .003 | .0003 | .05 | 0 | 0 | 1 | 0 | 0 | 1 |
| 610 | .002 | .0005 | >.05 | 0 | 0 | 2 | 0 | 0 | 1 |
| 611 | .008 | .0002 | >.05 | 0 | 0 | 1 | 0 | 0 | 1 |
| 612 | .002 | .001 | >.05 | 0 | 0 | 1 | 0 | 0 | 1 |
| 613 | .003 | .001 | .05 | 0 | 0 | 1 | 0 | 0 | 1 |
| 614 | .01 | .003 | >.05 | 0 | 0 | 1 | 0 | 0 | 1 |
| 615 | .001 | .002 | .04 | 0 | 0 | 2 | 0 | 0 | 2 |
| 616 | .004 | <.001 | >.05 | 0 | 0 | 1 | 0 | 0 | 2 |
| 617 | .003 | .01 | .05 | 0 | 0 | 1 | 0 | 0 | 2 |
| 618 | .001 | .005 | .05 | 0 | 0 | 2 | 0 | 0 | 1 |
| 619 | .002 | .005 | .05 | 0 | 0 | 1 | 0 | 0 | 2 |
| 620 | .002 | .002 | >.05 | 0 | 0 | 1 | 0 | 0 | 1 |
| 621 | .01 | .003 | .05 | 0 | 0 | 0 | 0 | 0 | 0 |
| 622 | .03 | .001 | >.05 | 0 | 0 | 1 | 0 | 0 | 1 |
| 623 | .002 | .01 | >.05 | 0 | 0 | 1 | 0 | 0 | 1 |
| 624 | .001 | .0008 | .03 | 0 | 0 | 0 | 0 | 0 | 1 |
| 625 | .003 | .001 | .05 | 0 | 0 | 0 | 0 | 0 | 0 |
| 626 | .003 | .0005 | .03 | 0 | 0 | 1 | 0 | 0 | 1 |
| 627 | .005 | .001 | .01 | 0 | 0 | 1 | 0 | 0 | 1 |
| 628 | .003 | .001 | >.05 | 0 | 0 | 0 | 0 | 0 | 0 |
| 629 | .001 | .0005 | >.05 | 0 | 0 | 0 | 0 | 0 | 0 |
| 630 | .003 | <.001 | .05 | 0 | 1 | 2 | 0 | 1 | 2 |
| 631 | >.05 | .01 | >.05 | 0 | 0 | 1 | 0 | 0 | 1 |
| 632 | .005 | .023 | .05 | 0 | 0 | 1 | 0 | 1 | 2 |
| 633 | .01 | .01 | .1 | 0 | 0 | 1 | 0 | 0 | 0 |
| 634 | .002 | .003 | .05 | 1 | 2 | 4 | 1 | 2 | 3 |
| 635 | .008 | .002 | >.05 | 0 | 0 | 1 | 0 | 0 | 1 |
| 635 | >.05 | .1 | .05 | 0 | 0 | 0 | 0 | 0 | 0 |
| 636 | >.05 | .1 | .05 | 0 | 0 | 0 | 0 | 0 | 0 |
| 637 | .002 | .003 | >.05 | 0 | 1 | 3 | 0 | 1 | 4 |
| 638 | .003 | .003 | >.05 | 0 | 1 | 3 | 0 | 2 | 4 |
| 639 | >.05 | .1 | >.05 | 0 | 0 | 0 | 0 | 0 | 0 |
| 640 | .008 | .05 | >.05 | 0 | 1 | 2 | 0 | 1 | 3 |
| 641 | >.05 | .15 | >.05 | 0 | 0 | 0 | 0 | 1 | 2 |
| 642 | >.05 | .2 | >.05 | 0 | 0 | 0 | 0 | 0 | 0 |
| 643 | .003 | .03 | >.05 | 0 | 0 | 1 | 1 | 2 | 3 |
| 644 | .01 | >.05 | >.05 | 0 | 0 | 0 | 0 | 0 | 0 |
| 645 | .01 | >.05 | >.05 | 0 | 0 | 0 | 0 | 0 | 0 |
| 646 | .03 | .05 | >.05 | 0 | 0 | 0 | 0 | 0 | 0 |
| 647 | .03 | >.05 | >.05 | 0 | 0 | 0 | 0 | 0 | 0 |
| 648 | .01 | >.05 | >.05 | 0 | 0 | 0 | 0 | 0 | 0 |
| 649 | .003 | >.05 | >.05 | 0 | 0 | 0 | 0 | 0 | 0 |
| 650 | .003 | .003 | >.05 | 0 | 1 | 2 | 0 | 1 | 3 |
| 651 | .05 | .03 | >.05 | 0 | 0 | 0 | 0 | 0 | 0 |
| 652 | .05 | .03 | >.05 | 0 | 0 | 0 | 0 | 0 | 0 |
| 653 | .002 | .002 | <.05 | 0 | 1 | 2 | 0 | 1 | 3 |
| 654 | >.05 | .4 | >.05 | 0 | 0 | 0 | 0 | 0 | 0 |
| 655 | >.05 | .2 | >.05 | 0 | 0 | 0 | 0 | 0 | 0 |
| 656 | >.05 | .1 | >.05 | 0 | 0 | 0 | 0 | 0 | 0 |
| 657 | .05 | >.05 | >.05 | 0 | 0 | 0 | 0 | 0 | 0 |
| 658 | .03 | >.05 | >.05 | 0 | 0 | 0 | 0 | 0 | 0 |
| 659 | >.05 | .05 | .03 | 0 | 0 | 0 | 0 | 0 | 0 |
| 660 | >.05 | .03 | >.05 | 0 | 0 | 0 | 0 | 0 | 0 |
| 661 | .03 | .01 | >.05 | 0 | 3 | 5 | 1 | 4 | 5 |
| 662 | >.05 | >.05 | >.05 | 0 | 0 | 0 | 0 | 0 | 0 |
| 663 | .002 | .005 | .05 | 0 | 0 | 1 | 0 | 1 | 2 |
| 664 | <.001 | .002 | >.05 | 0 | 0 | 0 | 0 | 0 | 0 |
| 665 | <.001 | .005 | .05 | 0 | 0 | 0 | 0 | 0 | 0 |
| 666 | <.001 | .001 | >.05 | 0 | 0 | 0 | 0 | 0 | 1 |
| 667 | .03 | >.05 | >.05 | 0 | 0 | 0 | 0 | 0 | 0 |
| 668 | .03 | .1 | >.05 | 0 | 0 | 0 | 0 | 0 | 0 |
| 669 | .002 | .002 | .05 | 0 | 1 | 2 | 1 | 3 | 4 |
| 670 | .03 | .05 | >.05 | 0 | 0 | 0 | 0 | 0 | 0 |
| 671 | .001 | <.001 | .05 | 0 | 0 | 0 | 0 | 0 | 0 |
| 672 | >.05 | >.05 | >.05 | 0 | 0 | 0 | 0 | 0 | 0 |
| 673 | >.05 | .5 | >.05 | 0 | 0 | 0 | 0 | 0 | 0 |
| 674 | >.05 | >.05 | >.05 | 0 | 0 | 0 | 0 | 0 | 0 |
| 675 | .05 | >.05 | >.05 | 0 | 0 | 0 | 0 | 0 | 0 |
| 676 | >.05 | >.05 | >.05 | 0 | 0 | 0 | 0 | 0 | 0 |
| 677 | >.05 | .2 | >.05 | 0 | 0 | 0 | 0 | 0 | 0 |
| 678 | >.05 | .1 | >.05 | 0 | 0 | 0 | 0 | 0 | 0 |
| 679 | .003 | .003 | >.05 | 0 | 0 | 1 | 0 | 1 | 2 |
| 680 | .002 | .002 | >.05 | 0 | 1 | 2 | 0 | 0 | 1 |
| 681 | >.05 | .1 | >.05 | 0 | 0 | 0 | 0 | 0 | 0 |
| 682 | >.05 | >.05 | >.05 | 0 | 0 | 0 | 0 | 0 | 0 |
| 683 | >.05 | >.05 | >.05 | 0 | 0 | 0 | 0 | 0 | 0 |
| 684 | >.05 | .1 | >.05 | 0 | 0 | 0 | 0 | 0 | 0 |
| 685 | >.05 | .15 | >.05 | 0 | 0 | 0 | 0 | 0 | 0 |
| 686 | >.05 | >.05 | >.05 | 0 | 0 | 0 | 0 | 0 | 0 |
| 687 | >.05 | >.05 | >.05 | 0 | 0 | 0 | 0 | 0 | 0 |
| 688 | .03 | .003 | >.05 | 0 | 0 | 1 | 0 | 0 | 1 |
| 689 | .01 | .03 | >.05 | 0 | 1 | 2 | 0 | 1 | 2 |
| 690 | >.05 | .1 | >.05 | 0 | 0 | 0 | 0 | 1 | 2 |
| 691 | .008 | .002 | >.05 | 0 | 0 | 0 | 0 | 0 | 0 |
| 692 | .008 | .008 | >.05 | 0 | 0 | 0 | 0 | 0 | 0 |
| 693 | .03 | .03 | >.05 | 0 | 0 | 0 | 0 | 0 | 0 |
| 694 | .0003 | .002 | .03 | 0 | 0 | 0 | 0 | 0 | 0 |
| 695 | .002 | .005 | .03 | 0 | 0 | 0 | 0 | 0 | 0 |
| 696 | .0005 | .0008 | >.05 | 0 | 0 | 0 | 0 | 0 | 0 |
| 697 | >.05 | .03 | >.05 | 0 | 0 | 0 | 0 | 0 | 0 |
| 698 | >.05 | .03 | >.05 | 0 | 0 | 0 | 0 | 0 | 0 |
| 699 | >.05 | .12 | >.05 | 0 | 0 | 0 | 0 | 1 | 2 |
| 700 | .008 | .03 | >.05 | 0 | 0 | 0 | 0 | 0 | 0 |
| 701 | >.05 | .4 | >.05 | 0 | 0 | 0 | 0 | 0 | 0 |
| 702 | >.05 | .4 | >.05 | 0 | 0 | 0 | 0 | 0 | 0 |
| 703 | .005 | .03 | >.05 | 0 | 0 | 0 | 0 | 0 | 0 |
| 704 | .002 | .001 | >.05 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 705 | .001 | .0008 | .05 | 0 | 0 | 0 | 0 | 0 | 0 |
| 706 | .01 | .005 | >.05 | 0 | 0 | 0 | 0 | 0 | 0 |
| 707 | .001 | .03 | >.05 | 0 | 0 | 0 | 0 | 0 | 1 |
| 708 | .0003 | .001 | >.05 | 0 | 0 | 0 | 0 | 0 | 0 |
| 709 | .003 | .008 | >.05 | 0 | 0 | 0 | 0 | 0 | 0 |
| 710 | .005 | .005 | >.05 | 0 | 0 | 0 | 0 | 0 | 0 |
| 711 | .03 | .03 | >.05 | 0 | 0 | 0 | 0 | 0 | 0 |
| 712 | .001 | .002 | >.05 | 0 | 0 | 0 | 0 | 0 | 0 |
| 713 | .002 | .002 | >.05 | 0 | 0 | 0 | 0 | 0 | 0 |
| 714 | .008 | .003 | >.05 | 0 | 0 | 0 | 0 | 0 | 0 |
| 715 | .0005 | .003 | >.05 | 0 | 0 | 0 | 0 | 0 | 0 |
| 716 | >.05 | >.05 | >.05 | 0 | 0 | 0 | 0 | 0 | 1 |
| 717 | .005 | .003 | >.05 | 0 | 0 | 0 | 0 | 0 | 1 |
| 718 | .001 | .0005 | .03 | 0 | 0 | 0 | 0 | 0 | 0 |
| 719 | .002 | .001 | <.05 | 0 | 0 | 0 | 0 | 0 | 0 |
| 720 | .002 | .003 | <.05 | 0 | 0 | 0 | 0 | 0 | 1 |
| 721 | .002 | .01 | <.05 | 0 | 0 | 0 | 0 | 0 | 0 |
| 722 | .001 | .005 | .1 | 0 | 0 | 0 | 0 | 0 | 0 |
| 723 | >.05 | >.05 | >.05 | 0 | 0 | 0 | 0 | 0 | 0 |
| 724 | .002 | .01 | .05 | 0 | 0 | 0 | 0 | 0 | 0 |
| 725 | .002 | .03 | >.05 | 0 | 0 | 0 | 0 | 0 | 0 |
| 726 | .0005 | .0008 | .04 | 0 | 0 | 0 | 0 | 0 | 0 |
| 727 | .03 | .01 | .05 | 0 | 0 | 0 | 0 | 0 | 0 |
| 728 | .03 | .03 | .05 | 0 | 0 | 0 | 0 | 0 | 0 |
| 729 | .001 | .001 | .01 | 0 | 0 | 0 | 0 | 0 | 0 |
| 730 | .05 | >.05 | >.05 | 0 | 0 | 0 | 0 | 0 | 0 |
| 731 | .0005 | .0005 | >.05 | 0 | 0 | 0 | 0 | 0 | 0 |
| 732 | >.05 | >.05 | >.05 | 0 | 0 | 0 | 0 | 0 | 0 |
| 733 | >.05 | >.05 | >.05 | 0 | 0 | 0 | 0 | 0 | 1 |
| 734 | >.003 | .12 | .05 | 0 | 0 | 0 | 0 | 0 | 0 |
| 735 | .01 | .008 | .1 | 0 | 0 | 0 | 0 | 0 | 0 |
| 736 | >.05 | .4 | >.1 | 0 | 0 | 0 | 0 | 1 | 2 |
| 737 | .01 | >.05 | >.1 | 0 | 0 | 0 | 0 | 0 | 0 |
| 738 | >.05 | .2 | .04 | 0 | 0 | 1 | 0 | 1 | 2 |
| 739 | >.05 | >.05 | .05 | 0 | 0 | 1 | 0 | 0 | 1 |
| 740 | >.05 | .1 | .04 | 0 | 0 | 0 | 0 | 1 | 2 |
| 741 | >.05 | .03 | .04 | 0 | 0 | 0 | 0 | 0 | 0 |
| 742 | >.05 | .03 | .05 | 0 | 0 | 0 | 0 | 0 | 0 |
| 743 | .05 | .005 | .04 | 0 | 0 | 0 | 0 | 0 | 0 |
| 744 | >.05 | .1 | >.05 | 0 | 0 | 0 | 0 | 1 | 2 |
| 745 | >.05 | .05 | .05 | 0 | 0 | 0 | 0 | 1 | 2 |
| 746 | .005 | .005 | .04 | 0 | 0 | 0 | 0 | 0 | 0 |
| 747 | .003 | .0005 | .05 | 0 | 0 | 0 | 0 | 0 | 0 |
| 748 | .05 | .1 | >.05 | 0 | 0 | 0 | 0 | 0 | 0 |
| 749 | >.05 | .005 | >.05 | 0 | 0 | 0 | 0 | 0 | 0 |
| 750 | .03 | >.05 | >.05 | 0 | 0 | 0 | 0 | 0 | 0 |
| 751 | .005 | <.001 | .05 | 0 | 0 | 0 | 0 | 0 | 0 |
| 752 | .01 | .008 | >.05 | 0 | 0 | 0 | 0 | 0 | 2 |
| 753 | .03 | .05 | >.05 | 0 | 0 | 0 | 0 | 0 | 0 |
| 754 | .005 | .03 | >.05 | 0 | 0 | 0 | 0 | 0 | 1 |
| 755 | .003 | .05 | >.05 | 0 | 0 | 0 | 0 | 0 | 1 |
| 756 | .008 | .03 | .05 | 0 | 0 | 0 | 0 | 0 | 1 |
| 757 | .03 | .03 | .05 | 0 | 0 | 0 | 0 | 1 | 2 |
| 758 | .008 | .03 | .05 | 0 | 0 | 0 | 0 | 0 | 2 |
| 759 | .01 | .15 | >.05 | 0 | 0 | 0 | 0 | 0 | 0 |
| 760 | .006 | .01 | .05 | 0 | 0 | 0 | 0 | 0 | 0 |
| 761 | >.05 | .5 | >.05 | 0 | 0 | 0 | 0 | 0 | 0 |
| 762 | .05 | .01 | >.05 | 0 | 0 | 0 | 0 | 0 | 0 |
| 763 | .05 | .05 | >.05 | 0 | 0 | 0 | 0 | 0 | 0 |
| 764 | >.05 | .03 | .05 | 0 | 0 | 0 | 0 | 0 | 0 |
| 765 | >.05 | .05 | >.05 | 0 | 0 | 0 | 0 | 0 | 0 |
| 766 | >.05 | >.05 | .05 | 0 | 0 | 0 | 0 | 0 | 0 |
| 767 | >.05 | .01 | >.05 | 0 | 0 | 0 | 0 | 0 | 0 |
| 768 | .05 | .05 | >.05 | 0 | 0 | 0 | 0 | 0 | 0 |
| 769 | >.05 | >.05 | >.05 | 0 | 0 | 0 | 0 | 0 | 0 |
| 770 | >.05 | .1 | >.05 | 0 | 0 | 0 | 0 | 0 | 0 |
| 771 | .01 | .1 | >.05 | 0 | 0 | 0 | 0 | 0 | 0 |
| 772 | .003 | .005 | .05 | 0 | 0 | 0 | 0 | 0 | 0 |
| 773 | .01 | .005 | >.05 | 0 | 0 | 0 | 0 | 0 | 0 |
| 774 | .0005 | .0008 | .01 | 0 | 0 | 1 | 0 | 0 | 0 |
| 775 | .0003 | .0004 | .003 | 0 | 0 | 1 | 0 | 0 | 2 |
| 776 | .0005 | .001 | .05 | 0 | 0 | 1 | 0 | 0 | 1 |
| 777 | .003 | .005 | >.05 | 0 | 1 | 3 | 0 | 1 | 2 |
| 778 | .0003 | .0003 | .05 | 0 | 0 | 1 | 0 | 0 | 1 |
| 779 | .05 | >.05 | >.05 | 0 | 0 | 0 | 0 | 0 | 0 |
| 780 | .03 | >.05 | >.05 | 0 | 0 | 0 | 0 | 0 | 0 |
| 781 | >.05 | >.05 | >.05 | 0 | 0 | 0 | 0 | 0 | 0 |
| 782 | .05 | >.05 | >.05 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 783 | .03 | >.05 | >.05 | 0 | 0 | 0 | 0 | 0 | 0 |
| 784 | .05 | >.05 | >.05 | 0 | 0 | 0 | 0 | 0 | 0 |
| 785 | >.05 | >.05 | >.05 | 0 | 0 | 0 | 0 | 0 | 0 |
| 786 | >.05 | >.05 | >.05 | 0 | 0 | 0 | 0 | 0 | 0 |
| 787 | >.05 | >.05 | >.05 | 0 | 0 | 0 | 0 | 0 | 0 |
| 788 | .008 | .01 | >.05 | 0 | 0 | 1 | 0 | 0 | 1 |
| 789 | .003 | >.003 | >.05 | 0 | 1 | 2 | 0 | 0 | 1 |
| 790 | .002 | .0005 | .02 | 0 | 1 | 3 | 1 | 2 | 4 |
| 791 | .003 | .001 | .05 | 0 | 0 | 1 | 0 | 0 | 1 |
| 792 | .01 | .003 | .05 | 0 | 0 | 1 | 0 | 0 | 1 |
| 793 | .0003 | .0005 | .05 | 0 | 0 | 0 | 0 | 0 | 0 |
| 794 | .001 | .003 | >.05 | 0 | 0 | 0 | 0 | 0 | 0 |
| 795 | .001 | .001 | >.05 | 0 | 0 | 0 | 0 | 0 | 0 |
| 796 | .002 | .003 | >.05 | 0 | 0 | 0 | 0 | 0 | 0 |
| 797 | >.05 | >.05 | >.05 | 0 | 0 | 0 | 0 | 0 | 0 |
| 798 | .002 | .008 | >.05 | 1 | 2 | 4 | 1 | 2 | 4 |
| 799 | .002 | .002 | >.05 | 0 | 0 | 0 | 0 | 0 | 0 |
| 800 | .002 | .002 | >.05 | 0 | 0 | 0 | 0 | 0 | 1 |
| 801 | .005 | .003 | .03 | 0 | 0 | 1 | 0 | 1 | 2 |
| 802 | .001 | .008 | >.05 | 0 | 0 | 2 | 0 | 1 | 2 |
| 803 | >.05 | .01 | >.05 | 0 | 1 | 2 | 0 | 0 | 1 |
| 804 | .002 | .001 | .01 | 1 | 2 | 4 | 1 | 2 | 4 |
| 805 | .01 | .003 | >.05 | 0 | 1 | 2 | 0 | 1 | 2 |
| 806 | .03 | .005 | >.05 | 0 | 1 | 2 | 0 | 1 | 2 |
| 807 | .005 | .003 | >.05 | 0 | 0 | 1 | 0 | 0 | 1 |
| 808 | .002 | .001 | .04 | 0 | 1 | 2 | 0 | 0 | 2 |
| 809 | .003 | .001 | .04 | 0 | 1 | 2 | 0 | 0 | 2 |
| 810 | .003 | .002 | .05 | 0 | 1 | 2 | 0 | 1 | 2 |
| 811 | .003 | .003 | >.05 | 0 | 0 | 1 | 0 | 0 | 0 |
| 812 | .003 | .005 | >.05 | 0 | 0 | 2 | 0 | 0 | 2 |
| 813 | .003 | .002 | .05 | 1 | 2 | 3 | 0 | 0 | 2 |
| 814 | >.05 | >.05 | >.05 | 0 | 0 | 0 | 0 | 0 | 0 |
| 815 | .003 | .005 | >.05 | 0 | 1 | 2 | 0 | 0 | 1 |
| 816 | .002 | .003 | >.05 | 0 | 1 | 3 | 0 | 1 | 2 |
| 817 | .002 | .0003 | .05 | 1 | 2 | 3 | 0 | 1 | 2 |
| 818 | .002 | .002 | .05 | 0 | 1 | 2 | 0 | 0 | 2 |
| 819 | .005 | .003 | >.05 | 0 | 1 | 2 | 0 | 0 | 1 |
| 820 | .002 | .002 | >.05 | 0 | 0 | 0 | 0 | 0 | 0 |
| 821 | >.05 | .03 | >.05 | 0 | 0 | 0 | 0 | 0 | 0 |
| 822 | .005 | .005 | >.05 | 0 | 0 | 0 | 0 | 0 | 0 |
| 823 | .003 | .003 | .05 | 0 | 0 | 0 | 0 | 0 | 0 |
| 824 | .005 | .005 | >.05 | 1 | 2 | 4 | 0 | 1 | 4 |
| 825 | .005 | .003 | .05 | 0 | 1 | 2 | 0 | 0 | 2 |
| 826 | .005 | .008 | >.05 | 0 | 0 | 1 | 0 | 0 | 1 |
| 827 | .003 | .03 | >.05 | 0 | 0 | 0 | 0 | 0 | 0 |
| 828 | .03 | .01 | >.05 | 0 | 1 | 3 | 0 | 1 | 3 |
| 829 | >.05 | .03 | >.05 | 0 | 0 | 0 | 0 | 0 | 0 |
| 830 | .008 | .005 | >.05 | 0 | 0 | 1 | 0 | 0 | 0 |
| 831 | .0005 | .0006 | .05 | 1 | 2 | 4 | 1 | 3 | 5 |
| 832 | .001 | .003 | .005 | 0 | 1 | 2 | 0 | 1 | 2 |
| 833 | .001 | .0007 | .005 | 0 | 1 | 3 | 0 | 1 | 3 |
| 834 | .001 | .001 | .02 | 0 | 0 | 2 | 0 | 0 | 2 |
| 835 | — | .03 | >.05 | 0 | 1 | 2 | 0 | 0 | 1 |
| 836 | .005 | .05 | >.05 | 0 | 1 | 2 | 0 | 0 | 0 |
| 837 | .003 | .01 | .05 | 0 | 0 | 0 | 0 | 0 | 0 |
| 838 | .002 | .001 | .03 | 0 | 1 | 2 | 0 | 1 | 2 |
| 839 | .01 | .01 | >.05 | 0 | 0 | 1 | 0 | 0 | 0 |
| 840 | .003 | .002 | .01 | 0 | 0 | 1 | 0 | 0 | 0 |
| 841 | .002 | .002 | .05 | 0 | 0 | 0 | 0 | 0 | 0 |
| 842 | .005 | .01 | >.05 | 0 | 0 | 0 | 0 | 0 | 0 |
| 843 | .003 | .002 | >.05 | 0 | 0 | 0 | 0 | 0 | 0 |
| 844 | .001 | .002 | >.05 | 0 | 0 | 0 | 0 | 0 | 0 |
| 845 | .001 | .003 | >.05 | 0 | 0 | 0 | 0 | 0 | 0 |
| 846 | .003 | .002 | .05 | 0 | 0 | 1 | 0 | 0 | 0 |
| 847 | .001 | .003 | .05 | 0 | 0 | 2 | 0 | 0 | 0 |
| 848 | .002 | .001 | >.05 | 0 | 0 | 0 | 0 | 0 | 0 |
| 849 | .001 | .002 | >.05 | 0 | 0 | 1 | 0 | 0 | 0 |
| 850 | .002 | .003 | .05 | 0 | 0 | 1 | 0 | 0 | 0 |
| 851 | .002 | .003 | .05 | 0 | 1 | 2 | 0 | 0 | 1 |
| 852 | .01 | .01 | >.05 | 0 | 0 | 0 | 0 | 0 | 0 |
| 853 | >.05 | .03 | >.05 | 0 | 0 | 0 | 0 | 0 | 0 |
| 854 | .01 | .03 | >.05 | 0 | 0 | 0 | 0 | 0 | 0 |
| 855 | .005 | .003 | >.05 | 0 | 1 | 3 | 0 | 0 | 2 |
| 856 | .001 | .0005 | .05 | 0 | 0 | 1 | 0 | 0 | 1 |
| 857 | .002 | .0002 | .03 | 0 | 1 | 3 | 0 | 1 | 2 |
| 858 | .05 | .01 | >.05 | 0 | 0 | 0 | 0 | 0 | 0 |
| 859 | .001 | .0008 | .01 | 0 | 0 | 0 | 0 | 0 | 0 |
| 860 | .003 | .0005 | .05 | 0 | 0 | 0 | 0 | 0 | 0 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 861 | .002 | .001 | >.05 | 0 | 0 | 1 | 0 | 0 | 0 |
| 862 | >.05 | .005 | >.05 | 0 | 0 | 2 | 0 | 0 | 2 |
| 863 | >.05 | .03 | >.05 | 0 | 0 | 0 | 0 | 0 | 0 |
| 864 | .003 | .003 | .05 | 0 | 0 | 0 | 0 | 0 | 0 |
| 865 | .001 | .001 | .05 | 0 | 0 | 2 | 0 | 0 | 1 |
| 866 | .001 | .001 | >.05 | 0 | 1 | 2 | 0 | 0 | 2 |
| 867 | .002 | .001 | >.05 | 0 | 0 | 1 | 0 | 0 | 0 |
| 868 | .0003 | .0003 | .05 | 0 | 0 | 1 | 0 | 0 | 1 |
| 869 | .0005 | .0003 | .008 | 0 | 0 | 1 | 0 | 0 | 2 |
| 870 | .0008 | .0005 | .01 | 0 | 0 | 1 | 0 | 0 | 0 |
| 871 | .008 | .001 | .01 | 0 | 2 | 3 | 0 | 1 | 2 |
| 872 | .01 | .002 | .05 | 0 | 1 | 2 | 0 | 0 | 2 |
| 873 | .002 | .0005 | .05 | 1 | 2 | 3 | 0 | 1 | 4 |
| 874 | .002 | .002 | .05 | 0 | 1 | 3 | 0 | 0 | 3 |
| 875 | .005 | .003 | .05 | 0 | 0 | 1 | 0 | 0 | 1 |
| 876 | .001 | .0002 | .008 | 1 | 2 | 3 | 1 | 2 | 3 |
| 877 | .001 | .0008 | .005 | 1 | 2 | 3 | 0 | 0 | 2 |
| 878 | .003 | .0005 | .008 | 1 | 2 | 3 | 0 | 2 | 3 |
| 879 | .03 | .003 | .03 | 0 | 1 | 3 | 0 | 0 | 2 |
| 880 | .002 | .0003 | .008 | 1 | 2 | 4 | 1 | 3 | 4 |
| 881 | .003 | .0003 | .008 | 1 | 2 | 3 | 1 | 2 | 3 |
| 882 | .003 | .0005 | .03 | 1 | 2 | 3 | 1 | 2 | 3 |
| 883 | .002 | .0005 | >.05 | 1 | 1 | 2 | 1 | 1 | 2 |
| 884 | .002 | .0003 | .03 | 1 | 2 | 3 | 1 | 2 | 3 |
| 885 | .002 | .0005 | .005 | 1 | 2 | 3 | 1 | 2 | 3 |
| 886 | .002 | .0003 | .003 | 0 | 1 | 2 | 0 | 1 | 3 |
| 887 | .0008 | .0005 | .05 | 1 | 2 | 3 | 1 | 2 | 2 |
| 888 | .001 | .0005 | .003 | 0 | 1 | 2 | 0 | 1 | 2 |
| 889 | .001 | .0002 | >.05 | 1 | 2 | 3 | 0 | 1 | 3 |
| 890 | .001 | .0002 | .03 | 1 | 2 | 3 | 0 | 1 | 3 |
| 891 | .001 | .0002 | .008 | 0 | 1 | 2 | 0 | 1 | 2 |
| 892 | .003 | .0002 | .03 | 1 | 2 | 3 | 0 | 1 | 3 |
| 893 | >.05 | >.05 | >.05 | 0 | 0 | 0 | 0 | 0 | 0 |
| 894 | >.05 | >.05 | >.05 | 0 | 0 | 1 | 0 | 0 | 0 |
| 895 | >.05 | >.05 | >.05 | 0 | 0 | 0 | 0 | 0 | 0 |
| 896 | .001 | .0008 | .03 | 1 | 2 | 3 | 1 | 2 | 3 |
| 897 | .0008 | .0005 | .03 | 0 | 1 | 3 | 0 | 1 | 3 |
| 898 | .001 | .0002 | .005 | 0 | 1 | 2 | 0 | 1 | 2 |
| 899 | .0008 | .0008 | .03 | 1 | 2 | 3 | 0 | 1 | 2 |
| 900 | .002 | .001 | .03 | 0 | 2 | 3 | 0 | 1 | 3 |
| 901 | .005 | .005 | .01 | 0 | 0 | 0 | 0 | 0 | 0 |
| 902 | .002 | .002 | .01 | 1 | 2 | 4 | 0 | 2 | 4 |
| 903 | .03 | .002 | >.05 | 1 | 2 | 3 | 0 | 2 | 3 |
| 904 | >.05 | .005 | >.05 | 0 | 1 | 2 | 0 | 1 | 3 |
| 905 | .005 | .002 | .03 | 1 | 2 | 3 | 0 | 1 | 2 |
| 906 | .002 | .0005 | .01 | 1 | 2 | 3 | 1 | 2 | 4 |
| 907 | .002 | .0005 | .01 | 1 | 2 | 3 | 1 | 2 | 3 |
| 908 | .002 | .0002 | .01 | 0 | 1 | 2 | 0 | 1 | 2 |
| 909 | .005 | .0005 | >.05 | 1 | 2 | 3 | 0 | 1 | 3 |
| 910 | >.05 | .002 | .05 | 1 | 2 | 2 | 1 | 2 | 3 |
| 911 | .05 | .005 | >.05 | 1 | 2 | 3 | 0 | 1 | 2 |
| 912 | .002 | .0002 | .01 | 1 | 2 | 4 | 1 | 2 | 4 |
| 913 | .002 | .0005 | .003 | 1 | 2 | 4 | 1 | 3 | 4 |
| 914 | .002 | .0002 | .03 | 1 | 2 | 4 | 1 | 3 | 4 |
| 915 | .003 | .002 | >.05 | 1 | 2 | 3 | 0 | 1 | 2 |
| 916 | .0008 | .0003 | .03 | 0 | 1 | 2 | 0 | 2 | 3 |
| 917 | .0008 | .0002 | >.05 | 0 | 0 | 0 | 0 | 0 | 0 |
| 918 | .0002 | .0002 | >.05 | 0 | 1 | 2 | 0 | 1 | 3 |
| 919 | .0001 | .0002 | .05 | 0 | 1 | 2 | 0 | 1 | 2 |
| 920 | >.05 | >.05 | >.05 | 0 | 0 | 0 | 0 | 0 | 0 |
| 921 | .002 | .002 | >.05 | 1 | 2 | 3 | 1 | 2 | 4 |
| 922 | .001 | .001 | .05 | 1 | 2 | 4 | 1 | 2 | 4 |
| 923 | .002 | .001 | .03 | 1 | 2 | 3 | 1 | 2 | 4 |
| 924 | .002 | .005 | >.05 | 1 | 2 | 3 | 0 | 2 | 4 |
| 925 | .002 | .002 | >.05 | 1 | 2 | 3 | 1 | 2 | 4 |
| 926 | .0003 | .001 | >.05 | 0 | 0 | 0 | 0 | 0 | 0 |
| 927 | .002 | .002 | >.05 | 0 | 1 | 2 | 0 | 1 | 2 |
| 928 | .001 | .001 | >.05 | 0 | 0 | 0 | 0 | 0 | 0 |
| 929 | .002 | .002 | >.05 | 0 | 1 | 2 | 0 | 1 | 2 |
| 930 | .001 | .001 | >.05 | 0 | 1 | 3 | 1 | 2 | 4 |
| 931 | .003 | .03 | >.05 | 0 | 0 | 0 | 0 | 0 | 0 |
| 932 | .003 | .002 | >.05 | 1 | 2 | 3 | 0 | 1 | 3 |
| 933 | .0005 | .002 | >.05 | 1 | 2 | 3 | 1 | 3 | 4 |
| 934 | .002 | .0008 | .05 | 0 | 1 | 2 | 1 | 2 | 3 |
| 935 | .005 | .002 | >.05 | 1 | 1 | 2 | 0 | 0 | 1 |
| 936 | .005 | .0002 | >.05 | 0 | 1 | 2 | 0 | 0 | 1 |
| 937 | .003 | .002 | .05 | 0 | 1 | 2 | 0 | 0 | 2 |
| 938 | .003 | .0005 | >.05 | 0 | 0 | 1 | 0 | 0 | 1 |
| 939 | .002 | .0005 | >.05 | 0 | 0 | 0 | 0 | 0 | 0 |
| 940 | .001 | .0005 | .05 | 0 | 1 | 2 | 0 | 1 | 3 |
| 941 | .002 | .0005 | >.05 | 0 | 1 | 2 | 0 | 0 | 1 |
| 942 | .002 | .0005 | >.05 | 1 | 2 | 3 | 1 | 2 | 3 |
| 943 | .002 | .0002 | >.05 | 1 | 2 | 3 | 1 | 2 | 3 |
| 944 | .003 | .002 | >.05 | 0 | 1 | 2 | 0 | 1 | 2 |
| 945 | .008 | .002 | >.05 | 0 | 1 | 2 | 0 | 0 | 1 |
| 946 | .002 | .002 | >.05 | 0 | 0 | 0 | 0 | 0 | 1 |
| 947 | .002 | .002 | >.05 | 0 | 0 | 0 | 0 | 0 | 0 |
| 948 | .002 | .0005 | >.05 | 1 | 2 | 4 | 1 | 2 | 4 |
| 949 | .002 | .0008 | .05 | 0 | 1 | 2 | 0 | 1 | 3 |
| 950 | .0005 | .0005 | .03 | 0 | 1 | 2 | 0 | 0 | 1 |
| 951 | .0005 | .002 | .002 | 0 | 0 | 1 | 0 | 0 | 1 |
| 952 | .002 | .0005 | >.05 | 0 | 1 | 2 | 0 | 0 | 1 |
| 953 | .002 | .0005 | .05 | 0 | 0 | 0 | 0 | 0 | 0 |
| 954 | .003 | .0005 | .05 | 0 | 0 | 0 | 0 | 0 | 0 |
| 955 | .001 | .0005 | .05 | 0 | 1 | 2 | 0 | 1 | 2 |
| 956 | .0005 | .001 | .03 | 0 | 1 | 2 | 0 | 1 | 2 |
| 957 | .002 | .002 | .03 | 0 | 1 | 2 | 0 | 1 | 2 |
| 958 | .002 | .0002 | >.05 | 0 | 1 | 2 | 0 | 1 | 3 |
| 959 | >.05 | >.05 | >.05 | 0 | 0 | 1 | 0 | 0 | 0 |
| 960 | .005 | .002 | >.05 | 0 | 0 | 0 | 0 | 0 | 1 |
| 961 | .003 | .002 | >.05 | 0 | 1 | 2 | 0 | 0 | 1 |
| 962 | .0003 | .0005 | .03 | 0 | 1 | 2 | 0 | 1 | 2 |
| 963 | .0002 | .0005 | .05 | 1 | 2 | 3 | 1 | 2 | 3 |
| 964 | .0001 | .0001 | .01 | 0 | 1 | 2 | 0 | 1 | 2 |
| 965 | .001 | .002 | >.05 | 0 | 0 | 1 | 0 | 1 | 2 |
| 966 | .0008 | .003 | >.05 | 0 | 0 | 0 | 0 | 0 | 0 |
| 967 | .03 | .03 | >.05 | 0 | 0 | 0 | 0 | 0 | 0 |
| 968 | .03 | .005 | >.05 | 0 | 0 | 0 | 0 | 0 | 0 |
| 969 | .003 | .03 | >.05 | 0 | 0 | 0 | 0 | 0 | 0 |
| 970 | >.05 | >.05 | >.05 | 0 | 0 | 0 | 0 | 0 | 0 |
| 971 | >.05 | >.05 | >.05 | 0 | 0 | 0 | 0 | 0 | 0 |
| 972 | .03 | .005 | .05 | 0 | 0 | 0 | 0 | 0 | 0 |
| 973 | .008 | .03 | .05 | 0 | 0 | 0 | 0 | 0 | 0 |
| 974 | >.05 | .03 | >.05 | 0 | 0 | 0 | 0 | 0 | 0 |
| 975 | .003 | .002 | >.05 | 0 | 0 | 2 | 0 | 0 | 2 |
| 976 | .003 | .002 | >.05 | 0 | 0 | 1 | 0 | 0 | 2 |
| 977 | .0005 | .0003 | >.05 | 1 | 2 | 3 | 1 | 2 | 4 |
| 978 | .005 | .0005 | >.05 | 0 | 0 | 1 | 0 | 0 | 2 |
| 979 | .002 | .0008 | <.01 | 0 | 1 | 3 | 0 | 1 | 3 |
| 980 | .005 | .0005 | >.05 | 0 | 0 | 0 | 0 | 0 | 0 |
| 981 | .005 | .002 | >.05 | 0 | 0 | 1 | 0 | 0 | 0 |
| 982 | .003 | .0002 | >.05 | 0 | 1 | 2 | 0 | 1 | 3 |
| 983 | .005 | .0008 | .05 | 0 | 1 | 3 | 1 | 2 | 3 |
| 984 | .005 | .0005 | >.05 | 0 | 2 | 3 | 1 | 2 | 3 |
| 985 | .005 | .002 | .05 | 0 | 1 | 2 | 0 | 1 | 2 |
| 986 | .008 | .002 | .05 | 0 | 1 | 2 | 1 | 2 | 3 |
| 987 | .002 | .001 | .05 | 0 | 1 | 3 | 0 | 1 | 3 |
| 988 | .002 | .008 | >.05 | 0 | 2 | 3 | 0 | 2 | 3 |
| 989 | .002 | .001 | >.05 | 0 | 1 | 2 | 0 | 1 | 2 |
| 990 | .0005 | .002 | .05 | 0 | 0 | 1 | 0 | 0 | 1 |
| 991 | .0002 | .002 | >.05 | 1 | 2 | 3 | 1 | 2 | 4 |
| 992 | .0008 | .003 | .05 | 0 | 0 | 1 | 0 | 0 | 1 |
| 993 | .0005 | .0008 | >.05 | 0 | 0 | 0 | 0 | 0 | 0 |
| 994 | .002 | .0005 | >.05 | 1 | 2 | 3 | 1 | 2 | 3 |
| 995 | .002 | .002 | .03 | 1 | 2 | 3 | 1 | 2 | 3 |
| 996 | .0002 | .0003 | >.05 | 0 | 0 | 1 | 0 | 0 | 1 |
| 997 | .0005 | .001 | .05 | 1 | 2 | 3 | 0 | 1 | 3 |
| 998 | .0002 | .0008 | .05 | 0 | 0 | 0 | 0 | 0 | 0 |
| 999 | .002 | .002 | >.05 | 0 | 0 | 1 | 0 | 0 | 1 |
| 1000 | .0002 | .0001 | >.05 | 0 | 1 | 3 | 1 | 2 | 4 |
| 1001 | .001 | .0005 | >.05 | 0 | 0 | 1 | 0 | 0 | 1 |
| 1002 | .002 | .0005 | .05 | 0 | 0 | 2 | 0 | 0 | 2 |
| 1003 | .0005 | .002 | .05 | 0 | 1 | 3 | 1 | 2 | 3 |
| 1004 | .0003 | .0008 | >.05 | 0 | 1 | 3 | 1 | 2 | 4 |
| 1005 | .002 | .001 | >.05 | 0 | 0 | 0 | 0 | 0 | 0 |
| 1006 | .0005 | .0005 | .01 | 0 | 1 | 2 | 0 | 1 | 2 |
| 1007 | .002 | .0003 | >.05 | 0 | 1 | 2 | 0 | 1 | 2 |
| 1008 | .0005 | .0002 | .01 | 0 | 1 | 2 | 0 | 1 | 2 |
| 1009 | .0005 | .002 | .05 | 0 | 1 | 2 | 0 | 1 | 2 |
| 1010 | .0002 | .0005 | .05 | 0 | 1 | 2 | 0 | 0 | 1 |
| 1011 | .0005 | .003 | .03 | 0 | 0 | 1 | 0 | 0 | 0 |
| 1012 | .0008 | .002 | .05 | 0 | 0 | 1 | 0 | 0 | 0 |
| 1013 | .002 | .002 | >.05 | 0 | 0 | 1 | 0 | 0 | 1 |
| 1014 | .0008 | .002 | .05 | 0 | 1 | 2 | 0 | 0 | 1 |
| 1015 | .03 | .005 | >.05 | 0 | 0 | 0 | 0 | 0 | 1 |
| 1016 | .002 | .002 | .05 | 0 | 0 | 0 | 0 | 0 | 1 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 1017 | .0002 | .0005 | >.05 | 0 | 0 | 0 | 0 | 0 | 0 |
| 1018 | .0002 | .0005 | >.05 | 1 | 2 | 4 | 1 | 3 | 5 |
| 1019 | .001 | .0003 | >.05 | 1 | 2 | 4 | 1 | 3 | 5 |
| 1020 | .0008 | .0005 | >.05 | 0 | 0 | 1 | 0 | 0 | 0 |
| 1021 | .002 | .005 | >.05 | 0 | 0 | 1 | 0 | 0 | 0 |
| 1022 | .0003 | .0002 | .05 | 0 | 1 | 2 | 0 | 1 | 3 |
| 1023 | .0005 | .0002 | >.05 | 0 | 0 | 1 | 0 | 0 | 1 |
| 1024 | .002 | .002 | >.05 | 0 | 0 | 2 | 0 | 0 | 2 |
| 1025 | .001 | .0005 | >.05 | 0 | 1 | 2 | 0 | 0 | 1 |
| 1026 | .0008 | .002 | >.05 | 0 | 0 | 2 | 0 | 0 | 1 |
| 1027 | .0003 | .0005 | >.05 | 0 | 1 | 2 | 0 | 0 | 1 |
| 1028 | .0005 | .001 | >.05 | 1 | 2 | 4 | 1 | 3 | 5 |
| 1029 | .002 | .002 | >.05 | 0 | 0 | 1 | 0 | 0 | 0 |
| 1030 | .0005 | .0002 | .01 | 0 | 1 | 2 | 0 | 1 | 3 |
| 1031 | .0005 | .0002 | .05 | 0 | 0 | 1 | 0 | 0 | 0 |
| 1032 | .002 | .0005 | .03 | 0 | 0 | 1 | 0 | 0 | 2 |
| 1033 | .002 | .0002 | .008 | 0 | 1 | 2 | 0 | 1 | 2 |
| 1034 | .002 | .001 | .03 | 0 | 1 | 2 | 1 | 2 | 3 |
| 1035 | .001 | .0005 | .01 | 0 | 1 | 3 | 1 | 2 | 4 |
| 1036 | .001 | .0008 | .008 | 0 | 0 | 1 | 0 | 0 | 0 |
| 1037 | .0005 | .0005 | .03 | 0 | 1 | 2 | 0 | 1 | 2 |
| 1038 | .002 | .0008 | .01 | 0 | 1 | 2 | 0 | 1 | 2 |
| 1039 | .002 | .0003 | .05 | 0 | 1 | 2 | 0 | 1 | 2 |
| 1040 | .0005 | .0002 | .005 | 0 | 1 | 2 | 1 | 2 | 3 |
| 1041 | .002 | .002 | .05 | 0 | 0 | 0 | 0 | 0 | 0 |
| 1042 | .003 | .0005 | .008 | 1 | 2 | 3 | 0 | 1 | 3 |
| 1043 | .002 | .0005 | .03 | 0 | 1 | 2 | 1 | 2 | 4 |
| 1044 | .001 | .0005 | .008 | 0 | 1 | 3 | 1 | 2 | 4 |
| 1045 | .002 | .0005 | .008 | 0 | 1 | 2 | 0 | 1 | 3 |
| 1046 | .001 | .0005 | .01 | 0 | 1 | 3 | 0 | 1 | 3 |
| 1047 | .002 | .0005 | .008 | 0 | 1 | 2 | 0 | 1 | 3 |
| 1048 | .002 | .002 | .03 | | | | | | |
| 1049 | .0005 | .0005 | .03 | 1 | 2 | 5 | 2 | 4 | 5 |
| 1050 | .002 | .0005 | .03 | 0 | 1 | 3 | 1 | 2 | 4 |
| 1051 | .0005 | .002 | .03 | 0 | 1 | 2 | 0 | 1 | 2 |
| 1052 | .003 | .0005 | >.05 | 0 | 2 | 3 | 1 | 2 | 3 |
| 1053 | .0005 | .002 | .05 | 1 | 2 | 3 | 0 | 1 | 3 |
| 1054 | .0008 | .0005 | .03 | 1 | 2 | 4 | 1 | 3 | 4 |
| 1055 | .03 | >.05 | >.05 | 1 | 3 | 4 | 1 | 3 | 5 |
| 1056 | .002 | .005 | >.05 | 1 | 3 | 5 | 1 | 2 | 4 |
| 1057 | .005 | .005 | >.05 | 0 | 1 | 3 | 0 | 2 | 3 |
| 1058 | .005 | .03 | >.05 | 0 | 0 | 2 | 0 | 1 | 2 |
| 1059 | >.05 | >.05 | .05 | 0 | 0 | 0 | 0 | 0 | 0 |
| 1060 | .03 | .03 | >.05 | 0 | 0 | 1 | 0 | 0 | 0 |
| 1061 | >.05 | >.05 | >.05 | 0 | 0 | 0 | 0 | 0 | 0 |
| 1062 | >.05 | >.05 | >.05 | 0 | 0 | 0 | 0 | 0 | 0 |
| 1063 | >.05 | .01 | >.05 | 0 | 0 | 0 | 0 | 0 | 0 |
| 1064 | .005 | .005 | >.05 | 0 | 0 | 1 | 0 | 0 | 0 |
| 1065 | .008 | .005 | >.05 | 0 | 0 | 0 | 0 | 0 | 0 |
| 1066 | .03 | .03 | >.05 | 0 0 | 0 | 0 | 0 | 0 | |
| 1067 | >.05 | >.05 | >.05 | 0 | 0 | 0 | 0 | 0 | 0 |
| 1068 | .005 | .03 | >.05 | 0 | 1 | 3 | 0 | 1 | 3 |
| 1069 | .002 | .01 | >.05 | 1 | 3 | 5 | 1 | 3 | 5 |
| 1070 | .005 | .01 | >.05 | 0 | 0 | 1 | 0 | 0 | 1 |
| 1071 | .0002 | .0005 | .03 | 0 | 0 | 2 | 0 | 0 | 1 |
| 1072 | .002 | .0005 | >.05 | 0 | 0 | 1 | 0 | 0 | 0 |
| 1073 | .0005 | .0002 | .03 | 1 | 2 | 3 | 1 | 2 | 4 |
| 1074 | .0005 | .0005 | >.05 | 0 | 1 | 2 | 0 | 0 | 2 |
| 1075 | .002 | .0005 | .03 | 1 | 2 | 3 | 1 | 2 | 3 |
| 1076 | .0005 | .0002 | .008 | 0 | 1 | 2 | 0 | 1 | 3 |
| 1077 | .0003 | .0002 | .05 | 0 | 0 | 0 | 0 | 0 | 0 |
| 1078 | .0005 | .0005 | .01 | 1 | 1 | 3 | 0 | 2 | 3 |
| 1079 | .0005 | .0005 | .05 | 1 | 2 | 3 | 1 | 2 | 4 |
| 1080 | .0005 | .0005 | .01 | 0 | 0 | 1 | 0 | 0 | 1 |
| 1081 | .0005 | .0005 | .03 | 0 | 1 | 3 | 1 | 2 | 4 |
| 1082 | .0003 | .0005 | .01 | 1 | 2 | 4 | 1 | 3 | 5 |
| 1083 | .0005 | .0005 | .03 | 0 | 1 | 3 | 0 | 1 | 3 |
| 1084 | .002 | .0005 | .03 | 0 | 1 | 3 | 0 | 1 | 3 |
| 1085 | .0005 | .002 | .05 | 0 | 1 | 2 | 0 | 0 | 1 |
| 1086 | .0005 | .0005 | .03 | 0 | 0 | 2 | 0 | 0 | 2 |
| 1087 | .0005 | .0008 | >.05 | 0 | 1 | 2 | 0 | 1 | 2 |
| 1088 | .0005 | .0005 | .05 | 0 | 0 | 0 | 0 | 0 | 0 |
| 1089 | .0005 | .0005 | .01 | 0 | 0 | 2 | 0 | 1 | 3 |
| 1090 | .002 | .0005 | .03 | 0 | 1 | 2 | 0 | 1 | 3 |
| 1091 | .001 | .0005 | .05 | 0 | 1 | 2 | 0 | 0 | 2 |
| 1092 | .001 | .0008 | >.05 | 0 | 1 | 2 | 0 | 1 | 3 |
| 1093 | .002 | .0005 | .01 | 0 | 1 | 2 | 0 | 0 | 2 |
| 1094 | .002 | .0005 | .05 | 0 | 0 | 1 | 0 | 0 | 1 |

TABLE II-continued

| Compound No. | Lepidoptericidal Activity SMC | CL | TBW | Phytotoxicity Cotton ½ | 1 | 2 | Squash ½ | 1 | 2 |
|---|---|---|---|---|---|---|---|---|---|
| 1095 | .003 | .002 | .05 | 0 | 0 | 0 | 0 | 0 | 0 |
| 1096 | .002 | .0005 | .05 | 0 | 0 | 1 | 0 | 0 | 1 |
| 1097 | .03 | .003 | >.05 | 0 | 0 | 0 | 0 | 0 | 0 |
| 1098 | .03 | .002 | .05 | 0 | 0 | 0 | 0 | 0 | 0 |
| 1099 | >.05 | >.05 | >.05 | 0 | 0 | 0 | 0 | 0 | 0 |
| 1100 | .005 | .008 | >.05 | 0 | 0 | 0 | 0 | 0 | 0 |
| 1101 | >.05 | >.05 | >.05 | 0 | 0 | 0 | 0 | 0 | 0 |
| 1102 | >.05 | >.05 | >.05 | 0 | 0 | 0 | 0 | 0 | 0 |
| 1103 | .005 | .005 | >.05 | 0 | 0 | 0 | 0 | 0 | 0 |
| 1104 | .005 | .005 | >.05 | 0 | 0 | 0 | 0 | 0 | 0 |
| 1105 | .002 | .0005 | — | 0 | 0 | 0 | 0 | 0 | 0 |
| 1106 | .003 | .0005 | >.05 | 0 | 0 | 0 | 0 | 0 | 0 |
| 1107 | .002 | .002 | >.05 | 0 | 0 | 0 | 0 | 0 | 0 |
| 1108 | .03 | .01 | >.05 | | | | | | |
| 1109 | .03 | .005 | .05 | | | | | | |
| 1110 | .01 | .002 | >.05 | | | | | | |
| 1111 | .03 | .005 | >.05 | | | | | | |
| 1112 | .008 | .002 | >.05 | | | | | | |
| 1113 | .03 | .005 | .05 | | | | | | |
| 1114 | .005 | .002 | .05 | | | | | | |
| 1115 | .03 | .005 | <.05 | | | | | | |
| 1116 | .01 | .005 | >.05 | | | | | | |
| 1117 | .005 | .002 | .05 | | | | | | |
| 1118 | .03 | .005 | >.05 | | | | | | |
| 1119 | .01 | .005 | >.05 | | | | | | |
| 1120 | .01 | .008 | >.05 | | | | | | |
| 1121 | .01 | .005 | >.05 | | | | | | |
| 1122 | .01 | .002 | .05 | | | | | | |
| 1123 | .03 | .005 | >.05 | | | | | | |
| 1124 | .003 | .005 | <.05 | | | | | | |
| 1125 | .005 | .005 | >.05 | | | | | | |
| 1126 | .008 | .03 | >.05 | | | | | | |
| 1127 | .003 | .003 | >.05 | | | | | | |
| 1128 | <.001 | .005 | <.05 | | | | | | |
| 1129 | .002 | .005 | >.05 | | | | | | |
| 1130 | .002 | .005 | <.05 | | | | | | |
| 1131 | .002 | .005 | <.05 | | | | | | |
| 1132 | .002 | .003 | <.05 | | | | | | |
| 1133 | .001 | .002 | <.05 | | | | | | |
| 1134 | .01 | .005 | >.05 | 0 | 0 | 0 | 0 | 0 | 0 |
| 1135 | .01 | .01 | .05 | | | | | | |
| 1136 | — | <.003 | >.05 | | | | | | |

Symbols for Table II
SMC: salt-marsh caterpillar
CL: cabbage looper
TBW: tobacco budworm
>: greater than
<: less than

BIOCIDAL TESTS

In Vitro Vial Tests

Tubes of sterilized nutrient and malt extract broth were prepared. Aliquots of the toxicant, dissolved in an appropriate solvent, were injected through the stopper, into the broth, to provide concentrations ranging from 50 ppm downward. The test organisms consisted of one fungi, *Botrytus cinerea*, and one bacteria, *Staphylococcus aureus* (S.A.) Roseenbach.

Three drops of a spore suspension of each of the fungi were injected into the tubes of malt broth and three drops of the bacteria were injected into the nutrient broth. One week later and growth of each organism was observed and effectiveness of the chemical was recorded as the lowest concentration in ppm which provided 100 percent inhibition of growth as compared to untreated inoculated tubes. The results are shown in Table III.

FUNGICIDAL TESTS

Foliar Preventive Sprays

*Bean Powdery Mildew*—The chemicals were dissolved in an appropriate solvent and diluted with water containing several drops of a wetting agent. Test concentrations, ranging from 1000 ppm downward, were sprayed to runoff on the primary leaves of pinto beans *Phaseolus vulgaris* L.). After the plants were dry, the leaves were dusted with spores of the powdery mildew fungus (*Erysiphe polygoni* de Candolle) and the plants were retained in the greenhouse until the fungal growth appeared on the leaf surface. Effectiveness was recorded as the lowest concentration, in ppm, which will provide 75 percent or greater reduction in mycelial growth on the leaf surface as compared to untreated, inoculated plants. The results are shown in Table III.

TABLE III

| | Biocides LC-100 (ppm) | | Fungicides LC-75-100 (ppm) |
|---|---|---|---|
| Compound No. | *Staph aureus* | *Botyrytus cinerea* | Bean Powdery Mildew |
| 118 | (10) | 5 | 1 |
| 155 | — | — | 500 |
| 166 | — | — | 500 |
| 170 | — | — | 500 |
| 175 | — | — | 1000 |
| 183 | 5 | (10) | 500 |
| 213 | 10 | — | 500 |
| 279 | 0.125 | 5 | 500 |
| 309 | 25 | 10 | 500 |
| 310 | 0 | 5 | — |
| 554 | 10 | 0.125 | 500 |
| 662 | 25 | 10 | — |
| 733 | — | — | 500 |
| 741 | 50 | 50 | 10 |
| 769 | — | — | 500 |
| 878 | 10 | 5 | 5 |

( ) = partial control - 50% or greater

The primary screening level in each of the above tests was selected for purposes of convenience only, and none of the figures in the table are to be understood as representing the highest level at which a viable test for lepidoptericidal activity can be conducted.

The compounds of this invention are generally used in formulations suitable for convenient application. In general, such formulations will contain inert or other active ingredients or diluent carriers in addition to the active compound. Examples of such ingredients or carriers are organic solvents, such as sesame oil, xylene range solvents, and heavy petroleum; water; emulsifying agents; surface active agents; talc; pyrophyllite; diatomite; gypsum; clays; and propellants, such as dichlorodifluoromethane.

The active compounds can further be combined with dust carriers for application as dusts, with granular carriers for application by fertilizer spreaders or ground or airplane seeders. It also can be formulated as a wettable powder or a flowable for application as a water suspension, or with solvents and surface active materials for application as sprays, aerosols, or emulsions. The compounds or their formulated mixtures can be applied to any habitat of the pests. Examples of such habitats are insect dwellings, clothing, plant surfaces, and soil. If desired, however, the active compositions can be applied directly to organic matter, seeds or feedstuffs in general, upon which the pests feed, or directly to the pests themselves. When applied in such a manner, it will be advantageous to use a formulation which is not volatile.

Particularly preferred compositions are those comprising an insecticidally effective amount of the active compound in combination with an inert insoluble solid carrier vehicle. Examples of such compositions are wettable powders, dusts, and flowable formulations, in which the solid carrier is in finely divided form; and granular formulations, in which the solid carrier is a pre-formed granule.

These isothiourea compounds can also be formulated to include baits that induce feeding responses in the lepidoptera larva resulting in earlier ingestion of the lepidoptericidal isothioureas. Effective baits include cottonseed flour, cottonseed oil, extract of mature cottonseed, sucrose, invert sugar, citrus molasses, soybean oil, soy flour, corn oil, extract of corn kernels, extract of corn silks, extract of corn seed and mixtures thereof together with suitable emulsifiers and wetting agents.

The amount of active compound or formulation which is considered to be insecticidally effective is that amount which, when applied to the pest habitat or feedstuff, will kill or substantially injure a significant portion residing or feeding thereon. The active compounds of this invention can be employed either as the sole pesticide component of the formulations or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the pesticide composition will comprise not more than about 50.0 percent be weight of the formulation.

What is claimed is:

1. A compound having the formula

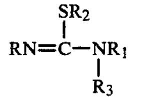

wherein

R and $R_1$ are independently selected from the group consisting of $C_2$–$C_{10}$ alkyl and; R and $R_1$ together contain from 12 to 22 carbon atoms;

$R_2$ is selected from the group consisting $C_1$–$C_{14}$ alkyl, $C_3$–$C_{10}$ alkenyl, and $C_3$–$C_4$ alkynyl; and $R_3$ is selected from the group consisting of

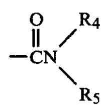

wherein $R_4$ is selected from the group consisting of hydrogen, $C_1$-$C_{22}$ alkyl, phenyl, and substituted phenyl wherein the substituents are independently selected from the group consisting of halogen, $C_1$-$C_5$ alkyl, $C_1$-$C_5$ alkoxy, nitro, cyano, —$N(CH_3)_2$ and —$CF_3$, and $R_5$ is selected from the group consisting of hydrogen, $C_1$-$C_4$ alkyl, and phenyl.

2. The compound of claim 1 wherein R and $R_1$ are independently selected from the group consisting of $C_5$-$C_9$ alkyl and R and $R_1$ together contain from 12 to 22 carbon atoms; wherein $R_2$ is selected from the group consisting of $C_1$14 $C_6$ alkyl, $C_3$-$C_5$ alkenyl and $C_3$-$C_4$ alkynyl.

3. The compound of claim 1 wherein R and $R_1$ are independently selected from the group consisting of $C_6$-$C_8$ alkyl and R and $R_1$ together contain from 12 to 22 carbon atoms; wherein $R_2$ is selected from the group consisting of $C_1$-$C_{13}$ alkyl, $C_2$-$C_3$ alkenyl, and $C_3$-$C_4$ alkynyl.

4. The compound of claims 1 or 2 or 3 wherein $R_3$ is selected from the group consisting of

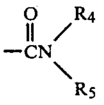

wherein $R_4$ is selected from the group consisting of hydrogen, $C_2$-$C_{12}$ alkyl, phenyl and substituted phenyl wherein the substituents are independently selected from the group consisting of chlorine, $C_1$14 $C_2$ alkyl, $C_1$14 $C_2$ alkoxy, cyano, nitro, —$N(CH_3)_2$ and —$CF_3$; and $R_5$ is selected from group consisting of hydrogen, $C_1$-$C_4$ alkyl and phenyl.

5. The compound of claims 1 or 2 or 3 wherein $R_3$ is selected from the group consisting of

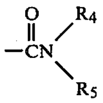

wherein $R_4$ is selected from the group consisting of hydrogen, $C_1$-$C_8$ alkyl, hydroxyethyl, naphthyl, phenyl, substituted phenyl wherein the substituents are independently selected from the group consisting of chlorine, $C_1$-$C_2$ alkyl, $C_1$-$C_2$ alkoxy, nitro, cyano, —$N(CH_3)_2$, and —$CF_3$; and $R^5$ is selected from the group consisting of hydrogen, $C_1$-$C_4$ alkyl, and phenyl.

6. The compound of claim 1 wherein R is —sec$C_7H_{15}$, $R_1$ is —$C_8H_{17}$, $R_2$ is —$C_1H_3$ and $R_3$ is

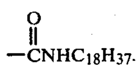

7. The compound of claim 1 wherein R is —sec$C_7C_{15}$, $R_1$ is —$C_8H_{17}$, $R_2$ is $C_1H_3$ and $R_3$ is

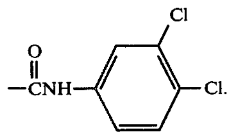

8. The compound of claim 1 wherein R is -2-ethylhexyl, $R_1$ is 2-ethylhexyl, $R_2$ is —$C_2H_5$ and $R_3$ is

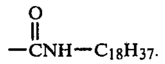

9. The compound of claim 1 wherein R is —sec$H_7H_{15}$, $R_1$ is —$C_8H_{17}$, $R_2$ is —$CH_2CH{=}CH_2$, and $R_3$ is

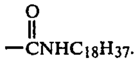

10. The compound of claim 1 wherein R is —sec$C_7H_{15}$, $R_1$ is —$C_8H_{17}$, $R_2$ is —$C_2H_5$and $R_3$ is

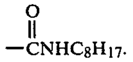

11. The compound of claim 1 wherein R is —sec$C_7H_{15}$, $R_1$ is —$C_8H_{17}$, $R_2$ is —$C_2H_4$ and $R_3$ is

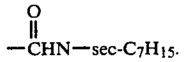

12. The compound of claim 1 wherein R is —sec$C_7H_{15}$, $R_1$ is —$C_8H_{17}$, $R_2$ is —$C_2H_5$ and $R_3$ is

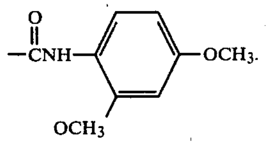

13. The compound of claim 1 wherein R is —sec $C_7H_{15}$, $R_1$ is —$C_8H_{17}$, $R_2$ is —$C_2H_5$ and $R_3$ is

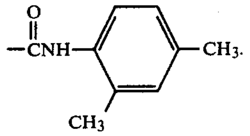

14. The compound of claim 1 wherein R is —sec$C_7H_{15}$, $R_1$ is —$C_8H_{17}$, $R_2$ is —$C_2H_5$ and $R_3$ is

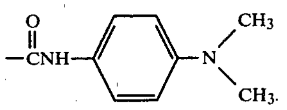

15. The compound of claim 1 wherein R is —sec $C_7H_{15}$, $R_1$ is —$C_8H_{17}$, $R_2$ is —$C_2H_5$ and $R_3$ is

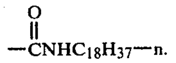

16. The compound of claim 1 wherein R is —$C_7H_{15}$, $R_1$ is —$C_7H_{15}$, $R_2$ is —$C_2H_5$ and $R_3$ is

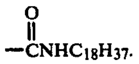

17. The compound of claim 1 wherein R is $—C_7H_{15}$, $R_1$ is $—C_8H_{17}$, $R_2$ is $—C_2H_5$, and $R_3$ is

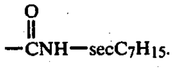

18. The compound of claim 1 wherein R is $—secC_7H_{15}$, $R_1$ is $—C_8H_{17}$, $R_2$ is $—CH_3$ and $R_3$ is

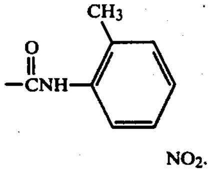

19. The compound of claim 1 wherein R is $—secC_7H_{15}$, $R_1$ is $—C_8H_{17}$, $R_3$ is $—CH_3$ and $R_3$ is

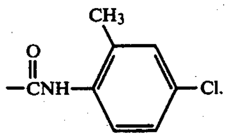

20. The compound of claim 1 wherein R is $—secC_7H_{15}$, $R_1$ is $—C_8H_{17}$, $R_2$ is $—C_2H_5$ and $R_3$ is

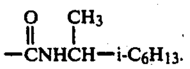

21. A lepidoptericidal composition comprising an effective amount of the compound of claim 1 and an inert carrier.

22. The lepidoptericidal composition of claim 21 wherein R is $—secC_7H_{15}$, $R_1$ is $—C_8H_{17}$, $R_2$ is $—C_1H_3$ and $R_3$ is

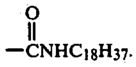

23. The lepidoptericidal composition of claim 21 wherein R is $—secC_7H_{15}$, $R_1$ is $—C_8H_{17}$, $R_2$ is $—C_1H_3$ and $R_3$ is

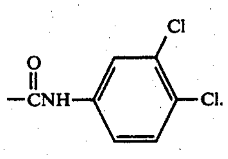

24. The lepidoptericidal composition of claim 21 wherein R is -2-ethylhexyl, $R_1$ is -2-ethylhexyl, $R_2$ is $—C_2H_5$ and $R_3$ is

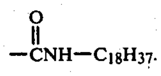

25. The lepidoptericidal composition of claim 21 wherein R is $—secC_7H_{15}$, $R_1$ is $—C_8H_{17}$, $R_2$ is $—CH_2CH{=}CH_2$ and $R_3$ is

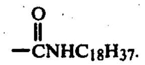

26. The lepidoptericidal composition of claim 21 wherein R is $—secC_7H_{15}$, $R_1$ is $—C_8H_{17}$, $R_2$ is $—C_2H_5$ and $R_3$ is

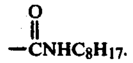

27. The lepidoptericidal composition of claim 21 wherein R is $—secC_7H_{15}$, $R_1$ is $—C_8H_{17}$, $R_2$ is $—C_2H_5$ and $R_3$ is

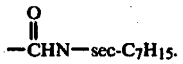

28. The lepidoptericidal composition of claim 21 wherein R is $—secC_7H_{15}$, $R_1$ is $—C_8H_{17}$, $R_2$ is $—C_2H_5$ and $R_3$ is

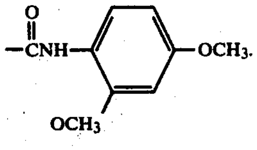

29. The lepidoptericidal composition of claim 21 wherein R is $—secC_7H_{15}$, $R_1$ is $—C_8H_{17}$, $R_2$ is $—C_2H_5$ and $R_3$ is

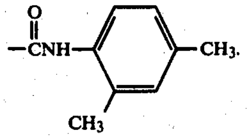

30. The lepidoptericidal composition of claim 21 wherein R is $—secC_7H_{15}$, $R_1$ is $—C_8H_{17}$, $R_2$ is $—C_2H_5$ and $R_3$ is

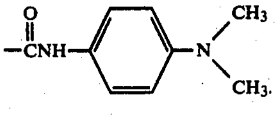

31. The lepidoptericidal composition of claim 21 wherein R is $—secC_7H_{15}$, $R_1$ is $—C_8H_{17}$, $R_2$ is $—C_2H_5$ and $R_3$ is

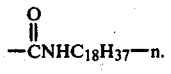

32. The lepidoptericidal composition of claim 21 wherein R is $—C_7H_{15}$, $R_1$ is $—C_7H_{15}$, $R_2$ is $—C_2H_5$ and $R_3$ is

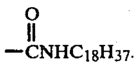

33. The lepidoptericidal composition of claim 21 wherein R is $—C_7H_{15}$, $R_1$ is $—C_8H_{17}$, $R_2$ is $—C_2H_5$ and $R_3$ is

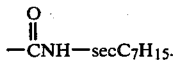

34. The lepidoptericidal composition of claim 21 wherein R is $—secC_7H_{15}$, $R_1$ is $—C_8H_{17}$, $R_2$ is $—CH_3$ and

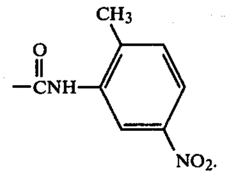

35. The lepidoptericidal composition of claim 21 wherein R is $—secC_7H_{15}$, $R_1$ is $—C_8H_{17}$, $R_2$ is $—CH_3$ and $R_3$ is

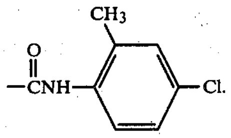

36. The lepiodoptericidal composition of claim 21 wherein R is $—secC_7H_{15}$, $R_1$ is $—C_8H_{17}$, $R_2$ is $—C_2H_5$ and $R_3$ is

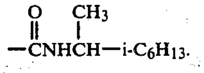

37. The lepidoptericidal compositions of claim 21 or 38 or 39 wherein $R_3$ is

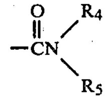

wherein $R_4$ is selected from the group consisting of hydrogen, $C_1$-$C_{12}$ alkyl, phenyl and substituted phenyl wherein the substituents are independently selected from the group consisting of halogen, $C_1$-$C_5$alkyl, $C_1$-$C_5$alkoxy, nitro, cyano, $—N(CH_3)_2$, and $—CF_3$; and $R_5$ is selected from the group consisting of hydrogen, $C_1$-$C_4$ alkyl, and phenyl.

38. A lepidoptericidal composition comprising an effective amount of the compound of claim 2 and an inert carrier.

39. A lepidoptericidal composition comprising an effective amount of the compound of claim 3 and an inert carrier.

40. The lepidoptericidal composition of claims 21, 38, or 39 wherein $R_3$ is

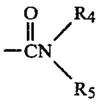

wherein $R_4$ is selected from the group consisting of hydrogen, $C_1$-$C_8$ alkyl, hydroxyethyl, naphthyl, phenyl, substituted phenyl wherein the substituents are independently selected from the group consisting of chlorine, $C_1$-$C_2$ alkyl, $C_1$-$C_2$ alkoxy, nitro, cyano, $—N(CH_3)_2$and $—CF_3$; and $R_5$ is selected from the group consisting of hydrogen, $C_1$-$C_4$ alkyl, and phenyl.

41. The method of controlling lepidoptera comprising applying to said lepidoptera or the locus or feedstuffs thereof a lepidoptericidally effective amount of the compound of claim 1.

42. The method of claim 41 wherein R is $—secC_7H_{15}$, $R_1$ is $—C_8H_{17}$, $R_2$ is $—C_1H_3$ and $R_3$ is

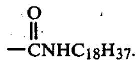

43. The method of claim 41 wherein R is $—secC_7H_{15}$, $R_1$ is $—C_8H_{17}$, $R_2$ is $—C_1H_3$ and $R_3$ is

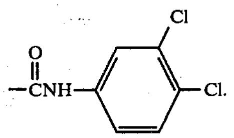

44. The method of claim 41 wherein R is -2-ethylhexyl, $R_1$ is -2-ethylhexyl, $R_2$ is $—C_2H_5$ and $R_3$ is

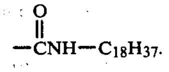

45. The method of claim 41 wherein R is $—secC_7H_{15}$, $R_1$ is $—C_8H_{17}$, $R_2$ is $—CH_2CH{=}CH_2$ and $R_3$ is

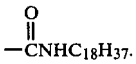

46. The method of claim 41 wherein R is $—secC_7H_{15}$, $R_1$ is $—C_8H_{17}$, $R_2$ is $—C_2H_5$ and $R_3$ is

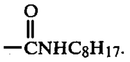

47. The method of claim 41 wherein R is $—secC_7H_{15}$, $R_1$ is $—C_8H_{17}$, $R_2$ is $—C_2H_5$ and $R_3$ is

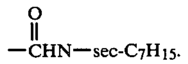

48. The method of claim 41 wherein R is $—secC_7H_{15}$, $R_1$ is $—C_8H_{17}$, $R_2$ is $—C_2H_5$ and $R_3$ is

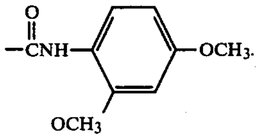

49. The method of claim 41 wherein R is —$secC_7H_{15}$, $R_1$ is —$C_8H_{17}$, $R_2$ is —$C_2H_5$ and $R_3$ is

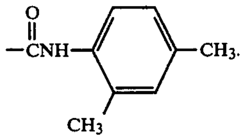

50. The method of claim 41 wherein R is —$secC_7H_{15}$, $R_1$ is —$C_8H_{17}$, $R_2$ is —$C_2H_5$ and $R_3$ is

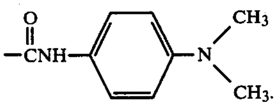

51. The method of claim 41 wherein R is —$secC_7H_{15}$, $R_1$ is —$C_8H_{17}$, $R_2$ is —$C_2H_5$ and $R_3$ is

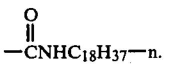

52. The method of claim 41 wherein R is —$C_7H_{15}$, $R_1$ is —$C_7H_{15}$, $R_2$ is —$C_2H_5$ and $R_3$ is

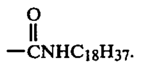

53. The method of claim 41 wherein R is —$C_7H_{15}$, $R_1$ is —$C_8H_{17}$, $R_2$ is —$C_2H_5$ and $R_3$ is

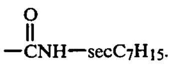

54. The method of claim 41 wherein R is —sec-$C_7H_{15}$, $R_1$ is —$C_8H_{17}$, $R_2$ is —$CH_3$ and $R_3$ is

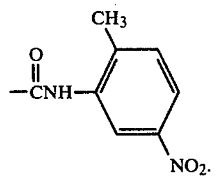

55. A method of claim 41 wherein R is —$secC_7H_{15}$, $R_1$ is —$C_8H_{17}$, $R_2$ is —$CH_3$ and $R_3$ is

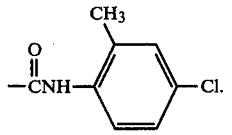

56. The method of claim 41 wherein R is —$secC_7H_{15}$, $R_1$ is —$C_8H_{17}$, $R_2$ is —$C_2H_5$ and $R_3$ is

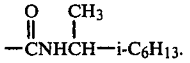

57. The method of controlling lepidoptera comprising applying to said lepidoptera or the locus or feedstuffs thereof a lepidoptericidally effective amount of the compound of claim 2.

58. The method of controlling lepidoptera comprising applying to said lepidoptera or the locus or feedstuffs thereof a lepidoptericidally effective amount of the compound of claim 3.

59. The method of claims 41, 57, 58 wherein $R_3$ is

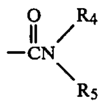

wherein $R_4$ is selected from the group consisting of hydrogen, $C_1$-$C_{12}$ alkyl, phenyl and substituted phenyl wherein the substituents are independently selected from the group consisting of halogen, $C_1$-$C_5$ alkyl, $C_1$-$C_5$ alkoxy, nitro, cyano, —$N(CH_3)_2$ and —$CF_3$; and $R_5$ is selected from the group consisting of hydrogen, $C_1$-$C_4$ alkyl, and phenyl.

60. The method of claims 41, 57, or 58 wherein $R_3$ is

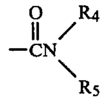

wherein $R_4$ is selected from the group consisting of hydrogen, $C_1$-$C_8$ alkyl, phenyl, and substituted phenyl wherein the substituents are independently selected from the group consisting of chlorine, $C_1$-$C_2$ alkyl, $C_1$-$C_2$ alkoxy, nitro, cyano, —$N(CH_3)_2$ and —$CF_3$; and $R_5$ is selected from the group consisting of hydrogen, $C_1$-$C_4$ alkyl and phenyl.

* * * * *

UNITED STATES PATENT AND TRADEMARK OFFICE

CERTIFICATE OF CORRECTION

PATENT NO. : 4,357,351

DATED : November 2, 1982

INVENTOR(S) : Fancher et al.

It is certified that error appears in the above-identified patent and that said Letters Patent is hereby corrected as shown below:

In Column 287, at line 13, "..of $C_1 14C_6$ alkyl...", should read ...of $C_1$-$C_6$ alkyl..."

In Column 287, at line 33, "...$C_1 14C_2$ alkyl,", should read ...$C_1$-$C_2$ alkyl, In column 287 at line 34, "$C_1 14C_2$ alkoxy...", should read ...$C_1$-$C_2$ alkoxy,

Signed and Sealed this

*Twenty-first* Day of *January 1986*

[SEAL]

*Attest:*

DONALD J. QUIGG

*Attesting Officer* *Commissioner of Patents and Trademarks*